(12) United States Patent
Knegtel et al.

(10) Patent No.: US 7,528,138 B2
(45) Date of Patent: May 5, 2009

(54) PYRAZOLO[1,5-A]PYRIMIDINES USEFUL AS INHIBITORS OF PROTEIN KINASES

(75) Inventors: Ronald Knegtel, Abindgon (GB);
Juan-Miguel Jimenez, Abindgon (GB);
Jean-Damien Charrier, Wantage (GB);
Dean Stamos, Framingham, MA (US);
Pan Li, Arlington, MA (US); Jon Come, Cambridge, MA (US); Alex Aronov, Watertown, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 227 days.

(21) Appl. No.: 11/266,935

(22) Filed: Nov. 4, 2005

(65) Prior Publication Data

US 2006/0135537 A1 Jun. 22, 2006

Related U.S. Application Data

(60) Provisional application No. 60/625,446, filed on Nov. 4, 2004.

(51) Int. Cl.
*C07D 487/04* (2006.01)
*A61K 31/519* (2006.01)
*A61P 35/00* (2006.01)

(52) U.S. Cl. .................................. 514/259.3; 544/281

(58) Field of Classification Search ................ 544/281; 514/259.3
See application file for complete search history.

(56) References Cited

FOREIGN PATENT DOCUMENTS

| WO | WO 98/54093 A1 | 12/1998 |
|---|---|---|
| WO | WO 00/53605 A1 | 9/2000 |
| WO | WO 02/066481 A1 | 8/2002 |
| WO | WO 2004/052315 A2 | 6/2004 |

OTHER PUBLICATIONS

Ho, "Studies on the Synthesis of the New 3-(3,5-diamino-1-substituted-pyrazol-4-yl)azo-thieno[2,3-b]pyridines and 3-(2-Amino-5,7-disubstituted-pyrazolo[1,5-a]pyrimidine-3-yl)azo-thieno[2,3-b]pyridines," J. Chin. Chem. Soc., 46(6) :955-962 (1999).
Elnagdi et al., "Synthesis of Substituted Azaindenes: Synthesis of New Pyrazolo-[1,5-a]pyrimidine Derivatives," 63(6):1854-1856 (1990).

*Primary Examiner*—Bruck Kifle
(74) *Attorney, Agent, or Firm*—Daniel A. Pearson

(57) ABSTRACT

The present invention relates to compounds useful as inhibitors of protein kinases. The invention also provides pharmaceutically acceptable compositions comprising said compounds and methods of using the compositions in the treatment of various disease, conditions, or disorders. The invention also provides processes for preparing the compounds of the invention.

15 Claims, No Drawings

PYRAZOLO[1,5-A]PYRIMIDINES USEFUL AS INHIBITORS OF PROTEIN KINASES

This application claims benefit of U.S. Provisional Application 60/625,446, filed Nov. 4, 2004, which is herein incorporated by reference in its entirety.

TECHNICAL FIELD OF THE INVENTION

The present invention relates to compounds useful as inhibitors of protein kinases, particularly Tec family kinases, Aurora kinases and c-Met. The invention also provides pharmaceutically acceptable compositions comprising the compounds of the invention and methods of using the compositions in the treatment of various disorders. The invention also provides processes for preparing the compounds of the invention.

BACKGROUND OF THE INVENTION

The Tec family of non-receptor tyrosine kinases plays a central role in signalling through antigen-receptors such as the TCR, BCR and Fcε receptors and are essential for T cell activation. Deletion of Itk in mice results in reduced T cell receptor (TCR)-induced proliferation and secretion of the cytokines IL-2, IL-4, IL-5, IL-10 and IFN-γ. Itk has been implicated in allergic asthma and a topic dermatitis.

Tec family kinases are also essential for B cell development and activation. Patients with mutations in Btk have a profound block in B cell development, resulting in the almost complete absence of B lymphocytes and plasma cells, severely reduced Ig levels and a profound inhibition of humoral response to recall antigens. Btk deletion in mice has a profound effect on B cell proliferation induced by anti-IgM, and inhibits immune responses to thymus-independent type II antigens.

Tec kinases also play a role in mast cell activation through the high-affinity IgE receptor (FcεRI). Itk and Btk are expressed in mast cells and are activated by FcεRI cross-linking. Btk deficient murine mast cells have reduced degranulation and decreased production of proinflammatory cytokines following FcεRI cross-linking. Btk deficiency also results in a decrease of macrophage effector functions.

The Aurora proteins are a family of three highly related serine/threonine kinases (termed Aurora-A, -B and -C) that are essential for a cell's progression through the mitotic phase of the cell cycle. Specifically Aurora-A plays a crucial role in centrosome maturation and segregation, formation of the mitotic spindle, and faithful segregation of chromosomes. Aurora-B is a chromosomal passenger protein that plays a central role in regulating the alignment of chromosomes on the meta-phase plate, in the spindle assembly checkpoint, and also in the correct completion of cytokinesis.

Overexpression of Aurora-A (Aurora-2), Aurora-B (Aurora-1) or Aurora-C has been observed in a range of human cancers including colorectal, ovarian, gastric, and invasive duct adenocarcinomas.

A number of studies have now demonstrated that depletion or inhibition of Aurora-A or -B in human cancer cell lines by siRNA, dominant negative or neutralizing antibodies, disrupts progression through mitosis with accumulation of cells with 4N DNA. In some cases, this is followed by endoreduplication and cell death.

The c-Met receptor tyrosine kinase is overexpressed in a significant percentage of human cancers and is amplified during the transition between primary tumors and metastasis. The various cancers in which c-Met is implicated include, but are not limited to, gastric adenocarcinoma, renal cancer, small cell lung carcinoma, colorectal cancer, colon cancer, prostate cancer, brain cancer, liver cancer, pancreatic cancer, and breast cancer. c-Met is also implicated in atherosclerosis, lung fibrosis, allergic disorders, autoimmune disorders, and conditions associated with organ transplantation.

Accordingly, there is a great need to develop compounds useful as inhibitors of protein kinases. In particular, it would be desirable to develop compounds that are useful as inhibitors of Tec family (e.g.,Tec, Btk, Itk/Emt/Tsk, Bmx, Txk/Rlk) and Aurora family protein kinases, as well as c-Met, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors Tec family (e.g.,Tec, Btk, Itk/Emt/Tsk, Bmx, Txk/Rlk) protein kinases, Aurora family kinases and/or c-Met. These compounds have the formulae I, I', II, III or IV as defined herein, or a pharmaceutically acceptable salt thereof.

These compounds and pharmaceutically acceptable compositions thereof are useful for treating or preventing a variety of diseases, disorders or conditions. The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

The present invention relates to a compound of formula I:

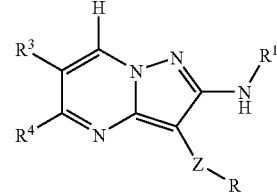

Formula I or a pharmaceutically accepted salt thereof, wherein
R is optionally substituted —(C=Q)$R^{2a}$ or optionally substituted Y;
Y is a 5-10 membered monocyclic or bicyclic heterocyclyl, aryl, or heteroaryl ring;
Q is a heteroatom selected from O, N, or S; and
$R^{2a}$ is $C_{1-6}$ aliphatic, aryl, heteroaryl, $OR^5$, or $N(R^5)_2$;
$R^1$ is H or $C_{1-6}$ aliphatic;
Z is a bond or $C_{1-6}$ aliphatic wherein up to two methylene units of the aliphatic chain are optionally and independently replaced by a heteroatom selected from O, N, or S in a chemically stable arrangement;
$R_3$ and $R_4$ are each independently H, halogen, $C_{1-6}$ aliphatic, $C_{1-6}$ alkoxy, $N(R^5)_2$, CN, $NO_2$, or $U_m$—V wherein m is 0 or 1;
V is H, aryl, heteroaryl, cycloaliphatic, heterocyclyl, or $C_{1-12}$ aliphatic wherein up to two methylene units of the alkylidene chain are optionally and independently replaced by a heteroatom selected from O, N, or S in a chemically stable arrangement; V is optionally substituted with $R^8$;

U is $C_{1-12}$ alkylidene chain wherein up to two methylene units of the chain are optionally and independently replaced by —$NR^5$—, —O—, —S—, —$CO_2$—, —OC(O)—, —C(O)CO—, —C(O)—, —$C(O)NR^5$—, —$NR^5CO$—, —$NR^5C(O)O$—, —$SO_2NR^5$—, —$NR^5SO_2$—, —$C(O)NR^5NR^5$—, —$NR^5C(O)NR^5$—, —$OC(O)NR^5$—, —$NR^5NR^5$—, —$NR^5SO_2NR^5$—, —SO—, —$SO_2$—, —PO—, —$PO_2$—, or —$POR^5$— in a chemically stable arrangement;

$R^5$ is H, $C_{1-4}$ haloalkyl, —$C(O)COR^6$, —$C(O)R^6$, —$C(O)OR^6$, —$C(O)N(R^6)_2$, —$SO_2R^6$, $C_{0-6}$alkyl-heterocyclyl, $C_{0-6}$alkyl-heteroaryl, $C_{0-6}$alkyl-aryl, $C_{0-6}$alkyl-cycloaliphatic or $C_{1-6}$ aliphatic wherein up to two methylene unit of the aliphatic chain are optionally and independently replaced by a heteroatom selected from O, N, or S in a chemically stable arrangement;

$R^6$ is H, $C_{1-6}$alkoxy, $C_{1-4}$haloalkyl, $C_{0-6}$alkyl-heterocyclyl, $C_{0-6}$alkyl-heteroaryl, $C_{0-6}$alkyl-aryl, $C_{0-6}$alkyl-cycloaliphatic, or $C_{1-6}$ aliphatic wherein up to two methylene units of the aliphatic chain are optionally and independently replaced by a heteroatom selected from O, N, or S in a chemically stable arrangement; or two $R^6$ groups taken together with the atom to which they are attached optionally join to form a 5-10 membered carbocycle or heterocycle;

$R^8$ is halogen, —$OR^6$, —$N(R^6)_2$, —$SR^6$, $NO_2$, CN, —$COOR^6$, —$C(O)N(R^6)_2$, —$SO_2R^6$, —$SO_2N(R^6)_2$, —$NR^6C(O)R^6$, —$C(O)R^6$, —$OC(O)R^6$, —$NR^6C(O)O$—$R^6$, —$NR^6SO_2$—$R^6$, —$C(O)NR^6N(R^6)_2$, —$NR^6C(O)N(R^6)_2$, —$OC(O)N(R^6)_2$, —$NR^6N(R^6)_2$, —$NR^6SO_2N(R^6)_2$ or $C_{1-12}$ aliphatic, wherein up to three methylene units of the aliphatic chain can be optionally interrupted with —$C(O)N(R^6)$—, —$NR^6CO(R^6)$—, —O—, —$NR^6$—, or —S—; provided that when Z is a bond R is not 2-(phenylamino)-pyrimidin-4-yl wherein phenyl is optionally substituted;

when Z is a bond R is not —$(C=O)N(R^a)_2$, —$(C=O)R^b$, or —$(C=O)OR^b$, wherein $R^a$ is H, $C_{1-6}$aliphatic, $C_{3-10}$cycloaliphatic, aryl, heteroaryl, heterocyclyl, $C_{0-6}$alkyl-$(C=O)N(R^a)_2$, $C_{0-6}$alkyl-$SOR^b$, $C_{0-6}$alkyl-$SO_2R^b$, $C_{0-6}$alkyl-$CO_2R^b$, $C_{0-6}$alkyl-$CO_2H$, $C_{0-6}$alkyl-$OR^b$, $C_{0-6}$alkyl-OH, $C_{0-6}$alkyl-$N(R^a)_2$, $C_{0-6}$alkyl-$(C=O)$—$C_{0-6}$alkyl-$OR^b$, or $C_{0-6}$alkyl-$(C=O)$—$C_{0-6}$alkyl-OH; and $R^b$ is $C_{1-6}$ aliphatic, $C_{3-10}$ cycloapliphatic, aryl, heteroaryl, or heterocyclyl;

when Z is a bond R is not substituted with $C_{0-6}$alkyl-$(C=O)N(R^a)_2$, $C_{0-6}$alkyl-$SO_nR^b$, $C_{0-6}$alkyl-$SO_nH$, $C_{0-6}$alkyl-$CO_2R^b$, $C_{0-6}$alkyl-$CO_2H$, $C_{1-6}$alkyl-$OR^b$, $C_{1-6}$alkyl-OH, $C_{1-6}$alkyl-$N(R^a)_2$, $C_{0-6}$alkyl-$(C=O)$—$C_{0-6}$alkyl-$OR^b$, $C_{0-6}$alkyl-$(C=O)$—$C_{0-6}$alkyl-OH;

wherein n is 0, 1, or 2; and $R^a$ and $R^b$ are as defined above;

when Z is a bond $R^3$ is not an optionally substituted dihydropyrimidinone or dihydropyridinone ring;

when Z is a bond R is not optionally substituted phenyl.

In some embodiments, Z is a bond. In some embodiments, $R^1$ is H.

In some embodiments, Y is represented by the formula shown below:

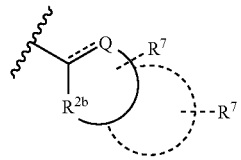

wherein
Q is a heteroatom selected from O, N, or S;
$R^7$ is halogen, —$OR^6$, —$N(R^6)_2$, —$SR^6$, $NO_2$, CN, —$COOR^6$, —$C(O)N(R^6)_2$, —$SO_2R^6$, —$SO_2N(R^6)_2$, —$NR^6C(O)R^6$, —$C(O)R^6$, —$OC(O)R^6$, or $C_{1-12}$ aliphatic, wherein up to three methylene units of the aliphatic chain can be optionally interrupted with —$C(O)N(R^6)$—, —$NR^6CO(R^6)$—, —O—, —$NR^6$—, or —S—;
⸺ is a single bond or a double bond;
$R^{2b}$ is carbon, or a heteroatom selected from O, N, or S;
$R^{2b}$ and Q, together with the carbon atom to which they are attached, form a 3-7 membered saturated or unsaturated monocyclic ring with 0-4 heteroatoms selected from O, N, or S; or a 8-10 membered saturated or unsaturated bicyclic ring with 0-6 heteroatoms selected from O, N, or S. In further embodiments, $R^{2b}$ is carbon.

In other embodiments, R is

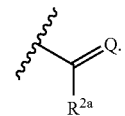

In further embodiments, Q is N or O.

In yet other embodiments, R is Y. In further embodiments, Y is a 5-10 membered heteroaryl or heterocyclyl. In further embodiments, Y is optionally substituted 5-6 membered heteroaryl or heterocyclyl. In further embodiments, Y is a pyridine ring optionally substituted with $R^7$. In still further embodiments, Y is a 2-pyridine ring optionally substituted with $R^7$. In some embodiments, $R^7$ is halogen, $OR^6$, —$N(R^6)_2$, —$SR^6$, $NO_2$, CN, —$OC(O)R^6$, —$NR^6C(O)R^6$, —$SO_2N(R^6)_2$, or —$NR^6SO_2$—.

In other embodiments, $R^3$ and $R^4$ are each independently $U_m$—V. In further embodiments, V is aryl, heteroaryl, cycloaliphatic, or heterocyclyl optionally substituted with $R^8$. In further embodiments, $R^3$ is H and $R^4$ is $U_m$—V; U is —$C(O)NR^5$; and m is 1. In other embodiments of $R^3$ and/or $R^4$, m is zero and V is aryl or heteroaryl. In further embodiments, V is unsubstituted phenyl. In other embodiments, V is phenyl substituted with $R^8$. In other embodiments, V is heteroaryl substituted with $R^8$. In further embodiments, V is heteroaryl substituted with $R^8$. In further embodiments, V is pyridyl substituted with $R^8$. In further embodiments, $R^8$ is halogen, OH, CN, $NH_2$, $OR^6$, or $C_{1-12}$ aliphatic. In further embodiments, $R^8$ is $C_{1-12}$ aliphatic, wherein up to three methylene units of the aliphatic chain can be optionally replaced with —$C(O)NR^6$—, —$NR^6CO$—, or a heteroatom selected from O, N, and S. In further embodiments, $R^8$ is —$(O)OR^6$ or —$C(O)N(R^6)_2$. In further embodiments, $R^6$ is H, $C_{1-6}$alkyl-heterocyclyl, $C_{1-6}$alkyl-heteroaryl, $C_{1-6}$alkyl-aryl, $C_{1-6}$alkyl-cycloaliphatic.

In some embodiments, Z is $C_{1-6}$ alkyl wherein zero methylene units are replaced by a heteroatom selected from O, N, or S; and V is aryl or heteroaryl. In further embodiments, Z is —$CH_2$—.
In some embodiments, the invention provides a compound selected from one of the following:
I-1
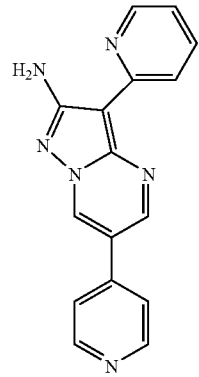
I-2
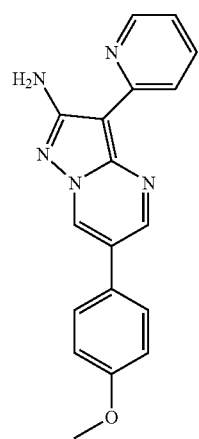
I-3
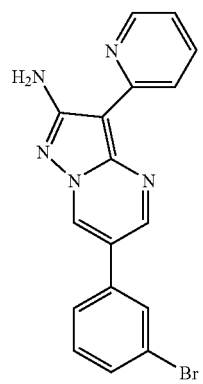
-continued
I-4
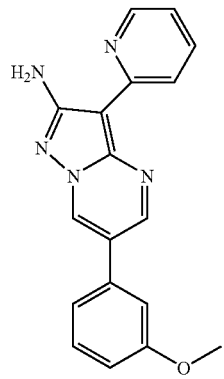
I-5
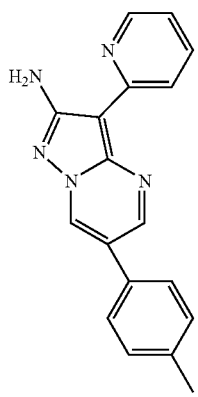
I-6
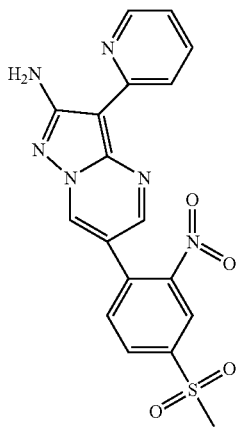
I-7
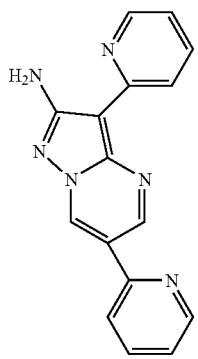

-continued
I-8
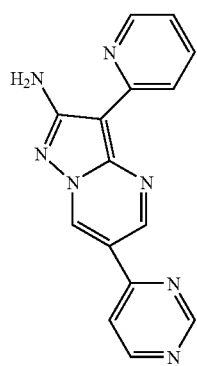
I-9
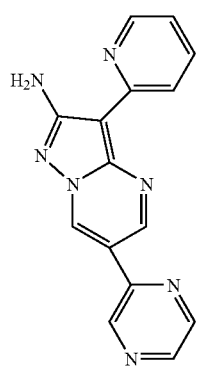
I-10
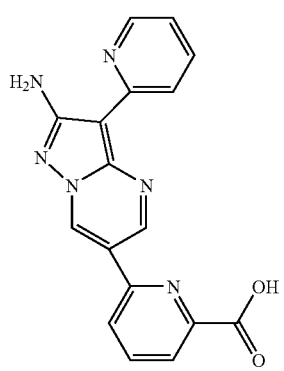
I-11
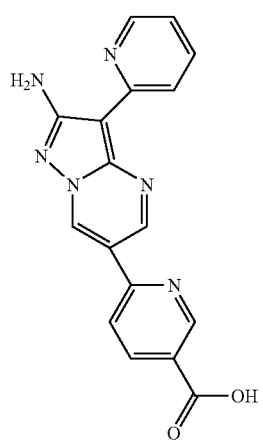
-continued
I-12
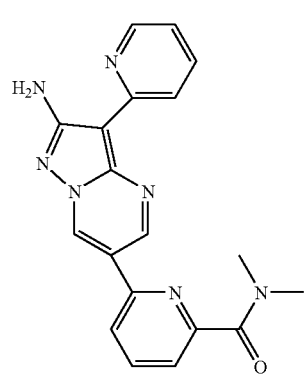
I-13
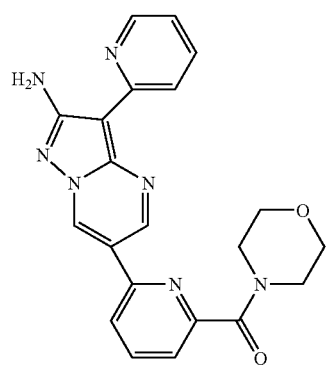
I-14
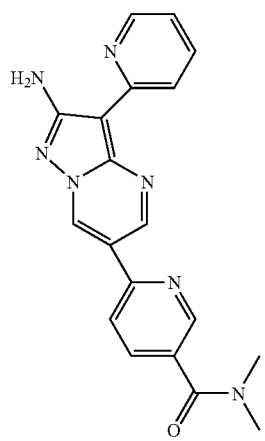
I-15
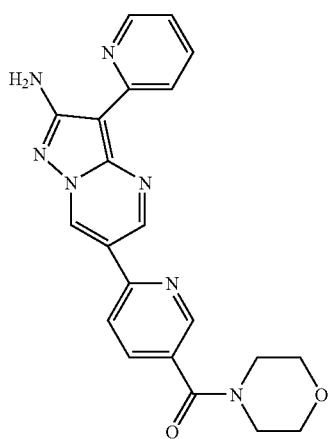

-continued
I-16
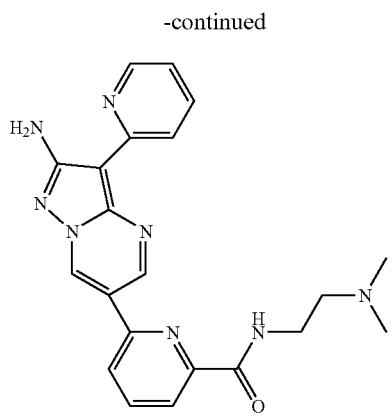
I-17
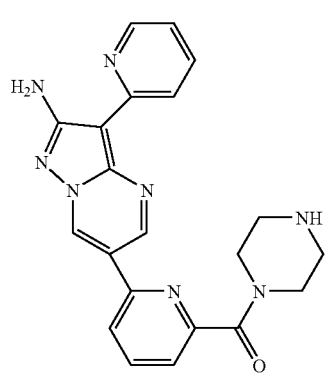
I-18
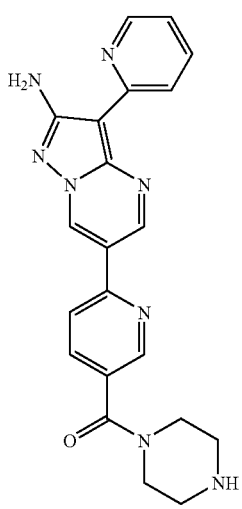
-continued
I-19
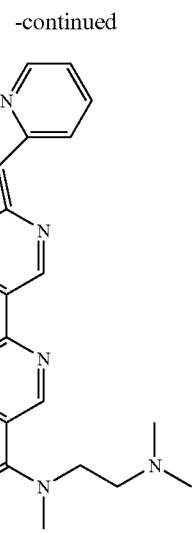
I-20
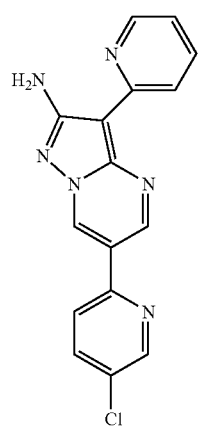
I-21
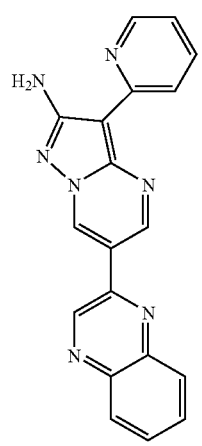

-continued
I-22
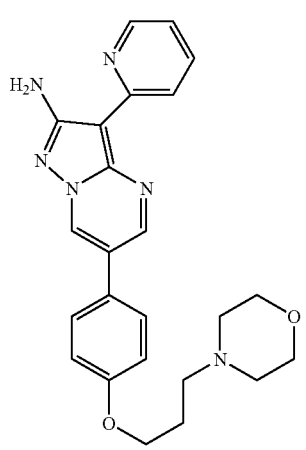
I-23
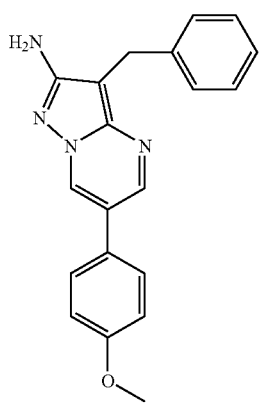
I-24
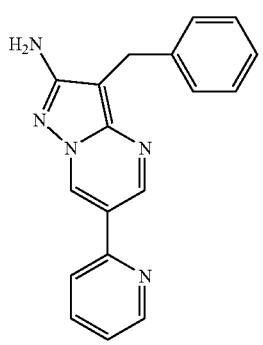
I-25
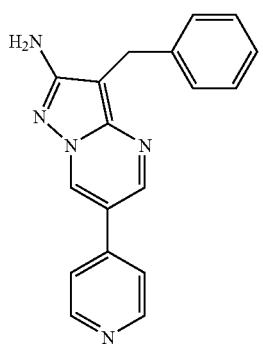
-continued
II-1
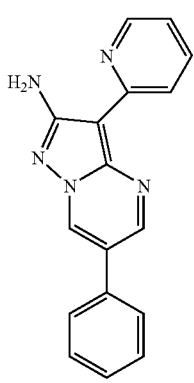
II-2
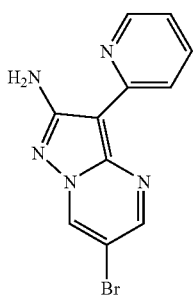
II-3
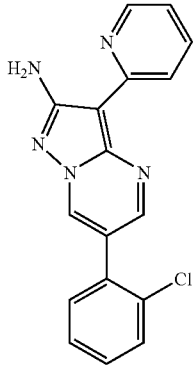
II-4
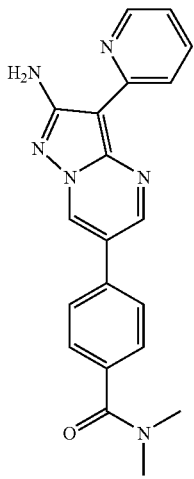

II-5
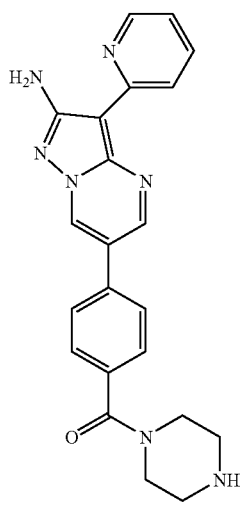
II-6
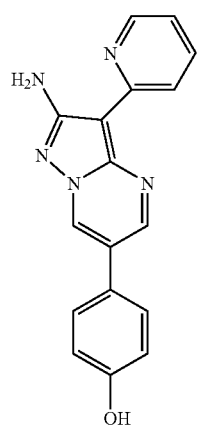
II-7
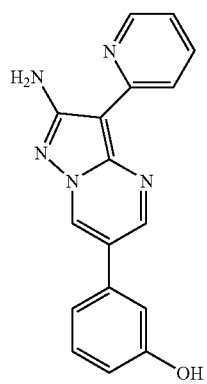
II-8
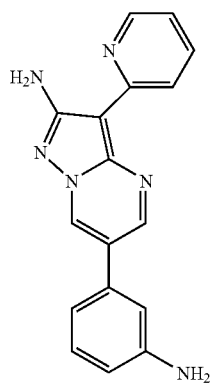
II-9
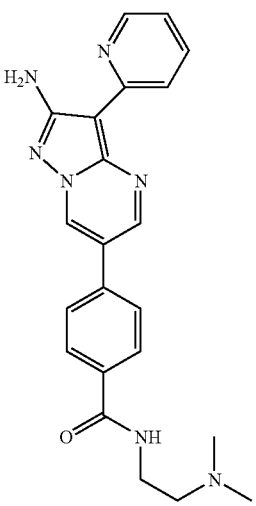
II-10
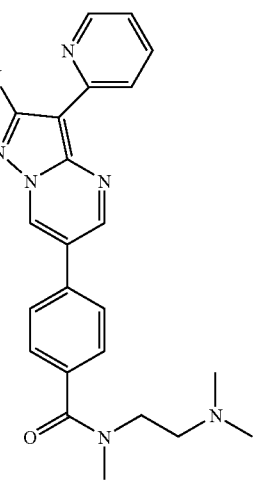

III-1
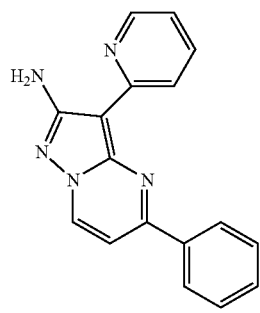
III-2
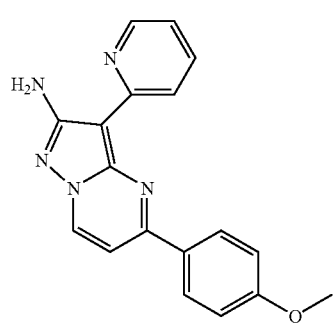
IV-1
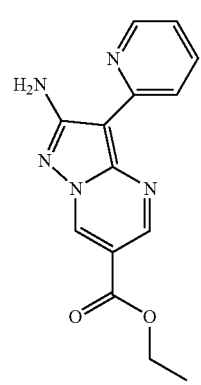
IV-2
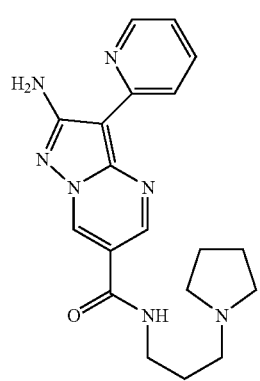
IV-3
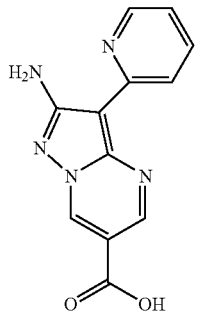
IV-4
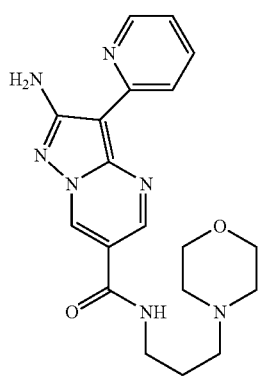
IV-5
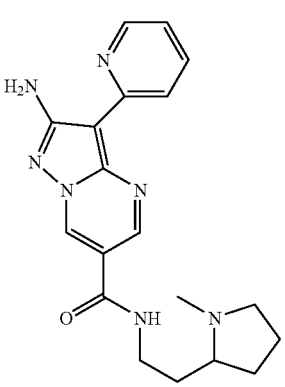
IV-6
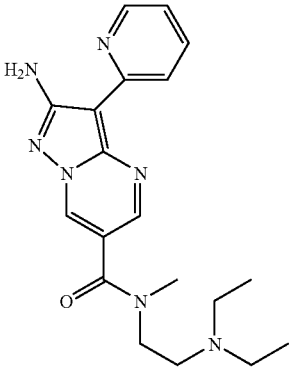

-continued

IV-7
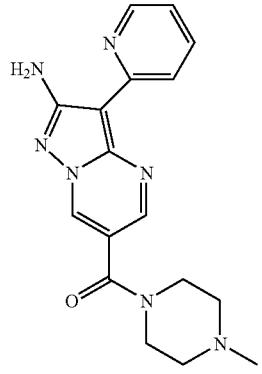

IV-8
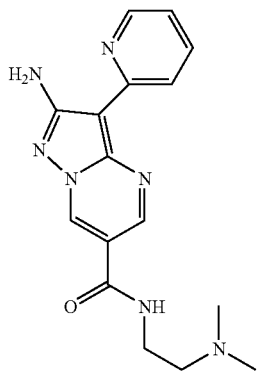

IV-9
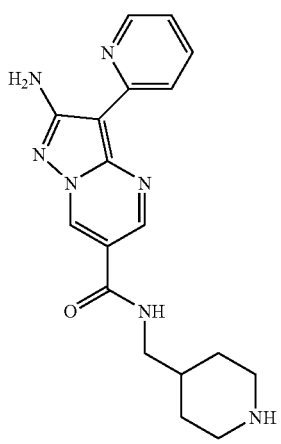

IV-10
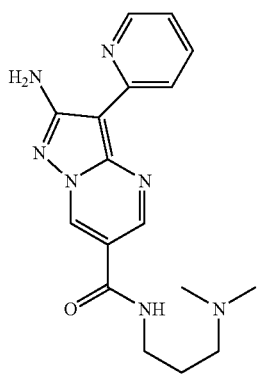

IV-11
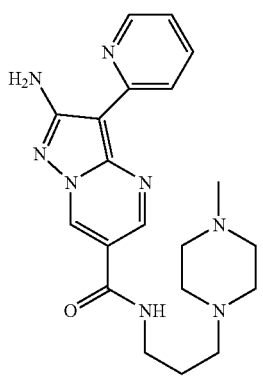

IV-12
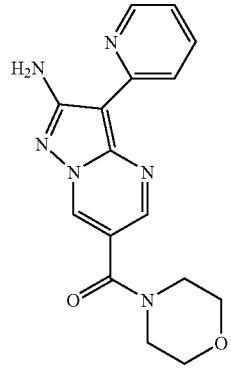

IV-13
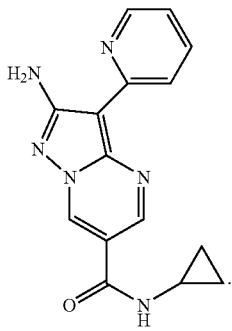

In some embodiments, the invention provides a composition comprising a compound of the invention, or a pharmaceutically acceptable salt thereof, and a pharmaceutically acceptable carrier or diluent. In further embodiments, the composition further comprises an agent for the treatment of an autoimmune, inflammatory, proliferative, hyperproliferative disease, or an immunologically-mediated disease including rejection of transplanted organs or tissues and Acquired Immunodeficiency Syndrome (AIDS).

The invention also provides methods of inhibiting Tec family kinase activity in a patient or a biological sample comprising administering to said patient, or contacting said biological sample with, a compound of the invention or a composition comprising said compound. In further embodiments, the method comprises inhibiting Itk activity. The invention also provides methods of treating or lessening the severity of a disease of condition selected from an autoimmune, inflammatory, proliferative, or hyperproliferative disease or an immunologically-mediated disease comprising administering to a patient in need thereof a compound of the present invention or a composition comprising said compound. In further embodiments, the method comprises administering to said patient an additional therapeutic agent selected from an agent for the treatment of an autoimmune, inflammatory, proliferative, hyperproliferative disease, or an immunologically-mediated disease including rejection of transplanted organs or tissues and Acquired Immunodeficiency Syndrome (AIDS), wherein said additional therapeutic agent is appropriate for the disease being treated; and said additional therapeutic agent is administered together with said composition as a single dosage form or separately from said composition as part of a multiple dosage form.

In further embodiments, the disease or disorder is asthma, acute rhinitis, allergic, atrophic rhinitis, chronic rhinitis, membranous rhinitis, seasonal rhinitis, sarcoidosis, farmer's lung, fibroid lung, idiopathic interstitial pneumonia, rheumatoid arthritis, seronegative spondyloarthropathis (including ankylosing spondylitis, psoriatic arthritis and Reiter's disease), Behcet's disease, Sjogren's syndrome, systernic sclerosis, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata vernal conjunctivitis, Coeliac disease, proctitis, eosinophilic gastro-enteritis, mastocytosis, pancreatitis, Crohn's disease, ulcerative colitis, food-related allergies, multiple sclerosis, artherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours, artherosclerosis, systemic lupus erythematosus, allograft rejection including, without limitation, acute and chronic allograft rejection following for example transplantation of kidney, heart, liver, lung, bone marrow, skin and cornea; and chronic graft versus host disease.

In other embodiments, the invention provides a compound of formula I':

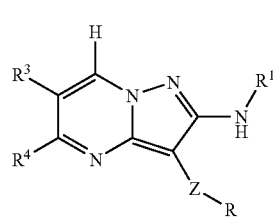

Formula I' or a pharmaceutically accepted salt thereof, wherein

R is —(C=Q)$R^{2a}$, CN, or Y; wherein

Y is a 5-10 membered monocyclic or bicyclic heterocyclyl, aryl, or heteroaryl ring; each Y is independently and optionally substituted with 0-5 $J^Y$;

Q is O, NH, NR', or S;

R' is $C_{1-6}$alkyl optionally substituted with 0-4 occurrences of halo, $C_{1-6}$aliphatic, $NO_2$, $NH_2$, —N($C_{1-6}$alkyl), —N($C_{1-6}$alkyl)$_2$, SH, —S($C_{1-6}$alkyl), OH, —O($C_{1-6}$alkyl), —C(O)($C_{1-6}$alkyl), —C(O)$NH_2$, —C(O)N($C_{1-6}$alkyl), or —C(O)N($C_{1-6}$alkyl)$_2$;

$R^{2a}$ is $C_{1-6}$aliphatic, $C_{6-10}$aryl, 5-10 membered heteroaryl, 5-10 membered heterocyclyl, $OR^5$, or N($R^5$)$_2$; each $R^{2a}$ is independently and optionally substituted with 0-5 $J^{2a}$;

$R^1$ is H, —C(O)($C_{1-6}$alkyl), —C(O)O($C_{1-6}$alkyl), —C(O)$NH_2$, —C(O)N($C_{1-6}$alkyl), —C(O)N($C_{1-6}$alkyl)$_2$; or $C_{1-6}$ aliphatic; each $R^1$ is optionally substituted with 0-4 occurrences of halo, $C_{1-6}$haloalkyl, $C_{1-6}$aliphatic, $NO_2$, $NH_2$, —N($C_{1-6}$alkyl), —N($C_{1-6}$alkyl)$_2$, SH, —S($C_{1-6}$alkyl), OH, or —O($C_{1-6}$alkyl);

Z is a bond or $C_{1-6}$ aliphatic wherein up to two methylene units of the aliphatic chain are optionally and independently replaced by a heteroatom selected from O, N, or S in a chemically stable arrangement;

$R_3$ and $R_4$ are each independently H, halogen, $C_{1-6}$ alkoxy, N($R^5$)$_2$, CN, $NO_2$, or $U_m$—V wherein m is 0 or 1;

V is H, $C_{6-10}$ aryl, 5-10 membered heteroaryl, $C_{3-10}$ cycloaliphatic, 5-10 membered heterocyclyl, or $C_{1-12}$ aliphatic wherein up to two methylene units of the alkylidene chain are optionally and independently replaced by a heteroatom selected from O, N, or S in a chemically stable arrangement; V is optionally substituted with 0-4 $R^8$;

U is $C_{1-12}$ alkylidene chain wherein up to two methylene units of the chain are optionally and independently replaced by —NH—, —$NR^5$—, —O—, —S—, —$CO_2$—, —OC(O)—, —C(O)CO—, —C(O)—, —C(O)NH—, —C(O)$NR^5$—, —C(=N—CN), —NHCO—, —$NR^5$CO—, —NHC(O)O—, —$NR^5$C(O)O—, —$SO_2$NH—, —$SO_2NR^5$—, —$NHSO_2$—, —$NR^5SO_2$—, —NHC(O)NH—, —$NR^5$C(O)NH—, —NHC(O)$NR^5$—, —$NR^5$C(O)$NR^5$, —OC(O)NH—, —OC(O)$NR^5$—, —NHNH—, —$NHNR^5$—, —$NR^5NR^5$—, —$NR^5$NH—, —$NHSO_2$NH—, —$NR^5SO_2$NH—, —$NHSO_2NR^5$—, —$NR^5SO_2NR^5$—, —SO—, —$SO_2$—, —PO—, —$PO_2$—, or —$POR^5$—; U is optionally substituted with 0-6 $J^U$;

$R^5$ is $C_{1-4}$haloalkyl, —C(O)$COR^6$, —C(O)$R^6$, —C(O)$OR^6$, —C(O)N($R^6$)$_2$, —$SO_2R^6$, $C_{0-6}$alkyl-heterocyclyl, $C_{0-6}$alkyl-heteroaryl, $C_{0-6}$alkyl-aryl, $C_{0-6}$alkyl-cycloaliphatic or $C_{1-6}$ aliphatic wherein up to three methylene unit of the aliphatic chain are optionally and independently replaced by —NR"—, —O—, —S—, —$CO_2$—, —OC(O)—, —C(O)CO—, —C(O)—, —C(O)NR"—, —NR"CO—, —NR"C(O)O—, —$SO_2$NR"—, —NR"$OS_2$—, —C(O)NR"NR"—, —NR"C(O)NR"—, —OC(O)NR"—, —NR"NR"—, —NR"$SO_2$NR"—, —SO—, —$SO_2$—, —PO—, —$PO_2$—, or —POR"— in a chemically stable arrangement; each $R^5$ is independently and optionally substituted with 0-5 $J^{R5}$; or two $R^5$ groups taken together with the atom to which they are attached optionally join to form a 5-10 membered carbocyclic or heterocyclic ring; wherein said ring is optionally substituted with 0-4 J';

$R^6$ is H, $C_{1-6}$alkoxy, $C_{1-4}$haloalkyl, $C_{0-6}$alkyl-heterocyclyl, $C_{0-6}$alkyl-heteroaryl, $C_{0-6}$alkyl-aryl, $C_{0-6}$alkyl-cycloaliphatic, or $C_{1-6}$ aliphatic wherein up to two methylene units of the aliphatic chain are optionally and independently replaced by a heteroatom selected from O, N, or S in a chemically stable arrangement; each $R^6$ is independently and optionally substituted with 0-5 $J^{R6}$; or two $R^6$ groups taken together with the atom to which they are attached optionally join to form a 5-10 membered carbocyclic or heterocyclic ring; wherein said ring is optionally substituted with 0-4 J";

$R^8$ is halogen, $C_{1-4}$haloalkyl, phenyl, 5-8 membered heterocyclyl, 5-6 membered heteroaryl, —$OR^6$, —N($R^6$)$_2$, —$SR^6$, $NO_2$, CN, —$COOR^6$, —C(O)N($R^6$)$_2$, —$SO_2R^6$, —$SO_2$N($R^6$)$_2$, —$NR^6$C(O)$R^6$, —C(O)$R^6$, —OC(O)$R^6$, —$NR^6$C(O)O—$R^6$, —$NR^6SO_2$—$R^6$, —C(O)$NR^6$N($R^6$)$_2$, —$NR^6$C(O)N($R^6$)$_2$, —OC(O)N($R^6$)$_2$, —$NR^6$N($R^6$)$_2$, —$NR^6SO_2$N($R^6$)$_2$ or $C_{1-12}$ aliphatic, wherein up to three methylene units of the aliphatic chain can be optionally interrupted with —C(O)R$^6$, —C(O)O—, —OC(O)—, —C(O)—, —C(O)N(R$^6$)—, —NR$^6$CO(R$^6$)—, —O—, —NR$_6$—, or —S—; each R$^8$ is independently and optionally substituted with 0-5 J$^{R8}$;

each J$^Y$, J$^{2a}$, J$^u$, J$^{R5}$, J$^{R6}$, J$^{R8}$, J', and J" is independently selected from N(R$^9$)$_2$, SR$^9$, OR$^9$, halo, CN, NO$_2$, COOR$^9$, C(O)R$^9$, SO$_2$R$^9$, SOR$^9$, —X—CF$_3$, —X—SH, —X—OH, C$_{1-4}$haloalkyl, C$_{6-10}$ aryl, —X—(C$_{6-10}$ aryl), 5-10 membered heteroaryl, —X-(5-10 membered heteroaryl), C$_{3-10}$ cycloaliphatic, —X—(C$_{3-10}$ cycloaliphatic), 5-10 membered heterocyclyl, —X-(5-10 membered heterocyclyl), or X;

X is C$_{1-12}$ aliphatic wherein up to two methylene units of the alkylidene chain are optionally and independently replaced by —NH—, —NR"—, —O—, —S—, —CO$_2$—, —OC(O)—, —C(O)CO—, —C(O)—, —C(O)NH—, —C(O)NR"—, —C(=N—CN), —NHCO—, —NR"CO—, —NHC(O)O—, —NR"C(O)O—, —SO$_2$NH—, —SO$_2$NR"—, —NHSO$_2$—, —NR"SO$_2$—, —NHC(O)NH—, —NR"C(O)NH—, —NHC(O)NR"—, —NR"C(O)NR"—, —OC(O)NH—, —OC(O)NR"—, —NHNH—, —NHNR"—, —NR"NR"—, —NR"NH—, —NHSO$_2$NH—, —NR"SO$_2$NH—, —NHSO$_2$NR"—, —NR"SO$_2$NR"—, —SO—, —SO$_2$—, —PO—, —PO$_2$—, or —POR"—; in a chemically stable arrangement; wherein R" is H or C$_{1-6}$ aliphatic; each J$^Y$, J$^{2a}$, J$^u$, J$^{R5}$, J$^{R6}$, J', and J" is optionally and independently substituted with 0-4 occurrences of N(R$^9$)$_2$, SR$^9$, OR$^9$, halo, CN, NO$_2$, COOR$^9$, C(O)R$^9$, SO$_2$R$^9$, SOR$^9$, —X—CF$_3$, —X—SH, —X—OH, C$_{1-4}$haloalkyl, C$_{6-10}$aryl, —X—(C$_{6-10}$ aryl), 5-10 membered heteroaryl, —X-(5-10 membered heteroaryl), C$_{3-10}$ cycloaliphatic, —X—(C$_{3-10}$ cycloaliphatic), 5-10 membered heterocyclyl, —X-(5-10 membered heterocyclyl), or X;

R$^9$ is H, C$_{1-6}$ aliphatic, C$_{1-4}$haloalkyl, C$_{6-10}$aryl, —X—(C$_{6-10}$ aryl), 5-10 membered heteroaryl, —X-(5-10 membered heteroaryl), C$_{3-10}$ cycloaliphatic, —X—(C$_{3-10}$ cycloaliphatic), 5-10 membered heterocyclyl, —X-(5-10 membered heterocyclyl) or X, or wherein two R$^9$, taken together with the atom to which they are attached, form a 5-10 membered heterocyclyl, wherein said heterocyclyl is optionally substituted with 0-4 occurrences of halo, CN, NO$_2$, —COOH, —COO(C$_{1-6}$alkyl), —C(O)H, SO$_2$H, SO$_2$(C$_{1-6}$alkyl), C$_{1-6}$haloaliphatic, NH$_2$, —NH(C$_{1-6}$alkyl), —N(C$_{1-6}$alkyl)$_2$, SH, —S(C$_{1-6}$alkyl), OH, —O(C$_{1-6}$alkyl), —C(O)(C$_{1-6}$alkyl), —C(O)NH$_2$, —C(O)NH(C$_{1-6}$alkyl), —C(O)N(C$_{1-6}$alkyl)$_2$, —C(O)NH$_2$, —C(O)NH(C$_{1-6}$alkyl), or —C(O)N(C$_{1-6}$alkyl)$_2$, C$_{1-4}$haloalkyl, C$_{6-10}$ aryl, —X—(C$_{6-10}$ aryl), 5-10 membered heteroaryl, —X-(5-10 membered heteroaryl), C$_{3-10}$ cycloaliphatic, —X—(C$_{3-10}$ cycloaliphatic), 5-10 membered heterocyclyl, —X-(5-10 membered heterocyclyl), or X.

In some embodiments of formula I', if R$^4$ is H, then R$^3$ is other than H. In further embodiments, R$^4$ is H and R$^3$ is other than H. In other embodiments, Z is a bond. In other embodiments, R$^1$ is H.

In some embodiments of formula I', R is

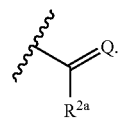

In further embodiments, Q is N or O. In further embodiments, R$^{2a}$ is OR$^5$, N(R$^5$)$_2$, or 5-8 membered heterocyclyl. In further embodiments, the 5-8 membered heterocyclyl contains 1-2 nitrogen atoms. In yet further embodiments, the 5-8 membered heterocyclyl is optionally substituted with 0-4 occurrences of C$_{1-6}$aliphatic, C$_{1-4}$haloalkyl, CN, halo, OH, O—(C$_{1-6}$aliphatic), NH$_2$, NH(C$_{1-6}$aliphatic), N(C$_{1-6}$aliphatic)$_2$, benzyl, —CH$_2$-(pyridyl), or —CH$_2$-pyrrolidinyl.

In some embodiments of formula I', R$^{2a}$ is N(R$^5$)$_2$. In further embodiments, R$^5$ is H or an optionally substituted group selected from 5-8 membered heterocyclyl, —(C$_{1-6}$alkyl)-(5-8 membered heterocyclyl), 5-6 membered heteroaryl —(C$_{1-6}$alkyl)-(5-6 membered heteroaryl), phenyl, —(C$_{1-6}$alkyl)-(phenyl), C$_{3-10}$cycloaliphatic, —(C$_{1-6}$alkyl)-(C$_{3-10}$cycloaliphatic) and C$_{1-6}$ aliphatic wherein up to three methylene unit of the aliphatic chain are optionally and independently replaced by —NR"—, —O—, or —S— in a chemically stable arrangement. In yet further embodiments, R$^5$ is H or an optionally substituted group selected from pyrrolidinyl, piperidinyl, piperazinyl, —CH$_2$-(5-6 membered heteroaryl), phenyl, benzyl, and C$_{1-6}$ aliphatic wherein up to one methylene unit of the aliphatic chain is optionally and independently replaced by —NR"—, —O—, or —S— in a chemically stable arrangement.

In some embodiments of formula I', J$^{R5}$ is halo, CN, C$_{1-4}$haloalkyl, or an optionally substituted group selected from phenyl, benzyl, 5-8 membered heterocyclyl, 5-6 membered heteroaryl, CH$_2$-(5-6 membered heteroaryl), CH$_2$-(5-8 membered heterocyclyl), and C$_{1-6}$aliphatic wherein up to two methylene units of the alkylidene chain are optionally and independently replaced by —NR"—, —O—, —S—, —C(O)—, —SO—, or —SO$_2$—, in a chemically stable arrangement. In further embodiments, J$^{R5}$ is halo, CN, phenyl, benzyl, CH$_2$-(pyridyl), CH$_2$-(pyrrolidinyl), or C$_{1-6}$aliphatic wherein up to two methylene units of the alkylidene chain are optionally and independently replaced by —NR"—, —O—, or —S—.

In some embodiments of formula I', R is Y. In further embodiments, Y is an optionally substituted 5-10 membered heteroaryl or heterocyclyl. In yet further embodiments, Y is an optionally substituted 5-6 membered heteroaryl or 5-8 membered heterocyclyl. In yet further embodiments, Y is a pyridine ring optionally substituted with 0-4 J$^Y$. In further embodiments, Y is a 2-pyridine ring optionally substituted with 0-4 J$^Y$.

In some embodiments of formula I', J$^Y$ is halo, CN, NO$_2$, C$_{1-6}$haloaliphatic, phenyl, benzyl, 5-6 membered heteroaryl, C$_{1-6}$alkyl-(5-6 membered heteroaryl), C$_{3-10}$ cycloaliphatic, (C$_{1-6}$alkyl)-(C$_{3-10}$ cycloaliphatic), 5-8 membered heterocyclyl, C$_{1-6}$alkyl-(5-8 membered heterocyclyl), or C$_{1-12}$ aliphatic wherein up to two methylene units of the alkylidene chain are optionally and independently replaced by —NR—, —O—, —S—, —C(O)—, —SO—, or —SO$_2$— in a chemically stable arrangement. In further embodiments, J$^Y$ is halo, CN, NO$_2$, CF$_3$, C$_{1-6}$ aliphatic, phenyl, benzyl, —O-benzyl, piperidinyl, pyrrolidinyl, —NR(C$_{1-6}$alkyl), —O(C$_{1-6}$alkyl), —S(C$_{1-6}$alkyl), OH, SH, or NH$_2$.

In some embodiments of formula I', R$^3$ and R$^4$ are each independently U$_m$—V. In further embodiments, V is H, C$_{6-10}$aryl, 5-10 membered heteroaryl, C$_{3-10}$cycloaliphatic, or 5-10 membered heterocyclyl optionally substituted with 0-4 R$^8$. In further embodiments, V is an optionally substituted group selected from phenyl, 5-6 membered heteroaryl, or 5-8 membered heterocyclyl. In yet further embodiments, V is an optionally substituted group selected from phenyl, pyrazolyl, pyridyl, pyrimidyl, pyrazinyl, pyridazinyl, pyrrolidinyl, piperidinyl, or morpholinyl. In still further embodiments, V is optionally substituted phenyl.

In some embodiments of formula I', $R^3$ is $U_m$—V; m is 1, and U is $C_{1-6}$aliphatic wherein up to two methylene units of the aliphatic chain are optionally and independently replaced by —C(O)—, —C(O)NR$^5$—, or —C(O)O—. In further embodiments, U is —C(O)NR$^5$—. In yet further embodiments, V is optionally substituted phenyl or optionally substituted pyridyl.

In some embodiments of formula I', $R^3$ is $U_m$—V, m is zero and V is aryl or heteroaryl.

In some embodiments of formula I', $R^8$ is halogen, $C_{1-4}$haloalkyl, phenyl, 5-8 membered heterocyclyl, 5-6 membered heteroaryl, —OR$^6$, —N(R$^6$)$_2$, —SR$^6$, NO$_2$, CN, —COOR$^6$, —C(O)N(R$^6$)$_2$, —SO$_2$R$^6$, —SO$_2$N(R$^6$)$_2$, —NR$^6$C(O)R$^6$, —C(O)R$^6$, —NR$^6$SO$_2$—R$^6$, —C(O)NR$^6$N(R$^6$)$_2$, or $C_{1-12}$ aliphatic, wherein up to three methylene units of the aliphatic chain can be optionally interrupted with —C(O)R$^6$, —C(O)O—, —OC(O)—, —C(O)—, —C(O)N(R$^6$)—, —NR$^6$CO(R$^6$)—, —O—, —NR$^6$—, or —S—. In further embodiments, $R^8$ is —OR$^6$, —N(R$^6$)$_2$, C(O)R$^6$, —C(O)N(R$^6$)$_2$, or 5-7 membered heterocyclyl. In still further embodiments, $R^8$ is —C(O)N(R$^6$)$_2$ or C(O)R$^6$ In certain embodiments of formula I', $R^6$ is H or an optionally substituted group selected from 5-8 membered heterocyclyl, —(C$_{1-6}$alkyl)-(5-8 membered heterocyclyl), benzyl, —(C$_{1-6}$alkyl)-(5-8 membered heteroaryl), and $C_{1-6}$ aliphatic wherein up to two methylene units of the aliphatic chain are optionally and independently replaced by a heteroatom selected from O, N, or S in a chemically stable arrangement. In further embodiments, $R^6$ is H or an optionally substituted group selected from a 5-8 membered heterocyclyl and $C_{1-6}$ aliphatic wherein up to two methylene units of the aliphatic chain are optionally and independently replaced by a heteroatom selected from O, N, or S in a chemically stable arrangement.

In some embodiments of formula I', $J^{R6}$ is selected from $C_{1-6}$alkyl, halo, CN, OH, —O(C$_{1-6}$alkyl), NH$_2$, —N(C$_{1-6}$alkyl), and —N(C$_{1-6}$alkyl)$_2$. In some embodiments of formula I', J" is selected from $C_{1-6}$aliphatic, halo, CN, OH, —O(C$_{1-6}$alkyl), NH$_2$, —N(C$_{1-6}$alkyl), —N(C$_{1-6}$alkyl)$_2$, —C(O)OH, —C(O)O(C$_{1-6}$alkyl), 5-6 membered heteroaryl, —CH$_2$-(5-6 membered heteroaryl), 5-6 membered heterocyclyl, —CH$_2$-(5-6 membered heterocyclyl), and $C_{1-6}$aliphatic wherein up to two methylene units of the aliphatic chain are optionally and independently replaced by a heteroatom selected from O, N, or S in a chemically stable arrangement.

In some embodiments of formula I', Z is a bond and R is selected from

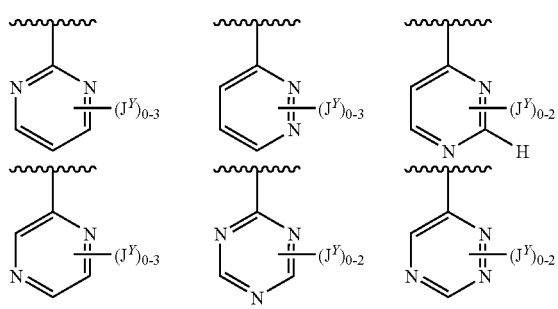

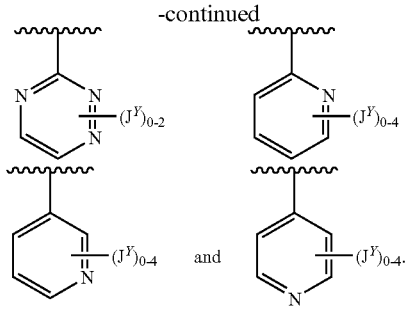

In certain embodiments, R is selected from

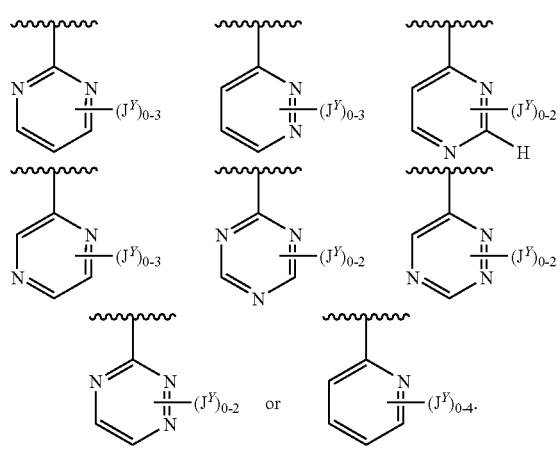

In further embodiments, R is

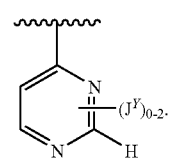

In some embodiments of formula I', $J^Y$ is selected from —X—(C$_{6-10}$ aryl), —X-(5-10 membered heteroaryl), —X—C$_{3-10}$ cycloaliphatic), —X-(5-10 membered heterocyclyl), or X. In some embodiments, X is $C_{1-12}$ aliphatic wherein up to two methylene units of the alkylidene chain are optionally and independently replaced by —NR"—, —O—, —S—, —C(O)—, —SO—, or —SO$_2$—. In further embodiments, X is $C_{1-12}$ aliphatic wherein up to one methylene unit is optionally and independently replaced by —NR"—. In yet further embodiments, at least one —NR"— is directly attached to R.

In other embodiments of formula I', $J^Y$ is an optionally substituted group selected from $C_{6-10}$ aryl, 5-10 membered heteroaryl, $C_{3-10}$ cycloaliphatic, and 5-10 membered heterocyclyl. In other embodiments, $J^Y$ is halo, CN, NO$_2$, CF$_3$, OR", SR", or N(R")$_2$.

In some embodiments of formula I', R is substituted with 2 occurrences of $J^Y$ wherein one $J^Y$ is selected from —X—(C$_{6-10}$ aryl), —X-(5-10 membered heteroaryl), —X-(C$_{3-10}$ cycloaliphatic), —X-(5-10 membered heterocyclyl), or X and the other $J^Y$ is selected from H, halo, CN, NO$_2$, CF$_3$, OR", SR", N(R")$_2$, $C_{6-10}$ aryl, 5-10 membered heteroaryl, $C_{3-10}$ cycloaliphatic, or 5-10 membered heterocyclyl. In further embodiments, R is substituted with 2 occurrences of $J^Y$ wherein one $J^Y$ is selected from X and the other $J^Y$ is selected from H, halo, CN, $NO_2$, $CF_3$, OR", SR", or $N(R")_2$.

In some embodiments, the invention provides a compound of formula II:

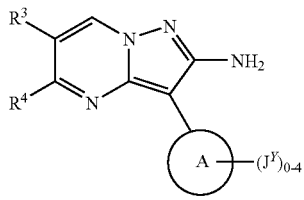

II or a pharmaceutically accepted salt thereof, wherein Ring A is Y.

In further embodiments of formula II, if $R^4$ is H, then $R^3$ is other than H. In further embodiments, $R^4$ is H and $R^3$ is other than H.

In some embodiments, the invention provides a compound of formula III:

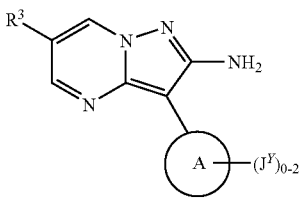

III or a pharmaceutically accepted salt thereof, wherein
$R^3$ is halogen, $C_{1-6}$ aliphatic, $C_{1-6}$ alkoxy, $N(R^5)_2$, CN, $NO_2$, or $U_m$—V;
Ring A is a 5-8 membered monocyclic heteroaryl ring.

In some embodiments of formula III, Ring A has the formula

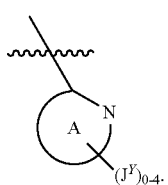

In further embodiments, Ring A has a formula selected from the group consisting of:

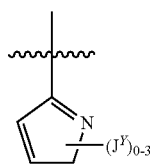 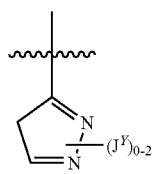 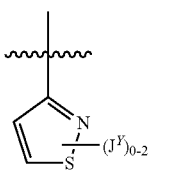

-continued

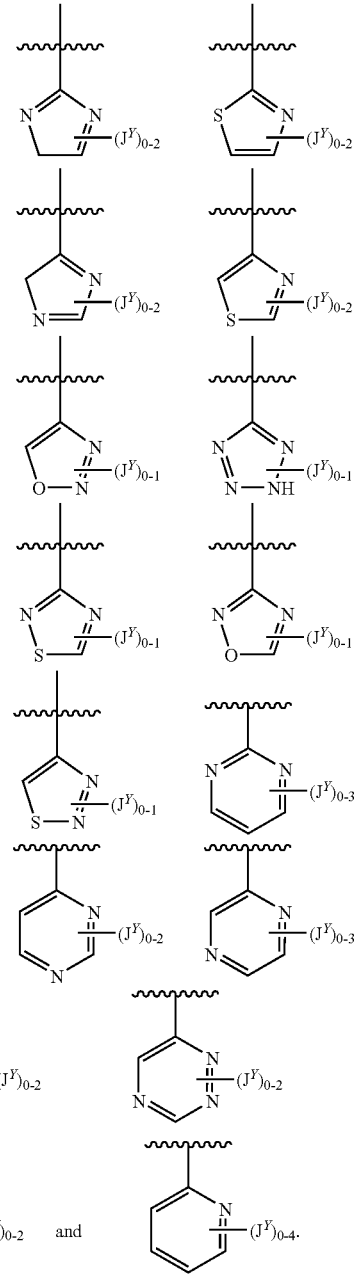

In some embodiments, the invention provides a compound of formula IV:

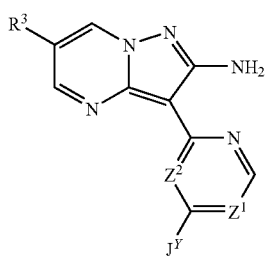

wherein each of $Z^1$ and $Z^2$ is CH or N and $R^3$ is as defined for formula III.

In some embodiments of formula IV, $Z^2$ is CH. In some embodiments, $Z^1$ is N or CH. In further embodiments, $Z^1$ is N and $Z^2$ is CH. In further embodiments, $Z^1$ and $Z^2$ are both CH.

In some embodiments of formula IV, $R^3$ is $C_{1-6}$ aliphatic. In further embodiments, $R^3$ is $C_{1-3}$ alkyl.

In some embodiments of formula IV, $J^Y$ is optionally substituted —$N(R^9)_2$. In further embodiments, $J^Y$ is optionally substituted —$NHR^9$. In further embodiments, $J^Y$ is optionally substituted $N(R^9)_2$, wherein said two $R^9$ form an optionally substituted 5-8 membered heterocyclyl.

In some embodiments, the invention provides a compound selected from Table 5.

In some embodiments, the invention provides a composition comprising a compound of formulae I', II, III or IV, or a pharmaceutically acceptable salt thereof, and a pharmaceutically acceptable carrier or diluent. In further embodiments, the composition comprises an additional therapeutic agent selected from an agent for the treatment of an autoimmune, inflammatory, proliferative, hyperproliferative disease, or an immunologically-mediated disease including rejection of transplanted organs or tissues and Acquired Immunodeficiency Syndrome (AIDS).

In some embodiments, the invention provides a method of inhibiting Tec family kinase activity in a patient or a biological sample, which method comprises administering to said patient, or contacting said biological sample with, a compound of formulae I', II, III or IV, or a pharmaceutically acceptable salt thereof, or a composition comprising said compound. In further embodiments, the method comprises inhibiting Itk activity.

In some embodiments, the invention provides a method of treating or lessening the severity of a disease of condition in a patient in need thereof, wherein said disease or condition is selected from an autoimmune, inflammatory, proliferative, or hyperproliferative disease or an immunologically-mediated disease, which method comprises administering to said patient a compound of formulae I', II, III or IV, or a pharmaceutically acceptable salt thereof, or a composition comprising said compound. In further embodiments, the method comprises administering to said patient an additional therapeutic agent selected from an agent for the treatment of an autoimmune, inflammatory, proliferative, hyperproliferative disease, or an immunologically-mediated disease including rejection of transplanted organs or tissues and Acquired Immunodeficiency Syndrome (AIDS), wherein said additional therapeutic agent is appropriate for the disease being treated; and said additional therapeutic agent is administered together with said composition as a single dosage form or separately from said composition as part of a multiple dosage form.

In some embodiments, the disease or disorder to be treated is asthma, acute rhinitis, allergic, atrophic rhinitis, chronic rhinitis, membranous rhinitis, seasonal rhinitis, sarcoidosis, farmer's lung, fibroid lung, idiopathic interstitial pneumonia, rheumatoid arthritis, seronegative spondyloarthropathis (including ankylosing spondylitis, psoriatic arthritis and Reiter's disease), Behcet's disease, Sjogren's syndrome, systernic sclerosis, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata vernal conjunctivitis, Coeliac disease, proctitis, eosinophilic gastro-enteritis, mastocytosis, pancreatitis, Crohn's disease, ulcerative colitis, food-related allergies, multiple sclerosis, artherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours, artherosclerosis, systemic lupus erythematosus, allograft rejection including, without limitation, acute and chronic allograft rejection following for example transplantation of kidney, heart, liver, lung, bone marrow, skin and cornea; and chronic graft versus host disease.

In some embodiments, the invention provides a method of inhibiting c-Met kinase activity in a patient or a biological sample, which method comprises administering to said patient, or contacting said biological sample with, a compound of formulae I, I', II, III or IV, or a pharmaceutically acceptable salt thereof, or a composition comprising said compound.

In some embodiments, the invention provides a method of treating or lessening the severity of a cancer in a patient in need thereof, comprising the step of administering to said patient, which method comprises administering to said patient a compound of formulae I, I', II, III or IV, or a pharmaceutically acceptable salt thereof, or a composition comprising said compound. In further embodiments, the method further comprises administering to said patient a chemotherapeutic-agent, wherein chemotherapeutic agent is administered together with said composition as a single dosage form or separately from said composition as part of a multiple dosage form.

In further embodiments, the cancer is renal cancer. In other embodiments, the cancer is selected from a glioblastoma, a gastric carcinoma or a cancer selected from colon, breast, prostate, brain, liver, pancreatic or lung cancer. In further embodiments, the cancer is gastric carcinoma. In other embodiments, the cancer is glioblastoma or a cancer selected from breast, colon or liver.

In other embodiments, the invention provides a method of inhibiting or reducing the severity of tumor metastasis in a patient in need thereof, comprising the step of administering to said patient, which method comprises administering to said patient a compound of formulae I, I', II, III or IV, or a pharmaceutically acceptable salt thereof, or a composition comprising said compound.

In some embodiments, the invention provides a method of inhibiting Aurora kinase activity in a patient or a biological sample, which method comprises administering to said patient, or contacting said biological sample with, a compound of formulae I, I', II, III or IV, or a pharmaceutically acceptable salt thereof, or a composition comprising said compound.

In some embodiments, the invention provides a method of treating or lessening the severity of melanoma, myeloma, leukemia, lymphoma, neuroblastoma, or a cancer selected from colon, breast, gastric, ovarian, cervical, lung, central nervous system (CNS), renal, prostate, bladder, or pancreatic, in a patient in need thereof, comprising the step of administering to said patient, which method comprises administering to said patient a compound of formulae I, I', II, III or IV, or a pharmaceutically acceptable salt thereof, or a composition comprising said compound.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "optionally interrupted" refers to the replacement of one atom within an alkylidene chain with another atom. Unless otherwise specified, the second atom can replace the first atom at any position, including terminal atoms. For example, a $C_{1-3}$ alkyl chain optionally interrupted with —O— can form —OCH$_2$CH$_3$, —CH$_2$—OCH$_3$, or CH$_2$CH$_2$OH. Unless otherwise specified, the terminal groups are bonded to hydrogen on the terminal side.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N (R°)₂; —OC(O)N(R°)₂; —OC(O)R°; —C(O)N(OR°)R°; —C(NOR°)R°; —S(O)₂R°; —S(O)₃R°; —SO₂N(R°)₂; —S(O)R°; —NR°SO₂N(R°)₂; —NR°SO₂R°; —N(OR°)R°; —C(=NH)—N(R°)₂; or —(CH₂)₀₋₂NHC(O)R° wherein each independent occurrence of R° is selected from hydrogen, optionally substituted $C_{1-6}$ aliphatic, an unsubstituted 5-6 membered heteroaryl or heterocyclic ring, phenyl, —O(Ph), or —CH₂(Ph), or, notwithstanding the definition above, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R° are selected from NH₂, NH($C_{1-4}$aliphatic), N($C_{1-4}$aliphatic)₂, halogen, $C_{1-4}$aliphatic, OH, O($C_{1-4}$aliphatic), NO₂, CN, CO₂H, CO₂($C_{1-4}$aliphatic), O(halo$C_{1-4}$ aliphatic), or halo$C_{1-4}$aliphatic, wherein each of the foregoing $C_{1-4}$aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHCO₂(alkyl), =NNHSO₂(alkyl), or =NR*, where each R* is independently selected from hydrogen or an optionally substituted $C_{1-6}$ aliphatic. Optional substituents on the aliphatic group of R* are selected from NH₂, NH($C_{1-4}$ aliphatic), N($C_{1-4}$ aliphatic)₂, halogen, $C_{1-4}$ aliphatic, OH, O($C_{1-4}$ aliphatic), NO₂, CN, CO₂H, CO₂($C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein R⁺is hydrogen, an optionally substituted $C_{1-6}$ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R⁺, on the same substituent or different substituents, taken together with the atom(s) to which each R⁺ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R⁺ are selected from NH₂, NH($C_{1-4}$ aliphatic), N($C_{1-4}$ aliphatic)₂, halogen, $C_{1-4}$ aliphatic, OH, O($C_{1-4}$ aliphatic), NO₂, CN, CO₂H, CO₂($C_{1-4}$ aliphatic), O(halo $C_{1-4}$ aliphatic), or halo($C_{1-4}$ aliphatic), wherein each of the foregoing $C_{1-4}$aliphatic groups of R⁺ is unsubstituted.

The term "alkylidene chain" refers to a straight or branched carbon chain that may be fully saturated or have one or more units of unsaturation and has two points of attachment to the rest of the molecule, wherein one or more methylene units may optionally and independently be replaced with a group including, but not limited to, CO, CO₂, COCO, CONR, OCONR, NRNR, NRNRCO, NRCO, NRCO₂, NRCONR, SO, SO₂, NRSO₂, SO₂NR, NRSO₂NR, O, S; or NR.

As detailed above, in some embodiments, two independent occurrences of R° (or R⁺, or any other variable similarly defined herein), are taken together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of

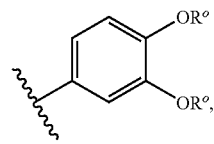

these two occurrences of R° are taken together with the oxygen atoms to which they are bound to form a fused 6-membered oxygen containing ring:

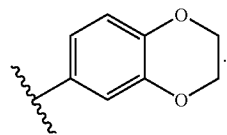

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

As described herein, a bond drawn from a substituent to the center of one ring within a multiple-ring system (as shown below), represents substitution of the substituent at any substitutable position in any of the rings within the multiple ring system. For example, Figure a represents possible substitution in any of the positions shown in Figure b.

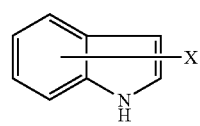

FIG. a

-continued

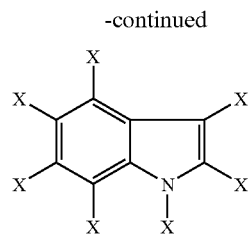

FIG. b

This also applies to multiple ring systems fused to optional ring systems (which would be represented by dotted lines). For example, in Figure c, X is an optional substituent both for ring A and ring B.

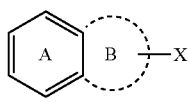

FIG. c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

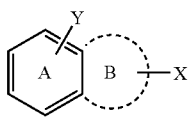

FIG. d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$— or $^{14}C$-enriched carbon are within the scope of this invention. Such compounds are useful, for example, as analytical tools or probes in biological assays.

The compounds of this invention may be prepared in general by methods known to those skilled in the art for analogous compounds, as illustrated by the general scheme below, and the preparative examples that follow.

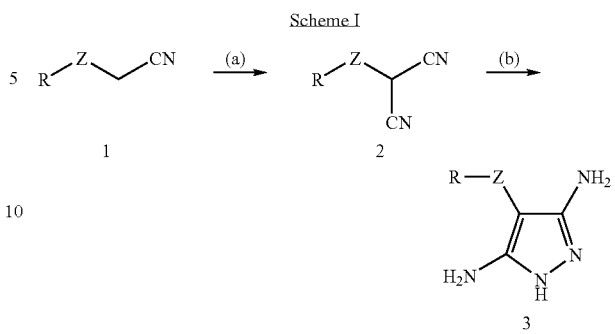

Reagents and conditions: (a) i) LDA, toluene, ii) o-ClC$_4$H$_6$CH$_2$SCN, toluene, 2 hours; (b) N$_2$H$_4$.H$_2$O, EtOH, reflux, 16 hours.

Scheme I above shows a general synthetic route that is used for preparing the compounds 3 of this invention when R and Z are as described herein. Intermediates 2 may be prepared by methods substantially similar to those described in the literature by Davis and Cava *J. Org. Chem.* 1983, 48, 2774. Cyclisation of the malononitrile 2 with hydrazine hydrate furnishes the desired diamino-pyrazoles 3.

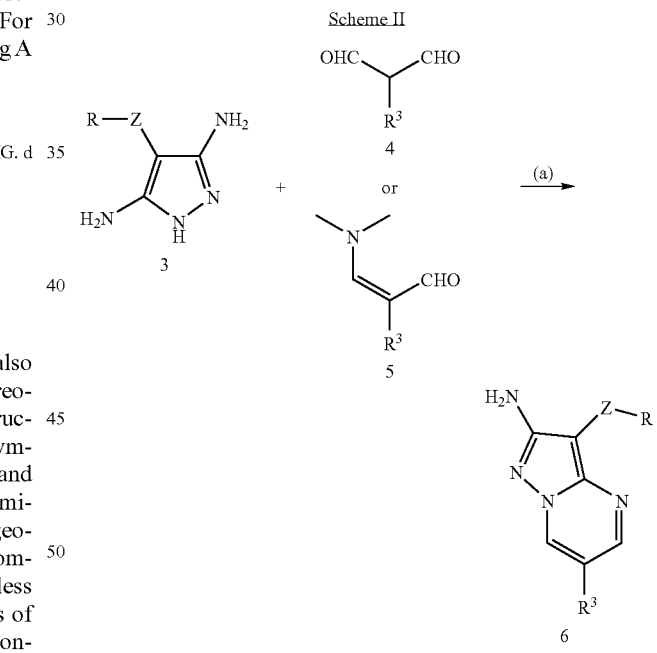

Reagents and conditions: (a) EtOH (in the case of 4), $^i$PrOH (in the case of 5), AcOH$_{cat.}$, microwave irradiation, 180° C., 15 minutes.

Scheme II above shows a general synthetic route that is used for preparing the compounds 6 of this invention when Z, R and R$^3$ are as described herein. Pyrazolo[1,5-a]pyrimidines 6 are prepared by microwave assisted cyclisation of diamino-pyrazoles 3 with either a commercially available malonaldehyde 4 or its equivalent 5. Derivative 5 may be prepared by methods described by Coppola, et al, *J. Het. Chem.* 1974, 44, 51.

Table 1 below depicts exemplary compounds prepared according to the general methods described in Schemes I and II.
TABLE 1
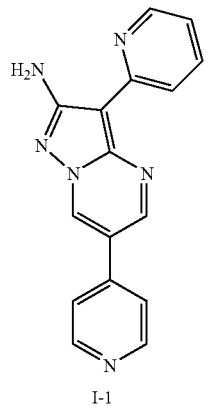
I-1
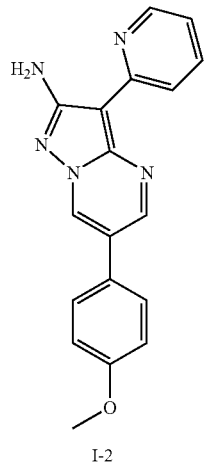
I-2
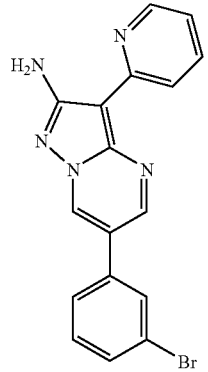
I-3
TABLE 1-continued
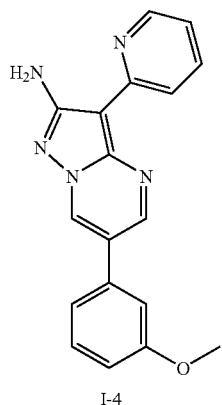
I-4
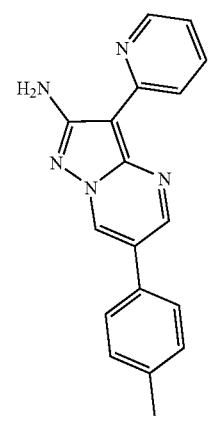
I-5
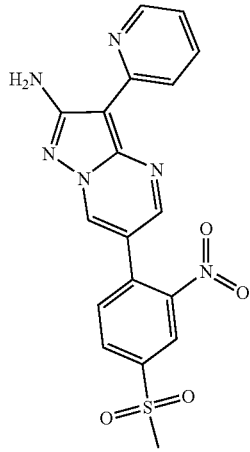
I-6

TABLE 1-continued
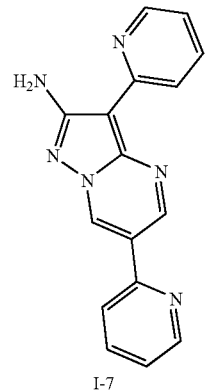
I-7
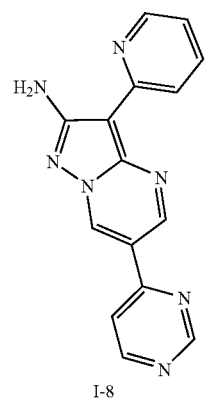
I-8
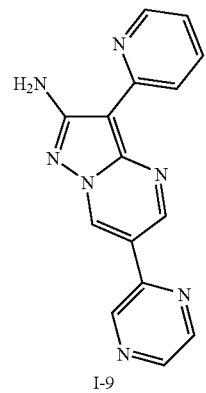
I-9
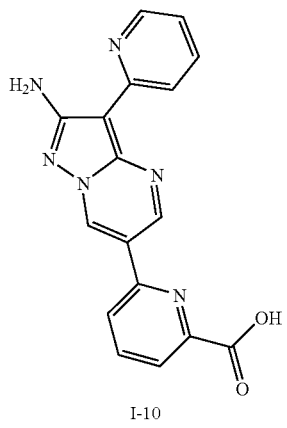
I-10
TABLE 1-continued
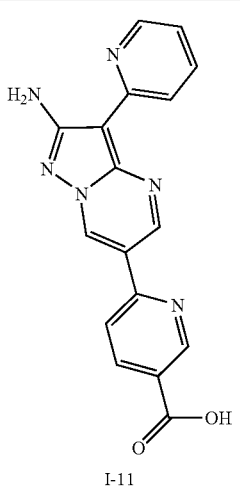
I-11
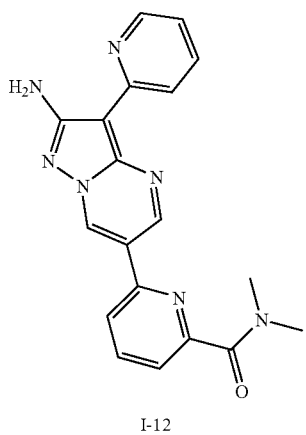
I-12
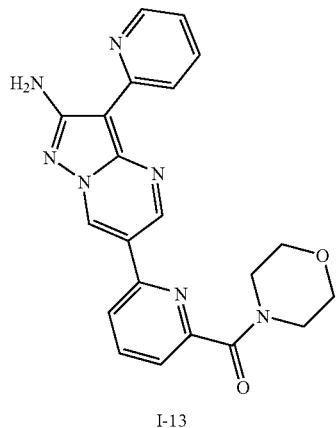
I-13

TABLE 1-continued
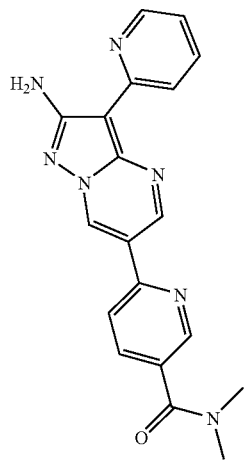
I-14
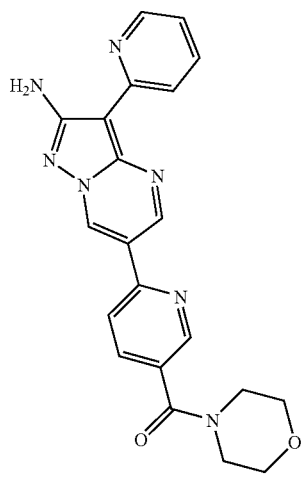
I-15
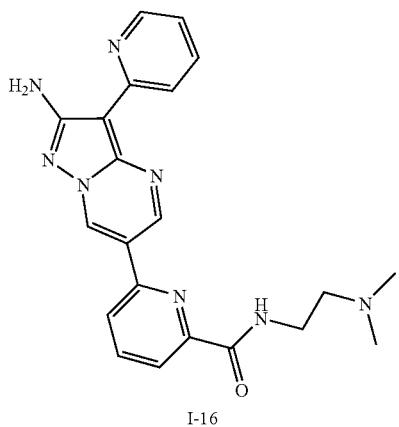
I-16
TABLE 1-continued
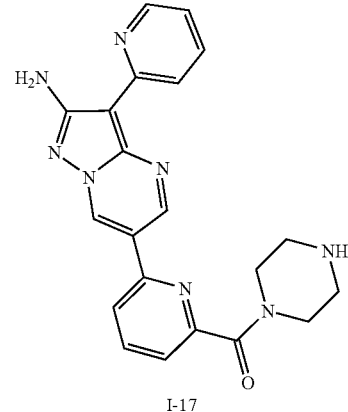
I-17
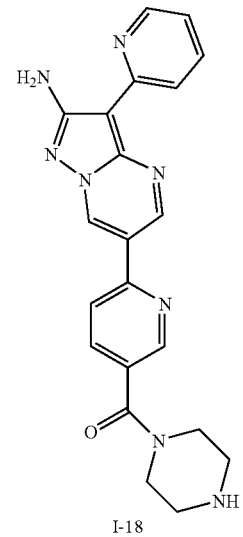
I-18
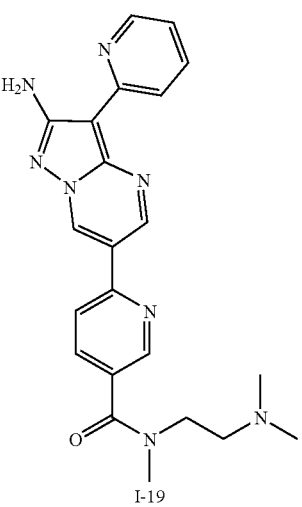
I-19

TABLE 1-continued
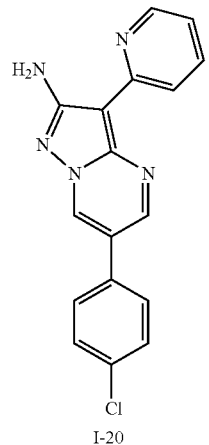
I-20
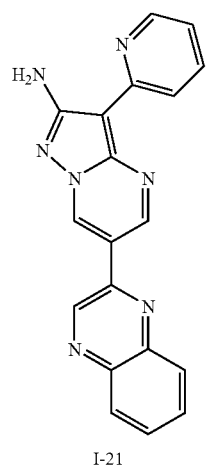
I-21
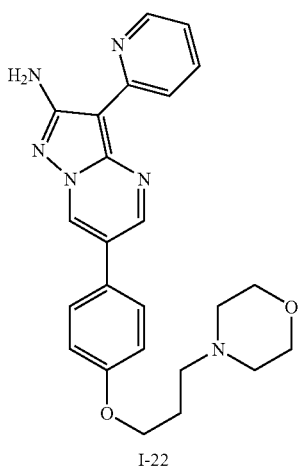
I-22
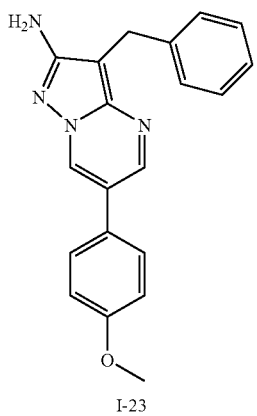
I-23
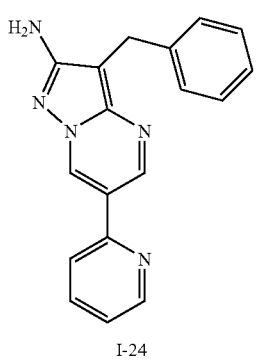
I-24
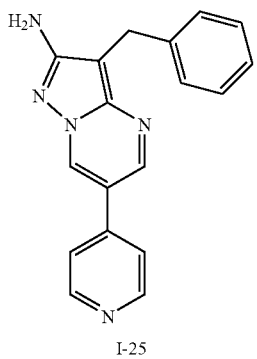
I-25
Scheme III
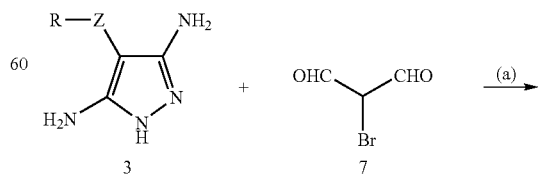

-continued

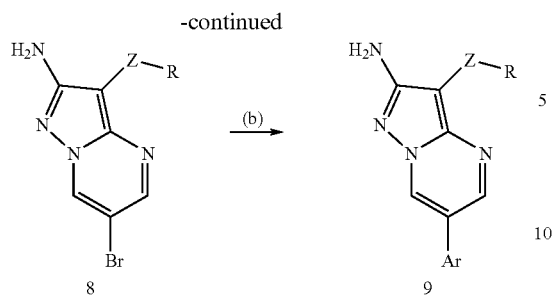

Reagents and conditions: (a) EtOH, AcOH$_{cat.}$, reflux, 3 hours; (b) ArB(OH)$_2$, Pd(dppf)$_2$Cl$_2$, 2M Na$_2$CO$_3$, microwave irradiation, 120° C., 20 minutes.

Scheme III above shows a general synthetic route that has been used for preparing compounds 9 of this invention when Z, R and Ar are as described herein. Pyrazolo[1,5-a]pyrimidines 8 are prepared by cyclisation of diamino-pyrazoles 3 with the commercially available 2-bromo-malonaldehyde 7. Finally, the formation of the biaryl link derivatives 9 is achieved by treating bromides 8 with the desired boronic acid derivative in the presence of palladium(0) as a catalyst by using the microwave-assisted Suzuki coupling methods that are well known in the art. The reaction is amenable to a variety of substituted aryl or heteroaryl boronic acids.

Table 2 below depicts exemplary compounds prepared according to the general methods described in Scheme III.

TABLE 2

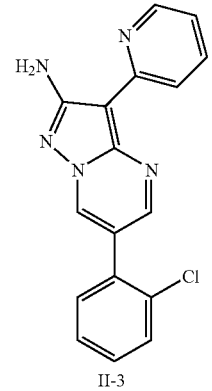

II-1

II-2

TABLE 2-continued

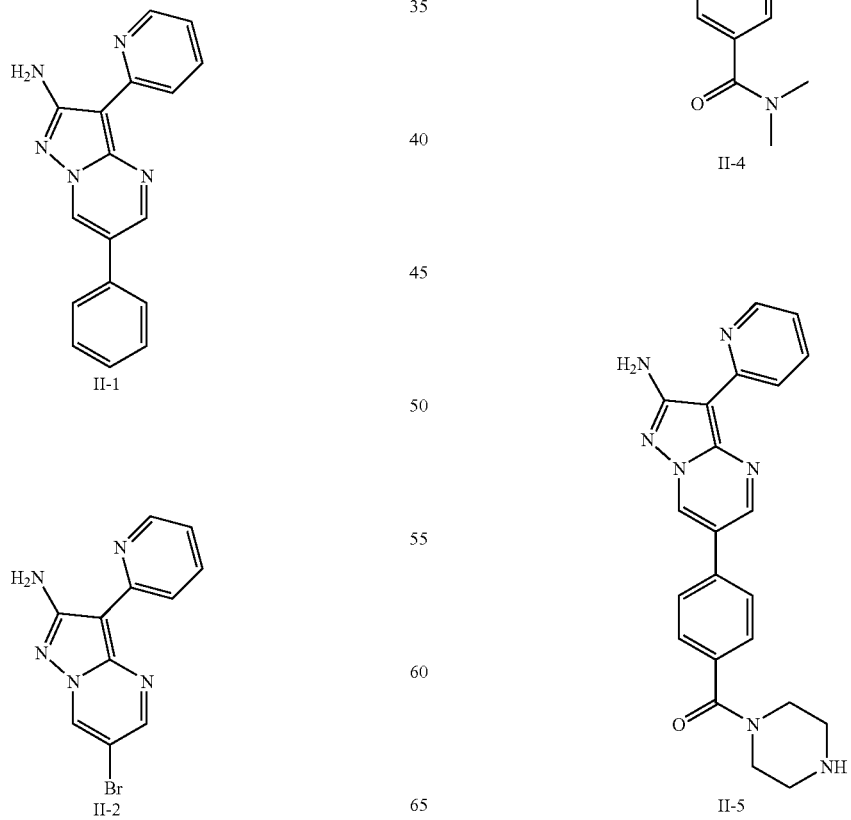

II-3

II-4

II-5

TABLE 2-continued
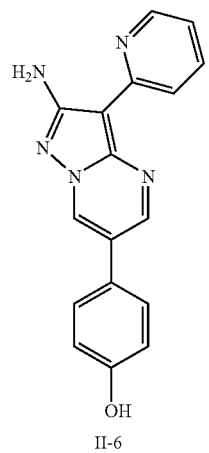
II-6
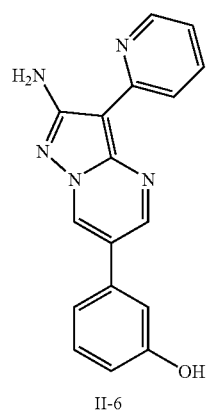
II-6
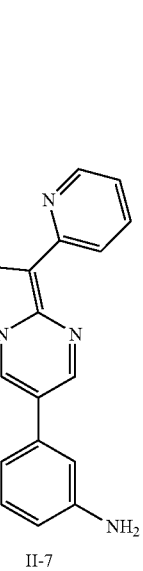
II-7
TABLE 2-continued
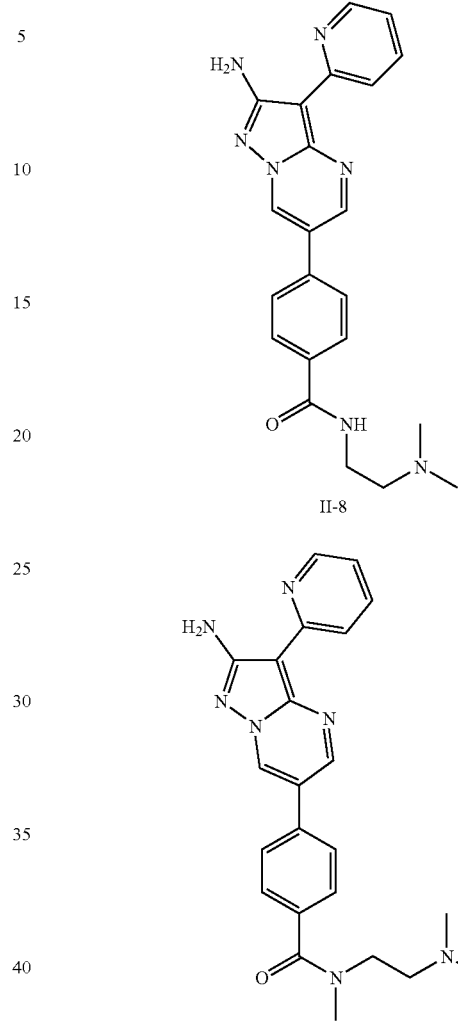
II-8
II-9
Scheme IV
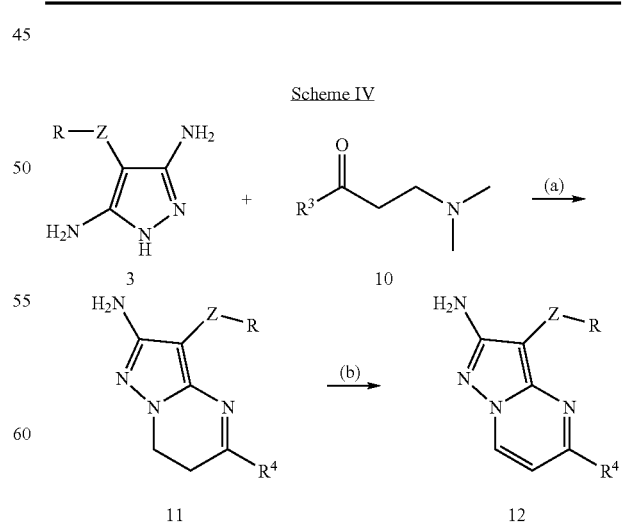
Reagents and conditions: (a) DMF, 160° C., 10 hours; (b) DDQ, 1,4-dioxane, reflux, 2-3 hours.

Scheme IV above shows a general synthetic route that has been used for preparing compounds 12 of this invention when Z, R and $R^4$ are as described herein. The cyclisation of diamino-pyrazoles 3 in presence of β-dimethylaminoketones 10 has been achieved by methods substantially similar to those described in the literature by Elnagdi and Erian *Bull. Chem. Soc. Jpn* 1990, 63, 1854. The reaction is amenable to a variety of diamino-pyrazoles 3 and β-dimethylaminoketones 10. Intermediates 11 are oxidized with DDQ according to step (b) of Scheme IV.

Table 3 below depicts exemplary compounds prepared according to the general methods described in Scheme IV.

TABLE 3

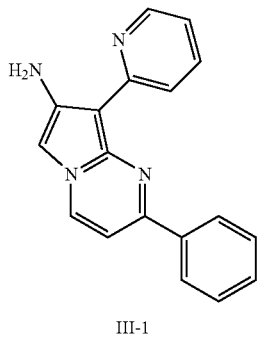

III-1

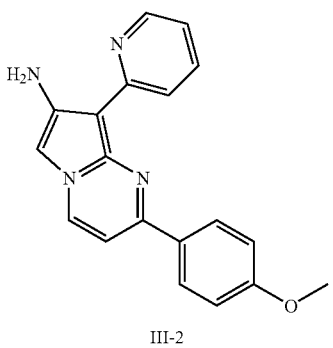

III-2

Scheme V

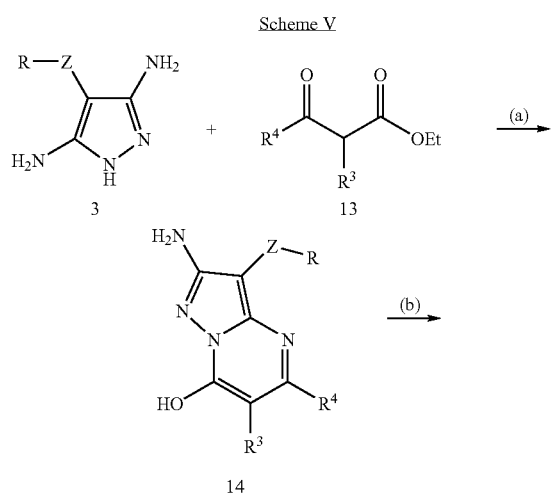

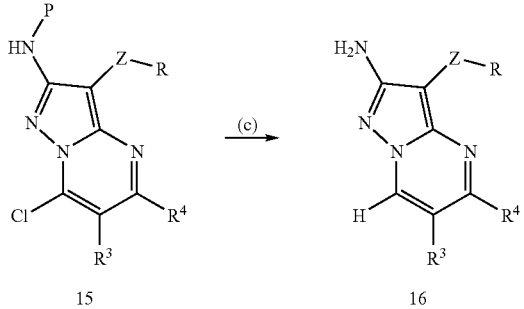

Reagents and conditions: (a) AcOH, reflux; (b) i) Protection conditions, ii) POCl$_3$, 90° C.; (c) i) H$_2$, Pd/C, NaOAc, EtOH, ii) Deprotection conditions.

Scheme V above shows a general synthetic route that has been used for preparing compounds 16 of this invention when Z, R, $R^3$ and $R^4$ are as described herein. Intermediate 14 may be prepared by methods described by Sofon, et al, *Pharmazie* 1994, 49, 482 and by Ram, et al, *Indian J. Chem. Sect. B* 1995, 34, 514. After protection of amines of formula 14, derivatives 15 are obtained by a method well known to one of skill in the art. Finally, chloro derivatives 15 are reduced according to Scheme V step (c) i), and the amine is deprotected to afford compounds of structure 16.

Scheme VI

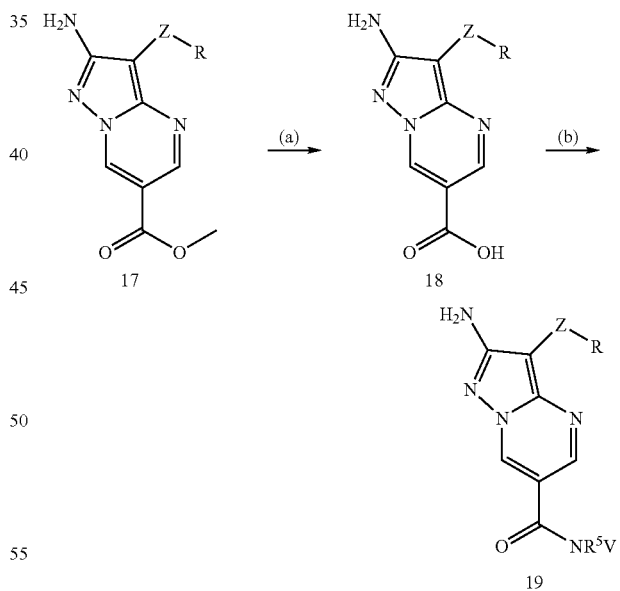

Reagents and conditions: (a) 1N NaOH, MeOH; (b) EDC, HOBt, DCM/DMF, HNR$^5$V.

Scheme VI above shows a general method for preparing compounds of formula 19 of this invention when Z, R, $R^5$ and V are as described herein. Each of the above steps is well known to one of skill in the art.

Table 4 below depicts exemplary compounds prepared according to the general methods described in Schemes VI.

TABLE 4
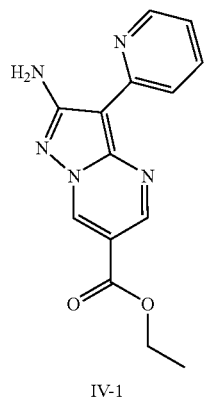
IV-1
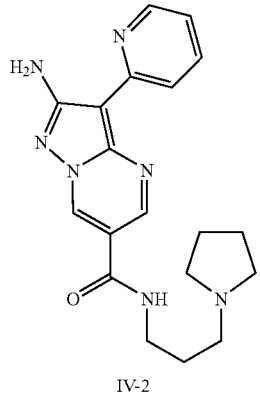
IV-2
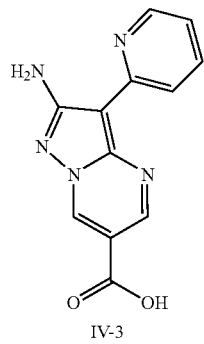
IV-3
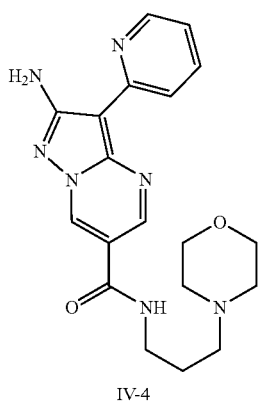
IV-4
TABLE 4-continued
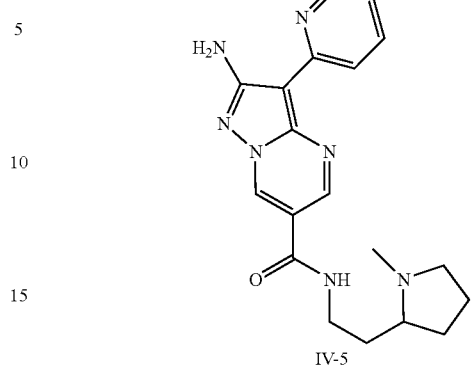
IV-5
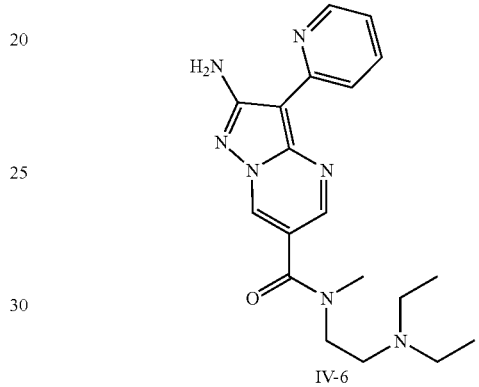
IV-6
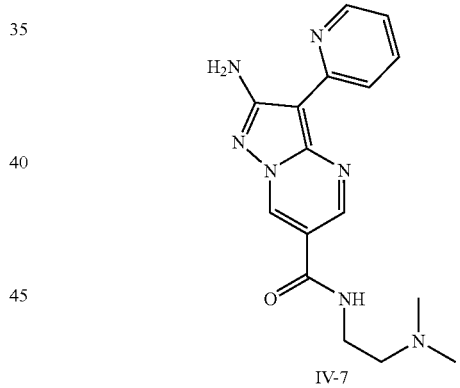
IV-7
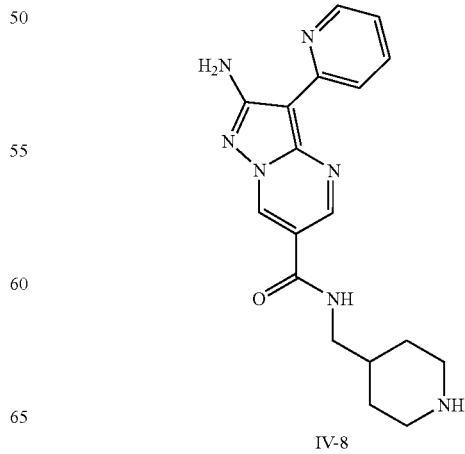
IV-8

TABLE 4-continued
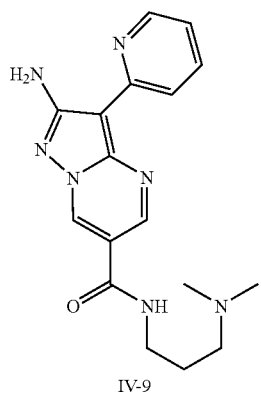
IV-9
IV-10
IV-11
IV-12
TABLE 4-continued
IV-13
Other compounds prepared according to schemes and examples described herein are provided in Table 5:
TABLE 5
Cmpd # (V-)   Compound
1
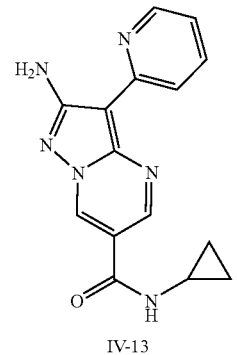
2
3

TABLE 5-continued
| Cmpd # (V-) | Compound |
|---|---|
| 4 | 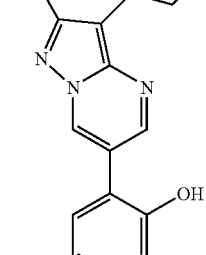 |
| 5 | |
| 6 | |
| 7 | |
| 8 | 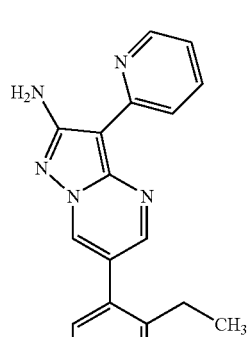 |
| 9 | |
| 10 | |
| 11 | |

TABLE 5-continued

| Cmpd # (V-) | Compound |
|---|---|
| 12 | 2-amino-3-(pyridin-2-yl)-6-(2-formylphenyl)pyrazolo[1,5-a]pyrimidine |
| 13 | 2-amino-3-(pyridin-2-yl)-6-(2-fluorophenyl)pyrazolo[1,5-a]pyrimidine |
| 14 | 2-amino-3-(pyridin-2-yl)-6-(2-methoxyphenyl)pyrazolo[1,5-a]pyrimidine |
| 15 | 2-amino-3-(pyridin-2-yl)-6-(biphenyl-2-yl)pyrazolo[1,5-a]pyrimidine |
| 16 | 2-amino-3-(pyridin-2-yl)-6-(2-(methylsulfonamido)phenyl)pyrazolo[1,5-a]pyrimidine |
| 17 | 2-amino-3-(pyridin-2-yl)-6-(2-((E)-3-methoxy-3-oxoprop-1-enyl)phenyl)pyrazolo[1,5-a]pyrimidine |
| 18 | 2-amino-3-(pyridin-2-yl)-6-(3-(methylsulfonamido)phenyl)pyrazolo[1,5-a]pyrimidine |
| 19 | 2-amino-3-(pyridin-2-yl)-6-(2-(difluoromethoxy)phenyl)pyrazolo[1,5-a]pyrimidine |

TABLE 5-continued

| Cmpd # (V-) | Compound |
|---|---|
| 20 | 2-amino-3-(pyridin-2-yl)-7-(2-aminophenyl)pyrazolo[1,5-a]pyrimidine |
| 21 | 2-amino-3-(pyridin-2-yl)-7-(2-nitrophenyl)pyrazolo[1,5-a]pyrimidine |
| 22 | 2-amino-3-(pyridin-2-yl)-7-(4-methoxypyridin-3-yl)pyrazolo[1,5-a]pyrimidine |
| 23 | 2-amino-3-(pyridin-2-yl)-7-(2-((dimethylamino)methyl)phenyl)pyrazolo[1,5-a]pyrimidine |
| 24 | ethyl 2-amino-7-(4-chlorophenyl)pyrazolo[1,5-a]pyrimidine-3-carboxylate |
| 25 | ethyl 2-amino-7-(pyridin-2-yl)pyrazolo[1,5-a]pyrimidine-3-carboxylate |
| 26 | ethyl 2-amino-7-(pyrazin-2-yl)pyrazolo[1,5-a]pyrimidine-3-carboxylate |
| 27 | ethyl 2-amino-7-(pyrimidin-4-yl)pyrazolo[1,5-a]pyrimidine-3-carboxylate |

TABLE 5-continued
| Cmpd # (V-) | Compound |
|---|---|
| 28 | 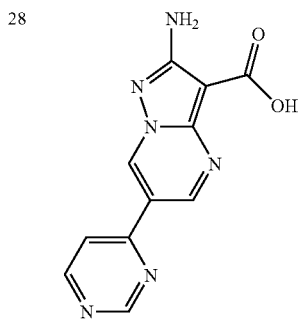 |
| 29 | 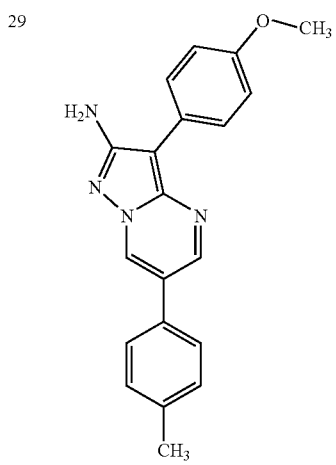 |
| 30 | 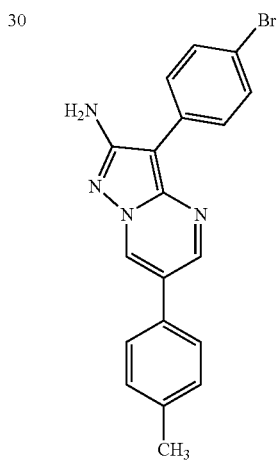 |
TABLE 5-continued
| Cmpd # (V-) | Compound |
|---|---|
| 29 | 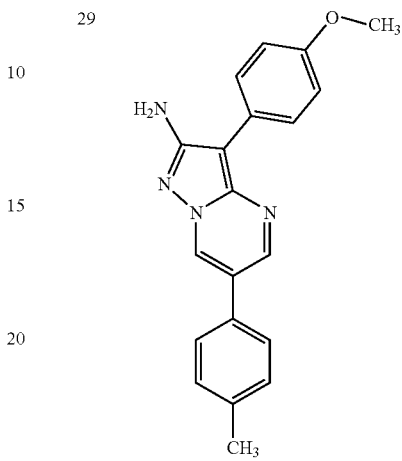 |
| 30 | 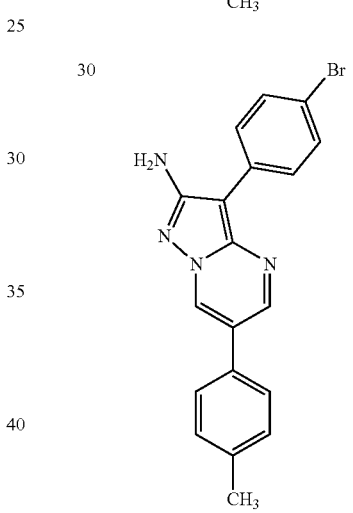 |
| 31 | 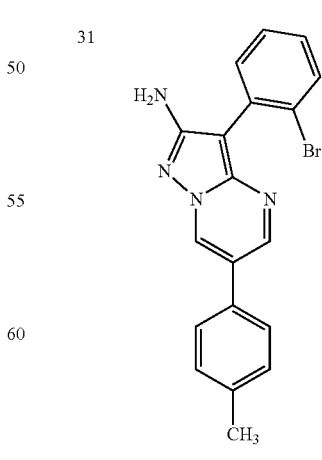 |

TABLE 5-continued
| Cmpd # (V-) | Compound |
|---|---|
| 32 | 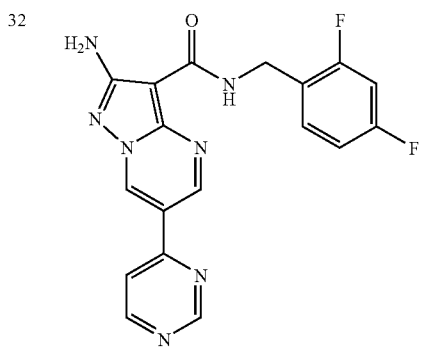 |
| 33 | 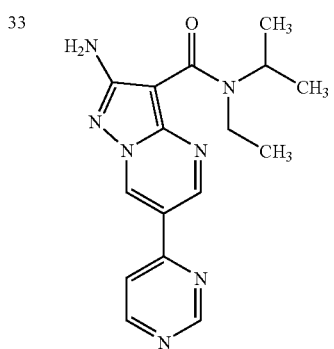 |
| 34 | 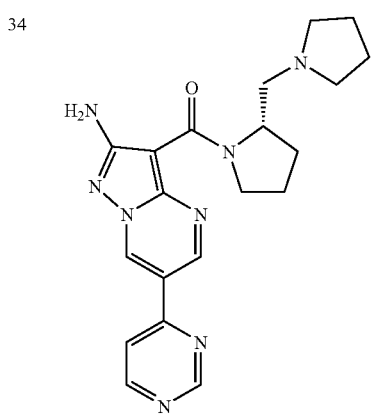 |
| 35 | 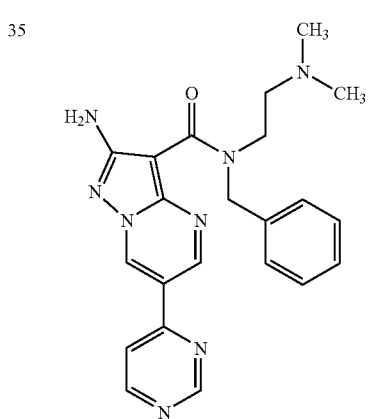 |
TABLE 5-continued
| Cmpd # (V-) | Compound |
|---|---|
| 36 | 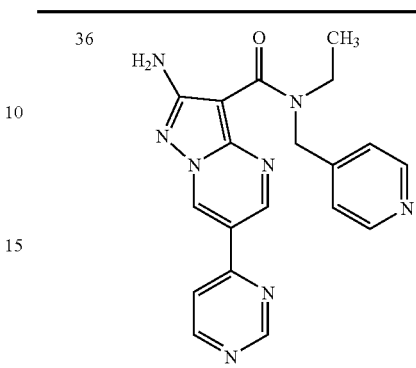 |
| 37 | 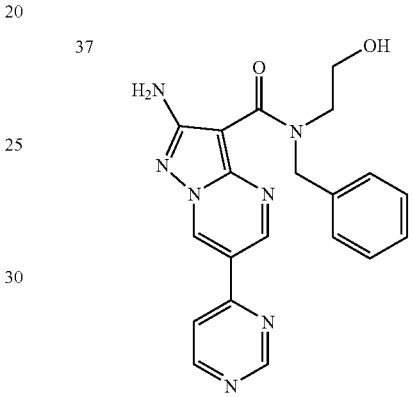 |
| 38 | 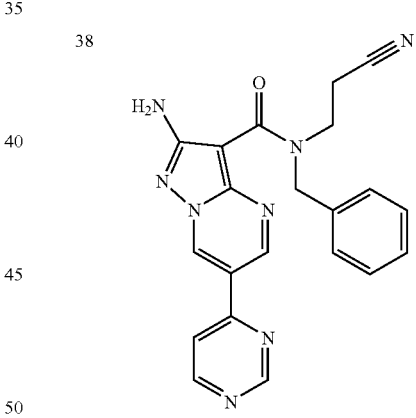 |
| 39 | 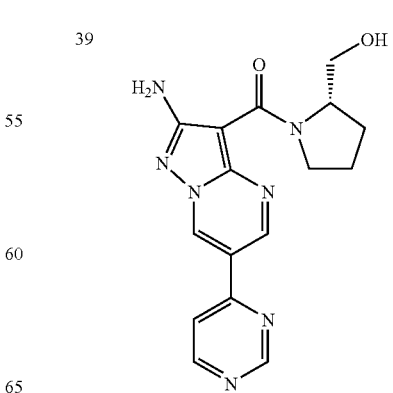 |

TABLE 5-continued
| Cmpd # (V-) | Compound |
|---|---|
| 40 | 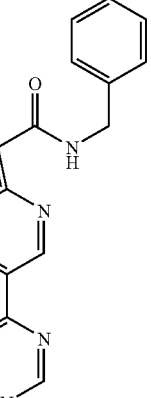 |
| 41 | |
| 42 | |
TABLE 5-continued
| Cmpd # (V-) | Compound |
|---|---|
| 43 | 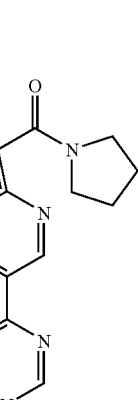 |
| 44 | |
| 45 | 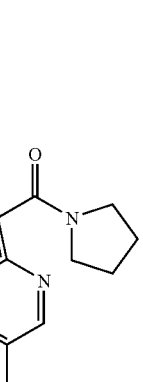 |

TABLE 5-continued
| Cmpd # (V-) | Compound |
|---|---|
| 46 | 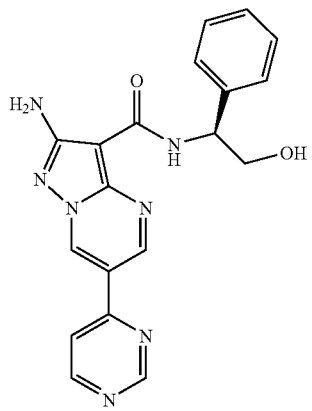 |
| 47 | 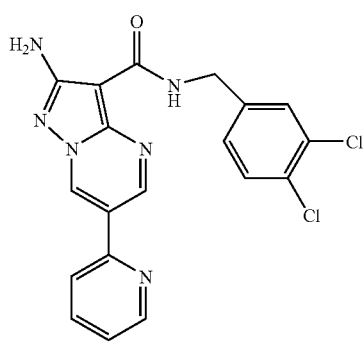 |
| 48 | 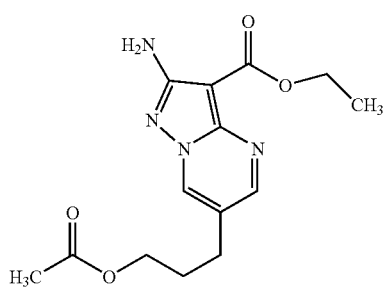 |
| 49 | 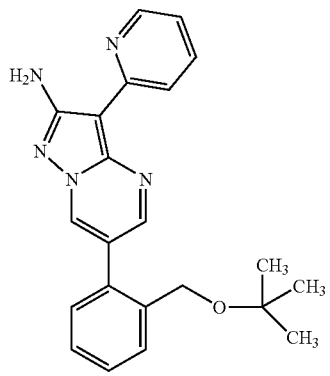 |
| 50 | 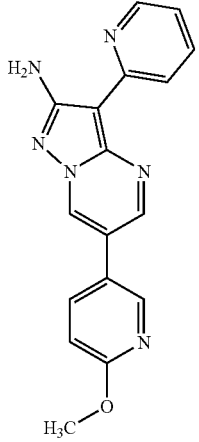 |
| 51 | 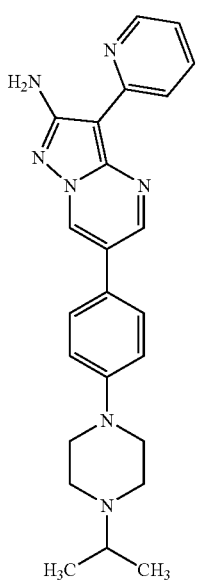 |
| 52 | 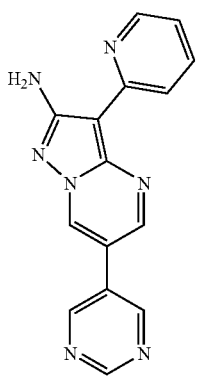 |

TABLE 5-continued
| Cmpd # (V-) | Compound |
|---|---|
| 53 | 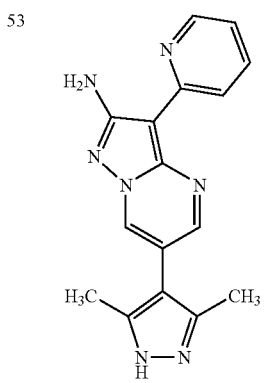 |
| 54 | 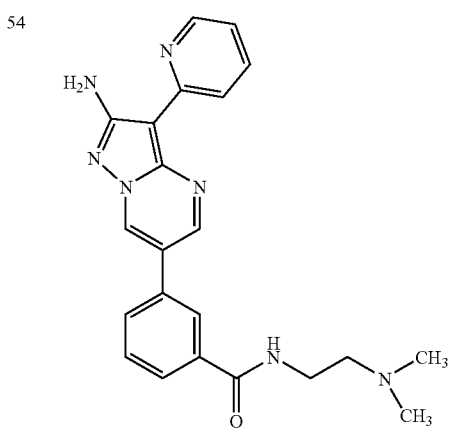 |
| 55 | 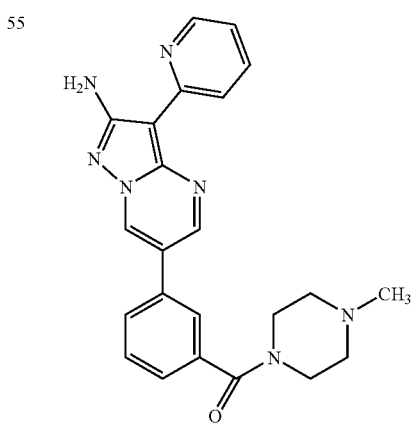 |
| 56 | 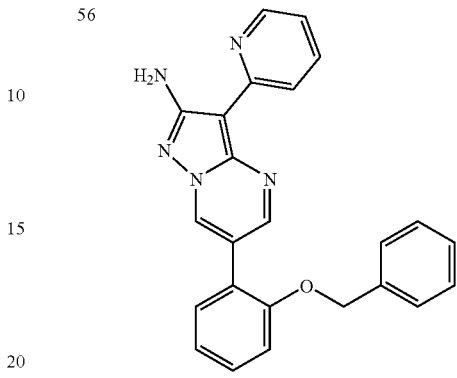 |
| 57 | 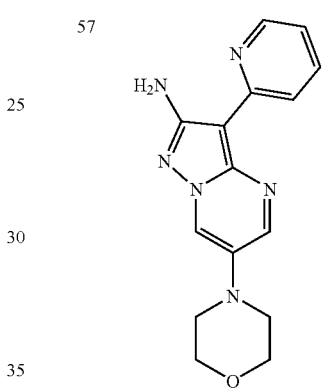 |
| 58 | 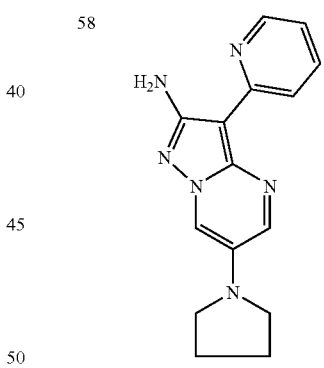 |
| 59 | 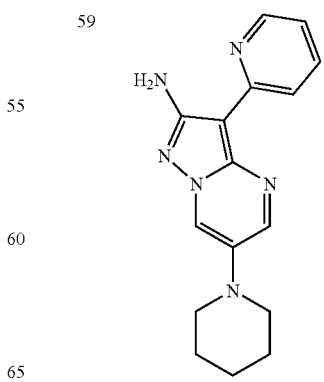 |

TABLE 5-continued
| Cmpd # (V-) | Compound |
|---|---|
| 60 | 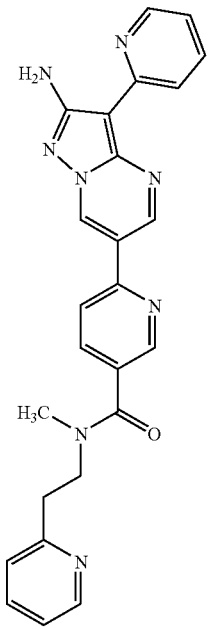 |
| 61 | 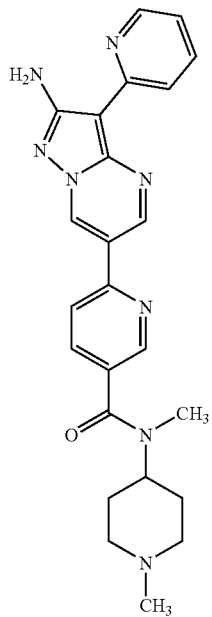 |
| 62 | 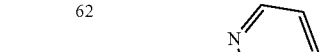 |
| 63 | 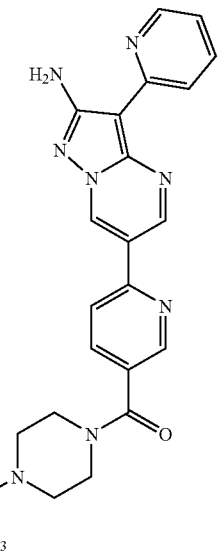 |

TABLE 5-continued
| Cmpd # (V-) | Compound |
|---|---|
| 64 | 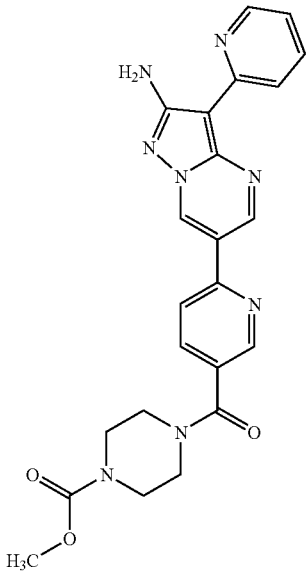 |
| 65 | 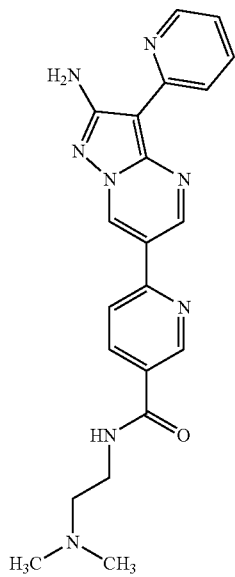 |在
TABLE 5-continued
| Cmpd # (V-) | Compound |
|---|---|
| 66 | 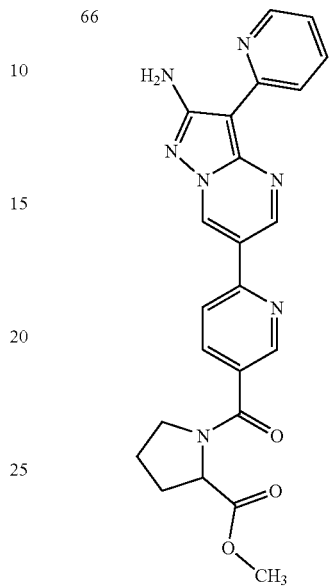 |
| 67 | 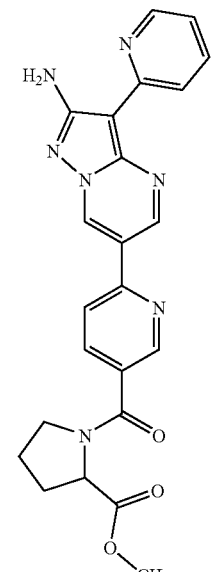 |

TABLE 5-continued
| Cmpd # (V-) | Compound |
|---|---|
| 68 | |
| 69 | 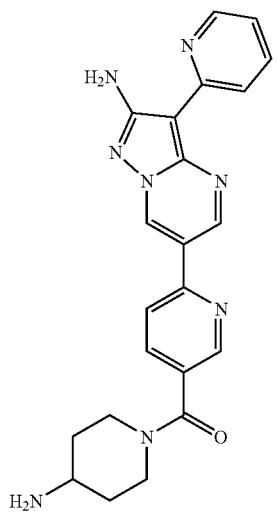 |
| 70 | |
| 71 | |

TABLE 5-continued
| Cmpd # (V-) | Compound |
|---|---|
| 72 | 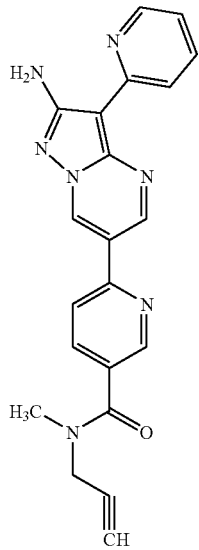 |
| 73 | 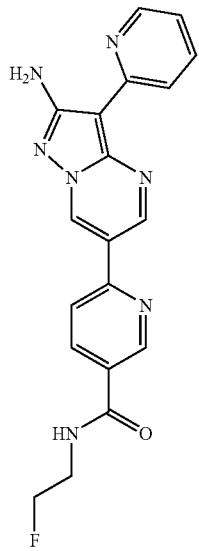 |
| 74 | 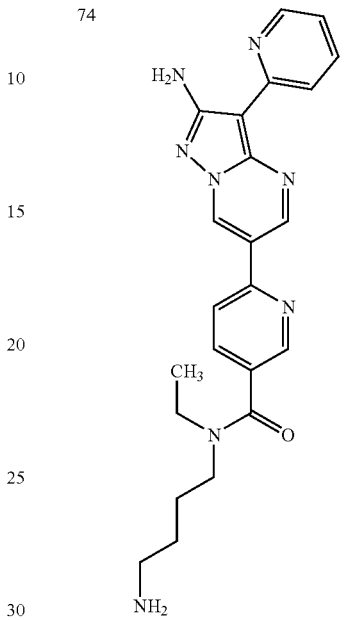 |
| 75 | 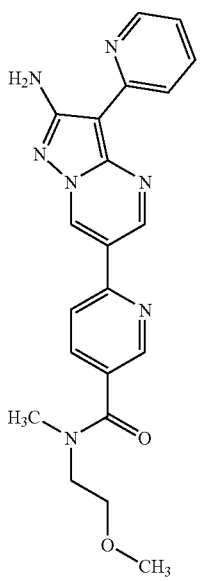 |

TABLE 5-continued
| Cmpd # (V-) | Compound |
|---|---|
| 76 | 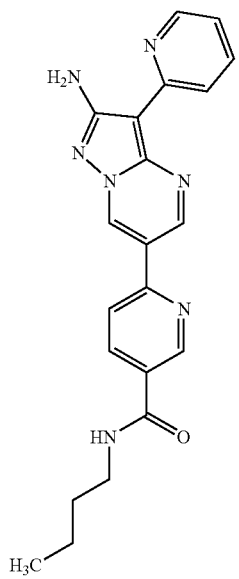 |
| 77 | |
TABLE 5-continued
| Cmpd # (V-) | Compound |
|---|---|
| 78 | |
| 79 | 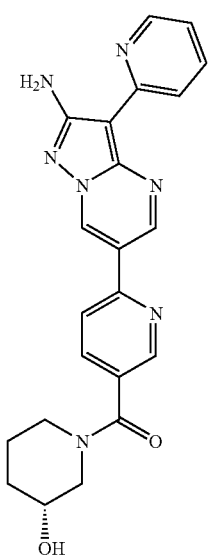 |

TABLE 5-continued
| Cmpd # (V-) | Compound |
|---|---|
| 80 | 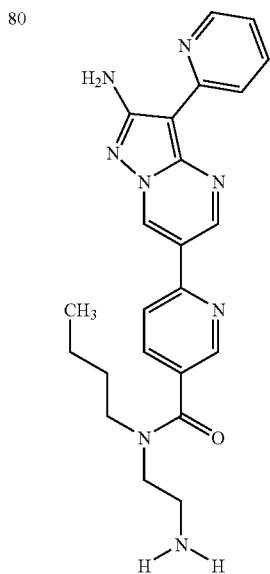 |
| 81 | 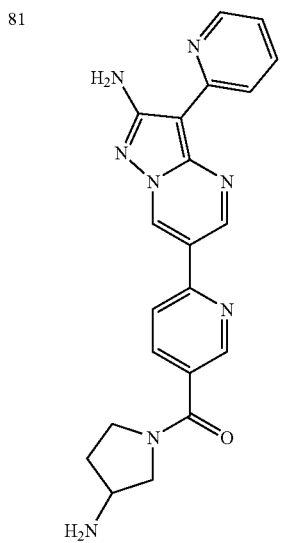 |
| 82 | 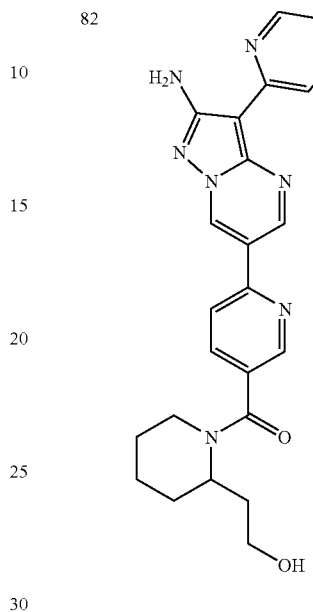 |
| 83 | 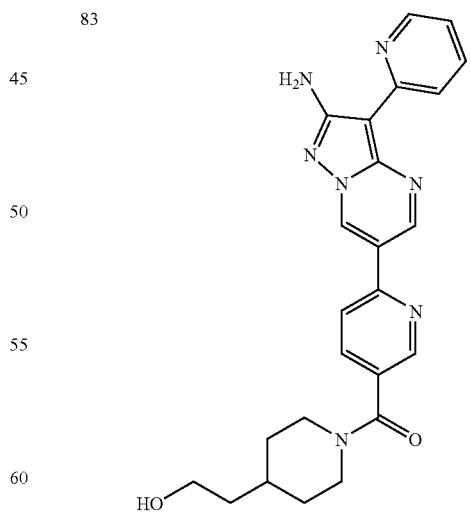 |

TABLE 5-continued
| Cmpd # (V-) | Compound |
|---|---|
| 84 | 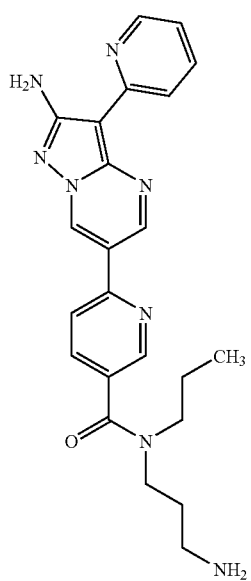 |
| 85 | |
| 86 | 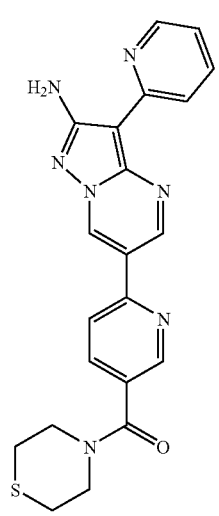 |
| 87 | |

TABLE 5-continued

| Cmpd # (V-) | Compound |
|---|---|
| 88 | *(structure)* |
| 89 | *(structure)* |
| 90 | *(structure)* |
| 91 | *(structure)* |

TABLE 5-continued
| Cmpd # (V-) | Compound |
|---|---|
| 92 | |
| 93 | 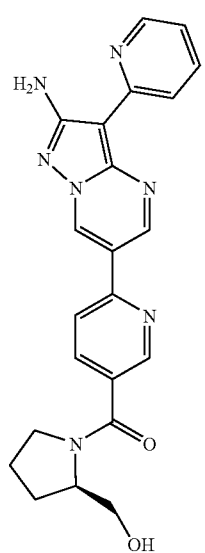 |
| 94 | |
| 95 | |

TABLE 5-continued

| Cmpd # (V-) | Compound |
|---|---|
| 96 | |
| 97 | |
| 98 | |
| 99 | |
| 100 | |

TABLE 5-continued
Cmpd #
(V-)  Compound
101
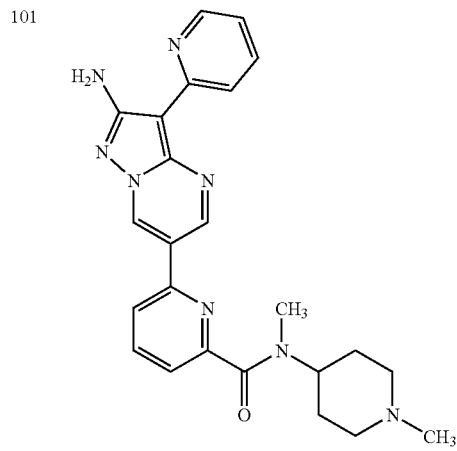
102
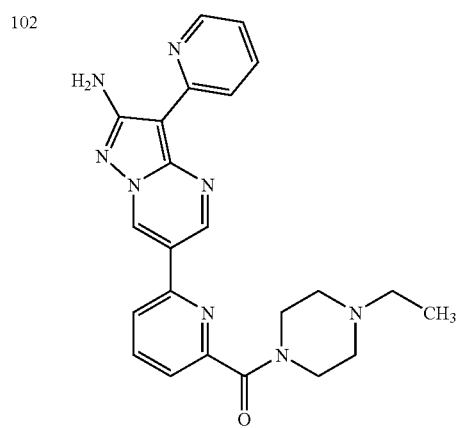
103
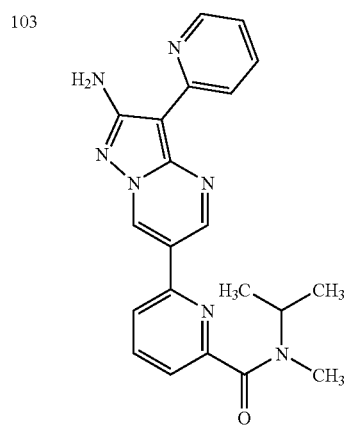
TABLE 5-continued
Cmpd #
(V-)  Compound
104
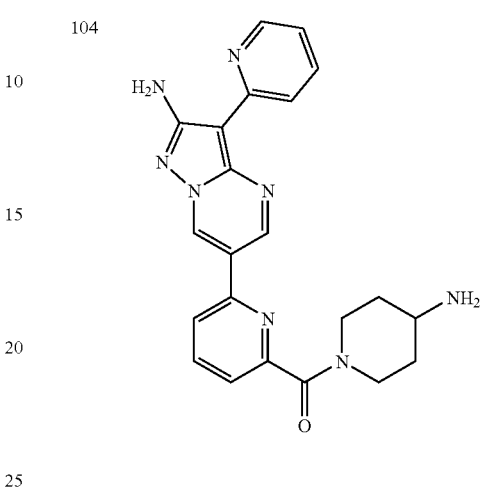
105
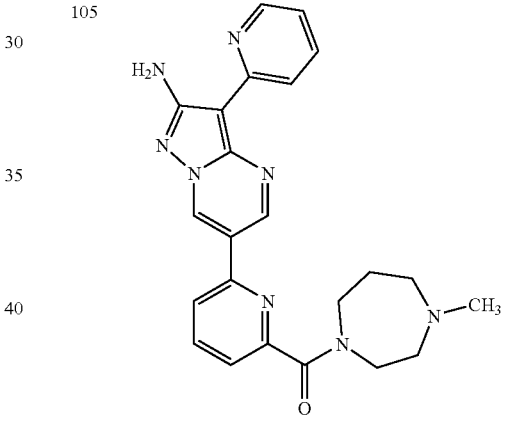
106
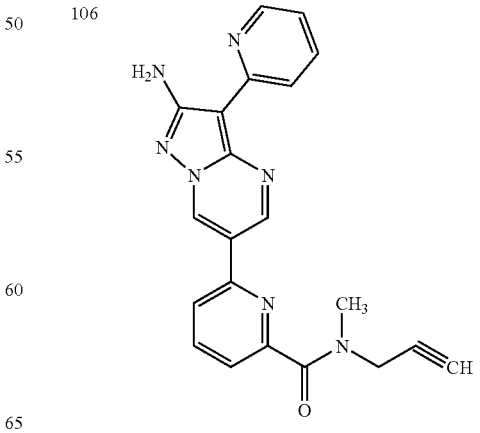

TABLE 5-continued
| Cmpd # (V-) | Compound |
|---|---|
| 107 | 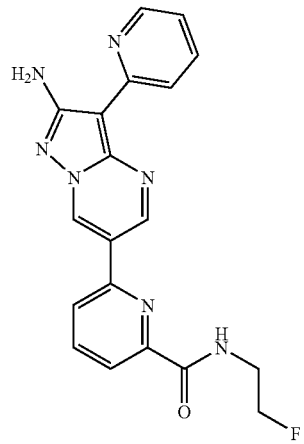 |
| 108 | 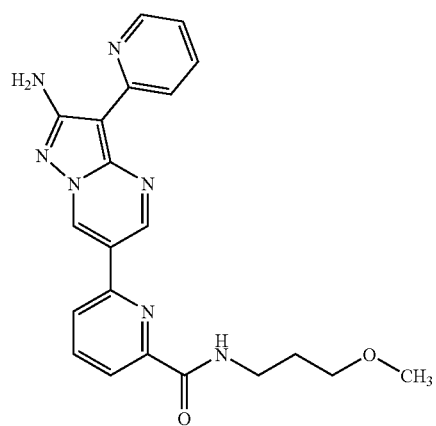 |
| 109 | 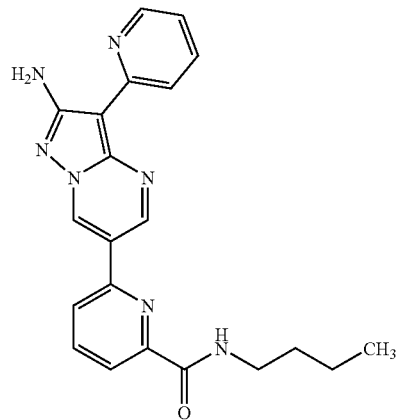 |
| 110 | 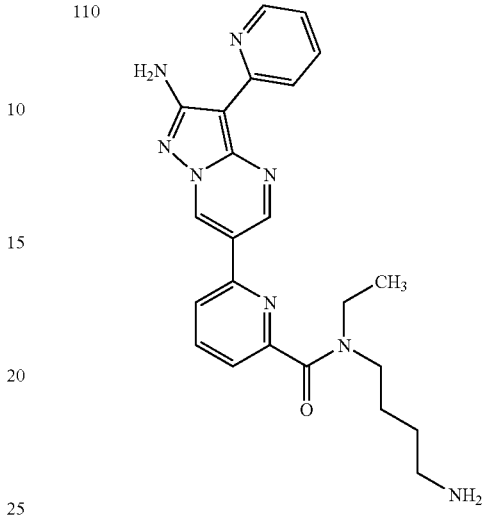 |
| 111 | 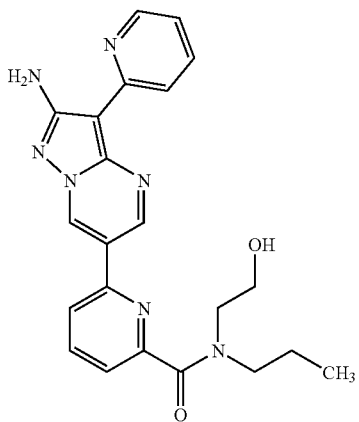 |
| 112 | 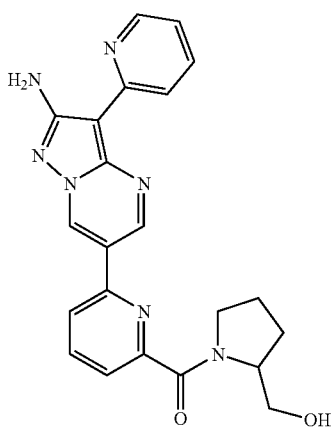 |

TABLE 5-continued
| Cmpd # (V-) | Compound |
|---|---|
| 113 | 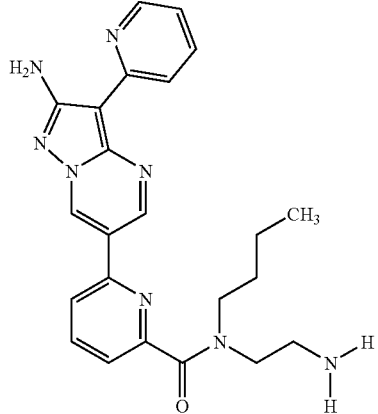 |
| 114 | 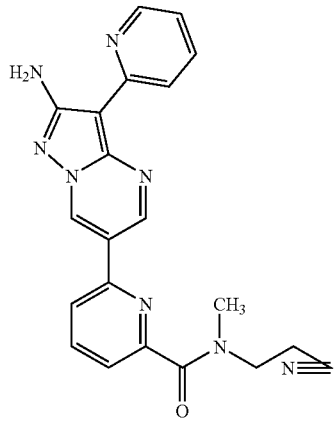 |
| 115 | 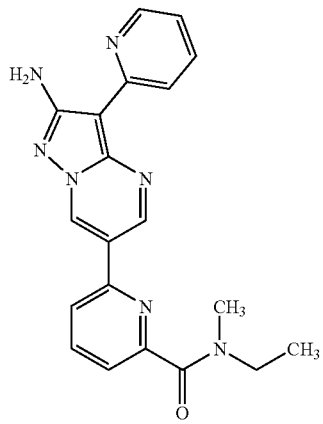 |
| 116 | 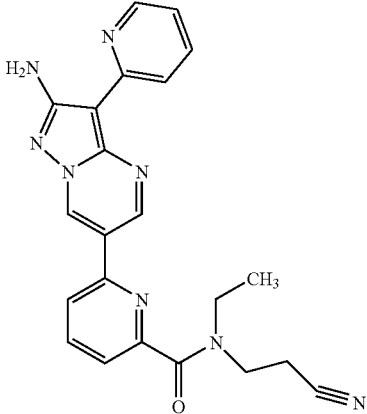 |
| 117 | 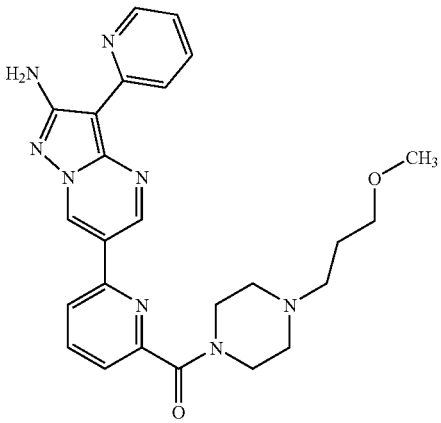 |
| 118 | 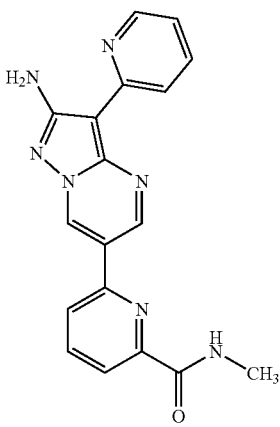 |

TABLE 5-continued
Cmpd # (V-) Compound
119
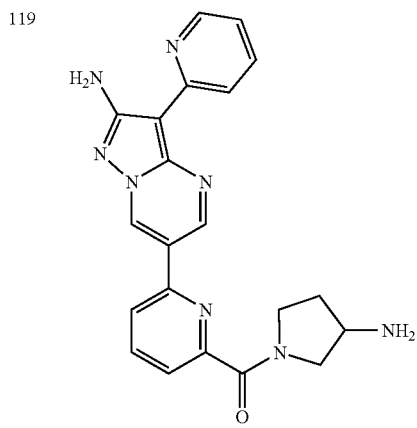
120
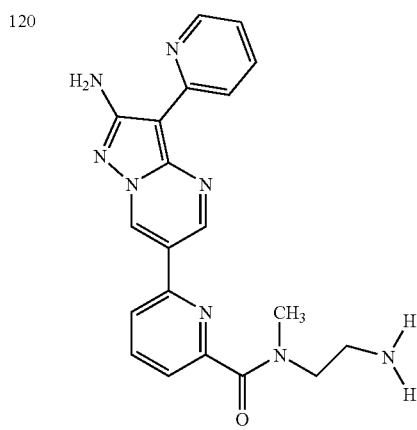
121
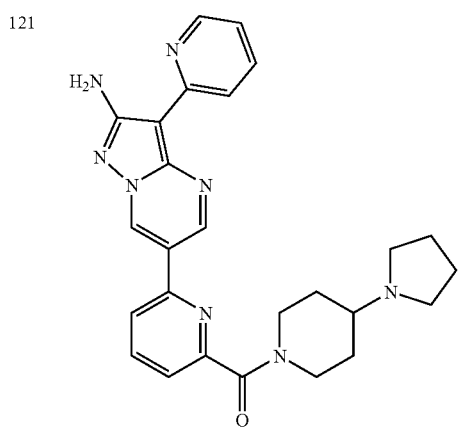
TABLE 5-continued
Cmpd # (V-) Compound
122
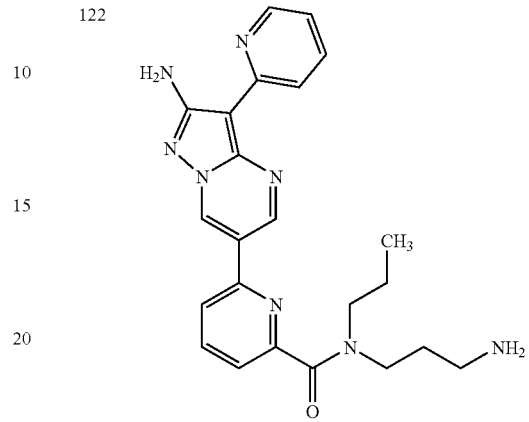
123
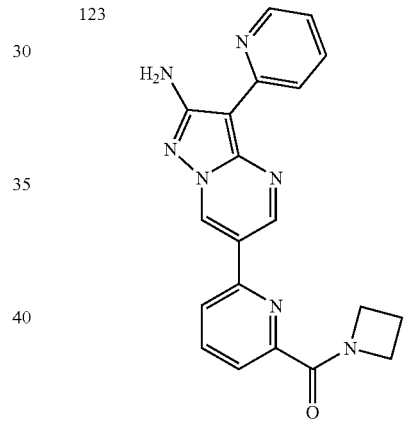
124
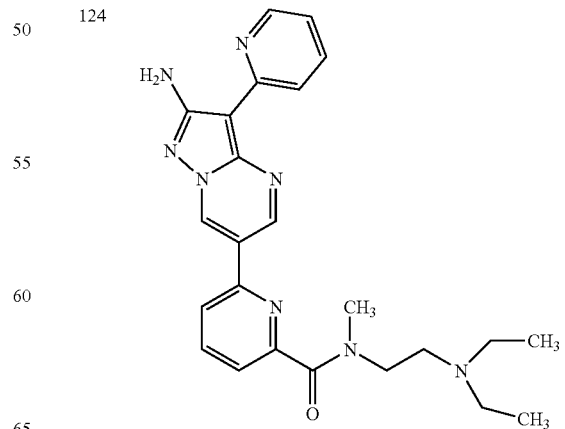

TABLE 5-continued
| Cmpd # (V-) | Compound |
|---|---|
| 125 | 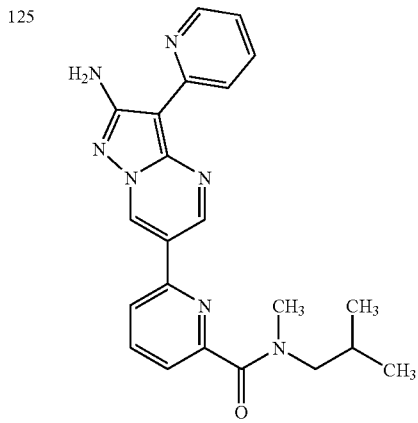 |
| 126 | 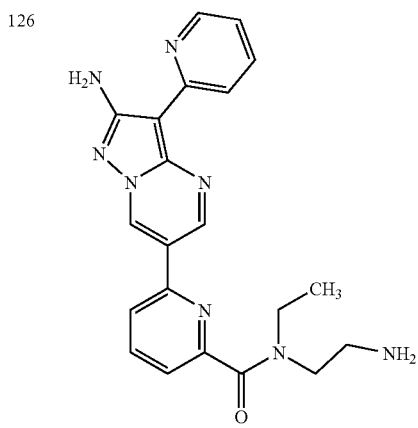 |
| 127 | 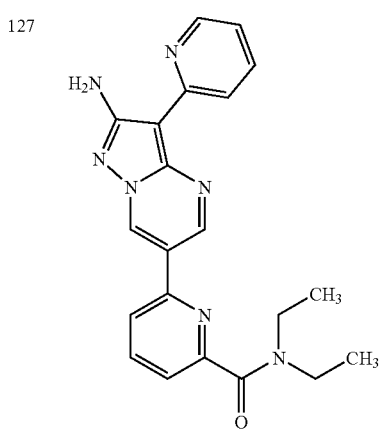 |
TABLE 5-continued
| Cmpd # (V-) | Compound |
|---|---|
| 128 | 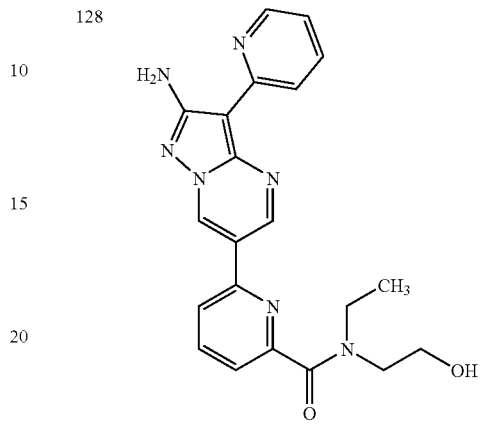 |
| 129 | 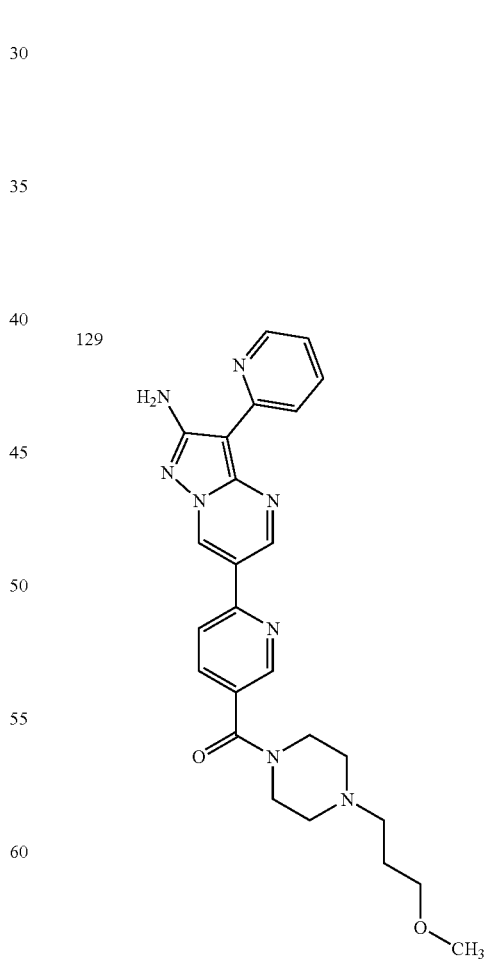 |

TABLE 5-continued
| Cmpd # (V-) | Compound |
|---|---|
| 130 | 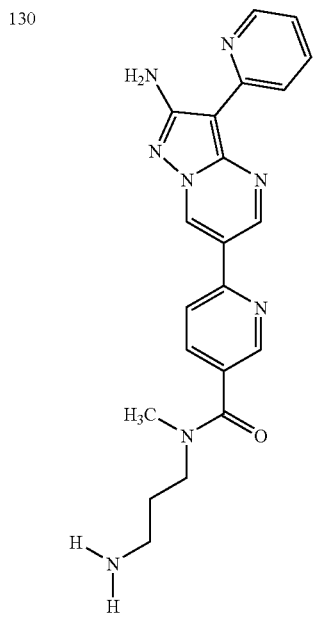 |
| 131 | 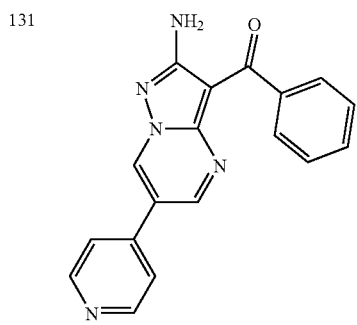 |
| 132 | 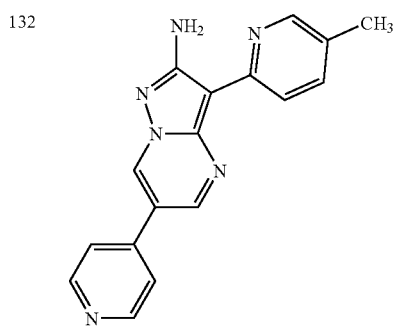 |
| 133 | 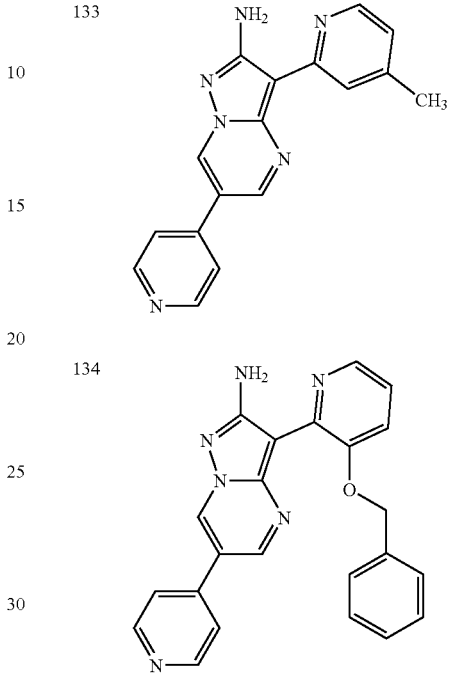 |
| 134 | |
| 135 | 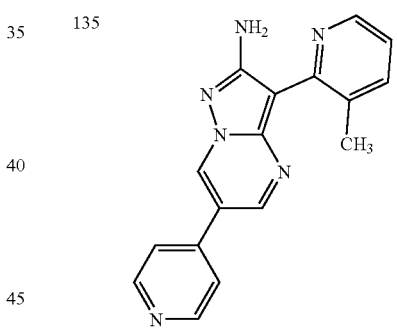 |
| 136 | 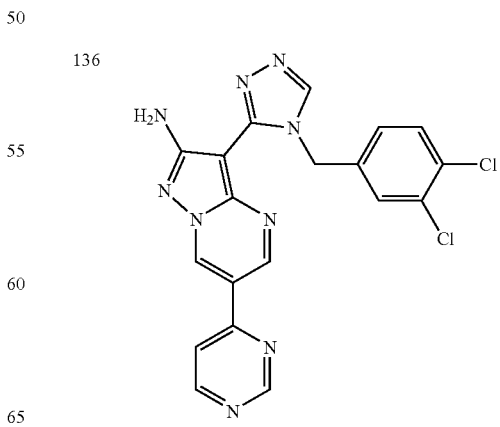 |

TABLE 5-continued
| Cmpd # (V-) | Compound |
|---|---|
| 137 | 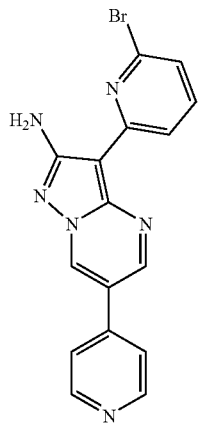 |
| 138 | 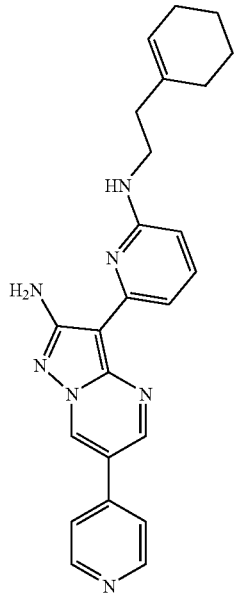 |
| 139 | 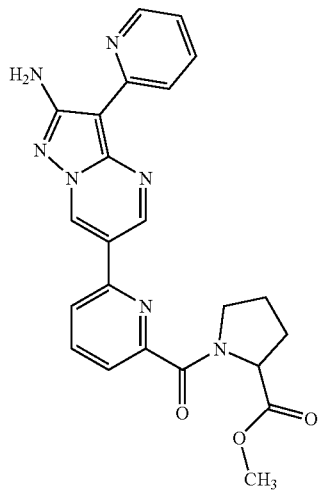 |
TABLE 5-continued
| Cmpd # (V-) | Compound |
|---|---|
| 140 |  |
| 141 |  |
| 142 | 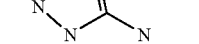 |

TABLE 5-continued
| Cmpd # (V-) | Compound |
|---|---|
| 143 | 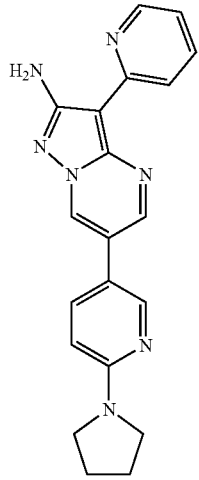 |
| 144 | 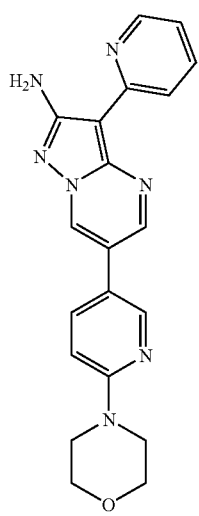 |
| 145 | 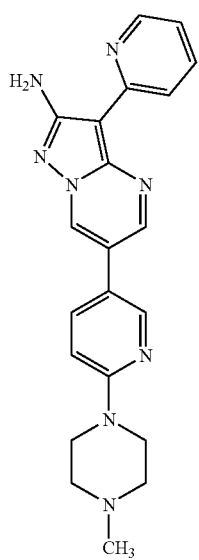 |
| 146 | 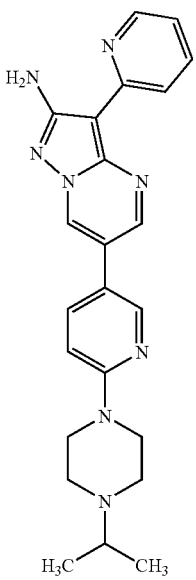 |
| 147 | 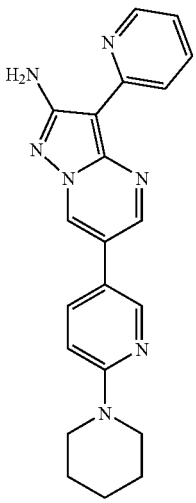 |

TABLE 5-continued
| Cmpd # (V-) | Compound |
|---|---|
| 148 | 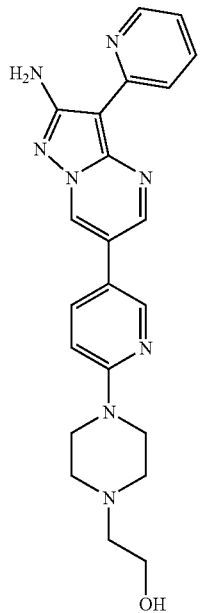 |
| 149 | 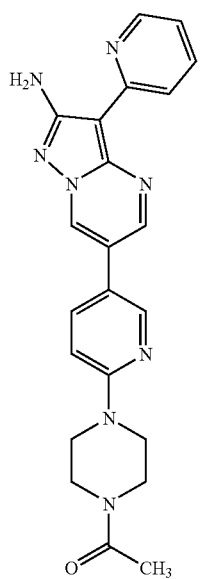 |
TABLE 5-continued
| Cmpd # (V-) | Compound |
|---|---|
| 150 | 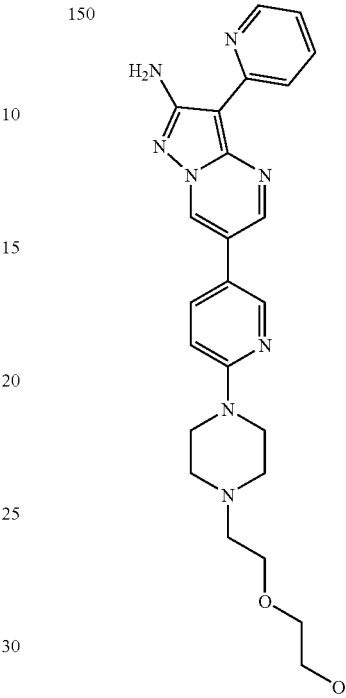 |
| 151 | 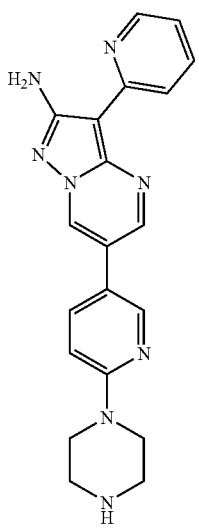 |

TABLE 5-continued
| Cmpd # (V-) | Compound |
|---|---|
| 152 | 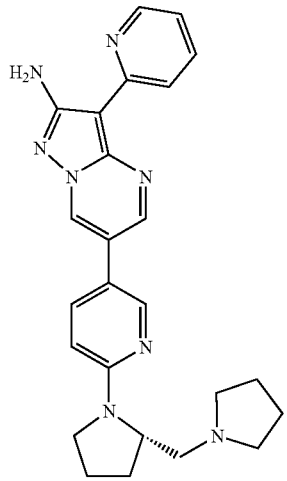 |
| 153 | 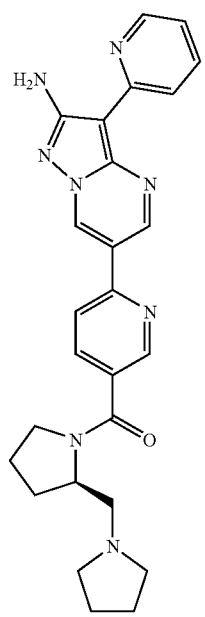 |
| 154 | 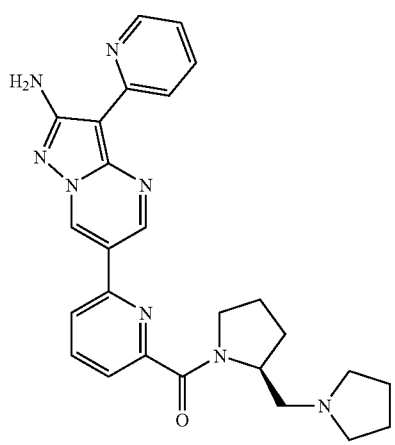 |
| 155 | 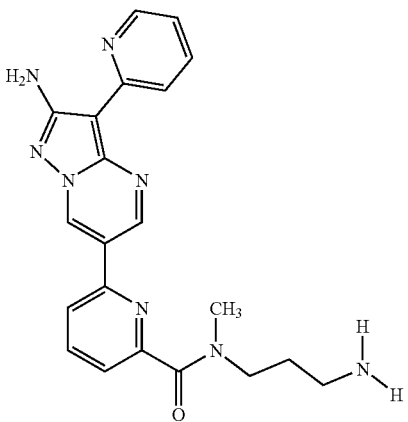 |
| 156 | 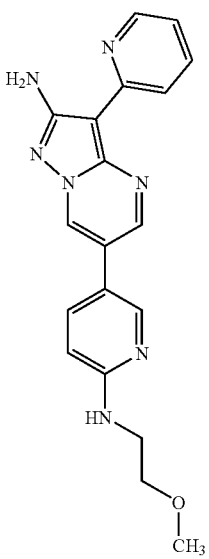 |
| 157 | 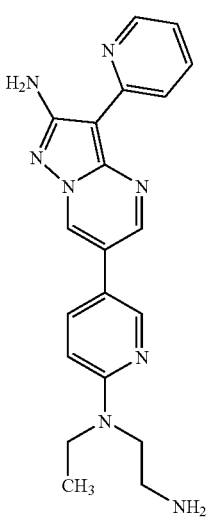 |

TABLE 5-continued
| Cmpd # (V-) | Compound |
|---|---|
| 158 | 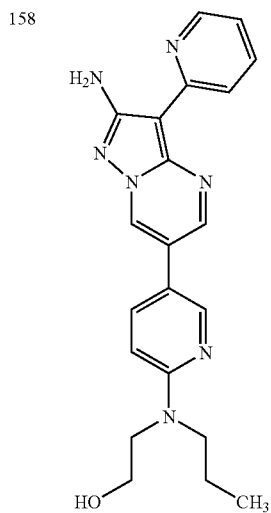 |
| 159 | 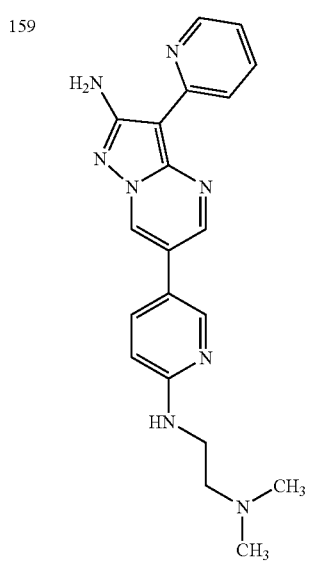 |
| 160 | 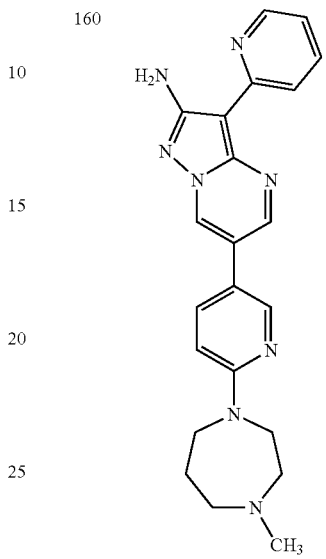 |
| 161 | 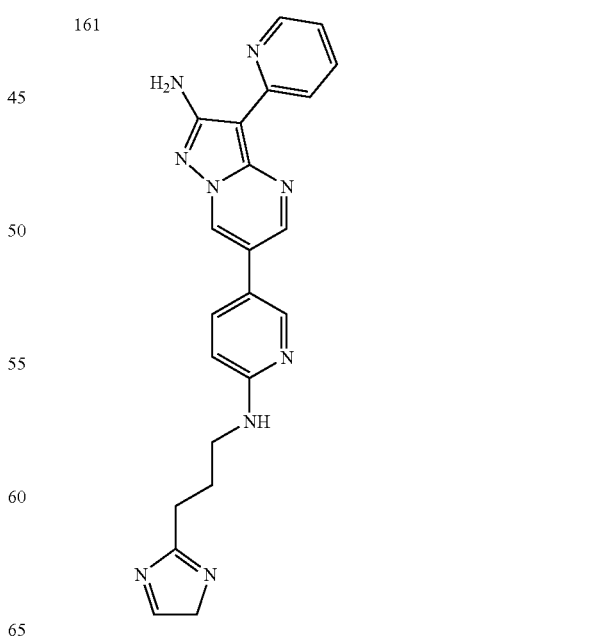 |

TABLE 5-continued
| Cmpd # (V-) | Compound |
|---|---|
| 162 | 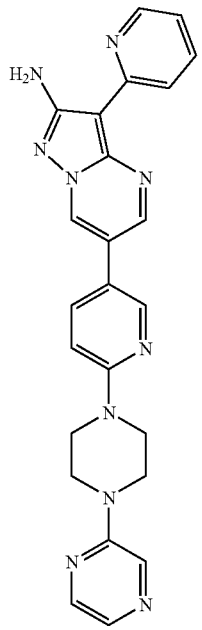 |
| 163 | 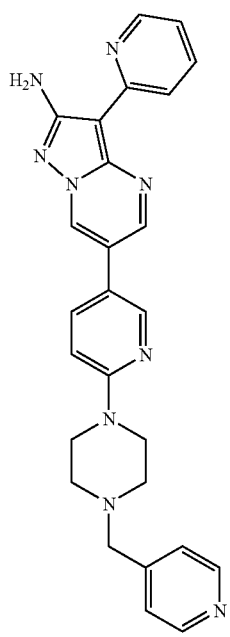 |
TABLE 5-continued
| Cmpd # (V-) | Compound |
|---|---|
| 164 | 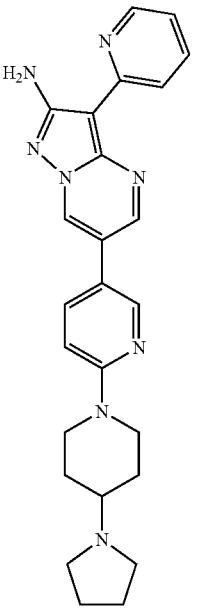 |
| 165 | 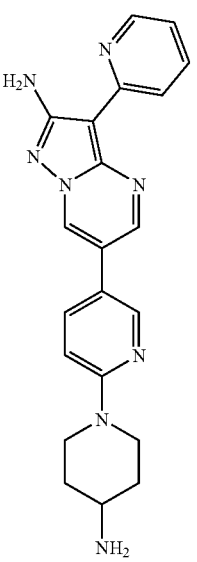 |

TABLE 5-continued
| Cmpd # (V-) | Compound |
|---|---|
| 166 | 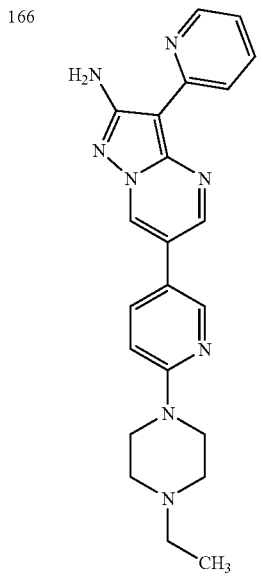 |
| 167 | 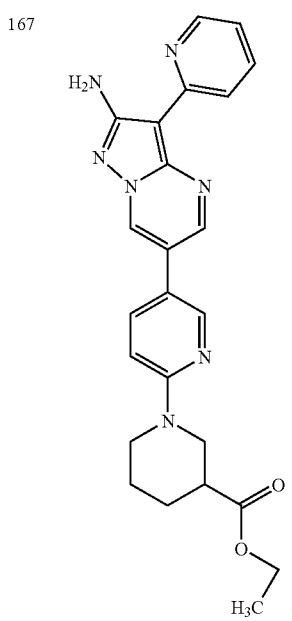 |
| 168 | 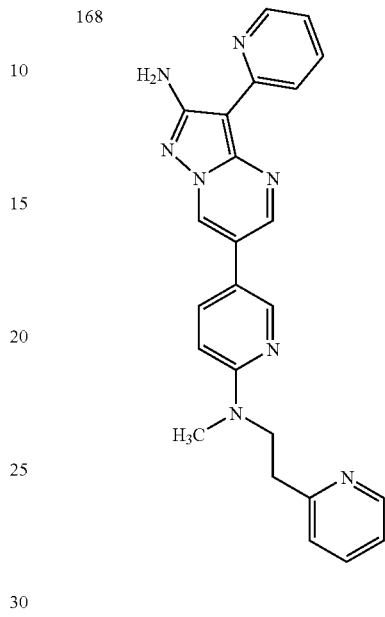 |
| 169 | 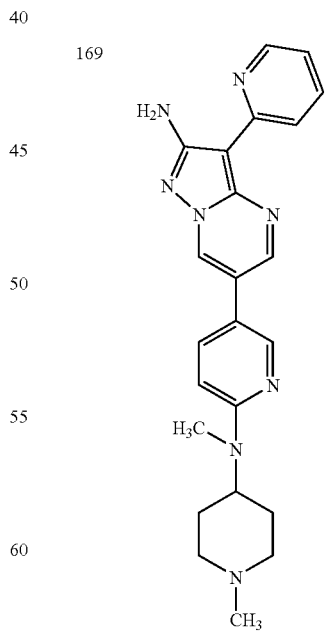 |

TABLE 5-continued
| Cmpd # (V-) | Compound |
|---|---|
| 170 | 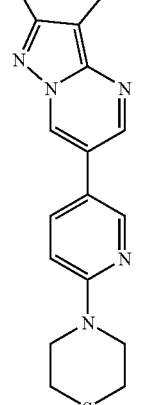 |
| 171 | 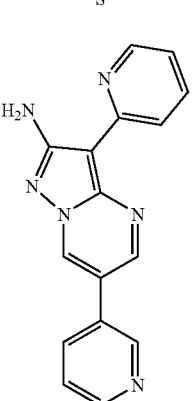 |
| 172 | 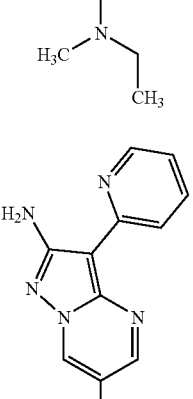 |
| 173 | 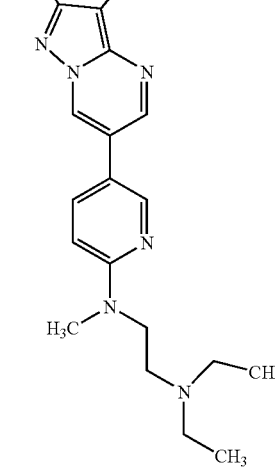 |
| 174 | 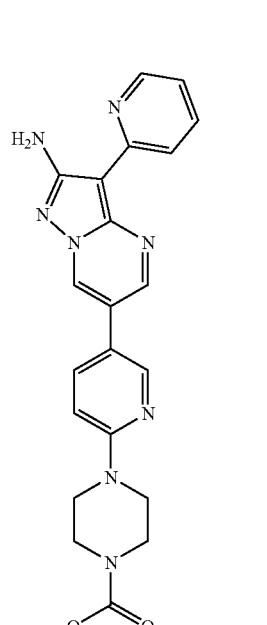 |

TABLE 5-continued
| Cmpd # (V-) | Compound |
|---|---|
| 175 | 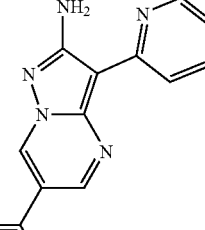 |
| 176 | |
| 177 | |
TABLE 5-continued
| Cmpd # (V-) | Compound |
|---|---|
| 178 | 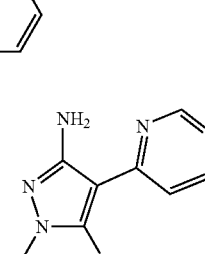 |
| 179 | |
| 180 | |
| 181 | |

TABLE 5-continued
| Cmpd # (V-) | Compound |
|---|---|
| 182 | 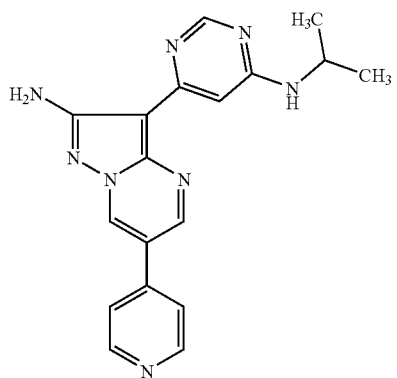 |
| 183 | 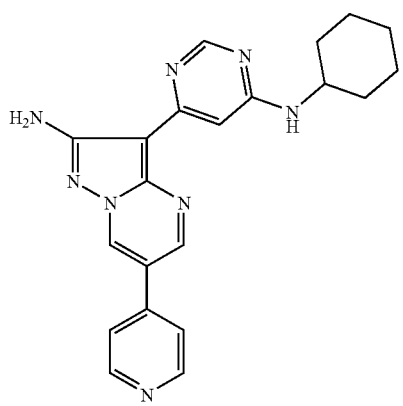 |
| 184 | 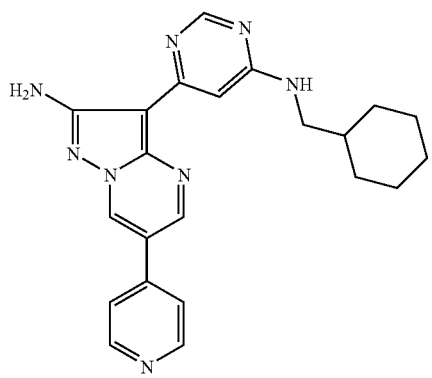 |
| 185 | 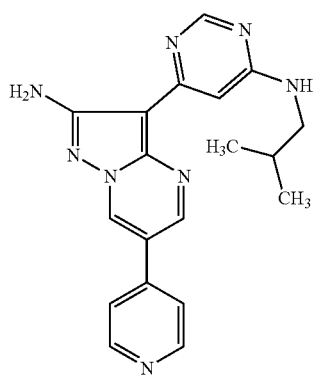 |
TABLE 5-continued
| Cmpd # (V-) | Compound |
|---|---|
| 186 | 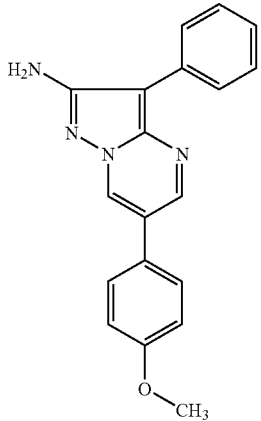 |
| 187 | 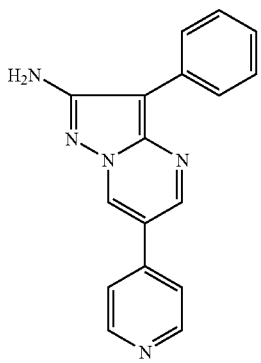 |
| 188 | 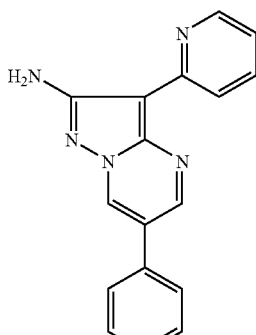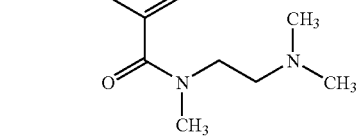 |

TABLE 5-continued
| Cmpd # (V-) | Compound |
|---|---|
| 189 | 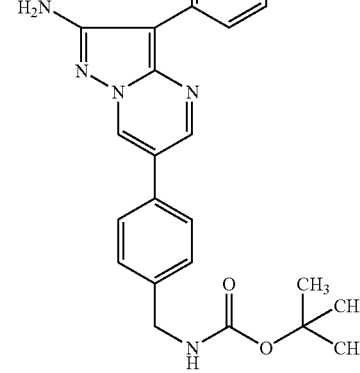 |
| 190 | |
| 191 | |
TABLE 5-continued
| Cmpd # (V-) | Compound |
|---|---|
| 192 | 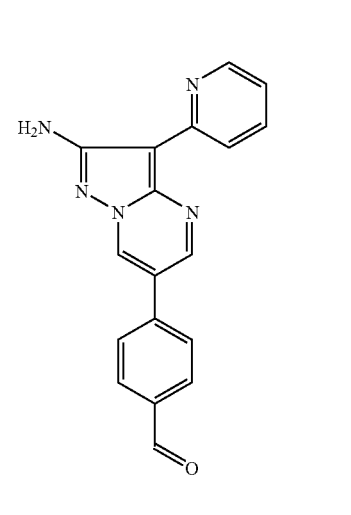 |
| 193 | |
| 194 | |

TABLE 5-continued
Cmpd #
(V-)    Compound
195
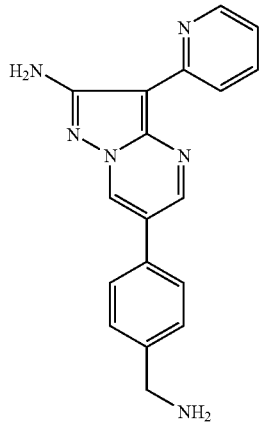
196
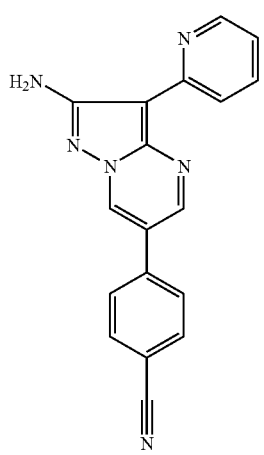
197
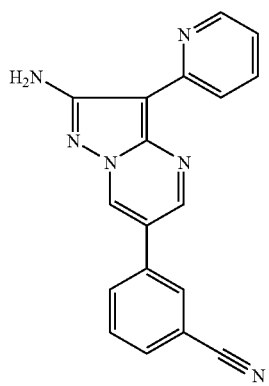
TABLE 5-continued
Cmpd #
(V-)    Compound
198
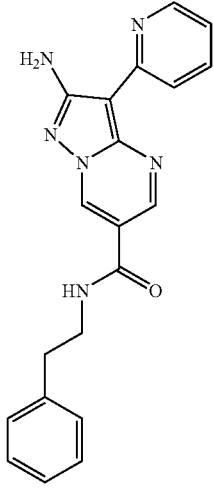
199
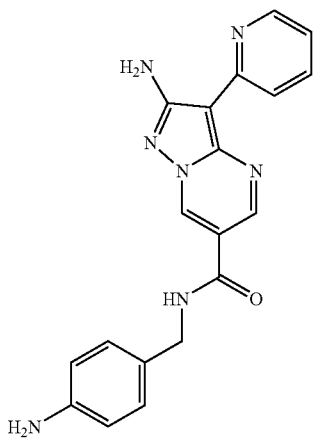
200
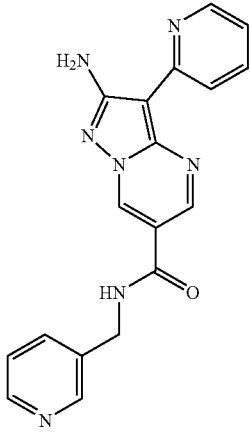

TABLE 5-continued

| Cmpd # (V-) | Compound |
|---|---|
| 201 | [structure: 2-amino-3-(pyridin-2-yl)pyrazolo[1,5-a]pyrimidine-6-carboxamide with N-((1-Boc-piperidin-4-yl)methyl) substituent] |
| 202 | [structure: 2-amino-3-(pyridin-2-yl)-6-(3-(aminomethyl)phenyl)pyrazolo[1,5-a]pyrimidine] |
| 203 | [structure: 2-amino-3-(pyridin-2-yl)-6-(4-(chloromethyl)phenyl)pyrazolo[1,5-a]pyrimidine] |
| 204 | [structure: 2-amino-3-(pyridin-2-yl)pyrazolo[1,5-a]pyrimidine-6-carboxamide with N-methyl substituent] |
| 205 | [structure: 2-amino-3-(pyridin-2-yl)pyrazolo[1,5-a]pyrimidine-6-carboxamide with N-isobutyl substituent] |
| 206 | [structure: 2-amino-3-(pyridin-2-yl)pyrazolo[1,5-a]pyrimidine-6-carboxamide with N-(piperidin-3-yl) substituent] |

TABLE 5-continued
| Cmpd # (V-) | Compound |
|---|---|
| 207 | 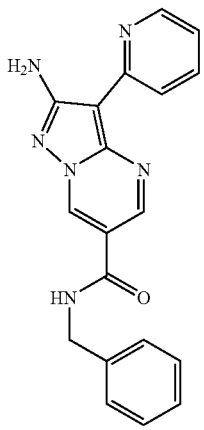 |
| 208 | 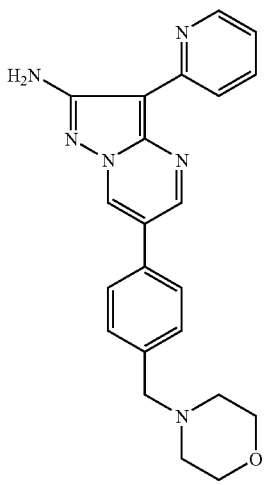 |
| 209 | 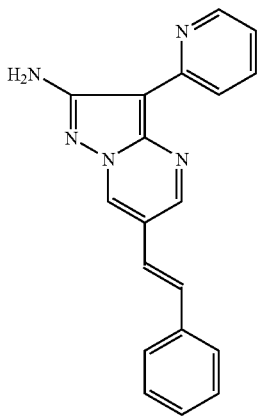 |
| 210 | 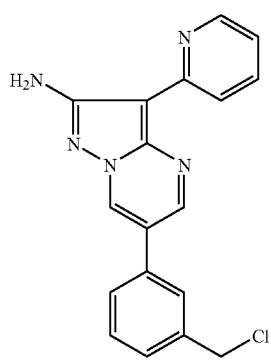 |
| 211 | 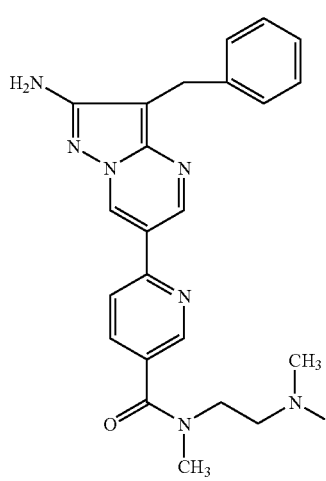 |
| 212 | 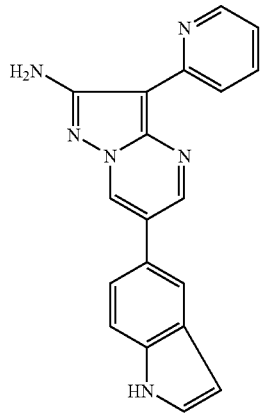 |

TABLE 5-continued
| Cmpd # (V-) | Compound |
|---|---|
| 213 | 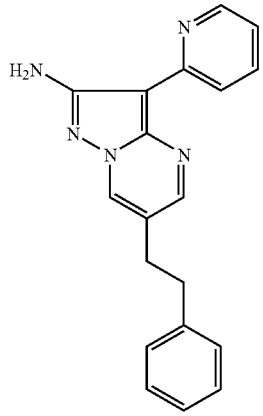 |
| 214 | 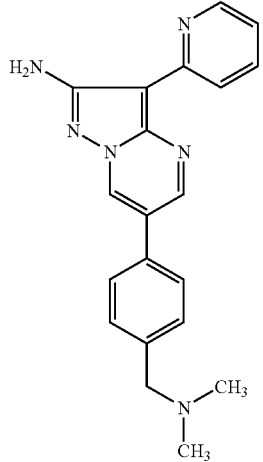 |
| 215 | 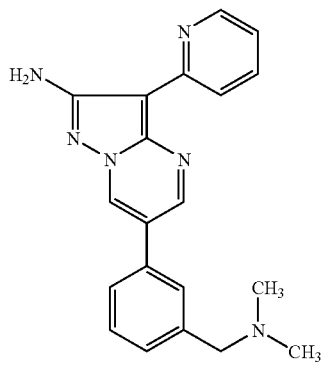 |
| 216 | 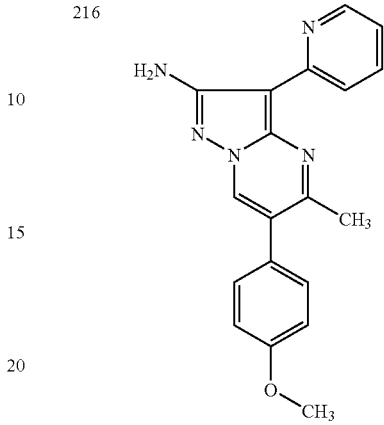 |
| 217 | 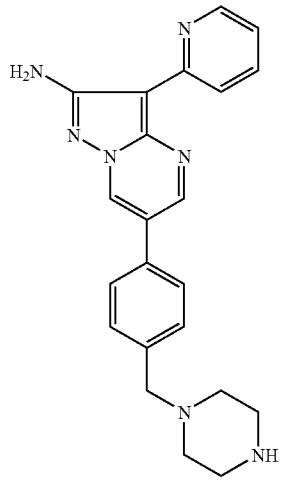 |
| 218 | 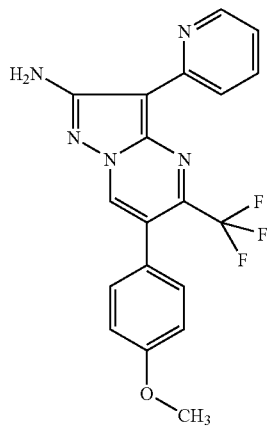 |

TABLE 5-continued
| Cmpd # (V-) | Compound |
|---|---|
| 219 | 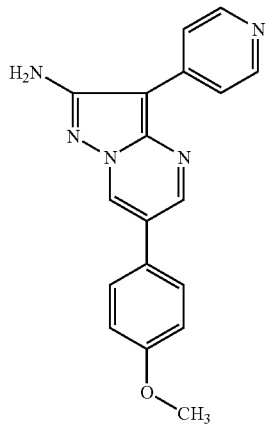 |
| 220 | 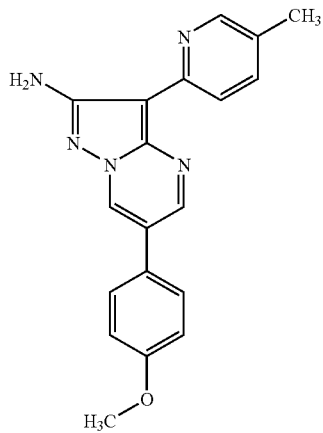 |
| 221 | 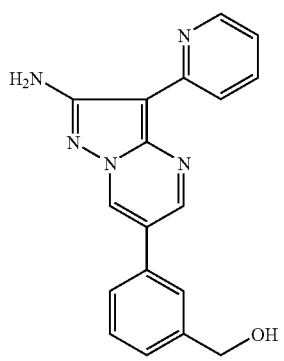 |
TABLE 5-continued
| Cmpd # (V-) | Compound |
|---|---|
| 222 | 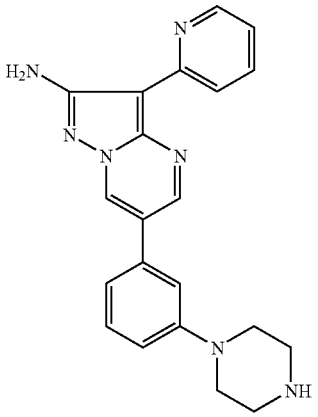 |
| 223 | 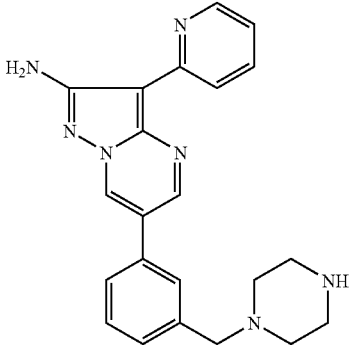 |
| 224 | 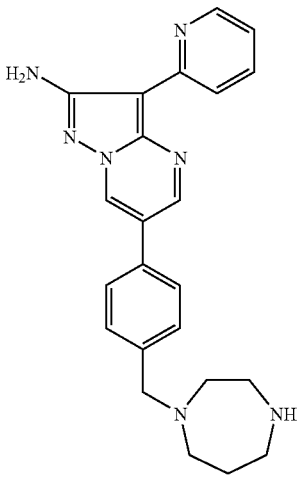 |

US 7,528,138 B2
TABLE 5-continued
| Cmpd # (V-) | Compound |
|---|---|
| 225 | 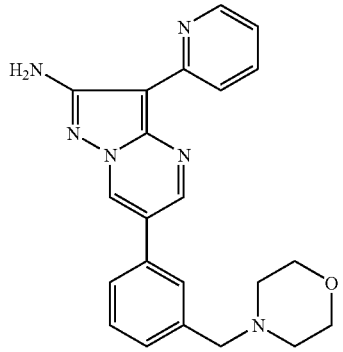 |
| 226 | 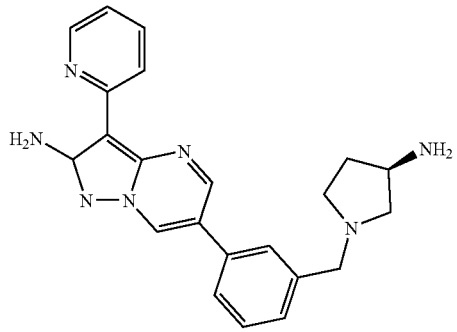 |
| 227 | 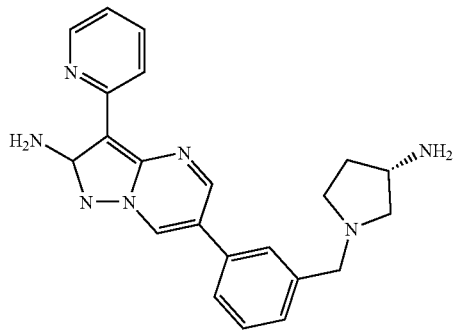 |
| 228 | 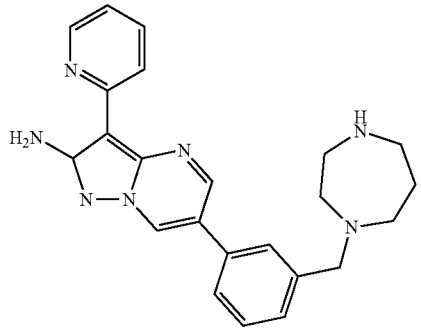 |
TABLE 5-continued
| Cmpd # (V-) | Compound |
|---|---|
| 229 | 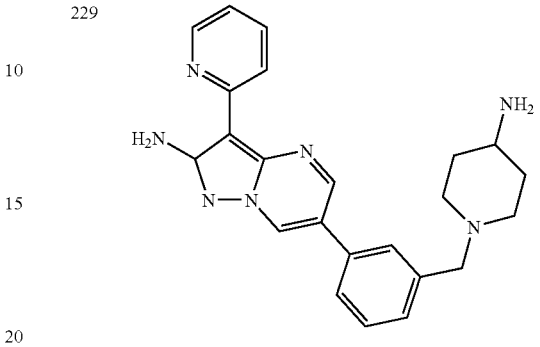 |
| 230 | 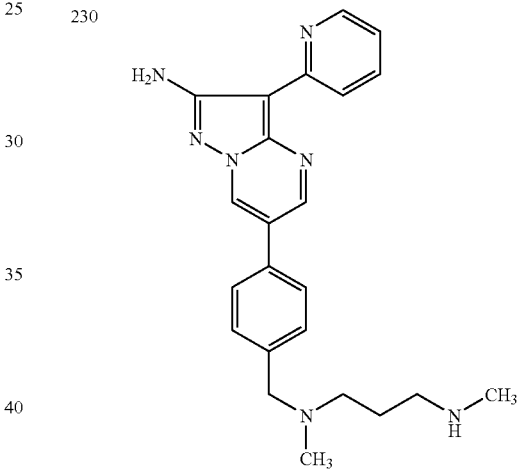 |
| 231 | 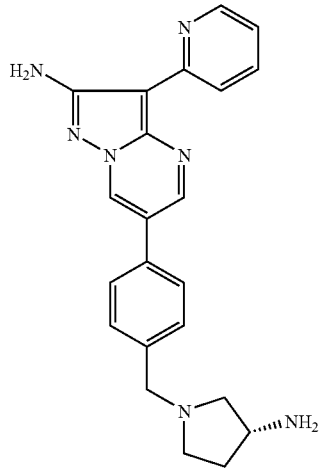 |

TABLE 5-continued
| Cmpd # (V-) | Compound |
|---|---|
| 232 | 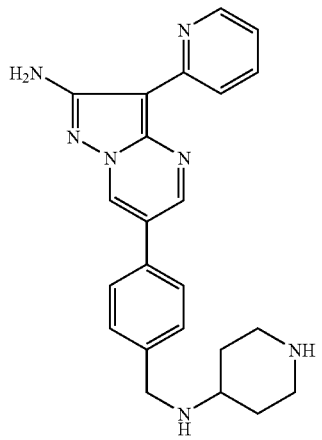 |
| 233 | 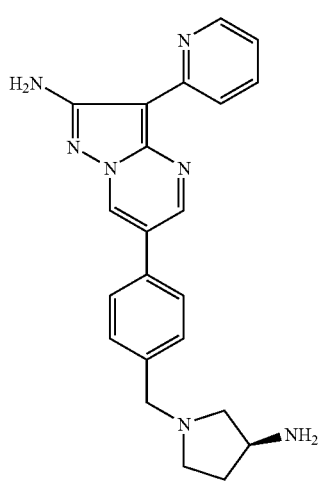 |
| 234 | 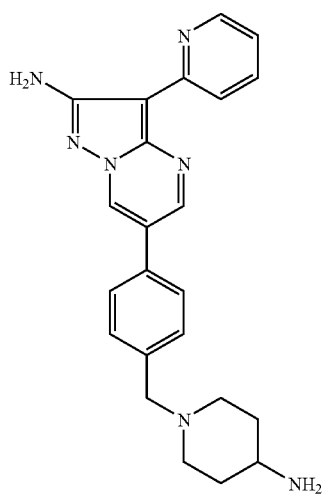 |
| 235 | 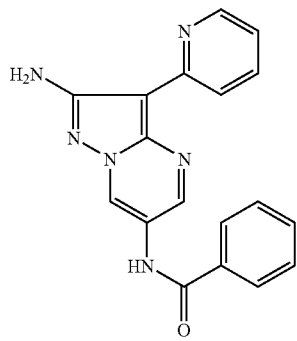 |
| 236 | 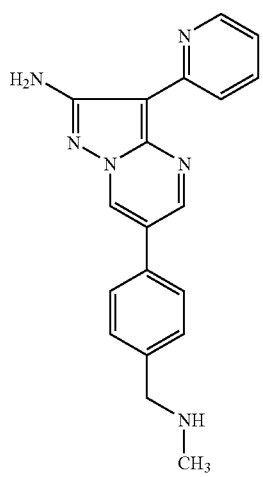 |
| 237 | 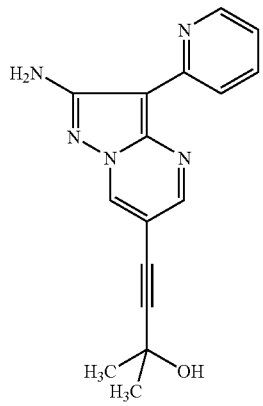 |

TABLE 5-continued
| Cmpd # (V-) | Compound |
|---|---|
| 238 | 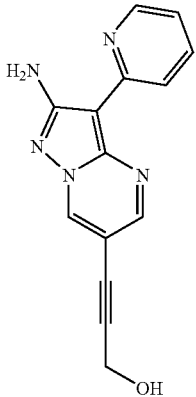 |
| 239 | 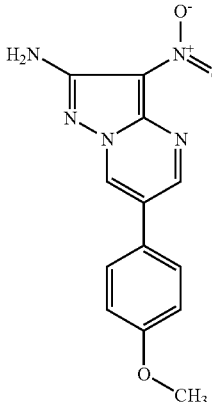 |
| 240 | 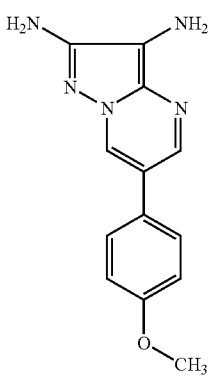 |
| 241 | 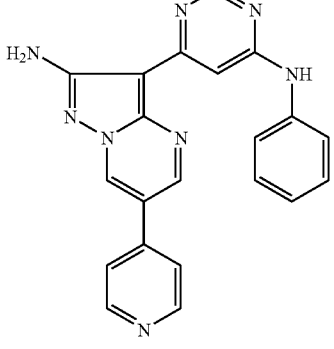 |
| 242 | 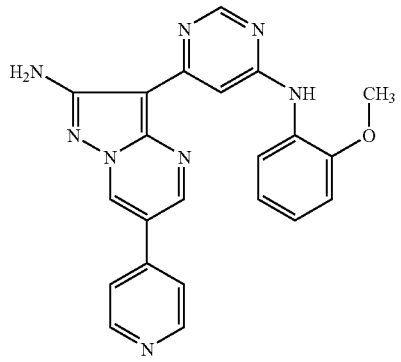 |
| 243 |  |
| 244 | 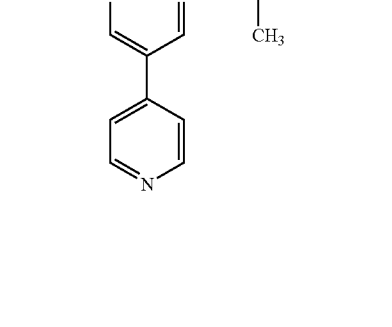 |

TABLE 5-continued
| Cmpd # (V-) | Compound |
|---|---|
| 245 | 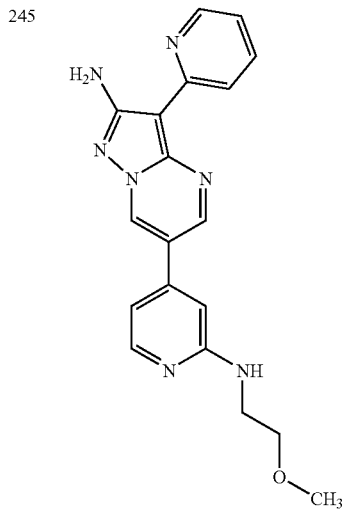 |
| 246 | 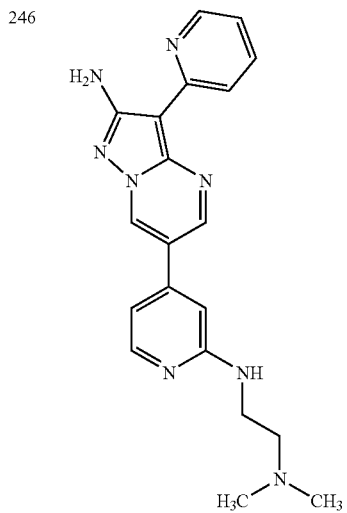 |
| 247 | 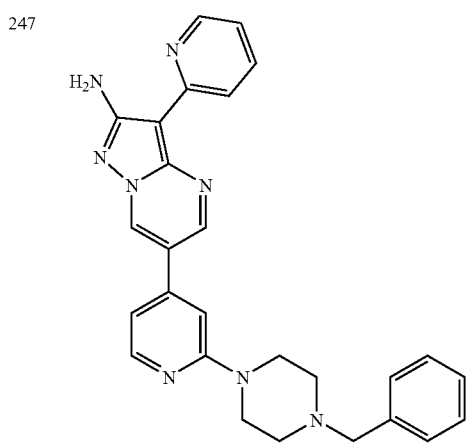 |
TABLE 5-continued
| Cmpd # (V-) | Compound |
|---|---|
| 248 | 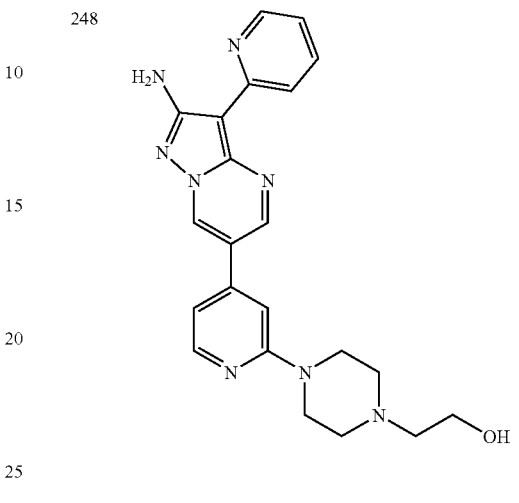 |
| 249 | 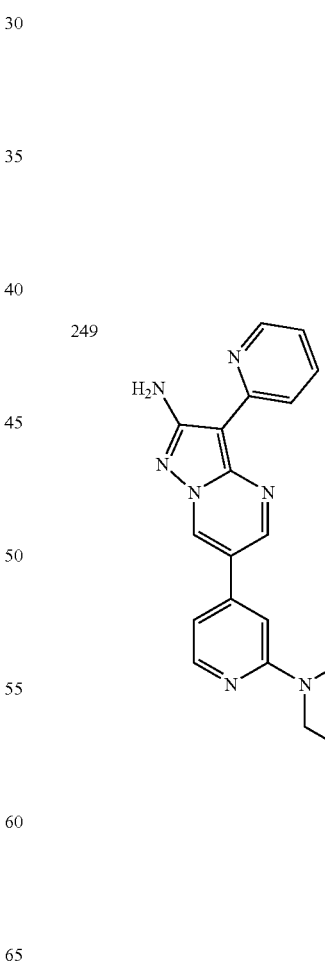 |

TABLE 5-continued
Cmpd #
(V-)  Compound
250
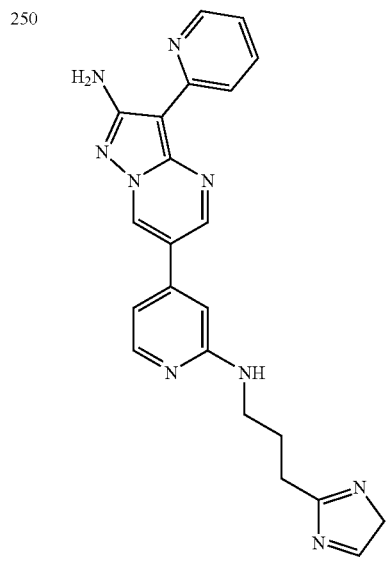
251
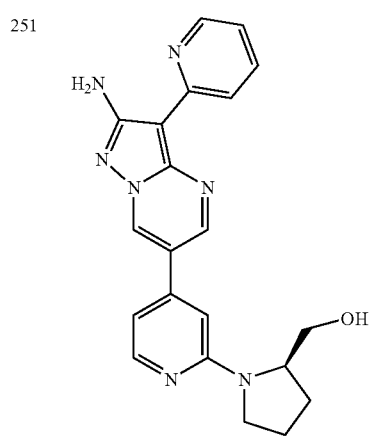
252
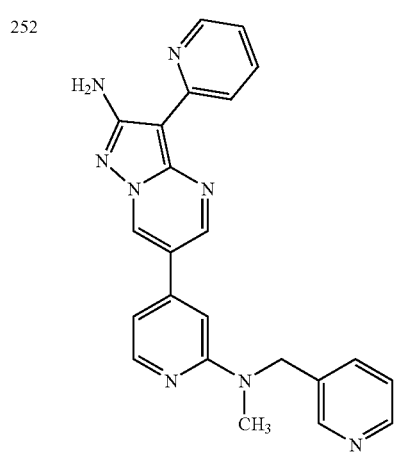
TABLE 5-continued
Cmpd #
(V-)  Compound
253
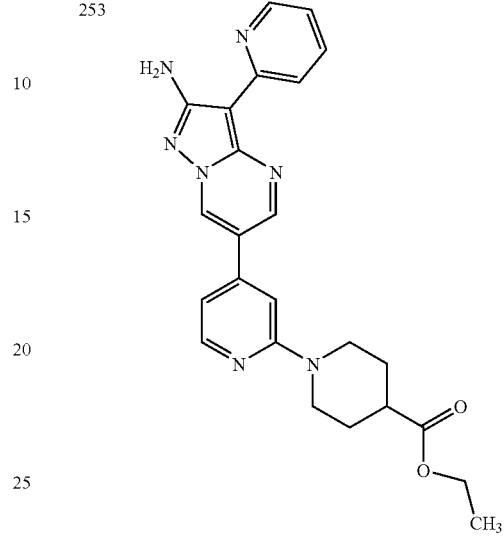
254
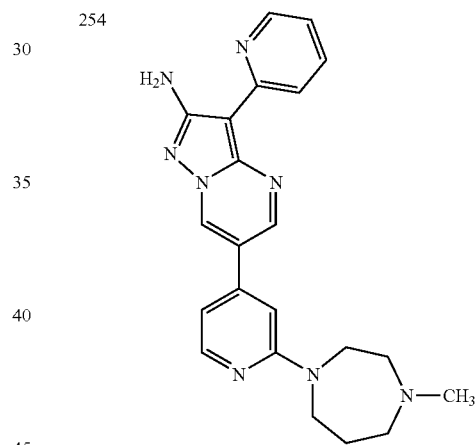
255
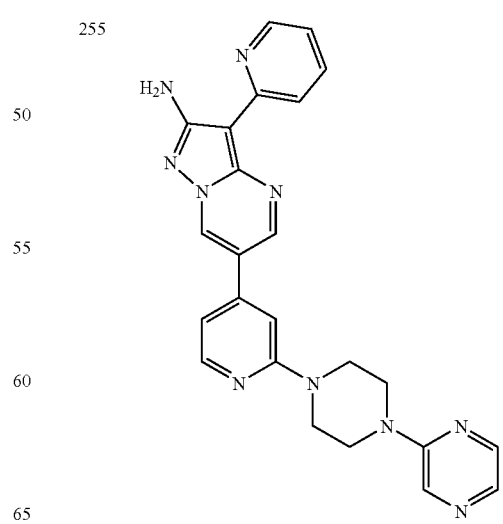

TABLE 5-continued
| Cmpd # (V-) | Compound |
|---|---|
| 256 | 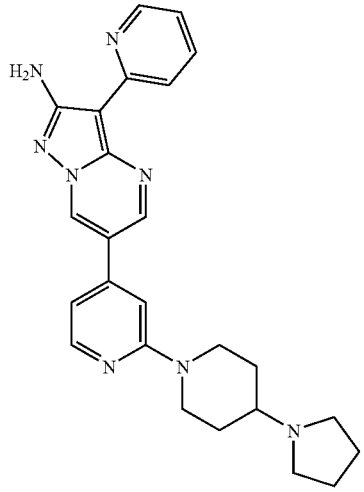 |
| 257 | 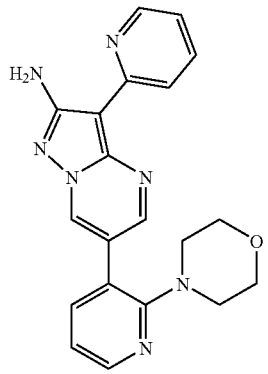 |
| 258 | 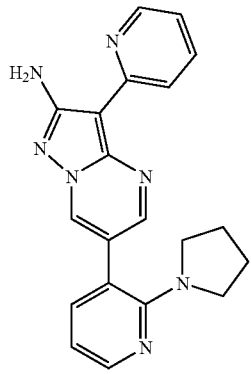 |
TABLE 5-continued
| Cmpd # (V-) | Compound |
|---|---|
| 259 | |
| 260 | |
| 261 | |
| 262 | |

TABLE 5-continued
| Cmpd # (V-) | Compound |
|---|---|
| 263 | 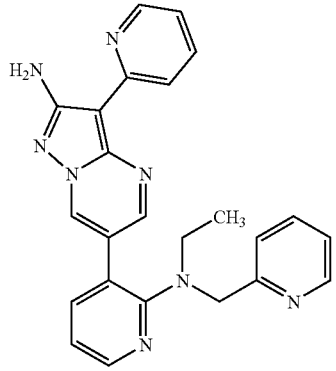 |
| 264 | 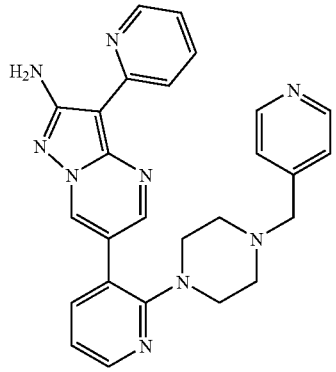 |
| 265 | 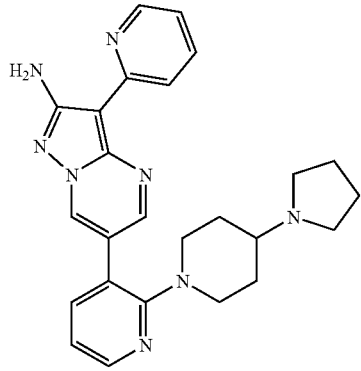 |
| 266 | 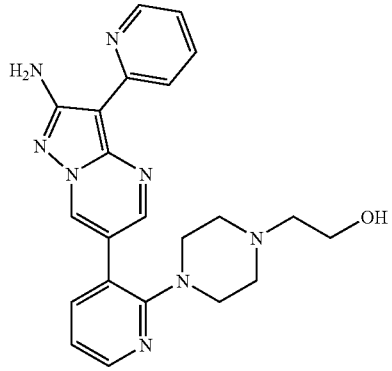 |
| 267 | 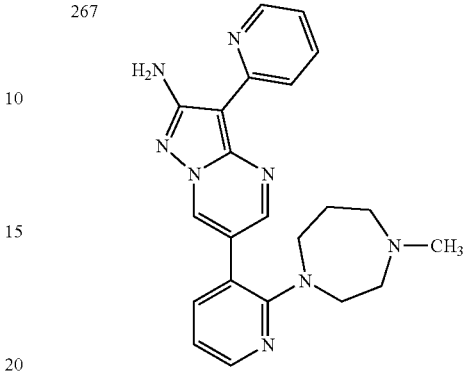 |
| 268 | 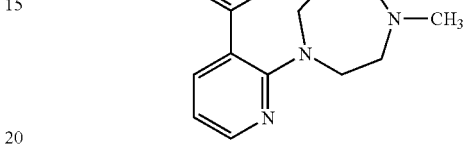 |
| 269 | 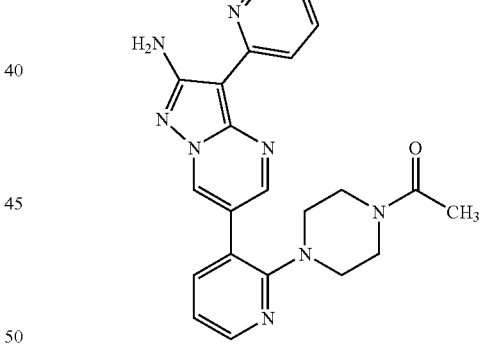 |
| 270 | 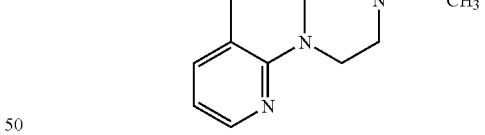 |

TABLE 5-continued
| Cmpd # (V-) | Compound |
|---|---|
| 271 | 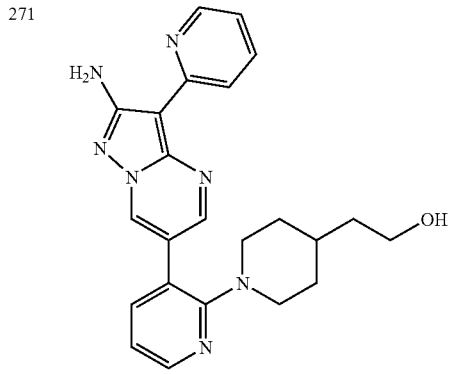 |
| 272 | 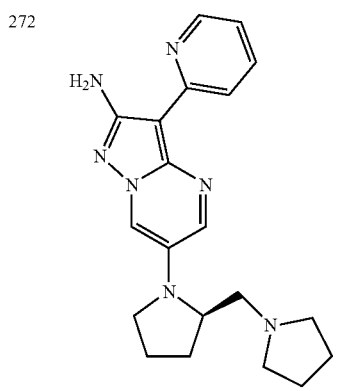 |
| 273 | 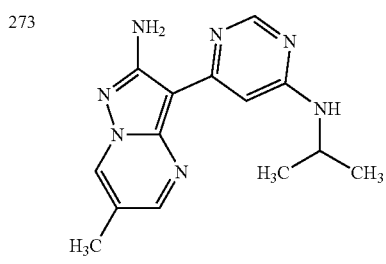 |
| 274 | 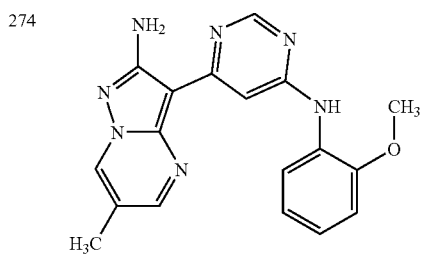 |
| 275 | 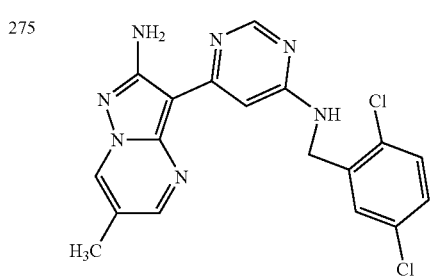 |
| 276 | 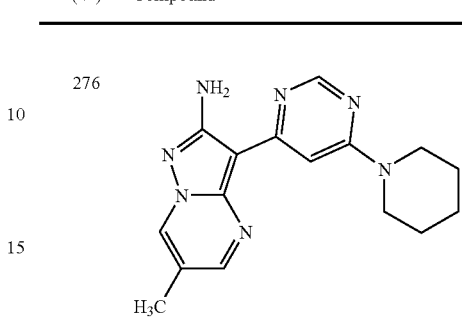 |
| 277 | 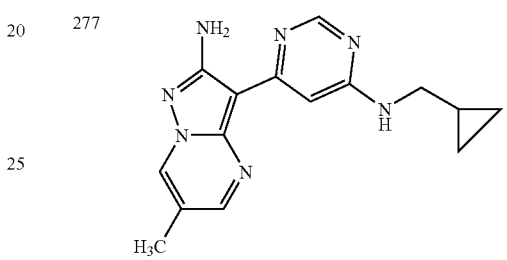 |
| 278 | 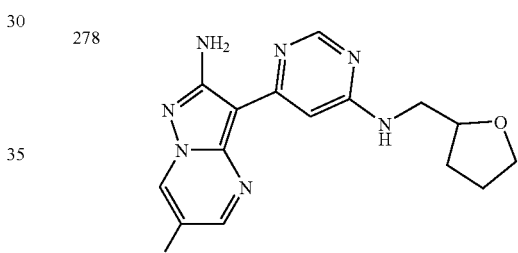 |
| 279 | 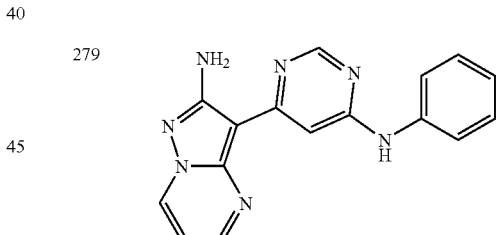 |
| 280 | 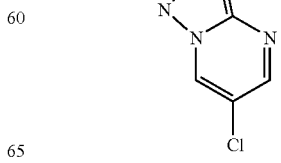 |
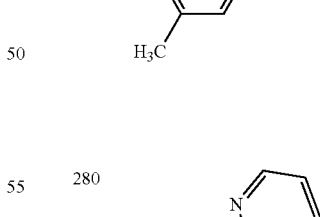

TABLE 5-continued

| Cmpd # (V-) | Compound |
|---|---|
| 281 | [structure] |
| 282 | [structure] |
| 283 | [structure] |
| 284 | [structure] |
| 285 | [structure] |

TABLE 5-continued

| Cmpd # (V-) | Compound |
|---|---|
| 286 | [structure] |
| 287 | [structure] |
| 288 | [structure] |
| 289 | [structure] |
| 290 | [structure] |

TABLE 5-continued

| Cmpd # (V-) | Compound |
|---|---|
| 291 | (structure) |
| 292 | (structure) |
| 293 | (structure) |
| 294 | (structure) |
| 295 | (structure) |
| 296 | (structure) |
| 297 | (structure) |
| 298 | (structure) |
| 299 | (structure) |
| 300 | (structure) |
| 301 | (structure) |

TABLE 5-continued

| Cmpd # (V-) | Compound |
|---|---|
| 302 | [structure] |
| 303 | [structure] |
| 304 | [structure] |
| 305 | [structure] |
| 306 | [structure] |
| 307 | [structure] |
| 308 | [structure] |
| 309 | [structure] |
| 310 | [structure] |

TABLE 5-continued
| Cmpd # (V-) | Compound |
|---|---|
| 311 | 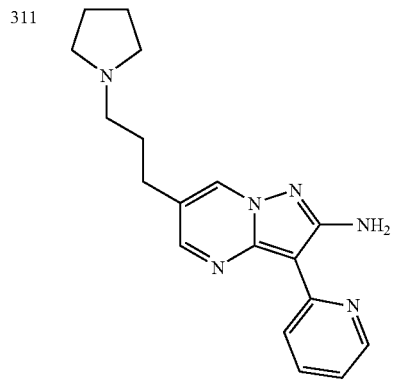 |
| 312 | 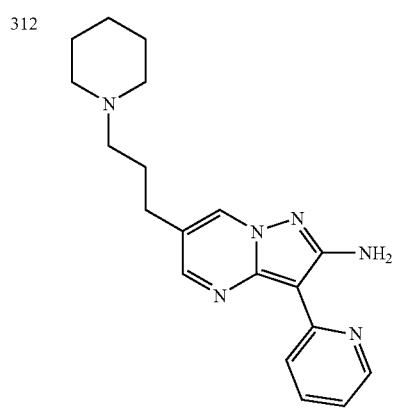 |
| 313 | 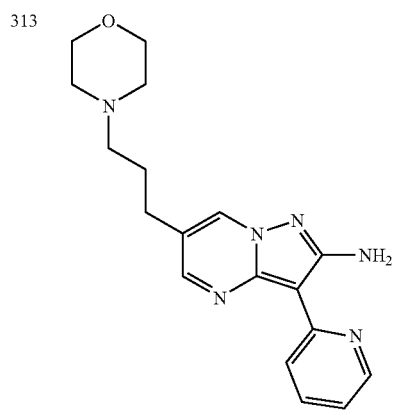 |
| 314 | 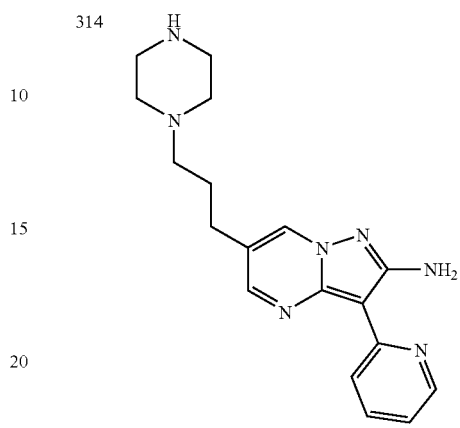 |
| 315 | 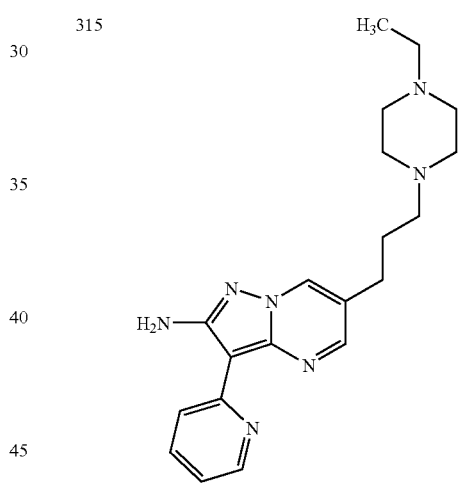 |
| 316 | 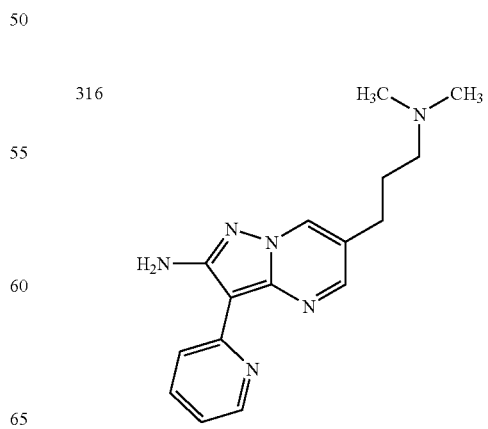 |

TABLE 5-continued
| Cmpd # (V-) | Compound |
| --- | --- |
| 317 | 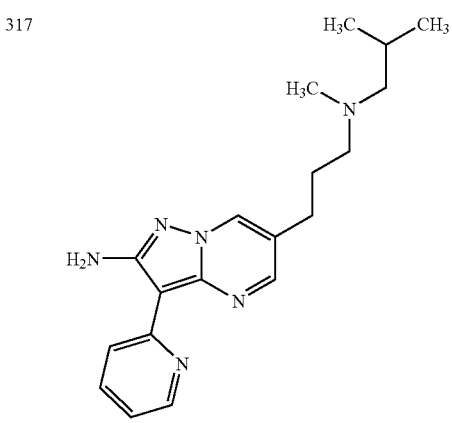 |
| 318 | 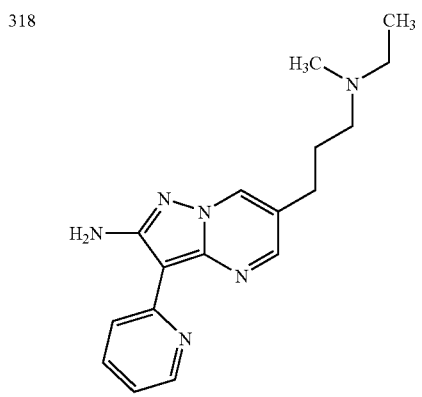 |
| 319 | 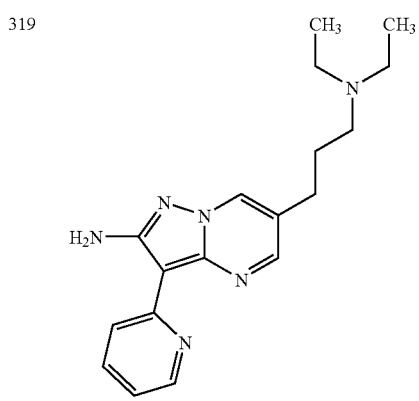 |
| 320 | 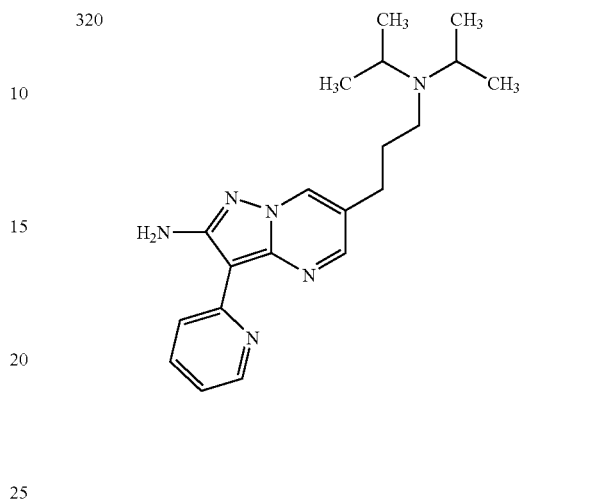 |
| 321 | 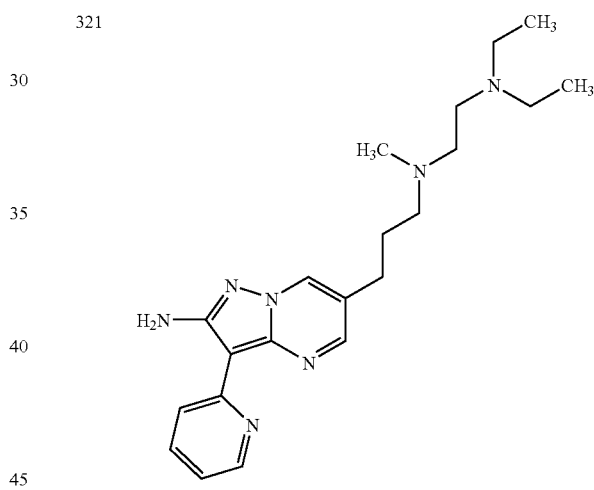 |
| 322 | 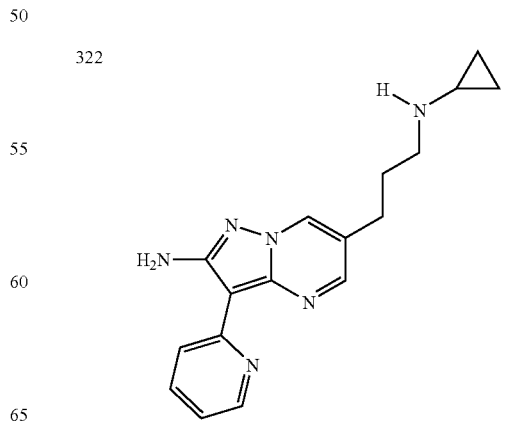 |

TABLE 5-continued
| Cmpd # (V-) | Compound |
|---|---|
| 323 | 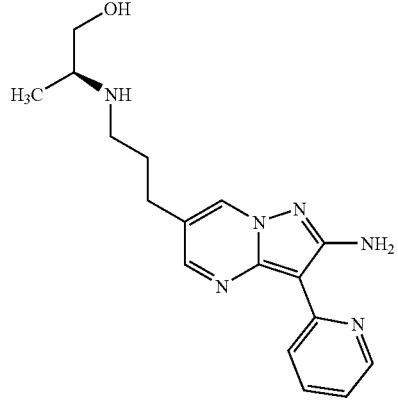 |
| 324 | 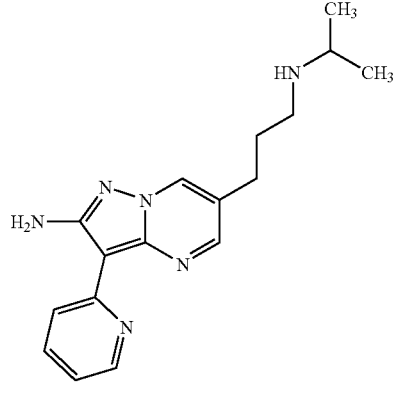 |
| 325 | 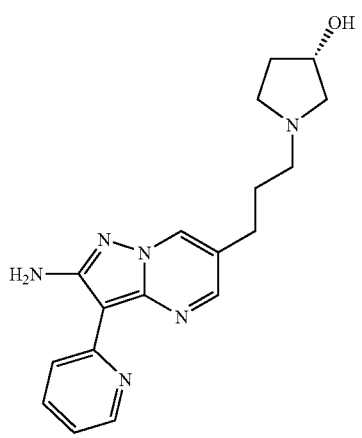 |
| 326 | |
| 327 | |
| 328 | 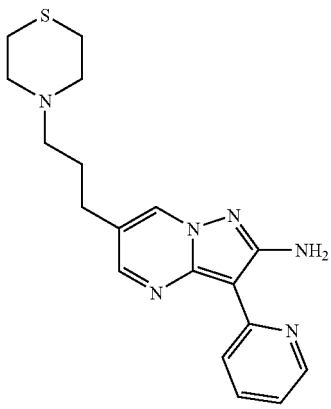 |

TABLE 5-continued

| Cmpd # (V-) | Compound |
|---|---|
| 329 | (structure) |
| 330 | (structure) |
| 331 | (structure) |
| 332 | (structure) |
| 333 | (structure) |
| 334 | (structure) |
| 335 | (structure) |
| 336 | (structure) |

TABLE 5-continued
| Cmpd # (V-) | Compound |
|---|---|
| 337 | |
| 338 | |
| 339 | |
| 340 | |
| 341 | |
| 342 | |
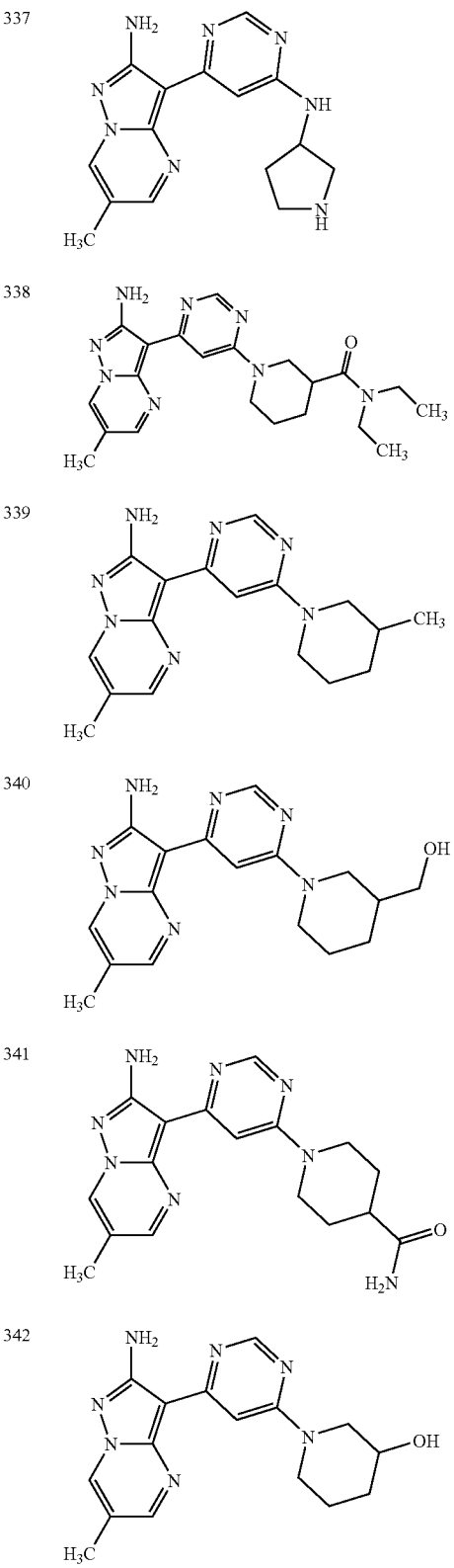
TABLE 5-continued
| Cmpd # (V-) | Compound |
|---|---|
| 343 | |
| 344 | |
| 345 | |
| 346 | |
| 347 | |
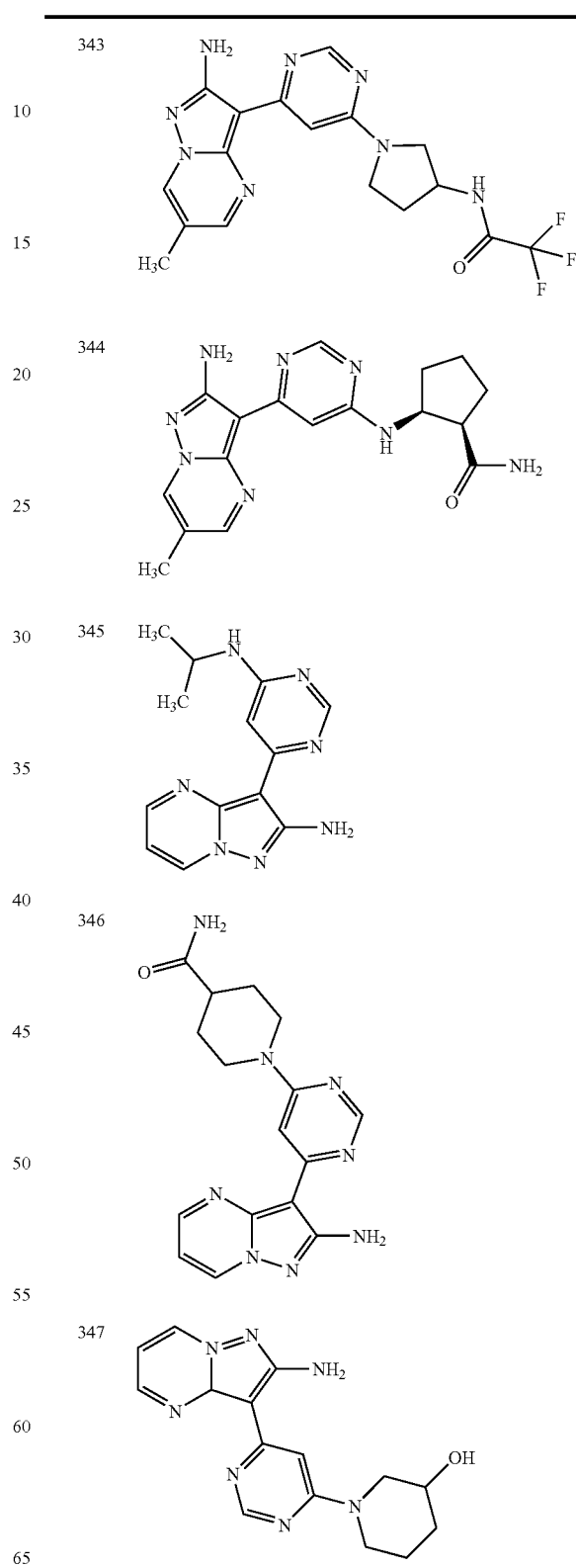

TABLE 5-continued

| Cmpd # (V-) | Compound |
|---|---|
| 348 | (structure) |
| 349 | (structure) |
| 350 | (structure) |
| 351 | (structure) |
| 352 | (structure) |
| 353 | (structure) |

As discussed above, the present invention provides compounds that are inhibitors of protein kinases, and thus the present compounds are useful for the treatment of diseases, disorders, and conditions including, but not limited to an autoimmune, inflammatory, proliferative, or hyperproliferative disease or an immunologically-mediated disease. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a Tec family (e.g., Tec, Btk, Itk/Emt/Tsk, Bmx, Txk/Rlk) protein kinase, an Aurora family kinase or c-Met.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for the treatment or lessening the severity of a Tec family (e.g., Tec, Btk, Itk/Emt/Tsk, Bmx, Txk/Rlk)-mediated disease, an Aurora family-mediated disease or a c-Met-mediated disease, is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for a Tec family (e.g., Tec, Btk, Itk/Emt/Tsk, Bmx, Txk/Rlk)-mediated disease, an Aurora family-mediated disease or a c-Met-mediated disease. The compounds and compositions, according to the method of the present invention, may be administered using any amount and any route of administration effective for treating or lessening the severity of a Tec family (e.g., Tec, Btk, Itk/Emt/Tsk, Bmx, Txk/Rlk)-mediated disease, an Aurora family-mediated disease or a c-Met-mediated disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of a Tec family (e.g., Tec, Btk, Itk/Emt/Tsk, Bmx, Txk/Rlk) kinase, an Aurora family kinase or a c-Met family kinase, and thus, without wishing to be bound by any particular theory, the compounds and compositions are particularly useful for treating or lessening the severity of a disease, condition, or disorder where activation of one or more of a Tec family (e.g., Tec, Btk, Itk/Emt/Tsk, Bmx, Txk/Rlk) kinase, an Aurora family kinase or c-Met is implicated in the disease, condition, or disorder. When activation of Tec family (e.g., Tec, Btk, Itk/Emt/Tsk, Bmx, Txk/Rlk) kinase, an Aurora family kinase or c-Met is implicated in a particular disease, condition, or disorder, the disease, condition, or disorder may also be referred to as a "Tec family (e.g., Tec, Btk, Itk/Emt/Tsk, Bmx, Txk/Rlk)-mediated disease", "an Aurora family-mediated disease" or "a c-Met-mediated disease" or disease symptom. Accordingly, in another aspect, the present invention provides a method for treating or lessening the severity of a disease, condition, or disorder where activation or one or more of Tec family (e.g., Tec, Btk, Itk/Emt/Tsk, Bmx, Txk/Rlk) kinase, an Aurora family kinase or c-Met is implicated in the disease state.

The activity of a compound utilized in this invention as an inhibitor of a Tec family (e.g., Tec, Btk, Itk/Emt/Tsk, Bmx, Txk/Rlk) kinase, an Aurora family kinase or c-Met may be assayed in vitro, in vivo or in a cell line. In vitro assays include assays that determine inhibition of either the phosphorylation activity or ATPase activity of activated Tec family (e.g., Tec, Btk, Itk/Emt/Tsk, Bmx, Txk/Rlk) kinase, an Aurora family kinase or c-Met. Alternate in vitro assays quantitate the ability of the inhibitor to bind to a Tec family (e.g., Tec, Btk, Itk/Emt/Tsk, Bmx, Txk/Rlk) kinase, an Aurora family kinase or c-Met. Inhibitor binding may be measured by radiolabelling the inhibitor prior to binding, isolating the inhibitor/kinase complex and determining the amount of radiolabel bound. Alternatively, inhibitor binding may be determined by running a competition experiment where new inhibitors are incubated with a Tec family (e.g., Tec, Btk, Itk/Emt/Tsk, Bmx, Txk/Rlk) kinase, an Aurora family kinase or c-Met bound to known radioligands.

The term "measurably inhibit", as used herein means a measurable change in kinase activity between a sample comprising a compound of the invention and a kinase of interest and an equivalent sample comprising the kinase in the absence of said compound.

The term "Tec family tyrosine kinases-mediated condition", as used herein means any disease or other deleterious condition in which Tec family kinases are known to play a role. Such conditions include, without limitation, autoimmune, inflammatory, proliferative, and hyperproliferative diseases and immunologically-mediated diseases including rejection of transplanted organs or tissues and Acquired Immunodeficiency Syndrome (AIDS).

For example, Tec family tyrosine kinases-mediated conditions include diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. Additionally, Tec family tyrosine kinases diseases include, without limitation, those conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

Tec family tyrosine kinases-mediated conditions also include diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

Tec family kinases-mediated conditions also include diseases and disorders of the skin, including, without limitation, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, areata and vernal conjunctivitis.

Tec family tyrosine kinases-mediated conditions also include diseases and disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema.

Tec family tyrosine kinases-mediated conditions also include those diseases and disorders of other tissues and systemic disease, including, without limitation, multiple sclerosis, atherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

Tec family tyrosine kinases-mediated conditions also include allograft rejection including, without limitation, acute and chronic allograft rejection following for example transplantation of kidney, heart, liver, lung, bone marrow, skin and cornea; and chronic graft versus host disease.

According to another embodiment, the invention provides methods for treating or preventing an Aurora-mediated condition comprising the step of administering to a patient one of the above-described pharmaceutical compositions.

Preferably, that method is used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease or disorder described above.

According to another embodiment, the invention relates to a method of inhibiting c-Met kinase activity in a biological sample comprising the step of contacting said biological sample with a compound of this invention, or a composition comprising said compound.

According to another embodiment, the invention relates to a method of inhibiting c-Met kinase activity in a patient comprising the step of administering to said patient a compound of the present invention, or a composition comprising said compound.

The term "c-Met-mediated disease" or "c-Met-mediated condition", as used herein, means any disease state or other deleterious condition in which c-Met is known to play a role. The terms "c-Met-mediated disease" or "c-Met-mediated condition" also mean those diseases or conditions that are alleviated by treatment with a c-Met inhibitor. Such conditions include, without limitation, renal, gastric, colon, brain, breast, prostate, and lung cancer, glioblastoma, atherosclerosis, lung fibrosis, conditions associated with organ transplantation, allergic disorders, and autoimmune disorders.

The term "c-Met" is synonymous with "cMet", "MET", "Met" or other designations known to one skilled in the art.

According to one embodiment, the present invention relates to a method of treating or lessening the severity of renal, gastric, colon, brain, breast, prostate, and lung cancer, glioblastoma, atherosclerosis, lung fibrosis, conditions associated with organ transplantation, allergic disorders, or autoimmune disorders in a patient in need thereof, comprising administering to said patient a compound of the present invention or composition thereof.

In an alternative embodiment, the present invention relates to a method of treating or lessening the severity of gastric or brain cancer in a patient in need thereof, comprising administering to said patient a compound of the present invention or composition thereof.

According to another embodiment, the present invention relates to a method of treating or lessening the severity of renal cancer in a patient in need thereof, comprising administering to said patient a compound of the present invention or composition thereof.

According to yet another embodiment, the present invention relates to a method of treating or lessening the severity of gastric cancer in a patient in need thereof, comprising administering to said patient a compound of the present invention or composition thereof.

Another aspect of the present invention relates to a method of inhibiting tumor metastasis in a patient in need thereof, comprising administering to said patient a compound of the present invention or composition thereof.

The term "biological sample", as used herein, means a sample outside a living organism, and includes, without limitation, cell cultures or extracts thereof; biopsied material obtained from a mammal or extracts thereof; and blood, saliva, urine, feces, semen, tears, or other body fluids or extracts thereof.

Inhibition of protein kinase, e.g., inhibition of c-Met, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound. Said protein kinases include, but are not limited to, the protein kinases listed above.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anticonvulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

EXAMPLES

As used herein, The term "Rt(min)" refers to the HPLC retention time, in minutes, associated with the compound. Unless otherwise indicated, the HPLC method utilized to obtain the reported retention time is as follows:

Column: Ace 5 C8, 15 cm×4.6 mm id

Gradient: 0-100% acetonitrile+methanol (50:50) (20 mM Tris phosphate at pH 7.0)

Flow rate: 1.5 ml/min

Detection: 225 nm

Example 1

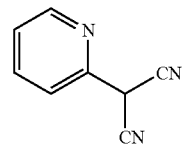

2-Pyridin-2-yl-malononitrile

To diisopropylamine (15.3 mL, 109 mmol) in toluene (500 mL), at 0-5° C., under nitrogen, was added drop wise over ~½ hour 1.6M" BuLi/THF (68.5 mL, 109 mmol). The reaction mixture was stirred for a further 15 minutes before the drop wise addition of 2-pyridylacetonitrile (5.55 mL, 49.6 mmol) over 1 hour. 2-Chlorobenzylthiocyanate (20.0 g, 109 mmol), described in the literature by Schlesinger *J. Am. Chem. Soc.* 1954, 76, 585, was then added in solution in toluene (100 mL) over a period of 1 hour. The reaction mixture was stirred for an additional 2 hours. Water was added and the layers were separated. The organic phase was extracted twice with 200 mL 2N NaOH. The combined aqueous phases were cooled down to 0° C and acidified to ~pH 1. The precipitate obtained was filtered and dried to give the title compound as a pale tan solid (4.50 g, 63% yield). δH (DMSO-$d_6$) 6.79 (1H, t), 7.09 (1H, d), 7.73 (1H, t), 7.79 (1H, dd), 12.95 (1H, br s).

Example 2

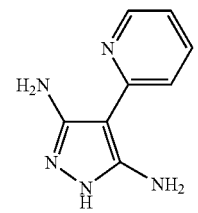

4-Pyridin-2-yl-1H-pyrazole-3,5-diamine

A mixture of 2-pyridin-2-yl-malononitrile (0.65 g, 4.59 mmol) and hydrazine hydrate (225 μL, 4.59 mmol) in EtOH (5 mL) was heated to reflux and stirred for 16 hours. The reaction mixture was cooled down to room temperature and filtered. The resulting solid was washed with $Et_2O$ to provide the title compound as a light tan solid (0.42 g, 52%). The filtrate was evaporated to dryness and purified by silica gel chromatography eluting with $NH_4OH$:MeOH:$CH_2Cl_2$ (0.5: 5:95) to give a further 63.3 mg (8%) of the desired product. MS (ES$^+$) 176, (ES$^-$) 174. δH (DMSO-$d_6$) 5.45 (4H, br s), 6.98 (1H, t), 7.57 (1H, d), 7.69 (1H, t), 8.46 (1H, d), 10.55 (1H, br s).

Example 3

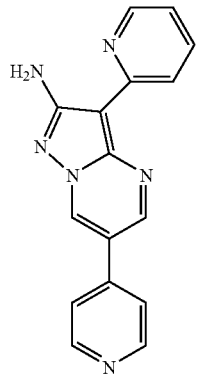

3-Pyridin-2-yl-6-pyridin-4-yl-pyrazolo[1,5-a]pyrimidin-2-ylamine I-1

A mixture of 4-pyridin-2-yl-1H-pyrazole-3,5-diamine (290 mg, 1.66 mmol) and 2-pyridin-4-yl-malonaldehyde (247 mg, 1.66 mmol) were placed in ethanol (5 mL) with a catalytic amount of acetic acid (6 drops). The reaction mixture was submitted to microwave irradiations at 140° C. for 15 minutes. The crude mixture was cooled down to room temperature and the resulting precipitate was filtered and washed with more ethanol to provide the title as a golden yellow solid (295 mg, 62%). MS (ES$^+$) 289, (ES$^-$) 287. δH (DMSO-d$_6$) 7.16 (1H, dd), 7.21 (2H, m), 7.84 (1H, m), 7.89 (2H, m), 8.57 (2H, br m), 8.65 (2H, d), 8.98 (1H, d), 9.44(1H, d).

A variety of other compounds have been prepared by methods substantially similar to those described herein Example 3. The characterization data for some of these compounds are summarized in Table 4 below and include HPLC, LC/MS (observed) and $^1$H NMR data.

$^1$H NMR data is summarized in Table 6 below wherein $^1$H NMR data was obtained at 400 MHz in deuterated DMSO, unless otherwise indicated, and was found to be consistent with structure. Compound numbers correspond to the compound numbers listed in Table 1.

TABLE 6

Characterization Data for Selected Compounds

| Cmpd # (I-) | M+1(obs) | Rt(min) | $^1$H-NMR |
|---|---|---|---|
| 2 | 318 | 9.68 | 3.81(3H, s), 7.07(4H, m), 7.12(1H, m), 7.75(2H, d), 7.84(1H, t), 8.54(1H, m), 8.58(1H, m) 8.82(1H, d) 9.15(1H, d) |
| 3 | 366 | / | (500MHz) 7.14(m, 3H), 7.46(t, 1H), 7.60(dd, 1H), 7.85(m, 2H), 8.06(m, 1H), 8.56(m, 2H), 8.86(d, 1H), 9.27(d, 1H) |
| 4 | 318 | / | (500MHz) 3.86(s, 3H), 6.97(m, 1H), 7.09(s, 2H), 7.13(m, 1H), 7.39(m, 3H), 7.84(m, 1H), 8.55(m, 1H), 8.58(d, 1H), 8.86(d, 1H), 9.23(d, 1H) |
| 5 | 302 | 10.12 | 2.40(3H, s), 7.15(3H, m), 7.35(2H, d), 7.75(2H, d), 7.90(1H, t), 8.60(2H, m), 8.90(1H, s), 9.20(1H, d) |
| 6 | 411 | 8.74 | 3.45(3H, s), 7.20(1H, m), 7.25(2H, s), 7.90(1H, t), 8.15(1H, d), 8.35(1H, d), 8.50(1H, s), 8.55(2H, m), 8.70(1H, s), 9.20(1H, d) |

TABLE 6-continued

Characterization Data for Selected Compounds

| Cmpd # (I-) | M+1(obs) | Rt(min) | $^1$H-NMR |
|---|---|---|---|
| 7 | 289 | 8.76 | 7.20(3H, m), 7.45(1H, m), 7.90(1H, t), 8.00(1H, t), 8.15(1H, d), 8.60(2H, m), 8.70(1H, m), 9.20(1H, s), 9.45(1H, s) |
| 8 | 290 | 8.29 | 7.20(1H, m), 7.35(2H, s), 7.90(1H, t), 8.20(1H, d), 8.60(2H, m), 8.90(1H, d), 9.25(2H, dd), 9.65(1H, s) |
| 9 | 290 | 8.44 | 7.20(1H, m), 7.30(2H, s), 7.95(1H, t), 8.70(3H, m), 8.80(1H, s), 9.30(1H, s), 9.45(1H, s), 9.60(1H, s) |
| 10 | 333 | 6.64 | 7.15(1H, m), 7.25(2H, s), 7.95(1H, t), 8.05(1H, d), 8.15(1H, t), 8.40(1H, d), 8.60(2H, m), 9.30(1H, s), 9.80(1H, s) |
| 11 | 333 | 6.65 | 7.15(1H, m), 7.25(2H, d), 7.90(1H, t), 8.25(1H, d), 8.35(1H, d), 8.60(2H, m), 9.15(1H, s), 9.25(1H, s), 9.55(1H, s) |
| 12 | 360 | 8.34 | 3.10(6H, s), 7.15(1H, m), 7.20(1H, d), 7.55(1H, d), 7.90(1H, t), 8.05(1H, t), 8.20(1H, d), 8.60(2H, m), 9.20(1H, s), 9.45(1H, s) |
| 13 | 402 | 8.26 | 3.60(4H, m), 3.75(4H, m), 7.15(1H, m), 7.20(1H, d), 7.60(1H, d), 7.90(1H, t), 8.00(1H, t), 8.20(1H, d), 8.60(2H, m), 9.20(1H, s), 9.45(1H, s) |
| 14 | 360 | 8.08 | 3.05(6H, s), 7.15(1H, m), 7.25(2H, s), 7.55(1H, d), 7.90(1H, t), 8.00(1H, d), 8.20(1H, d), 8.60(2H, m), 8.75(1H, s), 9.25(1H, s), 9.50(1H, s) |
| 15 | 402 | 8.06 | 3.65(8H, m), 7.15(1H, m), 7.25(2H, s), 7.90(1H, t), 8.00(1H, d), 8.20(1H, d), 8.60(2H, m), 8.75(1H, s), 9.20(1H, s), 9.50(1H, s) |
| 16 | 403 | 7.78 | 2.20(6H, s), 2.45(2H, m), 3.50(2H, m), 7.15(1H, m), 7.25(2H, s), 7.50(1H, t), 8.00(1H, d), 8.10(1H, t), 8.30(1H, d), 8.60(2H, m), 9.15(1H, s), 9.45(1H, s), 9.90(1H, s) |
| 17 | 401 | 7.27 | 2.80(4H, m), 3.40(2H, m), 3.60(2H, m), 7.15(1H, m), 7.20(2H, m), 7.50(1H, d), 7.85(1H, t), 8.05(1H, t), 8.20(1H, d), 8.60(2H, m), 9.20(1H, s), 9.45(1H, s) |
| 18 | 401 | 7.22 | 3.30(8H, m), 7.15(1H, m), 7.20(2H, br s), 7.90(1H, t), 8.10(1H, dd), 8.25(1H, d), 8.65(2H, m), 8.80(1H, s), 9.30(1H, s), 9.55(1H, s) |
| 19 | 417 | 7.62 | 2.00(3H, s), 2.20(3H, s), 2.40(2H, m), 3.00(3H, s), 3.60(2H, m), 7.15(1H, m), 7.25(2H, s), 7.90(2H, m), 8.15(1H, m), 8.55(2H, m), 8.70(1H, m), 9.20(1H, s), 9.50(1H, s) |
| 20 | 322 | / | (500MHz) 7.11(s, 2H), 7.14(m, 1H), 7.56(d, 2H), 7.83(m, 1H), 7.86(d, 2H), 8.55(m, 1H), 8.57(d, 1H), 8.85(d, 1H), 9.24(d, 1H) |
| 21 | 340 | / | (500MHz) 7.18(m, 1H), 7.28(s, 2H), 7.85(m, 1H), 7.89(m, 2H), 8.15(m, 2H), 8.59(m, 1H), 8.63(d, 1H), 9.40(d, 1H), 9.69(s, 1H), 9.78(s, 1H) |
| 22 | 417 | / | (500MHz) 3.25(m, 2H), 3.55(m, 2H), 3.62(m, 2H), 3.8(br, 2H), 4.05(be, 2H), 4.43(m, 2H), 7.16(m, 3H), 7.80(d, 2H), 7.85(t, 1H), 8.56(m, 2H), 8.83(d, 1H), 9.16(d, 1H) |
| 23 | 331 | 9.14 | 3.79(3H, s), 3.97(2H, s), 5.72(2H, s), 7.02–7.04(2H, m), 7.13(1H, m), 7.21–7.25(2H, m), 7.30–7.32(2H, m), 7.66(2H, d), 8.55(1H, s), 8.95(1H, s) |
| 24 | 302 | 8.17 | 3.96(2H, s), 5.89(2H, s), 7.15(1H, m), 7.22–7.25(2H, m), 7.31–7.32(3H, m), 7.90(1H, t), 8.00(1H, m), 8.65(1H, d), 8.97(1H, s), 9.25(1H, s) |
| 25 | 302 | 7.87 | 3.95(2H, s), 5.94(2H, s), 7.13(1H, m), 7.21–7.25(2H, m), 7.30–7.32(2H, m), 7.81(2H, d), 8.60(2H, m), 8.73(1H, s), 9.23(1H, s) |

Example 4

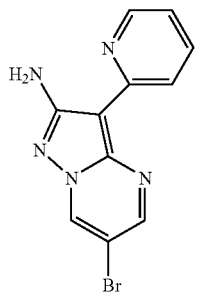

6-Bromo-3-pyridin-2-yl-pyrazolo[1,5-a]pyrimidin-2-ylamine II-2

4-(Pyridin-2-yl)-1H-pyrazole-3,5-diamine (2.54 g, 14.51 mmol) and 2-bromo-malonaldehyde (2.41 g, 15.97 mmol) were suspended in dry ethanol (35 mL). A small amount of glacial acetic acid (30 drops) was added and the mixture was heated at reflux for 3 hours. After allowing the reaction to cool to room temperature the mixture was concentrated under reduced pressure. The resulting solid was purified by silica gel chromatography eluting with EtOAc containing 2% NH$_3$ (aq) solution to afford the title compound as a yellow solid (0.82 g, 19% yield). MS (ES$^+$) 290/292. δH (DMSO-d$_6$) 7.2 (3H, m), 7.9 (1H, t), 8.5 (1H, d), 8.6 (2H, m), 9.3 (1H, s).

Example 5

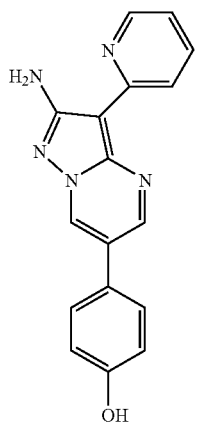

4-(2-Amino-3-pyridin-2-yl-pyrazolo[1,5-a]pyrimidin-6-yl)-phenol II-6

6-Bromo-3-pyridin-2-yl-pyrazolo[1,5-a]pyrimidin-2-ylamine (50 mg, 0.17 mmol) and 4-hydroxyphenylboronic acid (48 mg, 0.35 mmol) were suspended in dry DMF (1.4 ml). Aqueous 2M Na$_2$CO$_3$ (0.346 mL, 0.69 mmol) was added and the reaction mixture was degassed. [1,1-Bis(diphenylphosphino)ferrocene]dichloropalladium(II) complex in dichloromethane (1:1 ratio, 8 mg, 0.010 mmol) was added and the mixture was heated in a microwave at 120° C. for 20 minutes. After allowing the reaction to cool down to room temperature, the mixture was concentrated under reduced pressure. The resulting solid was purified by silica gel chromatography eluting with EtOAc to afford the title compound as a yellow solid (35 mg, 67% yield). MS (ES$^+$) 304. δH (DMSO-d$_6$) 6.8 (1H, d), 7.1 (3H, m), 7.2 (1H, d), 7.3 (1H, t), 7.9 (1H, t), 8.6 (2H, m), 8.8 (1H, s), 9.2 (1H, s), 9.7 (1H, s).

A variety of other compounds have been prepared by methods substantially similar to those described herein Example 5. The characterization data for some of these compounds are summarized in Table 5 below and include HPLC, LC/MS (observed) and $^1$H NMR data.

$^1$H NMR data is summarized in Table 7 below wherein $^1$H NMR data was obtained at 400 MHz in deuterated DMSO, unless otherwise indicated, and was found to be consistent with structure. Compound numbers correspond to the compound numbers listed in Table 2.

TABLE 7

Characterization Data for Selected Compounds

| Cmpd # (II-) | M+1(obs) | Rt(min) | $^1$H-NMR |
|---|---|---|---|
| 1 | 288 | 9.72 | 7.15(3H, m), 7.90(2H, m), 7.40(1H, t), 7.50(2H, m) 7.85(3H, m), 8.55(2H, m), 8.90(1H, s), 9.25(1H, s) |
| 3 | 322 | 10.14 | 7.15(3H, m), 7.50(1H, m), 7.65(1H, m) 7.90(1H, t), 8.60(3H, m), 9.05(1H, s) |
| 4 | 359 | 8.63 | 3.05(6H, m), 7.15(3H, m), 7.55(1H, d), 7.90(3H, m), 8.60(2H, m), 8.90(1H, s), 9.30(1H, s) |
| 5 | 401 | 8.06 | 2.40(4H, m), 3.20(4H, m), 7.15(2H, t), 7.70(1H, d), 7.90(3H, m), 8.60(2H, m), 8.85(2H, m), 8.90(1H, s), 9.30(1H, s) |
| 7 | 303 | 8.75 | 5.25(2H, s), 6.60(1H, d), 6.90(2H, m), 7.10(4H, m), 7.85(1H, t), 8.55(2H, m), 8.75(1H, s), 9.05(1H, s) |
| 8 | 402 | 8.60 | 2.20(6H, s), 2.45(2H, m), 3.40(2H, m), 7.15(3H, m), 7.85(1H, t), 7.95(4H, m), 8.60(3H, m), 8.95(1H, s), 9.30(1H, s) |
| 9 | 416 | 8.71 | 2.00(3H, m), 2.25(3H, m), 2.40(2H, m), 3.00(4H, m), 3.55(1H, m), 7.15(3H, m), 7.50(2H, d), 7.90(3H, m), 8.60(3H, m), 8.90(1H, s), 9.30(1H, s) |

Example 6

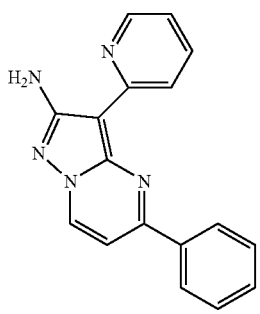

5-Phenyl-3-pyridin-2-yl-6,7-dihydro-pyrazolo[1,5-a]pyrimidin-2-ylamine

6-Bromo-3-pyridin-2-yl-pyrazolo[1,5-a]pyrimidin-2-ylamine (0.52 g, 3.01 mmol) and 3-dimethylamino-1-phenylpropan-1-one hydrochloride (0.64 g, 3.01 mmol) were suspended in dry DMF (10 mL). The mixture was heated at 160° C. for 3 hours with stirring. After allowing the reaction to cool down to room temperature, the mixture was poured into cold water. The resulting precipitate was filtered and dried to afford the title compound as a yellow solid (0.79 g, 93% yield). MS (ES⁺) 290. δH (DMSO-d₆) 3.3 (2H, m), 4.1 (2H, m), 6.1 (2H, s), 7.2 (1H, m), 7.7 (4H, m), 7.9 (1H, t), 8.2 (1H, m), 8.4 (1H, d), 8.6 (1H, d).

Example 7

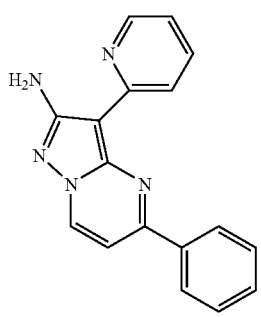

5-Phenyl-3-pyridin-2-yl-pyrazolo[1,5-a]pyrimidin-2-ylamine III-1 5-Phenyl-3-pyridin-2-yl-6,7-dihydro-pyrazolo[1,5-a]pyrimidin-2-ylamine (0.297 g, 1.03 mmol) and 2,3-dichloro-5,6-dicyano-1,4-benzoquinone (0.256 g, 1.13 mmol) were suspended in dry 1,4-dioxane (10 mL). The mixture was heated at 110° C. for 90 minutes. After allowing the reaction to cool to room temperature the mixture was concentrated under reduced pressure. The resulting solid was partitioned between ethyl acetate and 2M aqueous Na₂CO₃ solution. The organic layer was washed with further portions of 2M aqueous Na₂CO₃ solution (2×20 mL), H₂O (1×20), dried over Na₂SO₄, and filtered Purification by silica gel chromatography eluting with EtOAc/petroleum ether (1/1) afford the title compound as a yellow solid (0.15 g, 51% yield). MS (ES⁺) 288. δH (DMSO-d₆) 7.1 (3H, m), 7.6 (4H, m), 8.0 (1H, s), 8.4 (2H, d), 8.6 (1H, m), 8.8 (1H, d), 9.0 (1H, d).

A variety of other compounds have been prepared by methods substantially similar to those described herein Example 7. The characterization data for some of these compounds are summarized in Table 6 below and include HPLC, LC/MS (observed) and ¹H NMR data.

¹H NMR data is summarized in Table 8 below wherein ¹H NMR data was obtained at 400 MHz in deuterated DMSO, unless otherwise indicated, and was found to be consistent with structure. Compound numbers correspond to the compound numbers listed in Table 3.

TABLE 8

Characterization Data for Selected Compounds

| Cmpd # (III-) | M+1(obs) | Rt(min) | ¹H-NMR |
|---|---|---|---|
| 2 | 318 | 9.82 | 3.90(3H, s), 7.05(2H, m), 7.20(3H, m), 7.50(1H, d), 7.95(1H, t), 8.30(2H, d), 8.60(1H, m), 8.80(1H, d), 8.90(1H, d) |

Example 8

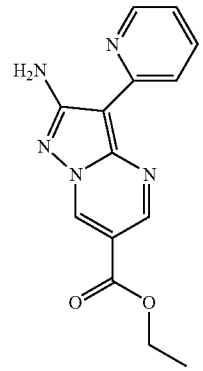

2-Amino-3-pyridin-2-yl-pyrazolo[1,5-a]pyrimidine-6-carboxylic acid ethyl ester IV-1

A mixture of 4-(pyridin-2-yl)-1H-pyrazole-3,5-diamine (0.10 g, 0.57 mmol), (ethoxycarbonyl)malondialdehyde (0.084 g, 0.57 mmol) and 2 drops acetic acid in 1-propanol (3 mL) was heated in the microwave for 15 min at 180° C. with stirring. The reaction was cooled down to room temperature and filtered, washing with ethanol and vacuum dried at 60° C. for 3 days to provide the title compound as a brown solid (0.098 g, 61 % yield). MS (ES⁺) 284. δH (500 Mhz, DMSO-d₆) 1.35 (3H, t), 4.36 (2H, q), 7.19 (1H, m), 7.36 (2H, s), 7.87 (1H, dt), 8.58 (2H, m), 8.82 (1H, d), 9.18 (1H, d).

Example 9

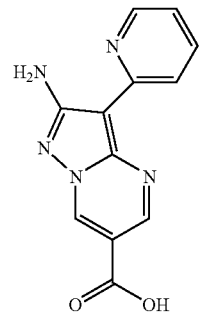

2-Amino-3-pyridin-2-yl-pyrazolo[1,5-a]pyrimidine-6-carboxylic acid IV-3

A solution of 2-amino-3-pyridin-2-yl-pyrazolo[1,5-a]pyrimidine-6-carboxylic acid ethyl ester (1.58 g, 5.58 mmol) and potassium hydroxide (0.95 g, 16.7 mmol) in ethanol (30 mL) was refluxed for 3 h, then cooled down to room temperature. The precipitate was filtered off, washed with ether, suspended in ether, treated with 2M HCl/Et2O (15 mL, 30 mmol), stirred 0.5 h, and filtered, washing with ether to provide an HCl salt of the title compound as a brown solid (0.88 g, 54% yield). MS (ES⁺) 256. δH (500 Mhz, DMSO-d₆) 7.25 (1H, m), 7.94 (1H, t), 8.56 (1H, d), 8.60 (1H, d), 8.83 (1H, d), 9.16 (1H, d).

Example 10

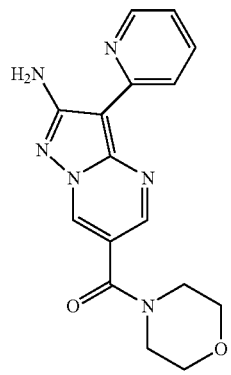

(2-Amino-3-pyridin-2-yl-pyrazolo[1,5-]pyrimidin-6-yl)morpholin-4-yl-methanone (IV-12)

A mixture of 2-amino-3-pyridin-2-yl-pyrazolo[1,5-a]pyrimidine-6-carboxylic acid (0.06 g, 0.20 mmol), morpholine (0.02 mL, 0.25 mmol) and HBTU (0.09 g, 0.25 mmol) in tetrahydrofuran (5 mL) was stirred at room temperature under nitrogen for 24 hours. The precipitate was filtered off and purified by silica gel chromatography eluting with NH₄OH: methanol:dichloromethane (0.5:5:95) to provide the title compound (0.02 g, 35% yield). ). MS (ES⁺) 325. δH (500 Mhz, DMSO-d₆) 3.63 (8H, m), 7.17 (3H, m), 7.85 (1H, m), 8.52 (1H, s), 8.56 (2H, m), 8.99 (1H, s).

A variety of other compounds have been prepared by methods substantially similar to those described herein. The characterization data for some of these compounds are summarized in Table 7 below and include HPLC, LC/MS (observed) and ¹H NMR data.

¹H NMR data is summarized in Table 9 below wherein ¹H NMR data was obtained at 500 MHz in deuterated DMSO, unless otherwise indicated, and was found to be consistent with structure. Compound numbers correspond to the compound numbers listed in Table 5.

TABLE 9

Characterization Data for Selected Compounds

| Cmpd # (IV-) | M+1(obs) | Rt(min) | ¹H-NMR |
|---|---|---|---|
| 2 | 366 | / | (500MHz) 1.70(6H, m), 2.50(6H, m), 3.34(2H, m), 7.16(1H, m), 7.23(2H, s), 7.86(1H, dt), 8.56(2H, m), 8.61(1H, t), 8.84(1H, d), 9.19(1H, d) |
| 4 | 382 | / | (500MHz) 1.71(2H, m), 2.35(6H, m), 3.33(2H, m), 3.58(4H, m), 7.16(1H, m), 7.23(2H, s), 7.86(1H, dt), 8.56(3H, m), 8.85(1H, d), 9.20(1H, d) |
| 5 | 366 | / | (500MHz) 1.49(2H, m), 1.67(2H, m), 1.92(1H, m), 1.98(1H, m), 2.15(2H, m), 2.29(3H, m), 3.00(1H, m), 3.34(2H, m), 7.16(1H, m), 7.23(2H, s), 7.86(1H, dt), 8.57(3H, m), 8.84(1H, d), 9.19(1H, d) |
| 6 | 368 | / | (500MHz) 1.2(6H, m), 2.50(4H, m), 3.12(5H, m), 3.75(2H, m), 7.18(3H, m), 7.85(1H, m), 8.56(3H, m), 9.05(1H, m) |
| 7 | 326 | / | (500MHz) 2.26(3H, br s), 2.70(2H, m), 3.05(3H, br s), 3.49(2H, m), 7.16(3H, m), 7.84(1H, dt), 8.54(4H, m), 9.10(1H, m) |
| 8 | 352 | / | (500MHz) 1.07(2H, m), 1.65(3H, m), 2.46(2H, m), 2.97(2H, m), 3.17(2H, m), 7.16, (1H, m), 7.23(2H, s), 7.86(1H, dt), 8.56(3H, m), 8.86(1H, d), 9.23(1H, d) |
| 9 | 340 | / | (500MHz) 1.72(2H, m), 2.24(6H, s), 2.41(2H, t), 3.33(2H, m), 7.17(1H, m), 7.23(2H, s), 7.86(1H, dt), 8.56(2H, m), 8.60(1H, t), 8.84(1H, d), 9.20(1H, d) |
| 10 | 395 | / | (500MHz) 1.70(2H, m), 2.17(3H, s), 2.36(10H, m), 3.33(2H, m), 7.16(1H, m), 7.23(2H, s), 7.56(1H, dt), 8.56(3H, m), 8.84(1H, d), 9.20(1H, d) |
| 11 | 338 | / | (500MHz) 2.21(3H, s), 2.36(4H, m), 3.59(4H, m), 7.16(3H, m), 7.84(1H, dt), 8.50(1H, d), 8.55(2H, m), 8.96(1H, d) |
| 13 | 295 | / | (500MHz,) 0.60(2H, m), 0.74(2H, m), 2.86(1H, m), 7.16(1H, m), 7.23(2H, s), 7.85(1H, dt), 8.55(3H, m), 8.82(1H, d), 9.18(1H, d) |

Example 11

Synthesis of Compounds According to Scheme VII

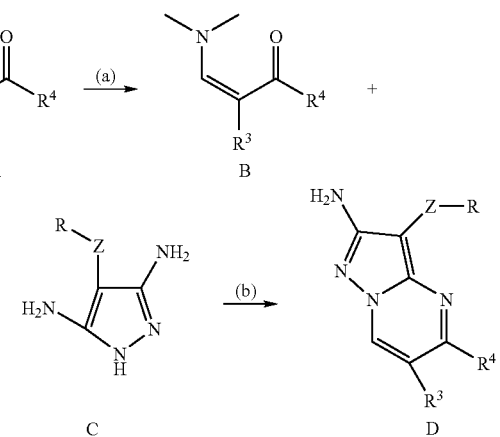

Reagents and conditions: (a) DMF-DMA, 85° C., 16 hours; (b) EtOH, AcOH, microwave irradiation, 120° C., 30 minutes.

Scheme VII above shows another general synthetic route that has been used for preparing compounds D of this invention when Z, R, R³ and R⁴ are as described herein. Intermediate B is prepared according to Scheme VII step (a) from Compound A. Pyrazolo[1,5-a]pyrimidines (D) are prepared by microwave assisted cyclization of diamino-pyrazoles C with enaminones B.

Exemplary compounds prepared according to the general methods described in Schemes VI and VII are shown below:

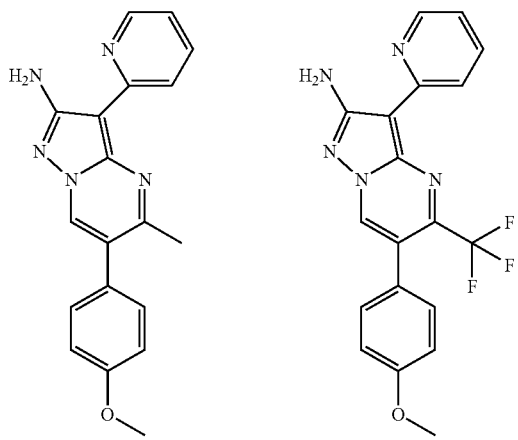

Example 12

Synthesis of 6-methyl-3-(6-(methylsulfinyl)pyrimidin-4-yl)pyrazolo[1,5-a]pyrimidin-2-amine

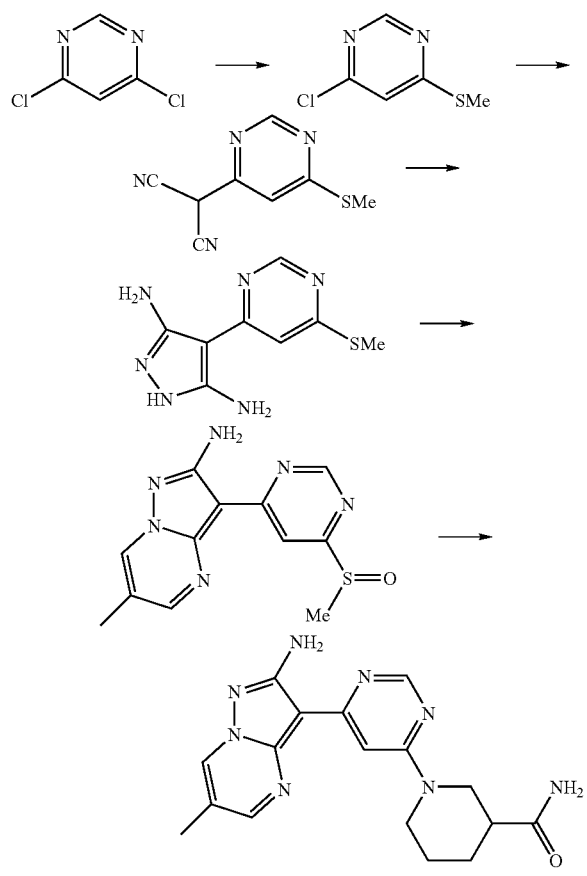

Synthesis of 4-chloro-6-(methylthio)pyrimidine 4,6 Dichloropyrimidine (15.4 g, 0.10 mol) was dissolved in THF (120 mL) at room temperature and NaSMe (8.5 g, 0.12 mol) was added as a solid. The reaction mixture was heated to 60° C. for 16 hours then let cool to room temperature and then diluted with ethyl acetate (300 mL) and water (300 mL). The organic layer was washed with brine, dried over sodium sulfate, and concentrated to an orange oil which was recrystalized from hexanes to give a pale yellow solid, 9.85 g, 0.061 mol, 61%. H NMR (500 MHz, CDCl3) 8.74 (s, 1H), 7.23 (s, 1H), 2.58 (s, 3H).

Synthesis of 2-(6-(methylthio)pyrimidin-4-yl)malononitrile

Sodium hydride (10.8 g, 0.27 mol) was suspended THF (100 mL) at 0° C. To this suspension, a solution of malonitrile (8.0 g, 0.122 mol) in 50 mL THF was added dropwise. After the addition was complete the reaction mixture was stirred an additional 10 minutes and then 4-chloro-6-(methylthio)pyrimidine (9.85 g, 0.61 mol) was added in 50 mL THF. Nitrogen was bubbled through the reaction mixture for 10 min. and the Pd(PPh3)4 (3.3 g, 3.0 mmol) was added as a solid and the reaction mixture was heated to 60° C. After heating for 4 hrs., the reaction mixture was let cool to room temperature and carefully quenched with water. The reaction mixture was then concentrated to a residue and 100 mL water added, followed by 6N HCl until the pH=1. A precipitate formed which was filtered, washed with water and diethyl ether, suspended in ethyl acetate (100 mL) and filtered again. This solid was dried to 11.4 g, 0.06 mol, 98%). %. H NMR (500 MHz, DMSO-d$_6$) 8.28 (s, 1H), 6.47 (s, 1H), 2.58 (s, 3H).

Synthesis of 4-(6-(methylthio)pyrimidin-4-yl)-1H-pyrazole-3,5-diamine 2-(6-(methylthio)pyrimidin-4-yl)malononitrile (11.4 g, 0.06 mol) was suspended in 150 mL EtOH and hydrazine hydrate (3 mL, 0.06 mol) was added. The reaction mixture was heated to reflux for 3 days. The reaction mixture was concentrated to a solid which was suspended in ethyl acetate (100 mL), and filtered. This solid was dried to give the product, 10.4 g, 46.8 mmol, 78%, ca. 80% pure).

Synthesis of 6-methyl-3-(6-(methylsulfinyl)pyrimidin-4-yl)pyrazolo[1,5-a]pyrimidin-2-amine 4-(6-(methylthio)pyrimidin-4-yl)-1H-pyrazole-3,5-diamine (1.0 g, 4.5 mmol) was combined with 3-ethoxy-2-methylacrylaldehyde (0.63 g, 5.3 mmol) in isopropanol (12 mL). Acetic acid (0.1 mL) was added to the reaction mixture which was then sealed in a microwave vessel and heated to 160° C. for 15 min. The reaction mixture was diluted with ethyl acetate (200 mL) and 1N NaOH (60 mL), the layers separated and the organic layer concentrated to 60 mL. This solution was cooled to 0° C. and 77% m-chloroperbenzoic acid (1.9 g, 8.5 mmol) was added. After 1 hr. a yellow precipitate formed which was filter off, washed with ethyl acetate and dried to give the product, 0.39 g, 30% yield. LCMS MH+289.29. H NMR (500 MHz, DMSO-d$_6$) 9.02 (s, 1H) 8.91 (s, 1H), 8.88 (s, 1H), 8.54 (s, 1H), 7.14 (s, 2H), 2.91 (s, 3H), 2.34 (s, 3H).

Synthesis 1-(6-(2-amino-6-methylpyrazolo[1,5-a]pyrimidin-3-yl)pyrimidin-4-yl)piperidine-3-carboxamide 6-methyl-3-(6-(methylsulfinyl)pyrimidin-4-yl)pyrazolo[1,5-a]pyrimidin-2-amine (60 mg, 0.21 mmol) was dissolved in NMP with nipecotamide (100 mg, 0.78 mmol) and heated to 200° C. in a microwave for 20 min. The reaction mixture was purified by RP HPLC (C18, CH3CN/H2O 0.1% TFA) and the pure fractions were poured into ethyl acetate/0.5 N NaOH. The organic phase was dried over sodium sulfate and concentrated to a yellow solid which was dissolved in 1N HCl in MeOH and concentrated to the HCl salt as a yellow solid, 20 mg, 0.052 mmol, 26%. LC/MS MH+353.4

$^1$H NMR (500 MHz, DMSO-$d_6$) 8.93 (s, 1H), 8.70 (s, 1H), 8.54 (d, J=1.9 Hz, 1H), 7.48 (s, 1H), 7.11 (s, 1H), 6.96 (s, 1H), 3.32-3.25 (m, 2H), 2.47 (m, 2H), 2.36 (s, 3H), 2.00-1.96 (m, 1H), 1.88-1.83 (m, 2H), 1.72 (m, 1H), 1.52 (s, 1H).

$^1$H NMR data is summarized in Table 10 below wherein $^1$H NMR data was obtained at 500 MHz in deuterated DMSO, unless otherwise indicated, and was found to be consistent with structure. Compound numbers correspond to the compound numbers listed in Table 5.

TABLE 10

Characterization Data for Selected Compounds

| Cmpd # (V-) | M+1(obs) | Rt(min) | $^1$H-NMR |
|---|---|---|---|
| 1 | 225.10 | 2.60 | (500MHz, dmso-d6) 8.59(d, 1H), 7.81(d, 2H), 7.40(t, 2H), 7.19(t, 1H), 6.65(d, 1H), 2.45(s, 3H) ppm |
| 2 | 265.90 | 2.62 | 1H NMR(500MHz, DMSO-d6) d 9.20(1H, s), 8.81(1H, s), 7.72(2H, d), 7.05(2H, d), 6.70(2H, br s), 3.80(3H, s) ppm. |
| 3 | 348.20 | 2.10 | |
| 4 | 316.20 | 2.30 | |
| 5 | 356.10 | 2.30 | |
| 6 | 330.20 | 1.90 | |
| 7 | 302.20 | 2.20 | |
| 8 | 304.20 | 1.90 | |
| 9 | 316.20 | 2.30 | |
| 10 | 313.10 | 2.00 | |
| 11 | 332.10 | 1.80 | |
| 12 | 316.20 | 2.30 | |
| 13 | 306.10 | 2.10 | |
| 14 | 318.20 | 2.10 | |
| 15 | 364.10 | 2.50 | |
| 16 | 381.20 | 1.80 | |
| 17 | 372.10 | 2.20 | |
| 18 | 380.10 | 1.90 | |
| 19 | 372.10 | 2.40 | |
| 20 | 303.20 | 1.70 | |
| 21 | 333.10 | 2.00 | |
| 22 | 319.10 | 1.80 | |
| 23 | 345.20 | 1.50 | |
| 24 | 317.00 | 3.00 | 1H NMR(500MHz, DMSO-d6) d 9.22(1H, s), 8.90(1H, s), 7.85(2H, d), 7.59(2H, d) 6.50(2H, br s), 4.30(2H, q), 1.30(3H, t) ppm. |
| 25 | 284.00 | 2.10 | 1H NMR(500MHz, DMSO-d6) d 9.40(1H, s), 9.22(1H, s), 8.70(1H, d), 8.10(1H, d), 7.91(1H, dd), 7.40(1H, dd), 6.55(2H, br s), 4.30(2H, q), 1.30(3H, t) ppm. |
| 26 | 285.00 | 2.00 | 1H NMR(500MHz, DMSO-d6) d 9.50(1H, s), 9.35(1H, s), 9.22(1H, s), 8.85(1H, d), 8.65(1H, d), 6.60(2H, br s), 4.30(2H, q), 1.30(3H, t) ppm. |
| 27 | 285.00 | 1.90 | 1H NMR(500MHz, DMSO-d6) d 9.55(1H, s), 9.30(1H, s), 9.25(1H, s), 8.90(1H, d), 8.21(1H, d), 6.62(2H, br s), 4.30(2H, q), 1.30(3H, t) ppm. |
| 28 | 257.00 | 1.50 | 1H NMR(500MHz, DMSO-d6) d 9.55(1H, s), 9.20(1H, s), 9.00(1H, s), 8.80(1H, d), 8.15(1H, d), 6.80(2H, br s) ppm. |
| 29 | 330.60 | 3.41 | H NMR(500MHz, DMSO-d6) 9.03(d, J=2.3Hz, 1H), 8.67(d, J=2.3Hz, 1H), 7.76(d, J=8.8Hz, 2H), 7.66(d, J=8.1Hz, 2H), 7.30(d, J=8.0Hz, 2H), 7.01(d, J=8.8Hz, 2H), 5.71(s, 2H), 3.79(s, 3H), 2.36(s, 3H) |
| 30 | 378.70 | 3.90 | H NMR(500MHz, DMSO-d6) 9.09(d, J=2.3Hz, 1H), 8.73(d, J=2.3Hz, 1H), 7.85(d, J=8.6Hz, 2H), 7.67(d, J=8.1Hz, 2H), 7.60(d, J=8.6Hz, 2H), 7.30(d, J=7.9Hz, 2H), 5.90(s, 2H), 2.36(s, 3H) |
| 31 | 378.60 | 3.41 | H NMR(500MHz, DMSO-d6)8.03(d, J=2.2Hz, 1H), 7.75(d, J=2.2Hz, 1H), 6.97(d, |

TABLE 10-continued

Characterization Data for Selected Compounds

| Cmpd # (V-) | M+1(obs) | Rt(min) | ¹H-NMR |
|---|---|---|---|
| 32 | 382.30 | 2.50 | J=8.0Hz, 1H), 6.76(d, J=8.1Hz, 2H), 6.67(m, 2H), 6.52(m, 3H), 1.60(s, 3H) 1H NMR(500MHz, DMSO-d6) d 9.65(1H, s), 9.25(2H, m), 8.9(1H, d), 8.20(2H, m), 7.45(1H, m), 7.20(1H, m), 7.05(1H, m), 6.70(2H, m), 4.60(2H, s) ppm. |
| 33 | 325.20 | 1.90 | 1H NMR(500MHz, DMSO-d6) d 9.50(1H, s), 9.20(1H, m), 9.15(1H, s), 8.85(1H, d), 8.20(1H, m), 7.45(1H, m), 3.4(3H, m), 1.20(6H, d), 1.1(3H, m) ppm. |
| 34 | 393.40 | 1.40 | 1H NMR(500MHz, DMSO-d6) d 9.60(1H, s), 9.25(1H, m), 9.20(1H, s), 8.85(1H, d), 8.20(1H, m), 4.5(1H, m), 3.90(1H, m), 3.80(1H, m), 3.60(2H, m), 3.45(1H, m), 3.30(1H, m), 3.15(1H, m), 3.05(1H, m), 2.15(1H, m), 1.95(2H, m), 1.90(4H, m), 1.75(2H, m) ppm. |
| 35 | 417.40 | 1.60 | 1H NMR(500MHz, DMSO-d6) d 9.60(1H, s), 9.21(2H, m), 8.89(1H, d), 8.20(1H, m), 7.35*3H, m), 7.29(2H, m), 4.85(2H, s), 3.74(2H, m), 3.35(2H, m), 2.80(6H, s) ppm. |
| 36 | 375.40 | 1.30 | 1H NMR(500MHz, DMSO-d6) d 9.55(1H, s), 9.21(1H, m), 8.89(1H, d), 8.80(2H, m), 8.20(1H, m), 7.80(2H, m), 4.97(2H, s), 3.55(2H, m), 1.15(3H, t) ppm. |
| 37 | 390.40 | 1.90 | 1H NMR(500MHz, DMSO-d6) d 9.55(1H, s), 9.21(2H, m), 8.85(1H, d), 8.20(1H, m), 7.30(5H, m), 4.80(2H, s), 4.0(2H, m), 3.50(2H, m) ppm. |
| 38 | 399.40 | 2.20 | 1H NMR(500MHz, DMSO-d6) d 9.55(1H, s), 9.21(2H, m), 8.85(1H, d), 8.20(1H, m), 7.25(5H, m), 4.80(2H, s), 3.70(2H, m), 2.85(2H, m) ppm. |
| 39 | 340.30 | 1.50 | 1H NMR(500MHz, DMSO-d6) d 9.55(1H, s), 9.21(1H, s), 9.20(1H, s), 8.85(1H, d), 8.20(1H, m), 3.55(2H, m), 3.35(1H, m), 1.95(2H, m), 1.90(2H, m), 1.70(2H, m) ppm. |
| 40 | 323.30 | 1.50 | 1H NMR(500MHz, DMSO-d6) d 9.55(1H, s), 9.25(2H, m), 8.89(1H, d), 8.20(1H, m), 3.70(2H, m), 3.20(3H, s), 2.95(2H, m) ppm. |
| 41 | 360.40 | 2.10 | 1H NMR(500MHz, DMSO-d6) d 9.55(1H, s), 9.25(2H, m), 8.89(1H, d), 8.20(1H, m), 7.30(5H, m), 4.70(2H, s), 3.0(3H, s) ppm. |
| 42 | 374.40 | 2.30 | 1H NMR(500MHz, DMSO-d6) d 9.55(1H, s), 9.25(2H, m), 8.89(1H, d), 8.20(1H, m), 7.30(5H, m), 4.75(2H, s), 3.40(2H, m), 1.10(3H, t) ppm. |
| 43 | 389.40 | 1.50 | 1H NMR(500MHz, DMSO-d6) d 9.60(1H, s), 9.22(2H, m), 8.89(1H, d), 8.20(1H, m), 8.0(1H, m), 7.20(2H, m), 6.75(3H, m), 4.45(2H, s), 2.90(6H, s) ppm. |
| 44 | 326.20 | 1.30 | 1H NMR(500MHz, DMSO-d6) d 9.55(1H, s), 9.22(2H, m), 8.89(1H, d), 8.20(1H, m), 3.90(2H, m), 3.40(1H, m), 2.20(1H, m), 1.95(2H, m) ppm. |
| 45 | 310.30 | 1.70 | 1H NMR(500MHz, DMSO-d6) d 9.55(1H, s), 9.22(2H, m), 8.89(1H, d), 8.20(1H, m), 3.70(2H, m), 3.55(2H, m), 1.85(4H, m) ppm. |
| 46 | 376.40 | 2.00 | 1H NMR(500MHz, DMSO-d6) d 9.60(1H, s), 9.30(1H, s), 9.25(1H, s), 8.89(1H, d), 8.40(1H, m), 8.20(1H, m), 7.30(5H, m), 5.20(1H, m), 3.75(2H, m) ppm. |
| 47 | 413.10 | 3.40 | 1H NMR(500MHz, DMSO-d6) d 9.50(1H, s), 9.20(1H, s), 8.70(1H, t), 8.30(1H, t), 8.10(1H, d), 7.91(1H, t), 7.60(2H, m), 7.40(1H, d), 7.35(1H, d), 6.61(2H, s), 4.55(2H, m) ppm. |
| 48 | 307.10 | 2.15 | 1H NMR(500MHz, DMSO-d6) d 8.79(1H, m), 8.46(1H, m), 6.32(2H, s), 4.30(2H, m), 4.05(2H, m), 2.69(2H, m), 2.0(3H, s), 1.91(2H, m), 1.29(3H, t) ppm. |

TABLE 10-continued

Characterization Data for Selected Compounds

| Cmpd # (V-) | M+1(obs) | Rt(min) | $^1$H-NMR |
|---|---|---|---|
| 49 | 373.90 | 3.90 | |
| 50 | 319.20 | 1.70 | |
| 51 | 414.20 | 1.50 | |
| 52 | 290.00 | 1.30 | |
| 53 | 306.20 | 1.30 | |
| 54 | 402.40 | 1.40 | |
| 55 | 414.40 | 1.30 | |
| 56 | 394.10 | 2.50 | |
| 57 | 296.70 | 2.62 | |
| 58 | 280.90 | 3.22 | |
| 59 | 294.00 | 3.36 | |
| 60 | 451.40 | 0.80 | |
| 61 | 443.50 | 1.30 | |
| 62 | 403.40; 401.20 | 1.30; 1.90 | |
| 63 | 429.00 | 1.30 | |
| 64 | 458.40 | 1.80 | |
| 65 | 403.40 | 1.30 | |
| 66 | 444.40 | 1.70 | |
| 67 | 388.40 | 1.70 | |
| 68 | 459.40 | 1.30 | |
| 69 | 415.50 | 1.30 | |
| 70 | 429.40 | 1.30 | |
| 71 | 430.40 | 1.50 | |
| 72 | 384.40 | 1.70 | |
| 73 | 378.40 | 1.70 | |
| 74 | 430.20 | 1.50 | |
| 75 | 404.40 | 1.60 | |
| 76 | 472.50; 473.50 | 1.90; 1.30 | |
| 77 | 388.40 | 1.90 | |
| 78 | 445.40 | 1.30 | |
| 79 | 416.40 | 1.50 | |
| 80 | 431.50 | 1.50 | |
| 81 | 401.40 | 1.20 | |
| 82 | 444.40 | 1.60 | |
| 83 | 444.40 | 1.60 | |
| 84 | 469.50 | 1.30 | |
| 85 | 431.40 | 1.40 | |
| 86 | 372.30 | 1.60 | |
| 87 | 418.40 | 1.80 | |
| 88 | 445.50 | 1.40 | |
| 89 | 374.40 | 1.60 | |
| 90 | 413.40 | 1.70 | |
| 91 | 400.40 | 1.80 | |
| 92 | 418.40 | 1.60 | |
| 93 | 415.20 | 1.50 | |
| 94 | 389.40 | 0.80 | |
| 95 | 432.40 | 1.60 | |
| 96 | 402.40 | 1.50 | |
| 97 | 402.40 | 1.90 | |
| 98 | 388.40 | 1.70 | |
| 99 | 404.40 | 1.50 | |
| 100 | 451.40 | 1.40 | |
| 101 | 443.50 | 1.30 | |
| 102 | 429.40 | 1.30 | |
| 103 | 388.40 | 1.78 | |
| 104 | 415.40 | 1.30 | |
| 105 | 429.40 | 1.30 | |
| 106 | 384.40 | 1.80 | |
| 107 | 378.30 | 1.80 | |
| 108 | 404.40 | 1.80 | |
| 109 | 388.40 | 2.10 | |
| 110 | 431.50 | 1.60 | |
| 111 | 418.40 | 1.60 | |
| 112 | 416.40 | 1.60 | |
| 113 | 431.50 | 1.60 | |
| 114 | 399.40 | 1.60 | |
| 115 | 373.20 | 1.70 | |
| 116 | 413.40 | 1.70 | |
| 117 | 473.50 | 1.40 | |
| 118 | 345.90 | 2.09 | |
| 119 | 401.40 | 1.30 | |
| 120 | 389.40 | 1.40 | |
| 121 | 469.50 | 1.40 | |
| 122 | 431.50 | 1.50 | |

TABLE 10-continued

Characterization Data for Selected Compounds

| Cmpd # (V-) | M+1(obs) | Rt(min) | ¹H-NMR |
|---|---|---|---|
| 123 | 372.40 | 1.70 | |
| 124 | 445.50 | 1.40 | |
| 125 | 402.40 | 2.00 | |
| 126 | 402.40 | 2.00 | |
| 127 | 388.40 | 1.80 | |
| 128 | 404.40 | 1.50 | |
| 129 | 473.50 | 1.30 | |
| 130 | 403.40 | 1.30 | |
| 131 | 315.70 | 1.61 | H NMR(500MHz, DMSO-d6) 9.61(d, J=2.3Hz, 1H), 8.95(d, J=2.3Hz, 1H), 8.78(dd, J=5.1, 1.4Hz, 2H), 8.13(d, J=6.3Hz, 2H), 7.76(d, J=7.0Hz, 2H), 7.57(m, 1H), 7.47(t, J=7.6Hz, 2H), 7.09(br s, 2H). |
| 132 | 302.80 | 1.62 | H NMR(500MHz, DMSO-d6) 9.56(d, J=2.3Hz, 1H), 9.04(d, J=2.3Hz, 1H), 8.79(m, 2H), 8.49(d, J=8.3Hz, 1H), 8.43(d, J=2.0Hz, 1H), 8.19(d, J=6.1Hz, 2H), 7.72(dd, J=8.4, 2.1Hz, 1H), 2.33(s, 3H). |
| 133 | 302.80 | 1.90 | H NMR(500MHz, DMSO-d6) 9.63(d, J=2.1Hz, 1H), 9.13(d, J=2.1Hz, 1H), 8.85(d, J=6.4Hz, 2H), 8.46(d, J=5.1Hz, 1H), 8.42(s, 1H), 8.30(d, J=6.1Hz, 2H), 7.08(d, J=4.5Hz, 1H, 2.42(s, 3H). |
| 134 | 395.00 | 1.67 | H NMR(500MHz, DMSO-d6) 9.60(d, J=2.2Hz, 1H), 9.00(d, J=2.2Hz, 1H), 8.85(d, J=6.6Hz, 2H), 8.41(d, J=4.8Hz, 1H), 8.30(d, J=6.5Hz, 2H), 8.00(d, J=8.4Hz, 1H), 7.67(dd, J=8.3, 5.3Hz, 1H), 7.49(d, J=7.2Hz, 2H), 7.33(m, 3H), 5.30(s, 2H). |
| 135 | 302.80 | 0.37 | H NMR(500MHz, DMSO-d6) 9.62(d, J=2.0Hz, 1H), 9.00(d, J=2.0Hz, 1H), 8.80(d, J=6.2Hz, 2H), 8.70(d, J=5.1Hz, 1H), 8.30(d, J=6.9Hz, 1H), 8.18(d, J=5.1Hz, 2H), 7.74(m, 1H), 2.43(s, 3H). |
| 136 | 438.10 | 2.46 | 1H NMR(500MHz, CDCl3) d 9.25(2H, m), 8.99(1H, s), 8.83(1H, d), 8.20(1H, s), 7.38(1H, d), 6.95(1H, d), 5.91(2H, s) ppm. |
| 137 | 367.20 | 2.00 | 500MHz, MeOD, 7.82(s, 1H), 7.49(s, 1H), 7.25(d, 2H), 7.11(d, 1H), 7.78(d, 2H), 6.18(t, 1H), 5.80(d, 1H) |
| 138 | 412.00 | 1.82 | |
| 139 | 444.40 | 1.80 | |
| 140 | 416.40 | 1.50 | |
| 141 | 444.50 | 1.60 | |
| 142 | 432.40 | 1.70 | |
| 143 | 358.40 | 1.40 | |
| 144 | 374.40 | 1.30 | |
| 145 | 387.50 | 1.30 | |
| 146 | 415.50 | 1.30 | |
| 147 | 371.20 | 1.50 | |
| 148 | 417.50 | 1.20 | |
| 149 | 415.50 | 1.30 | |
| 150 | 461.50 | 1.30 | |
| 151 | 373.40 | 1.20 | |
| 152 | 441.50 | 1.40 | |
| 153 | 469.50 | 1.40 | |
| 154 | 469.50 | 1.40 | |
| 155 | 403.40 | 1.40 | |
| 156 | 362.00 | 1.30 | |
| 157 | 375.40 | 1.10 | |
| 158 | 389.20 | 1.40 | |
| 159 | 375.40 | 1.20 | |
| 160 | 401.50 | 1.20 | |
| 161 | 412.50 | 1.10 | |
| 162 | 451.50 | 1.50 | |
| 163 | 464.20 | 1.20 | |
| 164 | 441.50 | 1.20 | |
| 165 | 387.40 | 1.10 | |
| 166 | 401.50 | 1.30 | |
| 167 | 444.20 | 1.60 | |
| 168 | 423.40 | 1.30 | |
| 169 | 415.50 | 1.10 | |
| 170 | 390.40 | 1.50 | |
| 171 | 346.30 | 1.30 | |
| 172 | 374.40 | 1.50 | |

TABLE 10-continued

Characterization Data for Selected Compounds

| Cmpd # (V-) | M+1(obs) | Rt(min) | ¹H-NMR |
|---|---|---|---|
| 173 | 417.50 | 1.40 | |
| 174 | 445.50 | 1.60 | |
| 175 | 469.50 | 1.50 | |
| 176 | 441.50 | 1.40 | |
| 177 | 469.50 | 1.40 | |
| 178 | 302.80 | 1.21 | H NMR(500MHz, DMSO-d6) 9.70(d, J=2.3Hz, 1H), 9.13(d, J=2.3Hz, 1H), 8.93(d, J=6.8Hz, 2H), 8.50(d, J=6.8Hz, 2H), 8.37(d, J=8.0Hz, 1H), 7.83(t, J=7.8Hz, 1H), 7.12(d, J=7.5Hz, 1H), 2.56(s, 3H) |
| 179 | 373.00 | 1.46 | H NMR(500MHz, DMSO-d6) 9.64(s, 1H), 9.16(s, 1H), 8.84(d, J=5.1Hz, 2H), 8.58(s, 1H), 8.27(d, J=5.1Hz, 2H), 7.59(s, 1H), 3.73(m, 4H), 1.65(m, 6H) |
| 180 | 361.00 | 1.35 | 500MHz, MeOD, 8.12(d, 1H), 7.77(d, 1H), 7.51(d, 2H), 7.28(s, 1H), 6.88(d, 2H), 5.89(s, 1H), 2.47(m, 4H), 1.01(t, 6H) |
| 181 | 319.30 | 1.19 | DMSO, 500MHz, 9.61(s, 1H), 9.052(s, 1H), 8.80(d, 2H), 8.55(s, 1H), 8.14(d, 2H), 7.47(s, 1H), 2.93(s, 3H) |
| 182 | 347.30 | 1.37 | DMSO, 500MHz, 9.58(s, 1H), 9.01(s, 1H), 8.79(d, 2H), 8.52(s, 1H), 8.08(d, 2H), 7.46(s, 1H), 4.15(m, 1H), 1.19(d, 6H) |
| 183 | 387.40 | 1.64 | DMSO, 500MHz, 9.56(s, 1H), 9.01(s, 1H), 8.78(d, 2H), 8.51(s, 1H), 8.10(d, 2H), 7.47(s, 1H), 1.91(m, 2H), 1.86(m, 1H), 1.62(m, 1H), 1.30(m, 6H) |
| 184 | 401.40 | 1.76 | DMOS, 500MHz, 9.58(s, 1H), 9.01(s, 1H), 8.77(d, 2H), 8.50(s, 1H), 8.11(d, 2H), 7.48(s, 1H), 3.20(s, 2H), 1.69(m, 6H), 1.18(m, 3H), 0.96(q, 2H) |
| 185 | 361.40 | 1.50 | DMSO, 500MHz, 9.59(s, 1H), 9.13(s, 1H), 8.81(d, 2H), 8.56(s, 1H), 8.18(d, 2H), 7.50(s, 1H), 3.21(s, 2H), 1.89(m, 1H), 0.94(d, 6H) |
| 186 | | | (400MHz, DMSO-d6) 3.81(3H, s), 5.83(2H, br s), 7.05(2H, d), 7.21(1H, m), 7.43(2H, t), 7.71(2H, d), 7.86(2H, d), 8.69(1H, s) and 9.05(1H, s). |
| 187 | | | (DMSO) 6.05(2H, m, NH2), 7.25(1H, m, ArH), 7.50(2H, m, 4×ArH), 7.90(4H, m, 4×ArH), 8.70(2H, d, ArH×2), 8.85(1H, s, ArH), 9.40(1H, s, ArH). |
| 188 | | | (DMSO) 2.65(1H, m), 2.91(6H, br s), 2.97(3H, s), 3.63(1H, m), 3.80(2H, m), 7.15(1H, t), 7.60(2H, d), 7.87(1H, t), 7.92(2H, d), 8.53–8.60(2H, m), 8.92(1H, s), 9.32(1H, s), 9.40(2H, br s). |
| 189 | | | (DMSO) 2.69(3H, s), 2.97(3H, s), 3.54–3.80(4H, m), 7.20(1H, m), 7.48–7.61(2H, m), 7.80–7.94(3H, m), 8.45(2H, br s), 8.54–8.58(2H, m), 8.88(1H, s), 9.28(1H, s) |
| 190 | 416.60 | 3.73 | |
| 191 | 416.61 | 3.79 | (DMSO) 1.91(2H, m), 2.61(2H, m), 2.96(6H, m), 3.52(2H, m), 7.15(1H, t), 7.55(2H, d), 7.86(1H, t), 7.90(2H, d), 8.39(2H, br s), 8.57(2H, m), 8.91(1H, s), 9.32(1H, s). (DMSO) 1.91–2.00(2H, m), 2.58–2.64(2H, m), 2.95–2.99(3H, m), 3.49–3.54(3H, br s), 3.64–3.74(2H, m), 7.15(1H, t), 7.55(2H, d), 7.86(1H, t), 7.90(2H, d), 8.39(2H, br s), 8.57(2H, m), 8.91(1H, s), 9.32(1H, s).; (DMSO) 1.91(2H, m), 2.61(2H, m), 2.96(6H, m), 3.52(2H, m), 7.15(1H, t), 7.55(2H, d), 7.86(1H, t), 7.90(2H, d), 8.39(2H, br s), 8.57(2H, m), 8.91(1H, s), 9.32(1H, s) |
| 192 | | | (DMSO) 1.38(9H, s), 4.17(2H, m), 7.08–7.15(3H, m), 7.34(2H, d), 7.48(1H, m), 7.78(2H, d), 7.84(1H, t), 8.52–8.58(2H, m), 8.85(1H, s), 9.21(1H, s) |
| 193 | 316.40 | 4.42 | (DMSO) 7.16(1H, t), 7.21(2H, br s), 7.88(1H, t), 8.01(2H, d), 8.10(2H, d), 8.56–8.60(2H, m), 8.98(1H, s), 9.40(1H, s), 10.09(1H, s). |
| 194 | | 4.14 | (DMSO) 4.55(2H, d), 5.27(1H, t), 7.10–7.18(3H, m), 7.45(2H, d), 7.79(2H, d), 7.86(1H, |

TABLE 10-continued

Characterization Data for Selected Compounds

| Cmpd # (V-) | M+1(obs) | Rt(min) | ¹H-NMR |
|---|---|---|---|
| | | | t), 8.54–8.60(2H, m), 8.89(1H, s), 9.23(1H, s) |
| 195 | 317.44 | 3.72 | (DMSO) 4.09(2H, m), 7.19(1H, t), 7.60(2H, d), 7.88–7.92(3H, m), 8.28(2H, br s), 8.55–8.59(2H, m), 8.92(1H, s), 9.32(1H, s). |
| 196 | | | DMSO 7.15(1H, t, ArH), 7.20(2H, br s, NH2), 7.70(1H, t, ArH), 7.90(2H, d, ArH×2), 8.20(2H, d, ArH×2), 8.60(2H, m, ArH×2), 8.95((1H, s, ArH), 9.40(1H, s, ArH). |
| 197 | | | DMSO 7.15(1H, t, ArH), 7.70(1H, t, ArH), 7.90(2H, d, ArH×2), 8.20(1H, d, ArH), 8.35(1H, s, ArH), 8.60(2H, m, ArH×2), 8.95((1H, s, ArH), 9.40(1H, s, ArH). |
| 198 | 359.80 | 4.42 | (DMSO) 2.9(2H, t), 3.6(2H, t), 7.1–7.3(6H, m), 7.9(1H, t), 8.5(2H, m), 8.8(1H, m), 8.9(1H, s), 9.2(1H, s) |
| 199 | 360.80 | 3.80 | (DMSO) 4.3(2H, d), 5.0(NH2), 6.5(2H, d), 7.1(2H, d), 7.2(1H, m), 7.3(NH2), 7.9(1H, m), 8.5(2H, m), 8.9(NH), 9.0(1H, m), 9.3(1H, s) |
| 200 | 346.70 | 3.75 | (DMSO) 4.6(2H, m), 7.2(1H, m), 7.3(NH2), 7.4(1H, m), 7.8(1H, m), 7.9(1H, m), 8.4–8.7(4H, m), 8.9(1H, s), 9.2(1H, m), 9.3(NH) |
| 201 | 452.90 | 4.65 | DMSO 1.1(2H, m), 1.4(9H, m), 1.7(3H, m), 2.7(2H, m), 4.0(2H, m), 7.1(1H, m), 7.3(NH2), 7.9(1H, m), 8.4–8.6(3H, m), 8.9(1H, s0, 9.3(1H, s) |
| 202 | 317.44 | 3.82 | (DMSO) 4.09–4.17(2H, m), 7.20(1H, t), 7.50(1H, d), 7.58(1H, t), 7.88(1H, d), 7.91(1H, t), 8.02(1H, s), 8.40(2H, br s), 8.58–8.62(2H, m), 8.92(1H, s), 9.29(1H, s). |
| 203 | 336.44 | 4.85 | (DMSO) 4.84(2H, s), 7.11–7.17(3H, m), 7.58(2H, d), 7.82–7.86(3H, m), 8.53–8.56(1H, m), 8.58(1H, d), 8.89(1H, s), 9.27(1H, s) |
| 204 | 269.70 | 3.50 | (DMSO) 2.8(3H, d), 7.1(1H, m), 7.3(2H, brs), 7.9(1H, m), 8.5–8.7(3H, m), 8.9(1H, s), 9.2(1H, s) |
| 205 | 311.74 | 4.24 | (DMSO) 0.9(6H, m), 1.9(1H, m), 3.1(2H, m), 7.1(1H, m), 7.2(NH2), 7.9(1H, t), 8.5–8.6(3H, m), 8.9(1H, s), 9.3(1H, s) |
| 206 | 338.75 | 3.30 | (DMSO) 0.8(2H, m), 1.6(1H, m), 2.0(2H, m), 2.9(2H, m), 3.1–3.3(2H, m), 7.2(1H, m), 8.0(1H, m), 8.4(1H, m), 8.6(1H, m), 8.7(NH2), 8.9(1H, s), 9.2(1H, s) |
| 207 | 345.75 | 4.30 | (DMSO) 4.6(2H, d), 7.2(1H, m), (7.3, 2H, s), 7.4(3H, m), 7.9(1H, m), 8.5(2H, m), 8.9(1H, s), 9.2(1H, m), 9.3(NH, s) |
| 208 | 387.54 | 4.59 | (DMSO) 2.40(4H, m), 3.52(2H, s), 3.59(4H, t), 7.09–7.15(3H, m), 7.45(2H, d), 7.78(2H, d), 7.84(1H, t), 8.55(1H, d), 8.59(1H, d), 8.86(1H, s), 9.22(1H, s). |
| 209 | | | (DMSO) 7.10(3H, m, ARH, NH2), 7.25(2H, m, ArH×2), 7.40(3H, m, ArH×3), 7.60(2H, m, ArH×2), 7.85(1H, t, ArH), 8.55(2H, m, ArH×2), 8.85(1H, s, ArH), 9.10(1H, s, ArH). |
| 210 | 336.42 | 4.85 | (DMSO) 4.84(2H, s), 7.12–7.17(3H, m), 7.47–7.56(2H, m), 7.81(1H, d), 7.86(1H, t), 7.91(1H, s), 8.56(1H, d), 8.59(1H, d), 8.86(1H, s), 9.24(1H, s). |
| 211 | | | 1H NMR(DMSO) 2.55(1H, m), 2.89(4H, m), 3.02(6H, br s), 3.82(2H, br s), 3.96(2H, s), 5.98(2H, s), 7.14(1H, m), 7.22–7.26(2H, m), 7.31–7.32(2H, m), 7.98(1H, m), 8.14(1H, m), 8.73(1H, m), 9.01(1H, m), 9.32(1H, s)1H NMR(DMSO) 2.55(1H, m), 2.89(4H, m), 3.02(6H, br s), 3.82(2H, br s), 3.96(2H, s), 5.98(2H, s), 7.14(1H, m), 7.22–7.26(2H, m), 7.31–7.32(2H, m), 7.98(1H, m), 8.14(1H, m), 8.73(1H, m), 9.01(1H, m), 9.32(1H, s) |
| 212 | | | DMSO 6.50(1H, s, ArH), 7.10(2H, s, NH2), 7.15(1H, t, ArH), 7.40(1H, d, ArH), 7.55(2H, dd, ArH×2), 7.85(1H, t, ArH), 8.00(1H, s, ArH), 8.50(1H, m, ArH), 8.60(1H, d, |

TABLE 10-continued

Characterization Data for Selected Compounds

| Cmpd # (V-) | M+1(obs) | Rt(min) | $^1$H-NMR |
|---|---|---|---|
| 213 | | | ArH), 8.90(1H, s, ArH), 9.15(1H, s, ArH). (DMSO) 3.00(2H, s, CH2), 3.30(2H, d, CH2), 6.95(2H, s, NH2), 7.10(1H, t, ArH), 7.30(5H, m, ArH×5), 7.80(1H, t, ArH), 8.40(1H, s, ArH), 8.50(2H, m, ArH×2), 8.70(1H, s, ArH). |
| 214 | 345.52 | 4.30 | (DMSO) 2.75(6H, s), 4.32(2H, s), 7.18(1H, t), 7.68(2H, d), 7.87–7.98(3H, m), 8.55–8.60(2H, m), 8.93(1H, s), 9.34(1H, s), 10.40(2H, m). |
| 215 | 345.52 | 4.32 | (DMSO) 2.75(6H, d), 4.36(2H, d), 7.25(1H, t), 7.59(1H, t), 7.61(1H, t), 7.92–8.00(2H, m), 8.13(1H, s), 8.57(1H, d), 8.60(1H, d), 8.99(1H, s), 9.38(1H, s), 10.83(2H, m). |
| 216 | | | (DMSO) 2.65(3H, s, CH3), 3.85(3H, s, CH3), 7.10(5H, m, ArH×3, NH2), 7.50(2H, d, ArH×2), 7.85(1H, t, ArH), 8.40(1H, s, ArH), 8.55(1H, d, ArH), 8.65(1H, d, ArH). |
| 217 | 386.56 | 2.97 | (DMSO) 2.56–2.65(4H, m), 3.09–3.14(4H, m), 3.61(2H, s), 7.10–7.18(2H, m), 7.43(2H, d), 7.81(2H, d), 7.85(1H, t), 8.53–8.61(3H, m), 8.88(1H, s), 9.22(1H, s). |
| 218 | | | (DMSO) 3.85(3H, s, CH3), 7.10(2H, d, ArH×2), 7.20(1H, t, ArH), 7.40(4H, m, ArH×2, NH2), 7.90(1H, t, ArH), 8.50(1H, s, ArH), 8.60(2H, m, ArH×2). |
| 219 | | | 1H NMR(DMSO) 3.81(3H, s), 6.14(2H, br s), 7.07(2H, d), 7.74(2H, d), 7.96(2H, d), 8.53(2H, d), 8.81(1H, s), 9.14(1H, s) |
| 220 | 332.73 | 3.73 | (DMSO) 2.3(3H, s), 3.9(3H, s), 7.0(NH2), 7.1(2H, m), 7.6–7.8(3H, m), 8.3(1H, s), 8.4(1H, m), 8.8(1H, s), 9.2(1H, s) |
| 221 | 318.42 | 3.22 | 4.60(2H, s), 7.10–7.16(3H, m), 7.38(1H, d), 7.49(1H, t), 7.68(1H, d), 7.71(1H, s), 7.85(1H, t), 8.53–8.57(1H, m), 8.59(1H, d), 8.85(1H, s), 9.19(1H, s) |
| 222 | | | (DMSO) 3.30(4H, s, CH2×2), 3.50(4H, s, CH2×2), 7.05(1H, d, ArH), 7.15(1H, d, ArH), 7.30(1H, d, ArH), 7.40(2H, m, ArH×2), 7.90(1H, t, ArH), 8.55(2H, m, ArH×2), 8.75(2H, s, NH2), 8.90(1H, s, ArH), 9.25(1H, s, ArH). |
| 223 | 386.52 | 3.05 | (DMSO) 2.31–2.37(4H, m), 2.70(4H, t), 3.50(2H, s), 7.08–7.13(3H, m), 7.33(1H, d), 7.46(1H, t), 7.68–7.71(2H, m), 7.83(1H, t), 8.54–8.60(2H, m), 8.83(1H, s), 9.20(1H, s). |
| 224 | 400.54 | 3.15 | (DMSO) 1.68(2H, m), 2.58(2H, m), 2.64(2H, m), 2.75(2H, m), 2.80(2H, m), 3.68(2H, s), 7.10(3H, m), 7.46(2H, d), 7.76(2H, d), 7.84(1H, t), 8.54(1H, d), 8.57(1H, d), 8.86(1H, s), 9.20(1H, s) |
| 225 | 387.50 | 3.50 | (DMSO) 2.39–2.43(4H, m), 3.54(2H, s), 3.59(4H, t), 7.09–7.16(3H, m), 7.37(1H, d), 7.48(1H, t), 7.68–7.73(2H, m), 7.85(1H, t), 8.56–8.60(2H, m), 8.87(1H, s), 9.22(1H, s). |
| 226 | | | (DMSO) 1.3–1.4(1H, m), 1.9–2.3(3H, m), 2.5–2.6(1H, m), 2.6–2.7(1H, m), 3.6–3.7(2H, m), 7.0–7.2(2.5H, m), 7.3–7.4(1H, m), 7.4–7.5(1H, m), 7.6–7.7(2H, m), 7.8–7.9(1H, m), 8.5–8.6(2H, m), 8.8–8.9(1H, s), 9.2(1H, s) |
| 227 | | | (DMSO) 1.3–1.4(1H, m), 1.6–2.2(3H, m), 2.5–2.6(1H, m), 2.6–2.7(1H, m), 3.6–3.7(2H, m), 7.0–7.2(2.5H, m), 7.3–7.4(1H, m), 7.4–7.5(1H, m), 7.6–7.7(2H, m), 7.8–7.9(1H, m), 8.5–8.6(2H, m), 8.8–8.9(1H, s), 9.2(1H, s) |
| 228 | | | (DMSO) 1.6–1.7(2H, m), 2.5–2.9(8H, m), 3.7(2H, m), 7.0–7.2(2.8H, m), 7.3–7.4(1H, m), 7.4–7.5(1H, m), 7.7(2H, m), 7.8–7.9(1H, m), 8.5–8.6(2H, m), 8.8–8.9(1H, s), 9.2(1H, s) |
| 229 | | | (DMSO) 1.2–1.3(2H, m), 1.6–1.7(2H, m), 1.9–2.0(2H, m), 2.4–2.6(1H, m), 2.7–2.9(2H, m), 3.5–3.6(2H, m), 7.0–7.2(3H, m), 7.3(1H, m), 7.4–7.5(1H, m), 7.7–7.8(2H, m), 7.8–7.9(1H, m), 8.5–8.6(2H, m), 8.8(1H, m), 9.2(1H, m) |

TABLE 10-continued

Characterization Data for Selected Compounds

| Cmpd # (V-) | M+1(obs) | Rt(min) | ¹H-NMR |
|---|---|---|---|
| 230 | | | (DMSO) 1.60(2H, quin), 2.12(3H, s), 2.27(2H, br s), 2.38(2H, t), 2.50(3H, m), 3.49(2H, s), 7.08–7.14(3H, m), 7.40(2H, d), 7.77(2H, d), 7.85(1H, t), 8.54–8.59(2H, m), 8.86(1H, s), 9.20(1H, s). |
| 231 | | | (DMSO) 1.40–1.48(1H, m), 2.00–2.10(1H, m), 2.22(dd), 2.41–2.49(2H, m), 2.58–2.69(2H, m), 3.37–3.43(2H, m), 3.58(2H, d), 3.64(2H, d), 7.09–7.15(3H, m), 7.42(2H, d), 7.75(2H, d), 7.84(1H, t), 8.53–8.59(2H, m), 8.86(1H, s), 9.21(1H, s). |
| 232 | | | (DMSO) 1.74–1.79(2H, m), 2.22–2.28(2H, m), 2.95(2H, t), 3.36–3.40(2H, m), 4.18–4.24(2H, m), 7.09–7.20(2H, m), 7.14(1H, t), 7.62(2H, d), 7.86(1H, t), 8.93(2H, d), 8.53–8.58(2H, m), 8.89(1H, s), 9.29(1H, s). |
| 233 | | | (DMSO) 1.40–1.48(1H, m), 2.00–2.10(1H, m), 2.22(dd), 2.41–2.49(2H, m), 2.58–2.69(2H, m), 3.37–3.43(2H, m), 3.58(2H, d), 3.64(2H, d), 7.09–7.15(3H, m), 7.42(2H, d), 7.75(2H, d), 7.84(1H, t), 8.53–8.59(2H, m), 8.86(1H, s), 9.21(1H, s). |
| 234 | | | (DMSO) 1.48–1.60(2H, m), 1.81–1.92(2H, m), 1.97–2.08(2H, m), 2.81–2.90(1H, m), 2.95–3.09(1H, m), 3.48–3.59(2H, m), 7.10–7.18(3H, m), 7.38–7.44(2H, m), 7.75–7.89(3H, m), 8.54–8.60(2H, m), 8.88(1H, br s), 9.22(1H, br s). |
| 235 | 331.80 | 3.23 | (DMSO) 7.0(NH2), 7.1(1H, m), 7.5–7.7(3H, m), 7.9(H, m), 8.0(2H, m), 8.5(2H, m), 8.7(1H, s), 9.4(1H, s), 10.7(NH) |
| 236 | 331.84 | 2.96 | (DMSO) 1.37(1H, s), 2.29(3H, s), 3.70(2H, s), 7.08–7.14(3H, m), 7.43(2H, d), 7.75(2H, d), 7.85(1H, t), 8.55(1H, d), 8.58(1H, d), 8.88(1H, s), 9.20(1H, s). |
| 237 | 294.73 | 3.22 | (DMSO) 1.49(6H, s), 5.54(1H, s), 7.12–7.19(3H, m), 7.85(1H, t), 8.44(1H, s), 8.50(1H, d), 8.56(1H, d), 9.01(1H, s). |
| 238 | 266.63 | 2.95 | (DMSO) 4.33(2H, d), 5.43(1H, t), 7.10–7.20(3H, m), 7.82(1H, t), 8.47–8.60(3H, m), 9.09(1H, s). |
| 239 | 286.69 | 2.69 | (DMSO) 3.83(3H, s), 7.08(2H, d), 7.34(2H, br s), 7.80(2H, d), 9.08(1H, s), 9.37(1H, s) |
| 240 | 256.68 | 2.54 | (DMSO) 3.79(3H, s), 7.02(2H, d), 7.64(2H, d), 8.49(1H, s), 8.84(1H, s) |
| 241 | 381.40 | 1.59 | DMSO, 500MHz, 9.73(s, 1H), 9.45(s, 1H), 9.101(s, 1h), 8.82(d, 2H), 8.66(s, 1H), 8.15(d, 2H), 7.93(s, 1H), 7.73(d, 2H), 7.38(t, 2H), 7.14(t, 1H) |
| 242 | 411.40 | 1.56 | DMSO, 500MHz, 9.61(s, 1H), 9.02(s, 1H), 8.84(d, 2H), 8.58(s, 1H), 8.24(d, 2H), 7.81(s, 1H), 7.77(d, 1H), 7.19(t, 1H), 7.14(d, 1H), 7.00(t, 1H), 3.86(s, 3H) |
| 243 | 375.40 | 1.56 | DMSO, 500MHz 9.61(s, 1H), 9.12(s, 1H), 8.80(d, 2H), 8.55(s, 1H), 8.19(d, 2H), 7.58(s, 1H), 3.51(m, 2H), 3.18(s, 3H), 2.11(m, 1H), 0.96(d, 6H) |
| 244 | 375.40 | 1.52 | DMSO, 500MHz, 9.63(s, 1H), 9.12(s, 1H), 8.79(d, 2H), 8.57(s, 1H), 8.21(d, 2H), 7.58(s, 1H), 3.66(m, 2H), 3.50(m, 2H), 1.68(q, 2H), 1.21(t, 3H), 0.96(t, 3H) |
| 245 | 362.40 | 1.40 | |
| 246 | 375.40 | 1.20 | |
| 247 | 463.20 | 1.30 | |
| 248 | 417.00 | 1.20 | |
| 249 | 461.50 | 1.20 | |
| 250 | 412.50 | 1.30 | |
| 251 | 388.40 | 1.40 | |
| 252 | 409.40 | 1.20 | |
| 253 | 444.50 | 1.60 | |
| 254 | 401.50 | 1.10 | |
| 255 | 451.50 | 1.40 | |
| 256 | 441.50 | 1.20 | |
| 257 | 374.40 | 1.30 | |
| 258 | 358.40 | 1.30 | |
| 259 | 372.20 | 1.40 | |

TABLE 10-continued

Characterization Data for Selected Compounds

| Cmpd # (V-) | M+1(obs) | Rt(min) | ¹H-NMR |
|---|---|---|---|
| 260 | 430.50 | 1.40 | |
| 261 | 441.50 | 1.50 | |
| 262 | 388.40 | 0.70 | |
| 263 | 423.20 | 1.30 | |
| 264 | 464.20 | 1.30 | |
| 265 | 441.50 | 1.20 | |
| 266 | 417.20 | 1.30 | |
| 267 | 401.50 | 1.20 | |
| 268 | 386.20 | 1.30 | |
| 269 | 415.50 | 1.30 | |
| 270 | 402.50 | 1.30 | |
| 271 | 416.50 | 1.30 | |
| 272 | 364.50 | 1.30 | |
| 273 | 284.30; 284.40 | 1.61; 1.53 | H NMR(500MHz, DMSO-d6) 8.71(s, 1H), 8.37(d, J=1.6Hz, 2H), 7.45(s, 1H), 7.20(s, 1H), 6.89(s, 2H), 4.10–4.07(m, 1H), 2.30(s, 3H), 1.16(d, J=6.4Hz, 3H). |
| 274 | 347.80 | 2.55 | |
| 275 | 399.70 | 2.86 | |
| 276 | 310.30; 310.44 | 1.80 | H NMR(500MHz, DMSO-d6) 8.90(m, 2H), 8.65(s, 1H), 8.52(d, J=1.7Hz, 1H), 3.81(m, 4H), 2.35(s, 3H), 1.69(m, 2H), 1.63(m, 4H). |
| 277 | 296.30 | 1.80 | |
| 278 | 326.30 | 1.60 | |
| 279 | 318.30 | 1.90 | |
| 280 | 245.70 | 2.20 | |
| 281 | 273.40 | 2.73 | DMSO, 500MHz, 8.70(s, 2H), 8.48(d, 1H), 8.31(s, 1H), 2.59(s, 3H), 2.31(s, 3H) |
| 282 | 298.50 | 1.95 | H NMR(500MHz, CDCl3) 9.93(brs, 1H), 8.45(s, 1H), 8.34(s, 1H), 8.29(s, 1H), 7.86(s, 1H), 3.69–3.67(m, 1H), 2.43(s, 3H), 1.85–1.68(m, 2H), 1.40(d, J=6.5Hz, 3H), 1.05(t, J=7.4Hz, 3H), |
| 283 | 300.28 | 1.41 | H NMR(500MHz, MeOD) 8.65(s, 1H), 8.55(s, 1H), 8.51(s, 1H), 8.48(s, 1H), 7.15(brs, 1H), 4.29(brs, 1H), 3.67–3.60(m, 2H), 2.40(s, 3H), 1.29(d, J=6.7Hz, 3H) |
| 284 | 339.36 | 1.19 | |
| 285 | 415.44 | 1.51 | H NMR(500MHz, MeOD) 8.67(s, 1H), 8.63(s, H), 8.52(s, 1H),) 7.54–7.50(m, 5H), 7.07(s, 1H), 4.34(s, 2H), 3.61(m, 2H), 3.33–3.30(m, 2H), 2.40(s, 3H), 2.33(m, 2H), 2.31(m, 1H), 1.91(m, 2H) |
| 286 | 401.44 | 1.48 | H NMR(500MHz, MeOD) 8.67(s, 1H), 8.63(s, H), 8.52(s, 1H), 8.51(s, 1H), 7.54–7.50(m, 5H), 7.07(s, 1H), 3.61(m, 2H), 3.33–3.30(m, 2H), 2.40(s, 3H), 2.33(m, 2H), 2.31(m, 1H), 1.91(m, 2H) |
| 287 | 314.13 | 1.52 | H NMR(500MHz, MeOD) 8.66(s, 1H), 8.55(s, 1H), 8.52(s, 1H), 8.51(1H), 7.27(s, 1H), 4.38(m, 1H), 3.71–3.62(,m, 2H), 2.65(s, 3H), 1.62–1.59(m, 2H), 1.02(t, J=7.4Hz, 3H) |
| 288 | 314.40 | 1.69 | H NMR(500MHz, MeOD) 8.65(s, 1H), 8.54(s, 1H), 8.50(s, 1H), 7.19(s, 1H), 3.72–3.62(m, 2H), 2.40(s, 3H), 2.2.02(d, J=10.5Hz, 1H), 1.80–1.75(m, 1H), 1.64–1.58(m, 1H), 1.02(t, J=7.4Hz, 3H) |
| 289 | 282.30 | 1.60 | |
| 290 | 296.30 | 1.70 | |
| 291 | 324.30 | 2.00 | |
| 292 | 314.30 | 1.60 | |
| 293 | 300.30 | 1.40 | |
| 294 | 298.30 | 1.80 | |
| 295 | 300.30 | 1.40 | |
| 296 | 312.30 | 2.00 | H NMR(500MHz, DMSO-d6) 8.84(s, 2H), 8.53(s, 1H), 8.47(s, 1H), 2.34(m, 4H), 1.81(d, J=6.6Hz, 1H), 1.14–1.11(m, 3H), 0.90(m, 6H). |
| 297 | 352.40 | 2.30 | |
| 298 | 342.30 | 1.80 | |
| 299 | 310.40 | 1.73 | |
| 300 | 346.40 | 2.17 | |
| 301 | 346.40 | 2.21 | |
| 302 | 340.30 | 2.70 | |

TABLE 10-continued

Characterization Data for Selected Compounds

| Cmpd # (V-) | M+1(obs) | Rt(min) | ¹H-NMR |
|---|---|---|---|
| 303 | 372.40 | 3.30 | |
| 304 | 400.40 | 3.70 | |
| 305 | 379.40 | 2.70 | |
| 306 | 326.30 | 2.20 | |
| 307 | 390.40 | 3.20 | |
| 308 | 374.30 | 1.90 | |
| 309 | 353.40 | 1.90; 1.40 | H NMR(500MHz, DMSO-d6) 8.93(s, 1H), 8.70(s, 1H), 8.54(d, J=1.9Hz, 1H), 7.48(s, 1H), 7.11(s, 1H), 6.96(s, 1H), 3.32–3.25(m, 2H), 2.47(m, 2H), 2.36(s, 3H), 2.00–1.96(m, 1H), 1.88–1.83(m, 2H), 1.72(m, 1H), 1.52(s, 1H). |
| 310 | 270.10 | 1.30 | |
| 311 | 323.40 | 1.12 | |
| 312 | 337.20 | 1.20 | |
| 313 | 339.40 | 0.90 | |
| 314 | 337.42 | 0.90 | |
| 315 | 366.50 | 1.00 | |
| 316 | 297.30 | 1.00 | |
| 317 | 339.40 | 1.30 | |
| 318 | 311.40 | 1.10 | |
| 319 | 325.40 | 1.20 | |
| 320 | 353.50 | 1.30 | |
| 321 | 382.50 | 1.10 | |
| 322 | 309.20 | 1.20 | |
| 323 | 351.50 | 1.40 | |
| 324 | 323.20 | 1.30 | |
| 325 | 339.40 | 1.00 | |
| 326 | 327.40 | 1.10 | |
| 327 | 311.40 | 1.90 | |
| 328 | 355.40 | 1.20 | |
| 329 | 353.40 | 1.20 | |
| 330 | 409.50 | 1.40 | |
| 331 | 380.50 | 1.10 | |
| 332 | 310.30 | 1.90 | |
| 333 | 336.40 | 2.10 | |
| 334 | 416.50 | 2.20 | |
| 335 | 312.30 | 1.50 | |
| 336 | 416.50 | 2.20 | |
| 337 | 311.43 | 1.48 | H NMR(500MHz, DMSO-d6) 8.80(s, 1H), 8.55(s, 1H), 8.44(d, J=1.8Hz, 1H), 8.09(m, 3H), 7.35(s, 1H), 3.99(m, 1H), 3.81(m, 1H), 3.79–3.58(m, 2H), 2.32(s, 3H), 2.19–2.13(m, 1H), 1.93–1.87(m, 1H). |
| 338 | 409.50 | 1.80 | |
| 339 | 324.30 | 2.00 | |
| 340 | 340.30 | 1.60 | |
| 341 | 353.40 | 1.40 | |
| 342 | 326.30 | 1.50 | |
| 343 | 407.40 | 1.68 | |
| 344 | 353.40 | 1.50 | |
| 345 | 270.30 | 1.50 | |
| 346 | 339.30 | 1.30 | |
| 347 | 312.30 | 1.40 | |
| 348 | 395.10 | 1.70 | |
| 349 | 296.30 | 1.70 | |
| 350 | 373.30 | 1.50 | |
| 351 | 346.20 | 1.50 | |
| 352 | 429.40 | 1.90 | |
| 353 | 373.30 | 1.50 | |

Example 13

ITK Inhibition Assay (Radiometric)

Compounds are screened for their ability to inhibit Itk using a radioactive-phosphate incorporation assay. Assays are carried out in a mixture of 100 mM HEPES (pH 7.5) 10 mM MgCl2, 25 mM NaCl, 0.01% BSA and 1 mM DTT. Final substrate concentrations are 15 µM [γ-33P]ATP (400 mCi 33P ATP/mmol ATP, Amersham Pharmacia Biotech/Sigma Chemicals) and 2 µM peptide (SAM68 protein D332-443). Assays carried out at 25° C. in the presence of 30 nM Itk. An assay stock buffer solution is prepared containing all of the reagents listed above, with the exception of ATP and the test compound of interest. 50 µL of the stock solution is placed in a 96 well plated followed by addition of 1.5 µL of DMSO stock containing serial dilutions of the test compound (typically starting from a final concentration of 15 µM with 2-fold serial dilutions) in duplicate (final DMSO concentration 1.5%). The plate is pre-incubated for 10 minutes at 25° C. and the reaction initiated by addition of 50 µL [γ-33P]ATP (final concentration 15 µM).

The reaction is stopped after 10 minutes by the addition of 50 μL of a TCA/ATP mixture (20% TCA, 0.4 mM ATP). A Unifilter GF/C 96 well plate (Perkin Elmer Life Sciences, Cat no. 6005174) is pretreated with 50 μL Milli Q water prior to the addition of the entire reaction mixture (150 μL). The plate is washed with 200 μL Milli Q water followed by 200 mL of a TCA/ATP mixture (5% TCA, 1 mM ATP). This wash cycle is repeated a further 2 times. After drying, 30 μL Optiphase 'SuperMix' liquid scintillation cocktail (Perkin Elmer) is added to the well prior to scintillation counting (1450 Microbeta Liquid Scintillation Counter, Wallac).

$IC_{50}$ data are calculated from non-linear regression analysis of the initial rate data using the Prism software package (GraphPad Prism version 3.0cx for Macintosh, GraphPad Software, San Diego Calif., USA).

Assays are carried out in a mixture of 20 mM MOPS (pH 7.0), 10 mM MgCl2, 0.1% BSA and 1 mM DTT. Final substrate concentrations in the assay are 7.5 μM [γ-33P]ATP (400 mCi 33P ATP/mmol ATP, Amersham Pharmacia Biotech/Sigma Chemicals) and 3 μM peptide (SAM68 protein D332-443). Assays are carried out at 25° C. in the presence of 50 nM Itk. An assay stock buffer solution is prepared containing all of the reagents listed above, with the exception of ATP and the test compound of interest. 50 μL of the stock solution is placed in a 96 well plate followed by addition of 2 μL of DMSO stock containing serial dilutions of the test compound (typically starting from a final concentration of 50 μM with 2-fold serial dilutions) in duplicate (final DMSO concentration 2%). The plate is pre-incubated for 10 minutes at 25° C. and the reaction initiated by addition of 50 μL [γ-33P]ATP (final concentration 7.5 μM).

The reaction is stopped after 10 minutes by the addition of 100 mL 0.2M phosphoric acid+0.01% TWEEN 20. A multiscreen phosphocellulose filter 96-well plate (Millipore, Cat no. MAPHN0B50) is pretreated with 100 μL 0.2M phosphoric acid +0.01% TWEEN 20 prior to the addition of 170 mL of the stopped assay mixture. The plate is washed with 4×200 μL 0.2M phosphoric acid+0.01% TWEEN 20. After drying, 30 μL Optiphase 'SuperMix' liquid scintillation cocktail (Perkin Elmer) is added to the well prior to scintillation counting (1450 Microbeta Liquid Scintillation Counter, Wallac).

Ki(app) data are calculated from non-linear regression analysis of the initial rate data using the Prism software package (GraphPad Prism version 3.0cx for Macintosh, GraphPad Software, San Diego Calif., USA).

Example 14

ITK Inhibition Assay (UV)

Compounds are screened for their ability to inhibit Itk using a standard coupled enzyme assay (Fox et al., Protein Sci., (1998) 7, 2249).

Assays are carried out in a mixture of 20 mM MOPS (pH 7.0), 10 mM MgCl2, 0.1% BSA, 1 mM DTT, 2.5 mM phosphoenolpyruvate, 300 μM NADH, 30 μg/ml pyruvate kinase and 10 μg/ml lactate dehydrogenase. Final substrate concentrations in the assay are 100 μM ATP (Sigma Chemicals) and 3 μM peptide (Biotinylated SAM68 D332-443). Assays are carried out at 25° C. and in the presence of 100 nM Itk.

An assay stock buffer solution is prepared containing all of the reagents listed above, with the exception of ATP and the test compound of interest. 60 μl of the stock solution is placed in a 96 well plate followed by addition of 2 μl of DMSO stock containing serial dilutions of the test compound (typically starting from a final concentration of 15 μM). The plate is preincubated for 10 minutes at 25° C. and the reaction initiated by addition of 5 μl of ATP. Initial reaction rates are determined with a Molecular Devices SpectraMax Plus plate reader over a 10 minute time course. IC50 and Ki data are calculated from non-linear regression analysis using the Prism software package (GraphPad Prism version 3.0cx for Macintosh, GraphPad Software, San Diego Calif., USA).

In general, compounds of the invention, including compounds in Table 1, are effective for the inhibition of ITK.

Example 15

BTK Inhibition Assay

Compounds are screened for their ability to inhibit Btk using a radioactive-phosphate incorporation assay at Vertex Pharmaceuticals. Assays are carried out in a mixture of 20 mM MOPS (pH 7.0), 10 mM MgCl2, 0.1% BSA and 1 mM DTT. Final substrate concentrations in the assay are 50 μM [γ-33P]ATP (200 mCi 33P ATP/mmol ATP, Amersham Pharmacia Biotech, Amersham, UK/Sigma Chemicals) and 2 μM peptide (SAM68 D332-443). Assays are carried out at 25° C. and in the presence of 25 nM Btk. An assay stock buffer solution is prepared containing all of the reagents listed above, with the exception of the peptide and the test compound of interest. 75 μL of the stock solution is placed in a 96 well plate followed by addition of 2 μL of DMSO stock containing serial dilutions of the test compound (typically starting from a final concentration of 15 μM) in duplicate (final DMSO concentration 2%). The plate is preincubated for 15 minutes at 25° C. and the reaction initiated by addition of 25 μL peptide (final concentration 2 μM). Background counts are determined by the addition of 100 mL 0.2M phosphoric acid+0.01% TWEEN to control wells containing assay stock buffer and DMSO prior to initiation with peptide.

The reaction is stopped after 10 minutes by the addition of 100 mL 0.2M phosphoric acid+0.01% TWEEN. A multiscreen phosphocellulose filter 96-well plate (Millipore, Cat no. MAPHN0B50) is pretreated with 100 μL 0.2M phosphoric acid+0.01% TWEEN 20 prior to the addition of 170 mL of the stopped assay mixture. The plate is washed with 4×200 μL 0.2M phosphoric acid+0.01% TWEEN 20. After drying, 30 μL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis using the Prism software package (GraphPad Prism version 3.0cx for Macintosh, GraphPad Software, San Diego Calif., USA).

Compounds are screened for their ability to inhibit Btk using an AlphaScreen™ phosphotyrosine assay at Vertex Pharmaceuticals. Assays are carried out in a mixture of 20 mM MOPS (pH 7.0), 10 mM MgCl2, 0.1% BSA and 1 mM DTT. Final substrate concentrations in the assay are 50 μM ATP (Sigma Chemicals) and 2 μM peptide (Biotinylated SAM68 D332-443). Assays are carried out at 25° C. and in the presence of 25 nM Btk. An assay stock buffer solution is prepared containing all of the reagents listed above, with the exception of peptide and the test compound of interest. 37.5 μL of the stock solution is placed in each well of a 96 well plate followed by 1 μL of DMSO containing serial dilutions of the test compound (typically starting from a final concentration of 15 μM) in duplicate (final DMSO concentration 2%). The plate is preincubated for 15 minutes at 25° C. and the reaction initiated by addition of 12.5 μL peptide (final concentration 2 μM). Background counts are determined by the addition of 5 μL 500 mM EDTA to control wells containing assay stock buffer and DMSO prior to initiation with Biotin-SAM68.

The reaction is stopped after 30 minutes by diluting the reaction 225-fold into MOPS buffer (20 mM MOPS (pH 7.0), 1 mM DTT, 10 mM MgCl2, 0.1% BSA) containing 50 mM EDTA to bring the final concentration of peptide to 9 nM.

AlphaScreen™ reagents are prepared according to the manufacturers instructions (AlphaScreen™ phosphotyrosine (P-Tyr-100) assay kit, PerkinElmer catalogue number 6760620C). Under subdued lighting, 20 μL of AlphaScreen™ reagents are placed in each well of a white half area 96 well plate (Corning Inc.—COSTAR 3693) with 30 μL of the stopped, diluted kinase reactions. Plates are incubated in the dark for 60 minutes prior to reading on a Fusion Alpha plate reader (PerkinElmer).

After removing mean background values for all of the data points, Ki(app) data are calculated from non-linear regression analysis using the Prism software package (GraphPad Prism version 3.0cx for Macintosh, GraphPad Software, San Diego Calif., USA).

In general, compounds of the invention, including compounds in Table 1, are effective for the inhibition of Btk.

Example 16

RLK Inhibition Assay

Compounds are screened for their ability to inhibit Rlk using a standard coupled enzyme assay (Fox et al., *Protein Sci.*, (1998) 7, 2249). Assays are carried out in a mixture of 20 mM MOPS (pH 7.0), 10 mM MgCl2, 0.1% BSA and 1 mM DTT. Final substrate concentrations in the assay are 100 μM ATP (Sigma Chemicals) and 10 μM peptide (Poly Glu:Tyr 4:1). Assays are carried out at 30° C. and in the presence of 40 nM Rlk. Final concentrations of the components of the coupled enzyme system are 2.5 mM phosphoenolpyruvate, 300 μM NADH, 30 μg/ml pyruvate kinase and 10 μg/ml lactate dehydrogenase.

An assay stock buffer solution is prepared containing all of the reagents listed above, with the exception of ATP and the test compound of interest. 60 μl of the stock solution is placed in a 96 well plate followed by addition of 2 μl of DMSO stock containing serial dilutions of the test compound (typically starting from a final concentration of 7.5 μM). The plate is preincubated for 10 minutes at 30° C. and the reaction initiated by addition of 5 μl of ATP. Initial reaction rates are determined with a Molecular Devices SpectraMax Plus plate reader over a 10 minute time course. IC50 and Ki data are calculated from non-linear regression analysis using the Prism software package (GraphPad Prism version 3.0cx for Macintosh, GraphPad Software, San Diego Calif., USA).

In general, compounds of the invention, including compounds in Table 1, are effective for the inhibition of RLK.

Example 17

JAK3 Inhibition Assays

Compound inhibition of JAK is assayed by the method described by G. R. Brown, et al, *Bioorg. Med. Chem. Lett.* 2000, vol. 10, pp 575-579 in the following manner. Into Maxisorb plates, previously coated at 4° C. with Poly (Glu, Ala, Tyr) 6:3:1 then washed with phosphate buffered saline 0.05% and Tween (PBST), is added 2 μM ATP, 5 mM MgCl2, and a solution of compound in DMSO. The reaction is started with JAK enzyme and the plates incubated for 60 minutes at 30° C. The plates are then washed with PBST, 100 μL HRP-Conjugated 4G10 antibody is added, and the plate incubated for 90 minutes at 30° C. The plate is again washed with PBST, 100 μL TMB solution is added, and the plates are incubated for another 30 minutes at 30° C. Sulfuric acid (100 μL of 1M) is added to stop the reaction and the plate is read at 450 nm to obtain the optical densities for analysis to determine $K_i$ values.

Compound inhibition of JAK may also be assayed in the following manner: Compounds are screened for their ability to inhibit JAK3 using the assay shown below. Reactions are carried out in a kinase buffer containing 100 mM HEPES (pH 7.4), 1 mM DTT, 10 mM MgCl$_2$, 25 mM NaCl, and 0.01% BSA. Substrate concentrations in the assay are 5 μM ATP (200 uCi/μmole ATP) and 1 μM poly(Glu)$_4$Tyr. Reactions are carried out at 25° C. and 1 nM JAK3. To each well of a 96 well polycarbonate plate is added 1.5 μl of a candidate JAK3 inhibitor along with 50 μl of kinase buffer containing 2 μM poly(Glu)$_4$Tyr and 10 μM ATP. This is then mixed and 50 μl of kinase buffer containing 2 nM JAK3 enzyme is added to start the reaction. After 20 minutes at room temperature (25 C), the reaction is stopped with 50 μl of 20% trichloroacetic acid (TCA) that also contained 0.4 mM ATP. The entire contents of each well are then transferred to a 96 well glass fiber filter plate using a TomTek Cell Harvester. After washing, 60 μl of scintillation fluid is added and $^{33}$P incorporation detected on a Perkin Elmer TopCount.

In general, compounds of the invention, including compounds in Table 1, are effective for the inhibition of JAK (e.g., JAK-3).

Example 18

Aurora B (Aurora-1) Inhibition Assay

An assay buffer solution is prepared which consists of 25 mM HEPES (pH 7.5), 10 mM MgCl$_2$, 0.1% BSA and 10% glycerol. A 22 nM Aurora-B solution, also containing 1.7 mM DTT and 1.5 mM Kemptide (LRRASLG), is prepared in assay buffer. To 22 μL of the Aurora-B solution, in a 96-well plate, is added 2 μl of a compound stock solution in DMSO and the mixture is allowed to equilibrate for 10 minutes at 25° C. The enzyme reaction is initiated by the addition of 16 μl stock [γ-$^{33}$P]-ATP solution (~20 nCi/μL) prepared in assay buffer, to a final assay concentration of 800 μM. The reaction is stopped after 3 hours by the addition of 16 μL 500 mM phosphoric acid and the levels of $^{33}$P incorporation into the peptide substrate is determined by the following method.

A phosphocellulose 96-well plate (Millipore, Cat no. MAPHNOB50) is pre-treated with 100 μL of a 100 mM phosphoric acid prior to the addition of the enzyme reaction mixture (40 μL). The solution is left to soak on to the phosphocellulose membrane for 30 minutes and the plate subsequently is washed four times with 200 μL of a 100 mM phosphoric acid. To each well of the dry plate is added 30 μL of Optiphase 'SuperMix' liquid scintillation cocktail (Perkin Elmer) prior to scintillation counting (1450 Microbeta Liquid Scintillation Counter, Wallac). Levels of non-enzyme catalysed background radioactivity are determined by adding 16 μL of the 500 mM phosphoric acid to control wells, containing all assay components (which acts to denature the enzyme), prior to the addition of the [γ-$^{33}$P]-ATP solution. Levels of enzyme catalysed $^{33}$P incorporation are calculated by subtracting mean background counts from those measured at each inhibitor concentration. For each Ki determination 8 data points, typically covering the concentration range 0-10 μM compound, are obtained in duplicate (DMSO stocks are prepared from an initial compound stock of 10 mM with subsequent 1:2.5 serial dilutions). Ki values are calculated from initial rate data by non-linear regression using the Prism software package (Prism 3.0, Graphpad Software, San Diego, Calif.).

Example 19

Aurora-A (Aurora-2) Inhibition Assay

Compounds are screened for their ability to inhibit Aurora-2 using a standard coupled enzyme assay (Fox et al., Protein Sci., (1998) 7, 2249). Assays are carried out in a mixture of 100 mM Hepes (pH7.5), 10 mM $MgCl_2$, 1 mM DTT, 25 mM NaCl, 2.5 mM phosphoenolpyruvate, 300 µM NADH, 30 µg/ml pyruvate kinase and 10 µg/ml lactate dehydrogenase. Final substrate concentrations in the assay are 400 µM ATP (Sigma Chemicals) and 570 µM peptide (Kemptide, American Peptide, Sunnyvale, Calif.). Assays are carried out at 30° C. and in the presence of 40 nM Aurora-2.

An assay stock buffer solution is prepared containing all of the reagents listed above, with the exception of Aurora-2 and the test compound of interest. 55 µl of the stock solution is placed in a 96 well plate followed by addition of 2 µl of DMSO stock containing serial dilutions of the test compound (typically starting from a final concentration of 7.5 µM). The plate is preincubated for 10 minutes at 30° C. and the reaction initiated by addition of 10 µl of Aurora-2. Initial reaction rates are determined with a Molecular Devices SpectraMax Plus plate reader over a 10 minute time course. IC50 and Ki data are calculated from non-linear regression analysis using the Prism software package (GraphPad Prism version 3.0cx for Macintosh, GraphPad Software, San Diego Calif., USA).

Example 20 c-Met Inhibition Assay

Compounds are screened for their ability to inhibit c-Met kinase activity using a standard coupled enzyme system (Fox et al., *Protein Sci.* 1998, 7, 2249). Reactions are carried out in a solution containing 100 mM HEPES (pH 7.5), 10 mM $MgCl_2$, 25 mM NaCl, 300 µM NADH, 1 mM DTT, and 1.5% DMSO. Final substrate concentrations in the assay are 200 µM ATP (Sigma Chemicals, St Louis, Mo.) and 10 µM poly-GluTyr (Sigma Chemical Company, St. Louis). Reactions are carried out at 30° C. and 80 nM c-Met. Final concentrations of the components of the coupled enzyme system are 2.5 mM phosphoenolpyruvate, 300 µM NADH, 30 µg/ml pyruvate kinase and 10 µg/ml lactate dehydrogenase.

An assay stock buffer solution is prepared containing all of the reagents listed above with the exception of ATP and a test compound of the present invention. The assay stock buffer solution (175 µl) is incubated in a 96 well plate with 5 µl of the test compound of the present invention at final concentrations spanning 0.006 µM to 12.5 µM at 30° C. for 10 minutes. Typically, a 12-point titration is conducted by preparing serial dilutions (from 10 mM compound stocks) with DMSO of the test compounds of the present invention in daughter plates. The reaction is initiated by the addition of 20 µl of ATP (final concentration 200 µM). Rates of reaction are obtained using a Molecular Devices Spectramax plate reader (Sunnyvale, Calif.) over 10 minutes at 30° C. The $K_i$ values are determined from the rate data as a function of inhibitor concentration.

Table 11 depicts enzyme inhibition data ($K_i$) for certain exemplary compounds. Compound numbers in Table 11 corresponds to those compounds depicted in Table 5. In Table 11, "A" represents a $K_i$ of less than 0.5 µM, "B" represents a $K_i$ of between 0.5 and less than 5.0 µM, and "C" represents a $K_i$ of greater than or equal to 5.0 µM for the indicated enzyme.

TABLE 11

Biological Characterization Data for Selected Compounds

| Cmpd # (V–) | AurA | AurB | ITK | JAK3 | Met | RLK |
|---|---|---|---|---|---|---|
| 1 | | | | C | | |
| 2 | B | | B | C | B | |
| 3 | | | B | C | B | |
| 4 | | | B | C | B | |
| 5 | | | B | C | B | |
| 6 | | | B | B | B | |
| 7 | | | B | C | B | |
| 8 | | | B | C | B | |
| 9 | | | B | C | B | |
| 10 | | | B | C | B | |
| 11 | | | B | C | B | |
| 12 | | | B | C | B | |
| 13 | | | B | C | B | |
| 14 | B | | B | C | B | |
| 15 | | | B | C | B | |
| 16 | | | B | C | B | |
| 17 | | | B | C | B | |
| 18 | A | | A | C | A | |
| 19 | | | B | C | B | |
| 20 | | | B | C | B | |
| 21 | | | B | C | B | |
| 22 | B | | B | C | A | |
| 23 | | | B | C | B | |
| 24 | B | | B | C | B | |
| 25 | | | B | C | B | |
| 26 | | | B | C | B | |
| 27 | | | B | C | B | |
| 28 | | | B | C | B | |
| 29 | | | B | C | B | |
| 30 | | | B | C | B | |
| 31 | | | B | C | B | |
| 32 | | | B | C | B | |
| 33 | B | | B | C | B | |
| 34 | | | B | C | B | |
| 35 | | | B | C | B | |
| 36 | | | B | C | B | |
| 37 | | | B | C | B | |
| 38 | | | B | C | B | |
| 39 | | | B | C | B | |
| 40 | | | B | C | B | |
| 41 | | | B | C | B | |
| 42 | | | B | C | B | |
| 43 | | | B | C | B | |
| 44 | | | B | C | B | |
| 45 | | | B | C | B | |
| 46 | | | B | C | B | |
| 47 | | | B | C | B | |
| 48 | | | B | C | B | |
| 49 | | | B | C | B | |
| 50 | | | B | C | A | |
| 51 | B | | A | B | A | |
| 52 | | | B | C | B | |
| 53 | | | B | C | A | |
| 54 | B | | B | C | A | |
| 55 | B | | B | C | A | |
| 56 | | | B | C | B | |
| 57 | B | | B | C | A | |
| 58 | | | B | C | A | |
| 59 | | | B | C | B | |
| 60 | | | B | B | A | |
| 61 | | | A | B | A | |
| 62 | B | | A | B | A | |
| 63 | A | | A | B | A | |
| 64 | A | | A | B | A | |
| 65 | B | | A | B | A | |
| 66 | | | B | B | A | |
| 67 | A | | B | B | A | |
| 68 | A | | A | B | A | |
| 69 | | | A | B | A | |
| 70 | A | | A | B | A | |
| 71 | A | | A | B | A | |

TABLE 11-continued

Biological Characterization Data for Selected Compounds

| Cmpd # (V−) | AurA | AurB | ITK | JAK3 | Met | RLK |
|---|---|---|---|---|---|---|
| 72 | A |  | A | B | A |  |
| 73 | B |  | B | C | A |  |
| 74 | B |  | A | B | A |  |
| 75 | A |  | B | C | A |  |
| 76 | A |  | A | B | A |  |
| 77 |  |  | B | C | B |  |
| 78 | A |  | A | B | A |  |
| 79 | A |  | A | B | A |  |
| 80 |  |  | A | C | A |  |
| 81 | A |  | A | B | A |  |
| 82 | B |  | A | C | A |  |
| 83 | A |  | A | B | A |  |
| 84 |  |  | A | B | A |  |
| 85 | B |  | A | B | A |  |
| 86 | B |  | B | C | A |  |
| 87 | A |  | A | B | A |  |
| 88 |  |  | A | B | A |  |
| 89 | A |  | A | B | A |  |
| 90 | A |  | A | B | A |  |
| 91 |  |  | A | A | A |  |
| 92 | A |  | A | B | A |  |
| 93 | A |  | A | B | A |  |
| 94 | B |  | A | C | A |  |
| 95 |  |  | A | B | A |  |
| 96 | B |  | B | C | A |  |
| 97 | A |  | A | B | A |  |
| 98 | A |  | A | B | A |  |
| 99 |  |  | A | B | A |  |
| 100 |  |  | B | C | A |  |
| 101 | B |  | B | C | A |  |
| 102 | B |  | B | C | A |  |
| 103 |  |  | B | C | A |  |
| 104 | B |  | B | C | A |  |
| 105 |  |  | B | C | A |  |
| 106 | B |  | B | C | A |  |
| 107 |  |  | B | B | A |  |
| 108 |  |  | B | C | A |  |
| 109 |  |  | B | C | A |  |
| 110 |  |  | A | B | A |  |
| 111 |  |  | B | C | A |  |
| 112 | B |  | B | C | A |  |
| 113 |  |  | A | B | A |  |
| 114 | B |  | B | C | A |  |
| 115 | B |  | B | C | A |  |
| 116 | B |  | B | C | A |  |
| 117 |  |  | B | C | A |  |
| 118 |  |  | B | C | A |  |
| 119 |  |  | B | B | A |  |
| 120 |  |  | A | B | A |  |
| 121 |  |  | B | C | A7 |  |
| 122 |  |  | A | B | A |  |
| 123 |  |  | B | C | A |  |
| 124 | B |  | B | C | A |  |
| 125 |  |  | B | C | A |  |
| 126 |  |  | B | C | A |  |
| 127 | B |  | B | C | A |  |
| 128 |  |  | B | C | A |  |
| 129 | A |  | A | B | A |  |
| 130 | B |  | A | C | A |  |
| 131 |  |  | B | B | B |  |
| 132 | B | B | B | C | A |  |
| 133 | A | B | B | B | A |  |
| 134 | B | B | B | C | B |  |
| 135 | B | B | B | C | B |  |
| 136 |  |  | B | C | B |  |
| 137 |  |  | B | C | B |  |
| 138 |  |  | B | C | B |  |
| 139 | B |  | B | C | A |  |
| 140 |  |  | B | C | A |  |
| 141 |  |  | B | C | A |  |
| 142 |  |  | B | B | A |  |
| 143 |  |  | B | C |  |  |
| 144 |  |  | B | C | A |  |
| 145 |  |  | A | C | A |  |
| 146 | B |  | A | C | A |  |
| 147 |  |  | B | C | B |  |
| 148 |  |  | A | B | A |  |
| 149 |  |  | B | B | A |  |
| 150 |  |  | A | C | A |  |
| 151 | B |  | A | C | A |  |
| 152 | B |  | A | C | A |  |
| 153 |  |  | A | B | A |  |
| 154 | B |  | B | C | A |  |
| 155 | B |  | A | B | A |  |
| 156 | B |  | B | C | A |  |
| 157 |  |  | A | C | A |  |
| 158 |  |  | B | C | A |  |
| 159 | B |  | A | B | A |  |
| 160 | B |  | B | C | A |  |
| 161 |  |  | B | C | A |  |
| 162 |  |  | B | C | B |  |
| 163 |  |  | B | C | A |  |
| 164 |  |  | A | C | A |  |
| 165 | A |  | A | C | A |  |
| 166 | B |  | A | C | A |  |
| 167 |  |  | B | C | A |  |
| 168 |  |  | B | C | B |  |
| 169 |  |  | A | C | A |  |
| 170 |  |  | B | C | B |  |
| 171 |  |  | B | C | A |  |
| 172 |  |  | B | C | B |  |
| 173 | B |  | A | B | A |  |
| 174 |  |  | B | C | B |  |
| 175 | B |  | B | B | A |  |
| 176 | B |  | A | B | A |  |
| 177 | A |  | A | B | A |  |
| 178 | A | B | A | C | B |  |
| 179 | A | A | A | A | A |  |
| 180 | A |  | A | A | A |  |
| 181 | A |  | A | A | A |  |
| 182 | A |  | A | A | A |  |
| 183 | A |  | A | B | A |  |
| 184 | A |  | A | B | A |  |
| 185 | A |  | A | A | A |  |
| 186 |  |  | A | C | B |  |
| 187 |  |  | B | C | A |  |
| 188 | A |  | A | B | A | A |
| 189 | B |  | A | B | A |  |
| 190 | B |  | A | B | A |  |
| 191 | A |  | A | B | A | A |
| 192 | A |  | A |  |  |  |
| 193 |  |  | A |  |  |  |
| 194 | A |  | A | B | A |  |
| 195 | A |  | A | B | A | B |
| 196 |  |  | A |  |  |  |
| 197 |  |  | A | C | A |  |
| 198 |  |  | B | C | B |  |
| 199 |  |  | B | C | B |  |
| 200 |  |  | B | C | B |  |
| 201 |  |  | B | C | B |  |
| 202 | B |  | A | C | A | B |
| 203 |  |  | A |  |  |  |
| 204 | B |  | B | C | B |  |
| 205 |  |  | B | C | B |  |
| 206 | B |  | B | C | B |  |
| 207 |  |  | B | C | B |  |
| 208 | A |  | A | B | B |  |
| 209 |  |  | A | C | B |  |
| 210 |  |  | A |  |  |  |
| 211 |  |  | B | C | B |  |
| 212 | A |  | A | C | A |  |
| 213 |  |  | B | C | B |  |
| 214 | A |  | A | B | A | B |
| 215 | B |  | A | C | A | B |
| 216 |  |  | B | C | B |  |
| 217 | A |  | A | B | A | A |
| 218 |  |  | B |  |  |  |
| 219 | B |  | B | C | B |  |
| 220 |  |  | B |  |  |  |
| 221 | B |  | B | B | A |  |

TABLE 11-continued

Biological Characterization Data for Selected Compounds

| Cmpd # (V−) | AurA | AurB | ITK | JAK3 | Met | RLK |
|---|---|---|---|---|---|---|
| 222 | A |  | A | B | A | B |
| 223 | B |  | A | B | A | B |
| 224 | A |  | A | N | A |  |
| 225 | B |  | B | C | A |  |
| 226 | B |  | A | C | A |  |
| 227 | B |  | A | C | A | B |
| 228 | B |  | A | C | A | B |
| 229 | B |  | A | C | A | B |
| 230 | A |  | A | B | A | A |
| 231 | A |  | A | B | A | B |
| 232 | B |  | A | C | A | B |
| 233 | A |  | A | B | A | B |
| 234 | A |  | A | B | A | B |
| 235 |  |  | B | C | B |  |
| 236 | A |  | A | B | A | B |
| 237 | B |  | A | B | A |  |
| 238 | B |  | B | B | A |  |
| 239 |  |  | B | C | B |  |
| 240 |  |  | B | C | B |  |
| 241 | A |  | A | A | A |  |
| 242 | A |  | A | A | A |  |
| 243 | A |  | A | A | A |  |
| 244 | A |  | A | A | A |  |
| 245 |  |  | B | C | A |  |
| 246 |  |  | B | C | A |  |
| 247 |  |  | B | C | A |  |
| 248 |  |  | B | B | A |  |
| 249 |  |  | B | B | A |  |
| 250 |  |  | A | B | A |  |
| 251 |  |  | B | C | A |  |
| 252 |  |  | B | C | B |  |
| 253 |  |  | B | C | B |  |
| 254 |  |  | B | C | B |  |
| 255 |  |  | B | C | B |  |
| 256 |  |  | B | C | B |  |
| 257 |  |  | B | C | B |  |
| 258 |  |  | B | C | B |  |
| 259 |  |  | B | C | B |  |
| 260 |  |  | B | C | B |  |
| 261 |  |  | B | C | B |  |
| 262 |  |  | B | C | B |  |
| 263 |  |  | B | C | B |  |
| 264 |  |  | B | C | B |  |
| 265 |  |  | B | C | B |  |
| 266 |  |  | B | C | B |  |
| 267 |  |  | B | C | B |  |
| 268 |  |  | B | C | B |  |
| 269 |  |  | B | C | B |  |
| 270 |  |  | B | C | B |  |
| 271 |  |  | B | C | B |  |
| 272 |  |  | B | C | B |  |
| 273 |  | B | B | B | B | A |
| 274 |  | B | B | A | B | A |
| 275 |  |  | B | C | B |  |
| 276 | B |  | A | B | A |  |
| 277 | B |  | B | B | A |  |
| 278 | B |  | B | B | A |  |
| 279 | A |  | A | A | A |  |
| 280 | A |  | B | C | B |  |
| 281 | B |  | B | B | A |  |
| 282 |  |  | B | B | A |  |
| 283 |  |  | B | B | B |  |
| 284 |  |  | B | B | A |  |
| 285 | B |  | B | B | A |  |
| 286 | B |  | B | B | A |  |
| 287 |  |  | B | B | A |  |
| 288 |  |  | A | B | A |  |
| 289 | B |  | B | B | A |  |
| 290 | B |  | B | B | A |  |
| 291 | B |  | B | B | A |  |
| 292 |  |  | B | B | A |  |
| 293 | B |  | B | B | A |  |
| 294 | B |  | B | B | A |  |
| 295 | B |  | B | B | A |  |
| 296 |  |  | A | B | A |  |
| 297 |  |  | B | B | A |  |
| 298 |  |  | A | B | A |  |
| 299 |  |  | A | A | A |  |
| 300 |  |  | B | A | A |  |
| 301 |  |  | B | C | B |  |
| 302 |  |  | A | B | A |  |
| 303 |  |  | B | B | B |  |
| 304 |  |  | B | C | B |  |
| 305 |  |  | B | C | B |  |
| 306 |  |  | B | B | A |  |
| 307 |  |  | B | B | A |  |
| 308 |  |  | A | A | A |  |
| 309 |  |  | B | A | A |  |
| 310 |  |  | B | C | B |  |
| 311 |  |  | B | C | A |  |
| 312 |  |  | B | C | B |  |
| 313 |  |  | B | C | B |  |
| 314 |  |  | B | C | B |  |
| 315 |  |  | B | C | B |  |
| 316 |  |  | B | C | B |  |
| 317 |  |  | B | C | B |  |
| 318 |  |  | B | C | B |  |
| 319 |  |  | B | C | A |  |
| 320 |  |  | B | C | B |  |
| 321 |  |  | B | C | B |  |
| 322 |  |  | B | C | B |  |
| 323 |  |  | B | C | B |  |
| 324 |  |  | B | C | A |  |
| 325 |  |  | B | C | B |  |
| 326 |  |  | B | C | B |  |
| 327 |  |  | B | C | B |  |
| 328 |  |  | B | C | B |  |
| 329 |  |  | B | C | A |  |
| 330 |  |  | B | C | B |  |
| 331 |  |  | B | C | B |  |
| 332 |  |  | A | B | A |  |
| 333 |  |  | A | B | A |  |
| 334 |  |  | B | B | A |  |
| 335 |  |  | B | B | A |  |
| 336 |  |  | B | B | A |  |
| 337 |  |  | A | A | A |  |
| 338 |  |  | B | B | A |  |
| 339 |  |  | A | A | A |  |
| 340 |  |  | B | B | A |  |
| 341 |  |  | B | B | B |  |
| 342 |  |  | B | B | A |  |
| 343 |  |  | B | B | B |  |

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

We claim:

1. A compound of formula I':

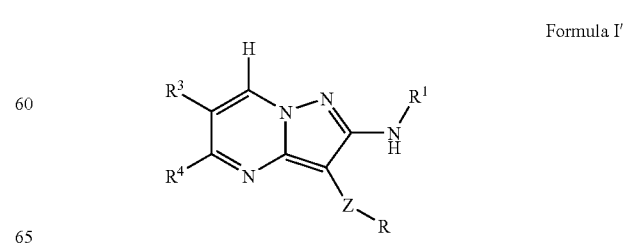

Formula I' or a pharmaceutically accepted salt thereof, wherein

R is —(C=Q)R$^{2a}$, CN, or Y; wherein
Y is a 5-6 membered aryl or heteroaryl ring; wherein said heteroaryl ring is selected from

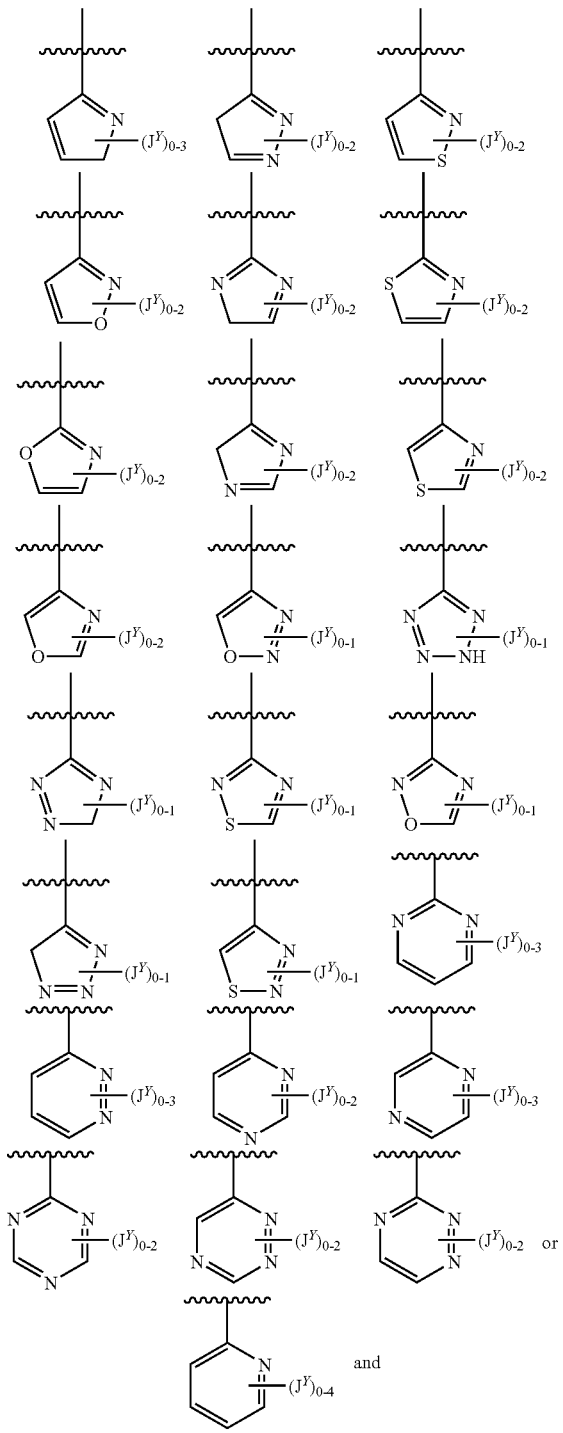

each Y is independently and optionally substituted with 0-4 J$^Y$;

Q is O, NH, NR', or S;

R' is C$_{1-6}$alkyl optionally substituted with 0-4 occurrences of halo, C$_{1-6}$aliphatic, NO$_2$, NH$_2$, —N(C$_{1-6}$alkyl), —N(C$_{1-6}$alkyl)$_2$, SH, —S(C$_{1-6}$alkyl), OH, —O(C$_{1-6}$alkyl), —C(O)(C$_{1-6}$alkyl), —C(O)NH$_2$, —C(O)N(C$_{1-6}$alkyl), or —C(O)N(C$_{1-6}$alkyl)$_2$;

R$^{2a}$ is C$_{1-6}$aliphatic, C$_{6-10}$aryl, 5-10 membered heteroaryl, 5-10 membered heterocyclyl, OR$^5$, or N(R$^5$)$_2$; and each R$^{2a}$ is independently and optionally substituted with 0-5 J$^{2a}$;

R$^1$ is H, —C(O)(C$_{1-6}$alkyl), —C(O)O(C$_{1-6}$alkyl), —C(O)NH$_2$, —C(O)N(C$_{1-6}$alkyl), —C(O)N(C$_{1-6}$alkyl)$_2$; or C$_{1-6}$aliphatic; each R$^1$ is optionally substituted with 0-4 occurrences of halo, C$_{1-6}$haloalkyl, C$_{1-6}$aliphatic, NO$_2$, NH$_2$, —N(C$_{1-6}$alkyl), —N(C$_{1-6}$alkyl)$_2$, SH, —S(C$_{1-6}$alkyl), OH, or —O(C$_{1-6}$alkyl);

Z is a bond;

R$^3$ and R$^4$ are each independently H, halogen, C$_{1-6}$alkoxy, N(R$^5$)$_2$, CN, NO$_2$, or U$_m$—V wherein m is 0 or 1;

V is H, C$_{6-10}$aryl, 5-10 membered heteroaryl, C$_{3-10}$cycloaliphatic, 5-10 membered heterocyclyl, or C$_{1-12}$aliphatic wherein: up to two methylene units of the alkylidene chain are optionally and independently replaced by a heteroatom selected from O, N, or S in a chemically stable arrangement; V is optionally substituted with 0-4 R$^8$;

U is C$_{1-12}$alkylidene chain wherein up to two methylene units of the chain are optionally and independently replaced by —NH—, —NR$^5$—, —O—, —S—, —CO$_2$—, —OC(O)—, —C(O)CO—, —C(O)—, —C(O)NH—, —C(O)NR$^5$—, —C(=N—CN), —NHCO—, —NR$^5$CO—, —NHC(O)O—, —NR$^5$C(O)O—, —SO$_2$NH—, —SO$_2$NR$^5$—, —NHSO$_2$—, —NR$^5$SO$_2$—, —NHC(O)NH—, —NR$^5$C(O)NH—, —NHC(O)NR$^5$—, —NR$^5$C(O)NR$^5$, —OC(O)NH—, —OC(O)NR$^5$—, —NHNH—, —NHNR$^5$—, —NR$^5$NR$^5$—, —NR$^5$NH—, —NHSO$_2$NH—, —NR$^5$SO$_2$NH—, —NHSO$_2$NR$^5$—, —NR$^5$SO$_2$NR$^5$—, —SO—, —SO$_2$—, —PO—, —PO$_2$—, or —POR$^5$—; U is optionally substituted with 0-6 J$^U$;

R$^5$ is C$_{1-4}$haloalkyl, —C(O)COR$^6$, —C(O)R$^6$, —C(O)OR$^6$, —C(O)N(R$^6$)$_2$, —SO$_2$R$^6$, C$_{0-6}$alkyl-heterocyclyl, C$_{0-6}$alkyl-heteroaryl, C$_{0-6}$alkyl-aryl, C$_{0-6}$alkyl-cycloaliphatic or C$_{1-6}$ aliphatic wherein up to three methylene unit of the aliphatic chain are optionally and independently replaced by —NR"—, —O—, —S—, —CO$_2$—, —OC(O)—, —C(O)CO—, —C(O)—, —C(O)NR"—, —NR"CO—, —NR"C(O)O—, —SO$_2$NR"—, —NR"SO$_2$—, —C(O)NR"NR"—, —NR"C(O)NR"—, —OC(O)NR"—, —NR"NR"—, —NR"SO$_2$NR"—, —SO—, —SO$_2$—, —PO—, —PO$_2$—, or —POR"— in a chemically stable arrangement; each R$^5$ is independently and optionally substituted with 0-5 J$^{R5}$; or two R$^5$ groups taken together with the atom to which they are attached optionally join to form a 5-10 membered carbocyclic or heterocyclic ring; wherein said ring is optionally substituted with 0-4 J';

R$^6$ is H, C$_{1-6}$alkoxy, C$_{1-4}$haloalkyl, C$_{0-6}$alkyl-heterocyclyl, C$_{0-6}$alkyl-heteroaryl, C$_{0-6}$alkyl-aryl, C$_{0-6}$alkyl-cycloaliphatic, or C$_{1-6}$ aliphatic wherein up to two methylene units of the aliphatic chain are optionally and independently replaced by a heteroatom selected from O, N, or S in a chemically stable arrangement; each R$^6$ is independently and optionally substituted with 0-5 J$^{R6}$; or two R$^6$ groups taken together with the atom to which they are attached optionally join to form a 5-10 membered carbocyclic or heterocyclic ring; wherein said ring is optionally substituted with 0-4 J";

R$^8$ is halogen, C$_{1-4}$haloalkyl, phenyl, 5-8 membered heterocyclyl, 5-6 membered heteroaryl, —OR$^6$, —N(R$^6$)$_2$, —SR⁶, NO₂, CN, —COOR⁶, —C(O)N(R⁶)₂, —SO₂R⁶, —SO₂N(R⁶)₂, —NR⁶C(O)R⁶, —C(O)R⁶, —OC(O)R⁶, —NR⁶C(O)O—R⁶, —NR⁶SO₂—R⁶, —C(O)NR⁶N (R⁶)₂, —NR⁶C(O)N(R⁶)₂, —OC(O)N(R⁶)₂, —NR⁶N (R⁶)₂, —NR⁶SO₂N(R⁶)₂ or $C_{1-12}$ aliphatic, wherein up to three methylene units of the aliphatic chain can be optionally interrupted with —C(O)R⁶, —C(O)O—, —OC(O)—, —C(O)—, —C(O)N(R⁶)—, —NR⁶CO (R⁶)—, —O—, —NR⁶—, or —S—; each R⁸ is independently and optionally substituted with 0-5 $J^{R8}$;

each $J^Y$, $J^{2a}$, $J^u$, $J^{R5}$, $J^{R6}$, $J^{R8}$, J', and J" is independently selected from N(R⁹)₂, SR⁹, OR⁹, halo, CN, NO₂, COOR⁹, C(O)R⁹, SO₂R⁹, SOR⁹, —X—CF3, —X—SH, —X—OH, $C_{1-4}$haloalkyl, $C_{6-10}$ aryl, —X—($C_{6-10}$ aryl), 5-10 membered heteroaryl, —X-(5-10 membered heteroaryl), $C_{3-10}$ cycloaliphatic, —X—($C_{3-10}$ cycloaliphatic), 5-10 membered heterocyclyl, —X-(5-10 membered heterocyclyl), or X;

X is $C_{1-12}$ aliphatic wherein up to two methylene units of the alkylidene chain are optionally and independently replaced by —NH—, —NR"—, —O—, —S—, —C₂—, —OC(O)—, —C(O)CO—, —C(O)—, —C(O) NH—, —C(O)NR"—, —C(=N—CN), —NHCO—, —NR"CO—, —NHC(O)O—, —NR"C(O)O—, —SO₂NH—, —SO₂NR"—, —NHSO₂—, —NR"SO₂—, —NHC(O)NH—, —NR"C(O)NH—, —NHC(O)NR"—, —NR"C(O)NR", —OC(O)NH—, —OC(O)NR"—, —NHNH—, —NHNR"—, —NR"NR"—, —NR"NH—, —NHSO₂NH—, —NR"SO₂NH—, —NHSO₂NR"—, —NR"SO₂NR"—, —SO—, —SO₂—, —PO—, —PO₂—, or —POR"—; in a chemically stable arrangement; wherein R" is H or $C_{1-6}$ aliphatic;

each $J^Y$, $J^{2a}$, $J^u$, $J^{R5}$, $J^{R6}$, J', and J" is optionally and independently substituted with 0-4 occurrences of N(R⁹)₂, SR⁹, OR⁹, halo, CN, NO₂, COOR⁹, C(O)R⁹, SO₂R⁹, SOR⁹, —X—CF₃, —X—SH, —X—OH, $C_{1-4}$haloalkyl, $C_{6-10}$ aryl, —X—($C_{6-10}$ aryl), 5-10 membered heteroaryl, —X-(5-10 membered heteroaryl), $C_{3-10}$ cycloaliphatic, —X—($C_{3-10}$ cycloaliphatic), 5-10 membered heterocyclyl, —X-(5-10 membered heterocyclyl), or X; and R⁹ is H, $C_{1-6}$ aliphatic, $C_{1-4}$haloalkyl, $C_{6-10}$ aryl, —X—($C_{6-10}$ aryl), 5-10 membered heteroaryl, —X-(5-10 membered heteroaryl), $C_{3-10}$ cycloaliphatic, —X—($C_{3-10}$ cycloaliphatic), 5-10 membered heterocyclyl, —X-(5-10 membered heterocyclyl) or X, or wherein two R⁹, taken together with the atom to which they are attached, form a 5-10 membered heterocyclyl, wherein said heterocyclyl is optionally substituted with 0-4 occurrences of halo, CN, NO₂, —COOH, —COO($C_{1-6}$ alkyl), —C(O)H, SO₂H, SO₂($C_{1-6}$alkyl), $C_{1-6}$haloaliphatic, NH₂, —NH($C_{1-6}$alkyl), —N($C_{1-6}$alkyl)₂, SH, —S($C_{1-6}$ alkyl), OH, —O($C_{1-6}$alkyl), —C(O)($C_{1-6}$ alkyl), —C(O)NH₂, —C(O)NH($C_{1-6}$alkyl), —C(O)N ($C_{1-6}$ alkyl)₂, —C(O)NH₂, —C(O)NH($C_{1-6}$alkyl), or —C(O)N($C_{1-6}$alkyl)₂, $C_{1-4}$haloalkyl, $C_{6-10}$ aryl, —X—($C_{6-10}$ aryl), 5-10 membered heteroaryl, —X-(5-10 membered heteroaryl), $C_{3-10}$ cycloaliphatic, —X—($C_{3-10}$ cycloaliphatic), 5-10 membered heterocyclyl, —X-(5-10 membered heterocyclyl), or X, wherein each of said heteroaryl heterocyclyl, or heterocyclic ring system contain one or more heteroatoms selected from nitrogen, oxygen, or sulfur.

2. The compound according to claim 1, wherein R⁴ is H and R³ is other than H.

3. The compound according to claim 1, wherein R¹ is H.

4. The compound according to claim 1, wherein R is

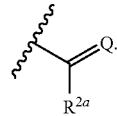

5. The compound according to claim 4, wherein $R^{2a}$ is OR⁵, N(R⁵)₂, or 5-8 membered heterocyclyl.

6. The compound according to claim 1, wherein R is Y.

7. The compound according to claim 1, wherein R³ and R⁴ are each independently $U_m$—V.

8. The compound according to claim 1, wherein Z is a bond and R is selected from

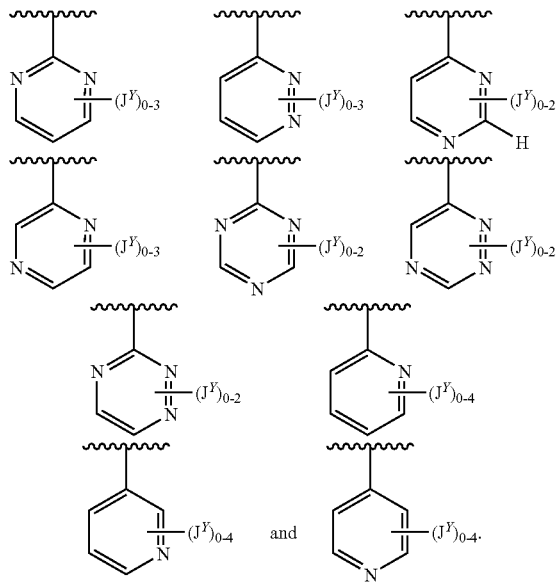

9. The compound according to claim 1, wherein said compound is of formula II:

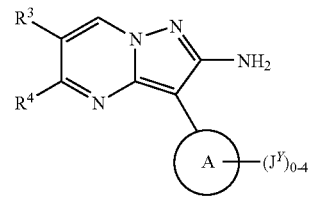

or a pharmaceutically accepted salt thereof, wherein Ring A is Y.

10. The compound according to claim 9, wherein said compound is of formula III:

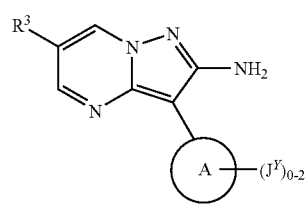

or a pharmaceutically accepted salt thereof, wherein $R^3$ is halogen, $C_{1-6}$ aliphatic, $C_{1-6}$ alkoxy, $N(R^5)_2$, CN, $NO_2$, or $U_m$—V.
11. The compound according to claim 10, wherein said compound is of formula IV:
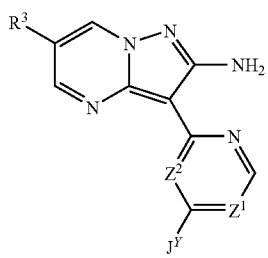
IV
wherein each of $Z^1$ and $Z^2$ is CH or N.
12. A compound according to claim 1 selected from any one of
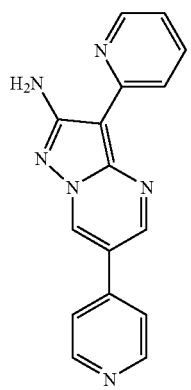
1-1
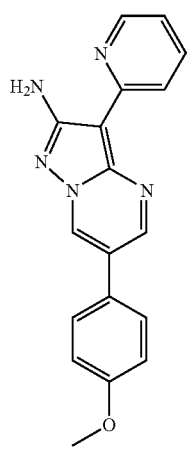
1-2
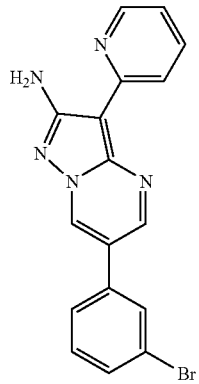
1-3
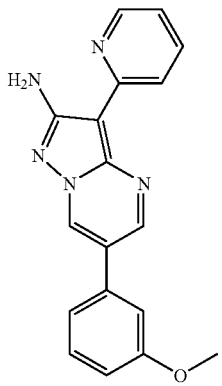
I-4
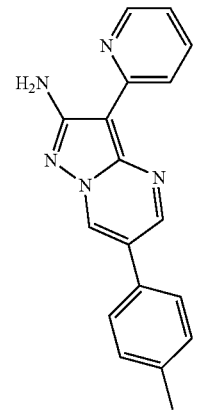
I-5
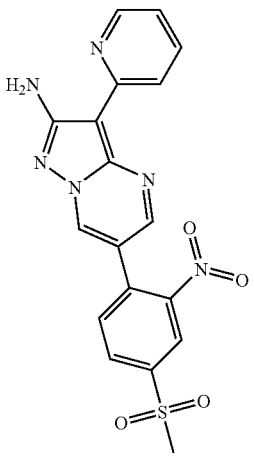
I-6

-continued
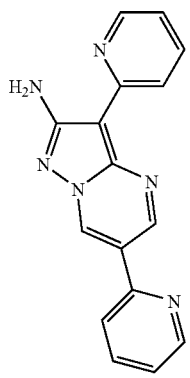
I-7
I-8
I-9
I-10
-continued
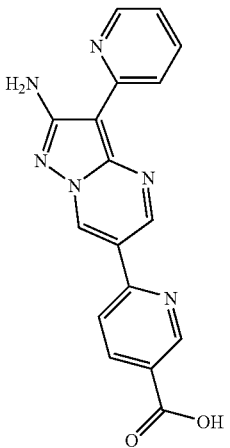
I-11
I-12
I-13

225
-continued
I-14
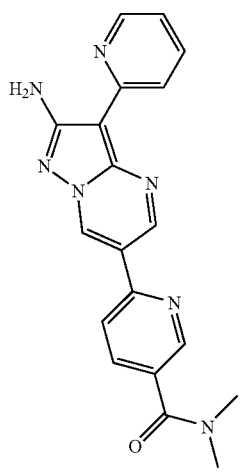
I-15
226
-continued
II-7
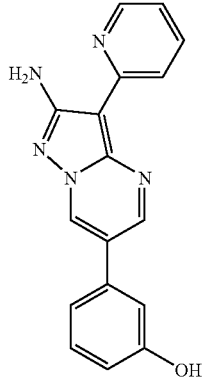
II-8
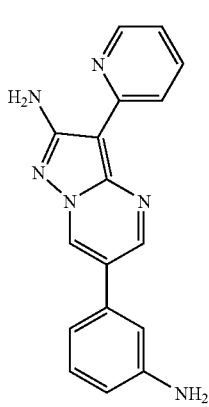
II-6
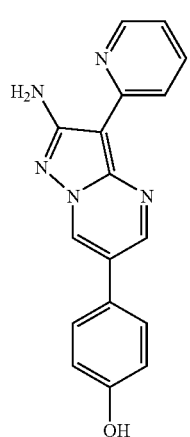
II-9
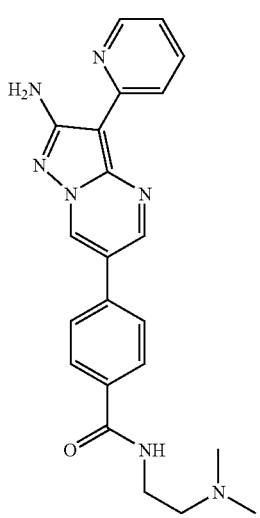

-continued
II-10
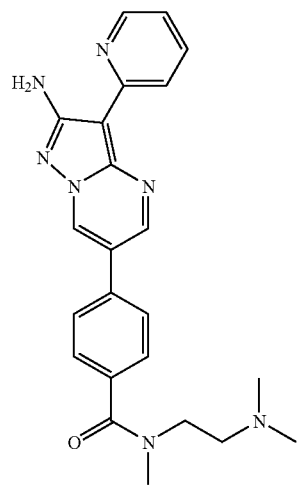
III-1
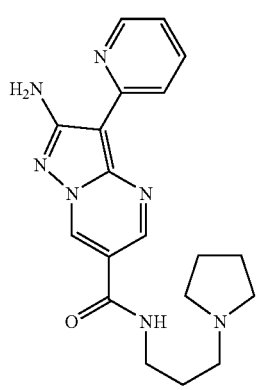
III-2
IV-1
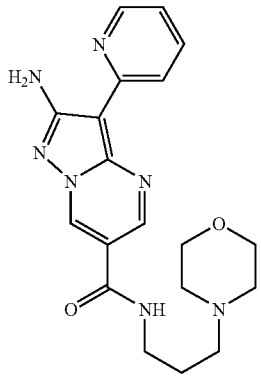
-continued
IV-2
IV-3
IV-4
IV-5
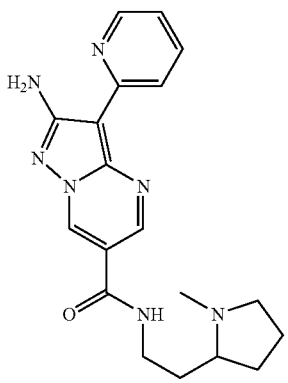

IV-6
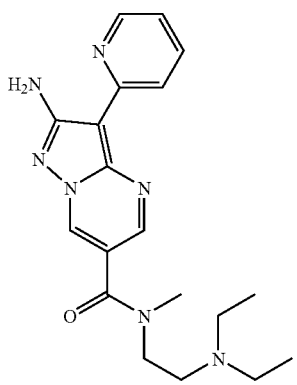
IV-7
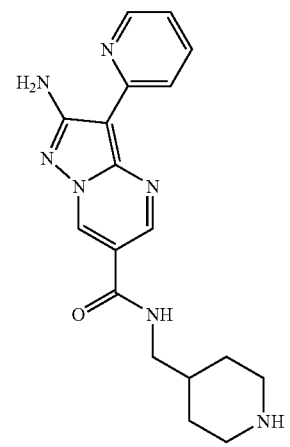
IV-8
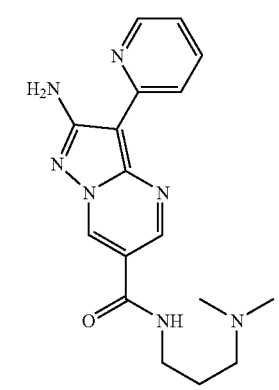
IV-9
IV-10
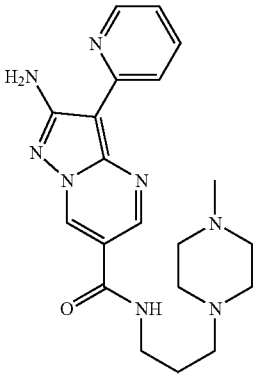
IV-11
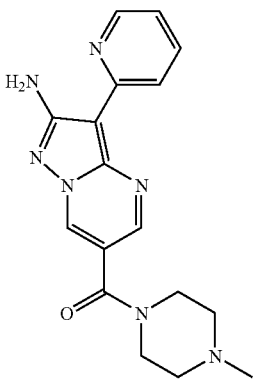
IV-12
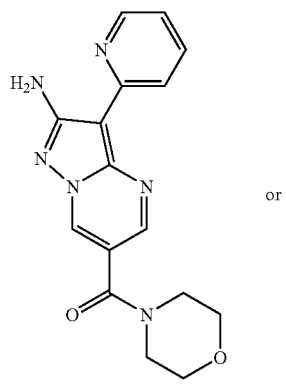
or
IV-13
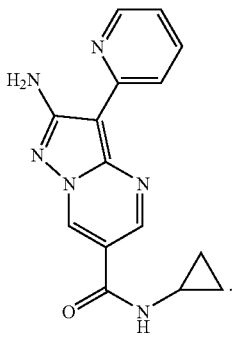

13. A compound according to claim 1 selected from
| Cmpd # (V-) | Compound |
|---|---|
| 1 | 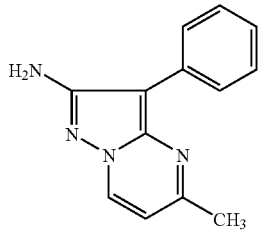 |
| 2 | 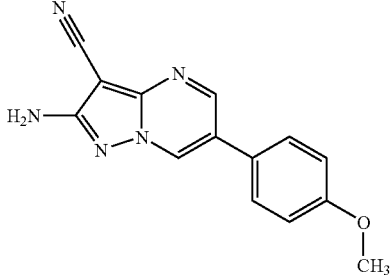 |
| 3 | 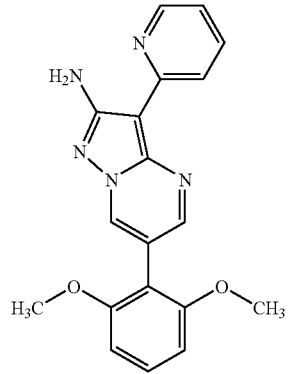 |
| 4 | 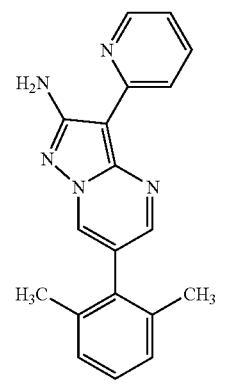 |
-continued
| Cmpd # (V-) | Compound |
|---|---|
| 5 | 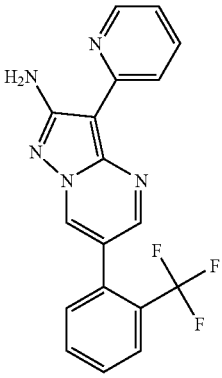 |
| 6 | 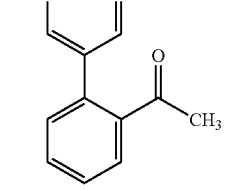 |
| 7 | 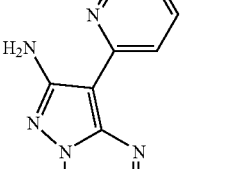 |
| 8 | 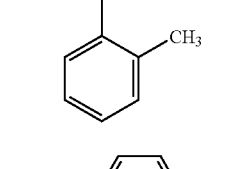 |

-continued
| Cmpd # (V-) | Compound |
|---|---|
| 9 | 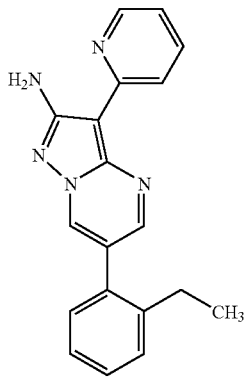 |
| 10 | 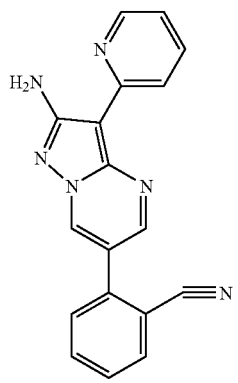 |
| 11 | 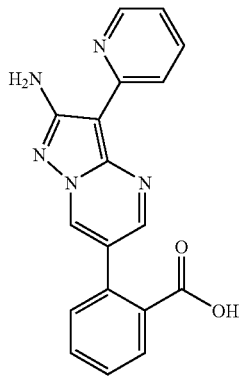 |
| 12 | 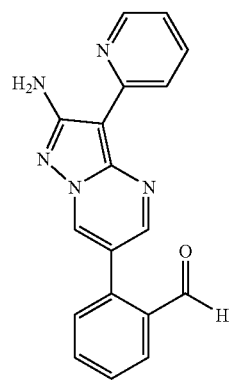 |
-continued
| Cmpd # (V-) | Compound |
|---|---|
| 13 | 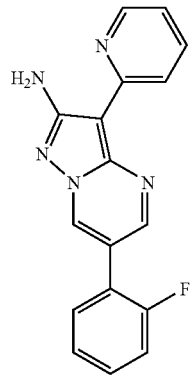 |
| 14 | 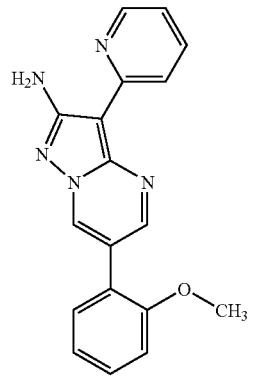 |
| 15 | 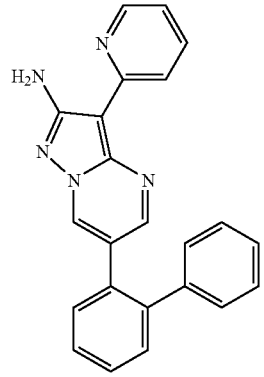 |
| 16 | 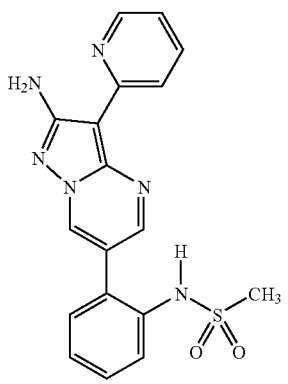 |

-continued

| Cmpd # (V-) | Compound |
|---|---|
| 17 | 3-(2-aminopyridin-3-yl)pyrazolo[1,5-a]pyrimidin-6-yl)phenyl acrylate methyl ester |
| 18 | N-(3-(2-amino-3-(pyridin-2-yl)pyrazolo[1,5-a]pyrimidin-6-yl)phenyl)methanesulfonamide |
| 19 | 2-amino-6-(2-(difluoromethoxy)phenyl)-3-(pyridin-2-yl)pyrazolo[1,5-a]pyrimidine |
| 20 | 2-(2-amino-3-(pyridin-2-yl)pyrazolo[1,5-a]pyrimidin-6-yl)aniline |

| Cmpd # (V-) | Compound |
|---|---|
| 21 | 2-amino-6-(2-nitrophenyl)-3-(pyridin-2-yl)pyrazolo[1,5-a]pyrimidine |
| 22 | 2-amino-6-(4-methoxypyridin-3-yl)-3-(pyridin-2-yl)pyrazolo[1,5-a]pyrimidine |
| 23 | (2-(2-amino-3-(pyridin-2-yl)pyrazolo[1,5-a]pyrimidin-6-yl)phenyl)-N,N-dimethylmethanamine |
| 24 | ethyl 2-amino-6-(4-chlorophenyl)pyrazolo[1,5-a]pyrimidine-3-carboxylate |

-continued

| Cmpd # (V-) | Compound |
|---|---|
| 25 | ethyl 2-amino-6-(pyridin-2-yl)pyrazolo[1,5-a]pyrimidine-3-carboxylate |
| 26 | ethyl 2-amino-6-(pyrazin-2-yl)pyrazolo[1,5-a]pyrimidine-3-carboxylate |
| 27 | ethyl 2-amino-6-(pyrimidin-4-yl)pyrazolo[1,5-a]pyrimidine-3-carboxylate |
| 29 | 2-amino-3-(4-methoxyphenyl)-6-(p-tolyl)pyrazolo[1,5-a]pyrimidine |

-continued

| Cmpd # (V-) | Compound |
|---|---|
| 30 | 2-amino-3-(4-bromophenyl)-6-(p-tolyl)pyrazolo[1,5-a]pyrimidine |
| 31 | 2-amino-3-(2-bromophenyl)-6-(p-tolyl)pyrazolo[1,5-a]pyrimidine |
| 32 | 2-amino-N-(2,4-difluorobenzyl)-6-(pyrimidin-4-yl)pyrazolo[1,5-a]pyrimidine-3-carboxamide |
| 33 | 2-amino-N-ethyl-N-isopropyl-6-(pyrimidin-4-yl)pyrazolo[1,5-a]pyrimidine-3-carboxamide |

| Cmpd # (V-) | Compound |
|---|---|
| 34 | 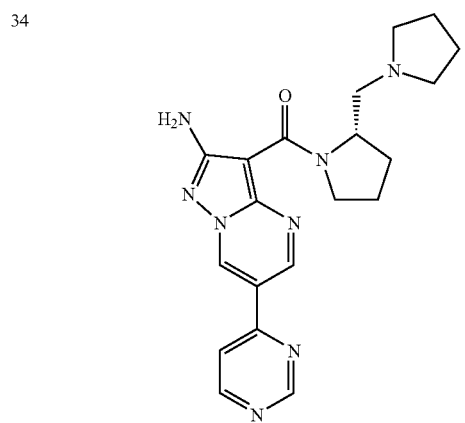 |
| 35 | |
| 36 | |
| 37 | |
| Cmpd # (V-) | Compound |
|---|---|
| 38 | 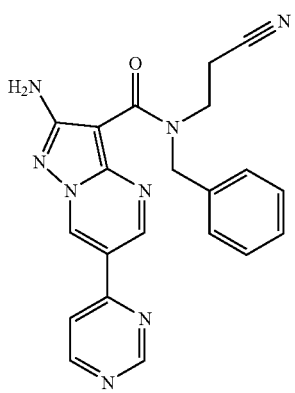 |
| 39 | 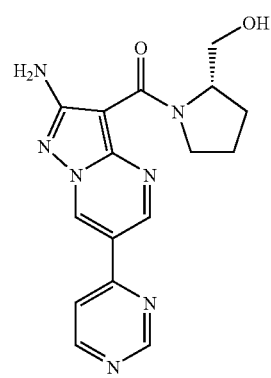 |
| 40 | 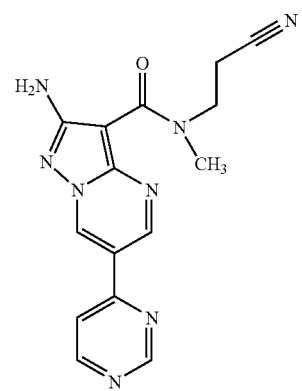 |

-continued

| Cmpd # (V-) | Compound |
|---|---|
| 41 | 2-amino-N-benzyl-N-methyl-6-(pyrimidin-4-yl)pyrazolo[1,5-a]pyrimidine-3-carboxamide |
| 42 | 2-amino-N-benzyl-N-ethyl-6-(pyrimidin-4-yl)pyrazolo[1,5-a]pyrimidine-3-carboxamide |
| 43 | 2-amino-N-(4-(dimethylamino)benzyl)-6-(pyrimidin-4-yl)pyrazolo[1,5-a]pyrimidine-3-carboxamide |
| 44 | (2-amino-6-(pyrimidin-4-yl)pyrazolo[1,5-a]pyrimidin-3-yl)(3-hydroxypyrrolidin-1-yl)methanone |
| 45 | (2-amino-6-(pyrimidin-4-yl)pyrazolo[1,5-a]pyrimidin-3-yl)(pyrrolidin-1-yl)methanone |
| 46 | (S)-2-amino-N-(2-hydroxy-1-phenylethyl)-6-(pyrimidin-4-yl)pyrazolo[1,5-a]pyrimidine-3-carboxamide |
| 47 | 2-amino-N-(3,4-dichlorobenzyl)-6-(pyridin-2-yl)pyrazolo[1,5-a]pyrimidine-3-carboxamide |

-continued
| Cmpd # (V-) | Compound |
|---|---|
| 48 | 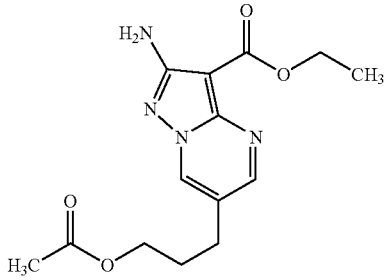 |
| 49 | 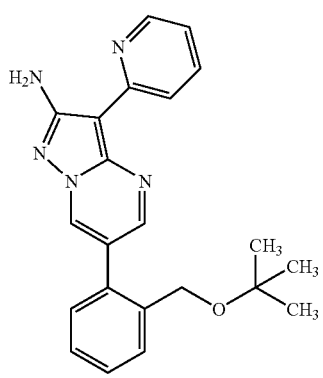 |
| 50 | 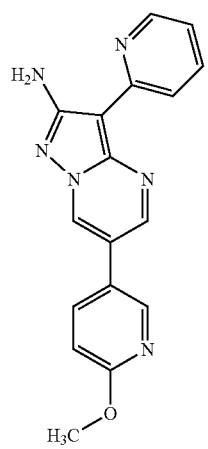 |
-continued
| Cmpd # (V-) | Compound |
|---|---|
| 51 | 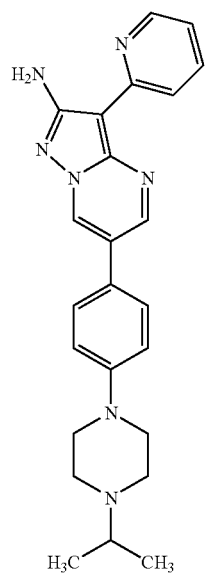 |
| 52 | 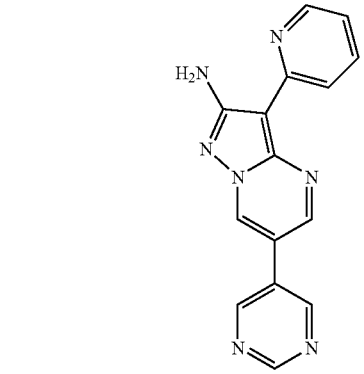 |
| 53 | 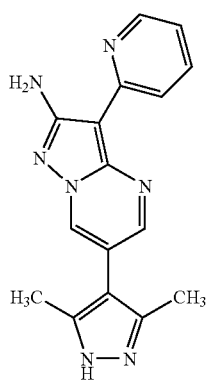 |

-continued
| Cmpd # (V-) | Compound |
|---|---|
| 54 | 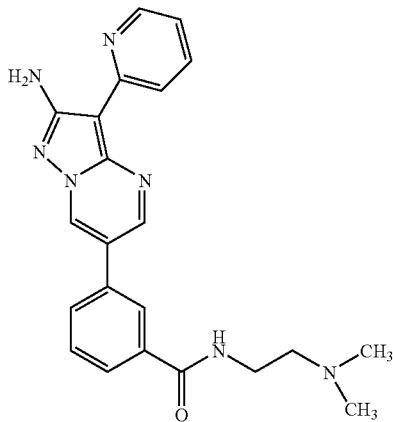 |
| 55 | 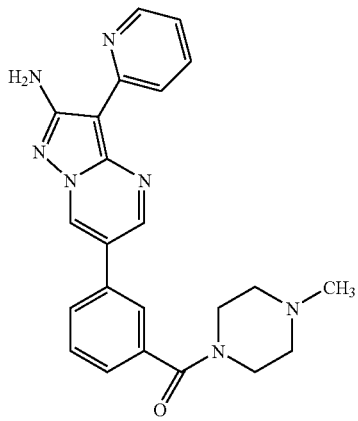 |
| 56 | 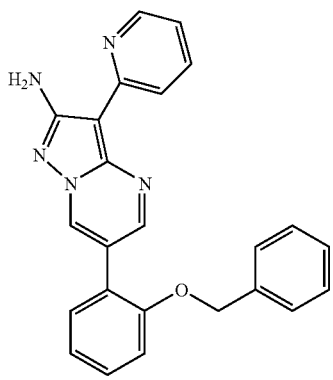 |
-continued
| Cmpd # (V-) | Compound |
|---|---|
| 57 | 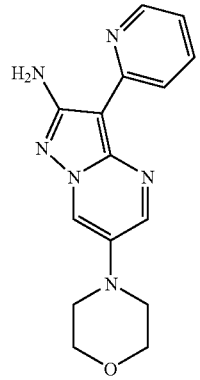 |
| 58 | 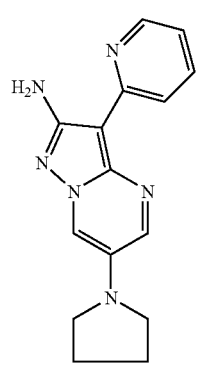 |
| 59 | 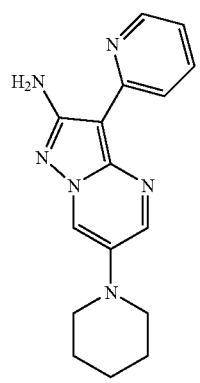 |

-continued
| Cmpd # (V-) | Compound |
|---|---|
| 60 | 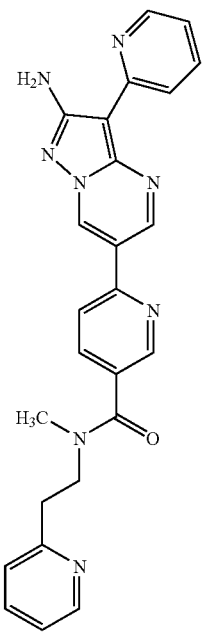 |
| 61 | 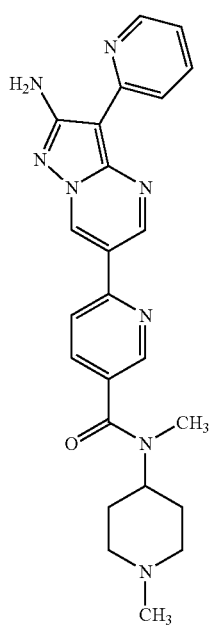 |
-continued
| Cmpd # (V-) | Compound |
|---|---|
| 62 | 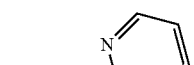 |
| 63 | 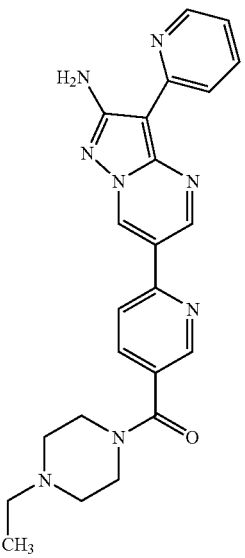 |

-continued
| Cmpd # (V-) | Compound |
|---|---|
| 64 | 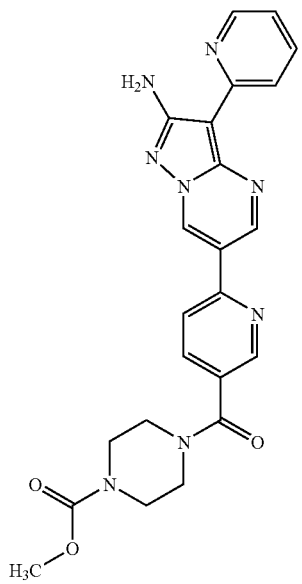 |
| 65 | 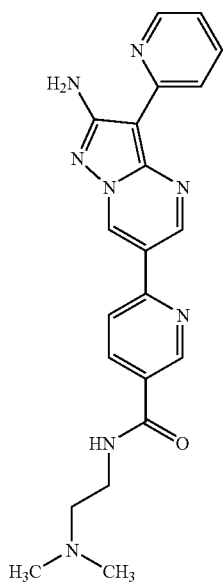 |
-continued
| Cmpd # (V-) | Compound |
|---|---|
| 66 | 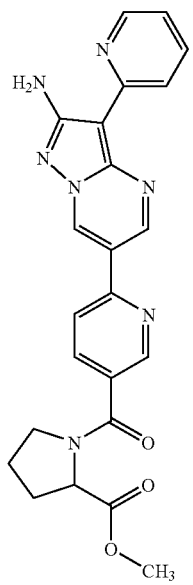 |
| 67 | 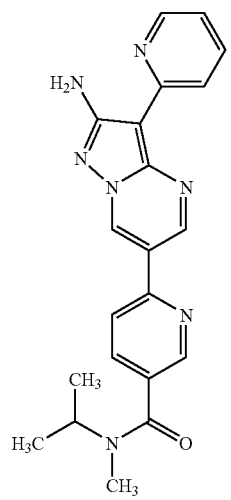 |

251
-continued
| Cmpd # (V-) | Compound |
|---|---|
| 68 | |
| 69 | 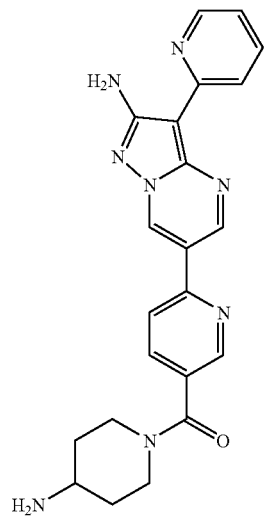 |
252
-continued
| Cmpd # (V-) | Compound |
|---|---|
| 70 | |
| 71 | 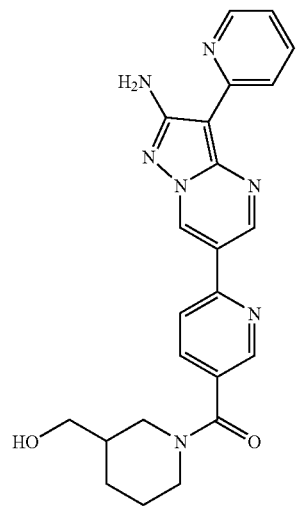 |

| Cmpd # (V-) | Compound |
|---|---|
| 72 | 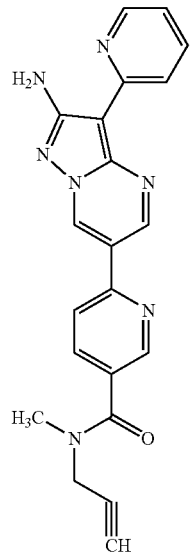 |
| 73 | 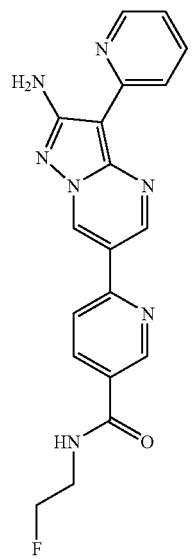 |
| Cmpd # (V-) | Compound |
|---|---|
| 74 | 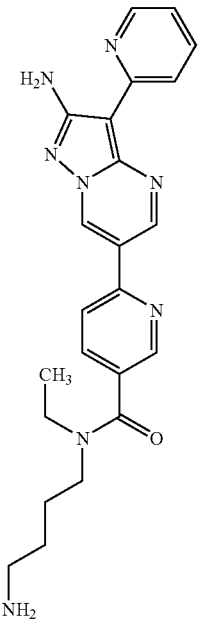 |
| 75 | 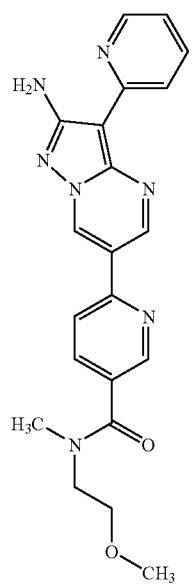 |

| Cmpd # (V-) | Compound |
|---|---|
| 76 | 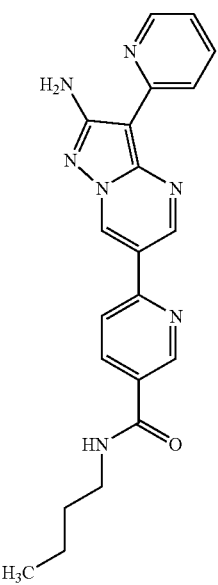 |
| 77 | |
| Cmpd # (V-) | Compound |
|---|---|
| 78 | 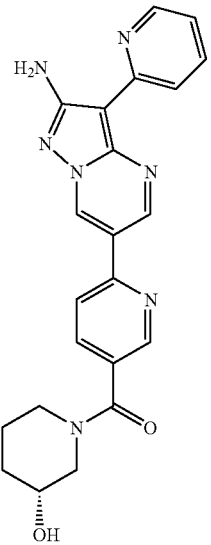 |
| 79 | |

-continued
| Cmpd # (V-) | Compound |
|---|---|
| 80 | 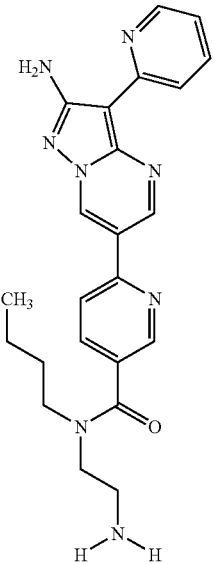 |
| 81 | 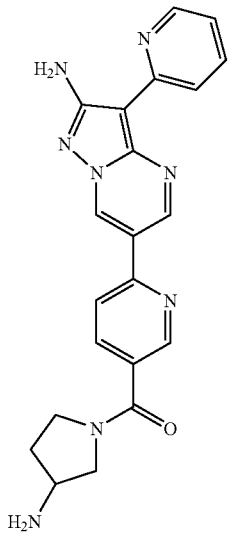 |
-continued
| Cmpd # (V-) | Compound |
|---|---|
| 82 | 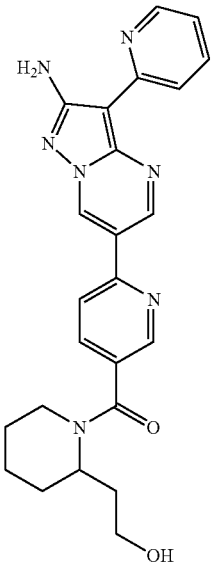 |
| 83 | 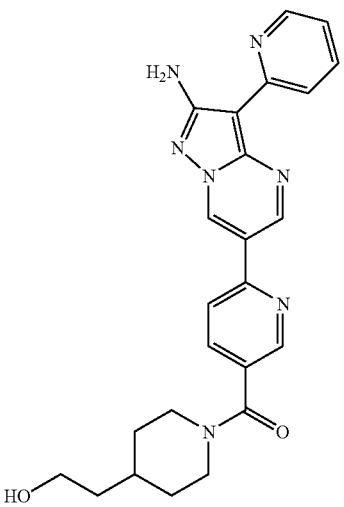 |

-continued
| Cmpd # (V-) | Compound |
|---|---|
| 84 | 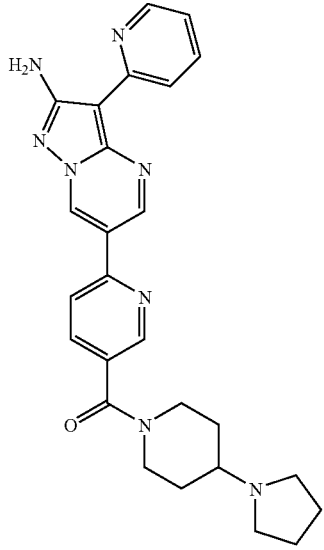 |
| 85 | 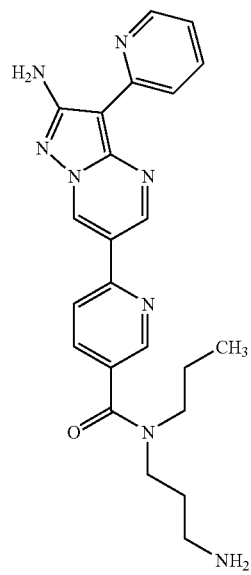 |
-continued
| Cmpd # (V-) | Compound |
|---|---|
| 87 | 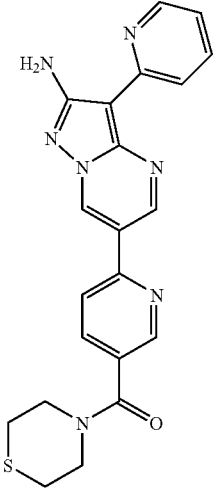 |
| 88 | 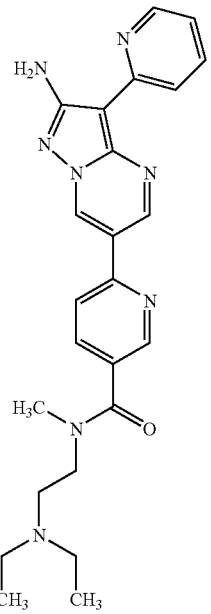 |

-continued

| Cmpd # (V-) | Compound |
|---|---|
| 89 | |
| 90 | |
| 91 | |

-continued

| Cmpd # (V-) | Compound |
|---|---|
| 92 | |
| 93 | |

-continued
| Cmpd # (V-) | Compound |
|---|---|
| 94 | 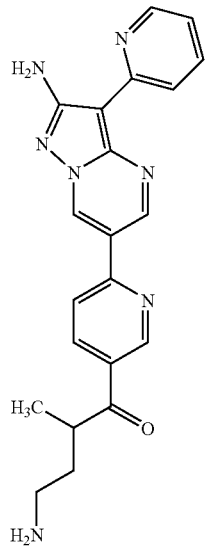 |
| 95 | 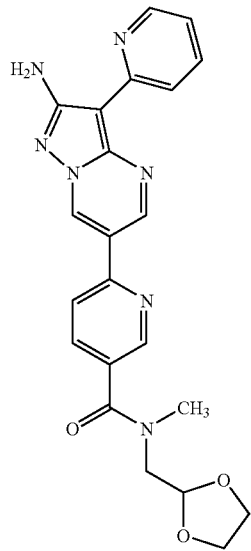 |
-continued
| Cmpd # (V-) | Compound |
|---|---|
| 96 | 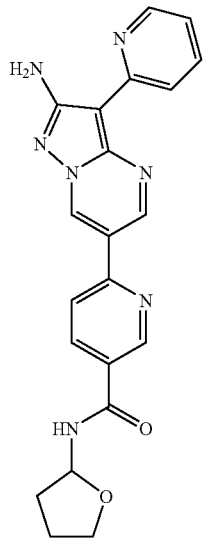 |
| 97 | 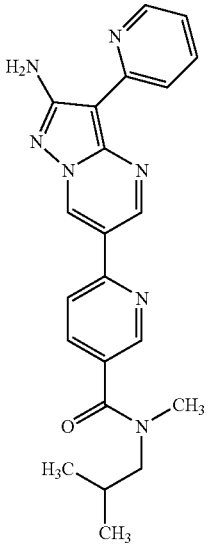 |

-continued

| Cmpd # (V-) | Compound |
|---|---|
| 98 | (structure) |
| 99 | (structure) |
| 100 | (structure) |

-continued

| Cmpd # (V-) | Compound |
|---|---|
| 101 | (structure) |
| 102 | (structure) |
| 103 | (structure) |

267 268
-continued
| Cmpd # (V-) | Compound |
|---|---|
| 104 | 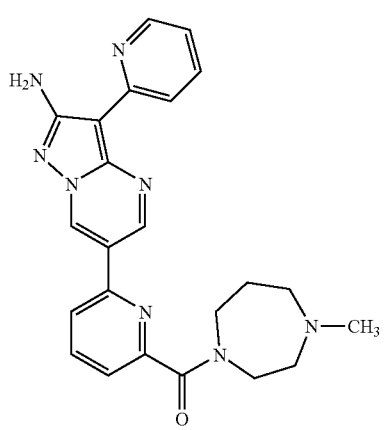 |
| 105 | |
| 106 | 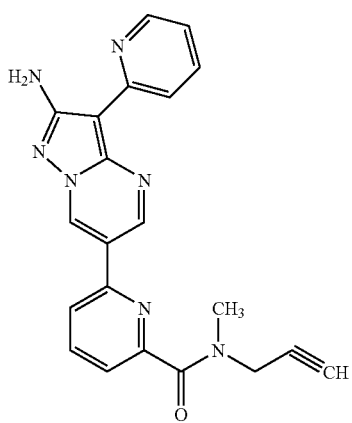 |
| Cmpd # (V-) | Compound |
|---|---|
| 107 | |
| 108 | |
| 109 | |

-continued
| Cmpd # (V-) | Compound |
|---|---|
| 110 | 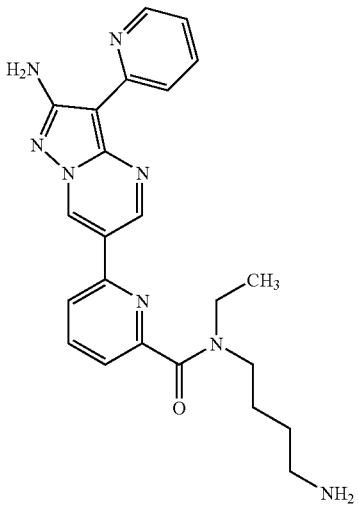 |
| 111 | 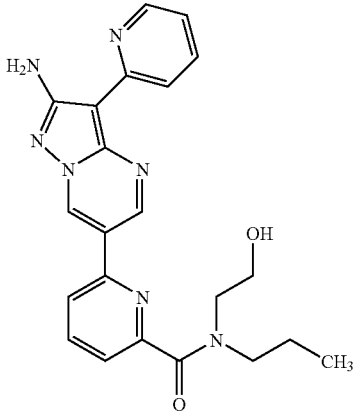 |
| 112 | 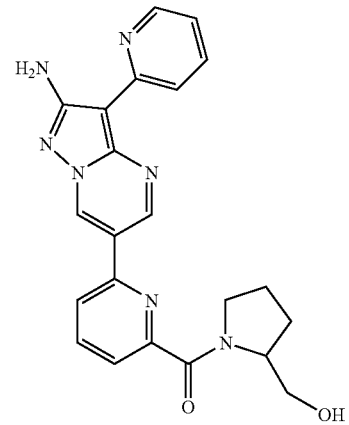 |
-continued
| Cmpd # (V-) | Compound |
|---|---|
| 113 | 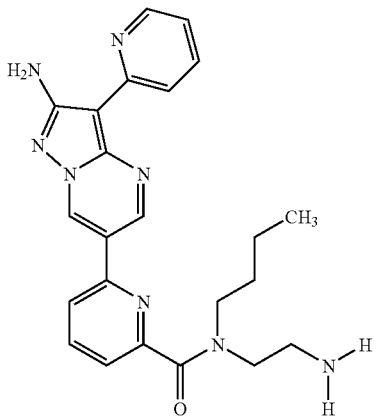 |
| 114 | 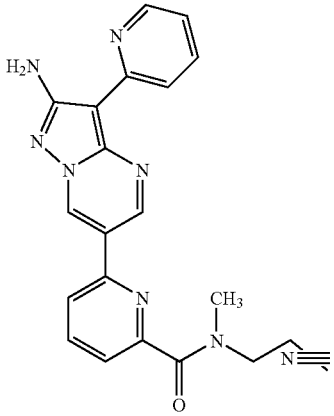 |
| 115 | 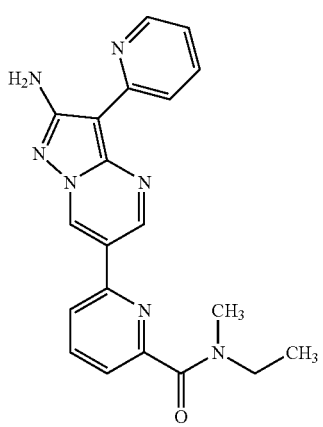 |

-continued

| Cmpd # (V-) | Compound |
|---|---|
| 116 | (structure) |
| 117 | (structure) |
| 118 | (structure) |

-continued

| Cmpd # (V-) | Compound |
|---|---|
| 119 | (structure) |
| 120 | (structure) |
| 121 | (structure) |

| Cmpd # (V-) | Compound |
|---|---|
| 122 | 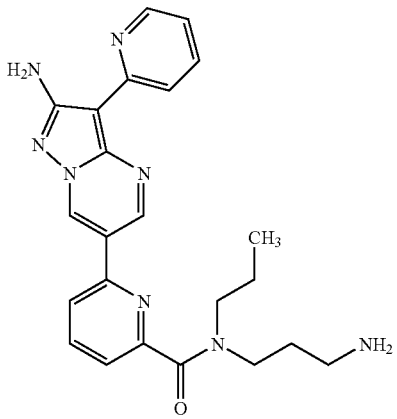 |
| 124 | 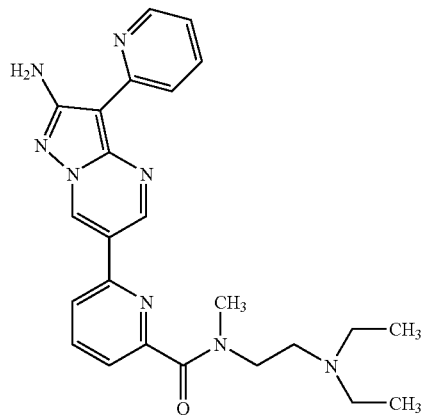 |
| 125 | 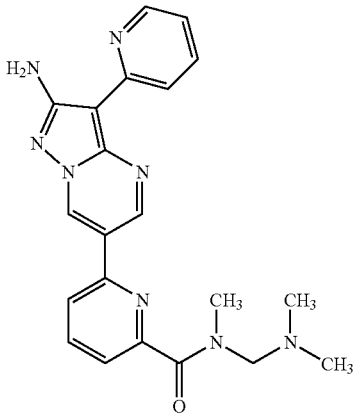 |
| Cmpd # (V-) | Compound |
|---|---|
| 126 | 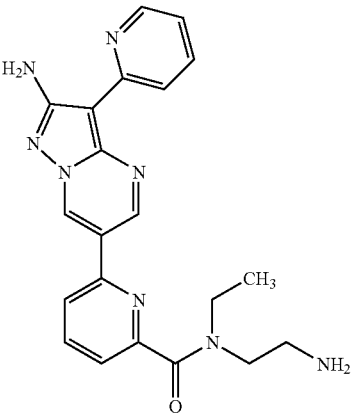 |
| 127 | 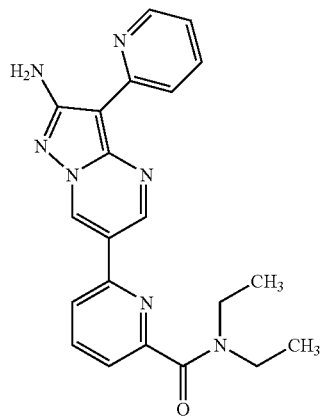 |
| 128 | 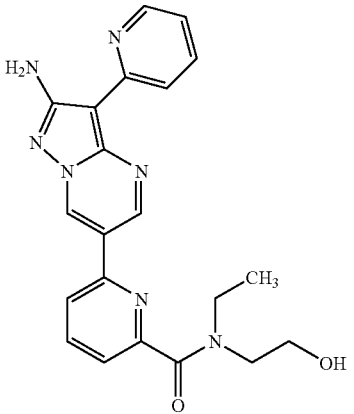 |

-continued
| Cmpd # (V-) | Compound |
|---|---|
| 129 | 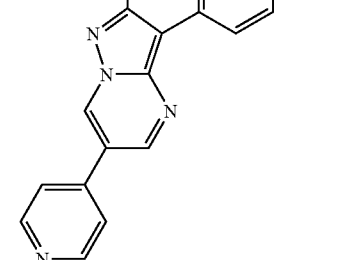 |
| 130 | |
| 131 | |
-continued
| Cmpd # (V-) | Compound |
|---|---|
| 132 | 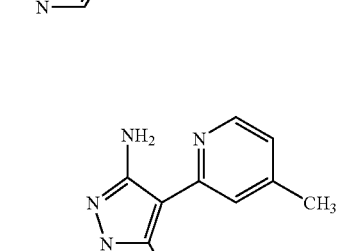 |
| 133 | |
| 134 | |
| 135 | |

| Cmpd # (V-) | Compound |
|---|---|
| 136 | 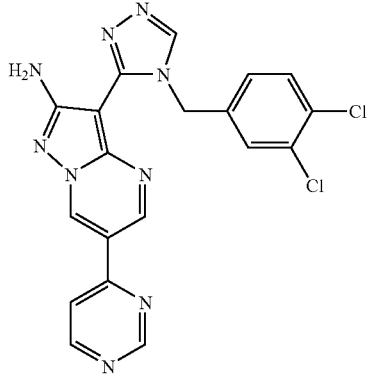 |
| 137 | 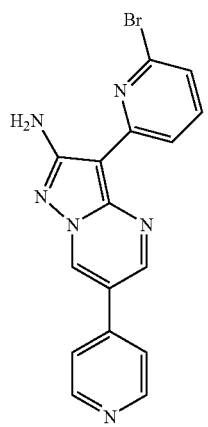 |
| 138 | 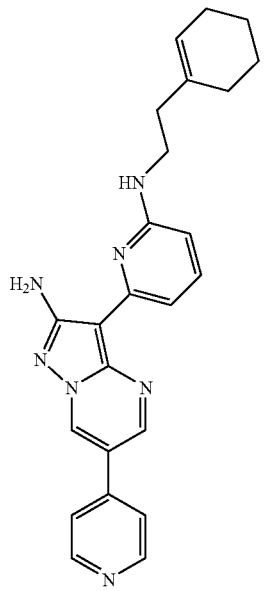 |
| Cmpd # (V-) | Compound |
|---|---|
| 139 | 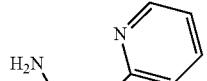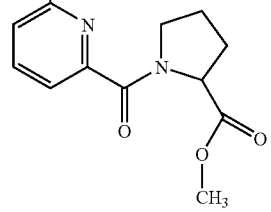 |
| 140 | 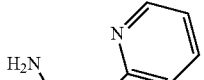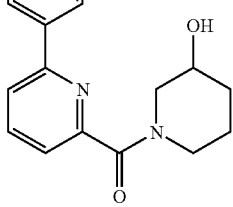 |
| 141 | 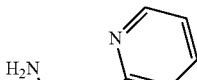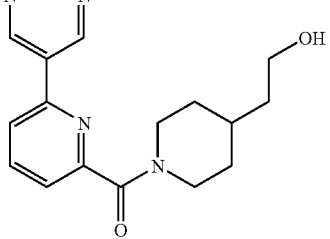 |

| Cmpd # (V-) | Compound |
|---|---|
| 142 | 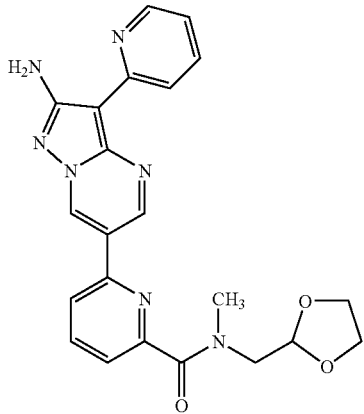 |
| 143 | 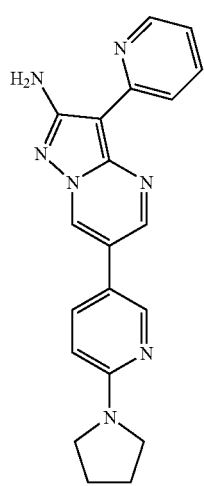 |
| 144 | 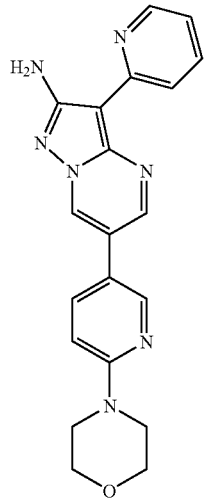 |
| Cmpd # (V-) | Compound |
|---|---|
| 145 | 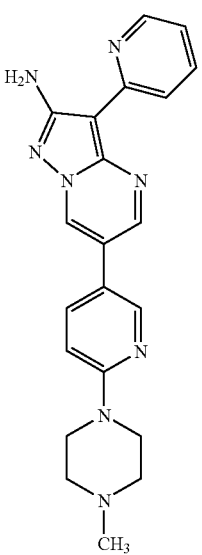 |
| 146 | 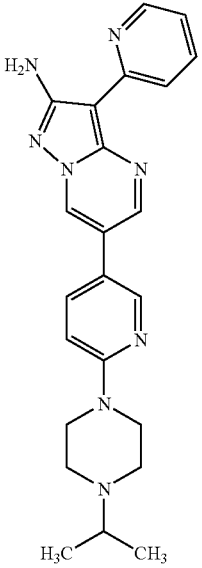 |

| Cmpd # (V-) | Compound |
|---|---|
| 147 | 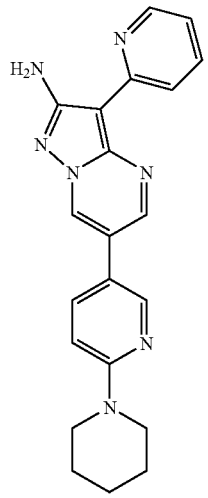 |
| 148 | 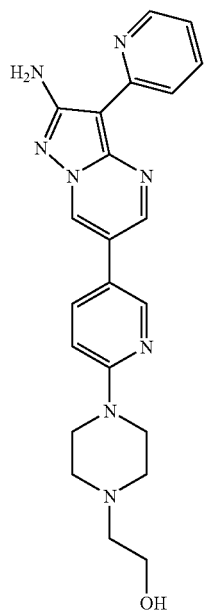 |
| Cmpd # (V-) | Compound |
|---|---|
| 149 | 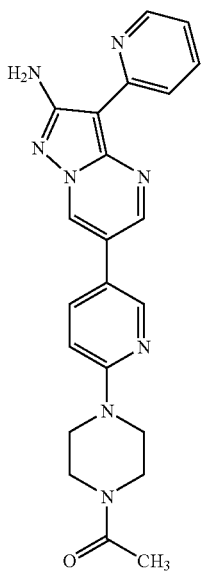 |
| 150 | 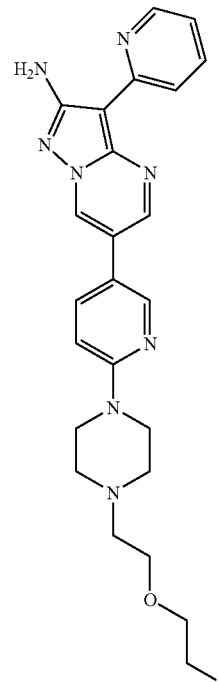 |

| Cmpd # (V-) | Compound |
|---|---|
| 151 | 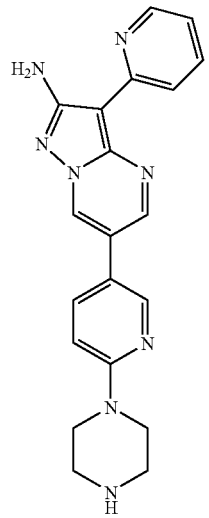 |
| 152 | 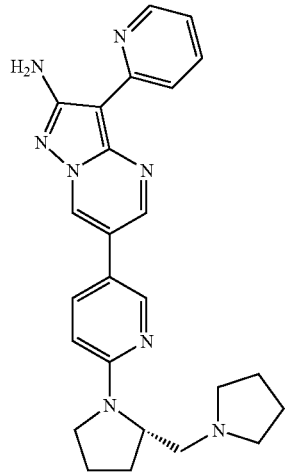 |
| Cmpd # (V-) | Compound |
|---|---|
| 153 | 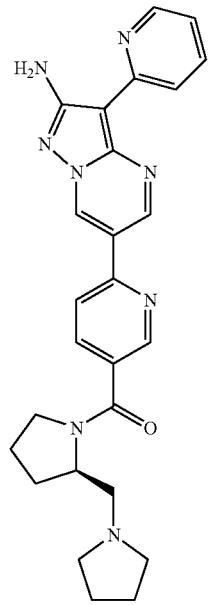 |
| 154 | 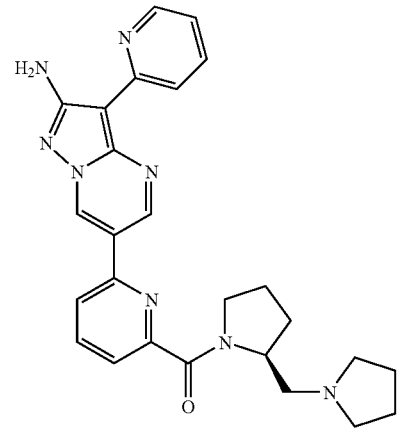 |
| 155 | 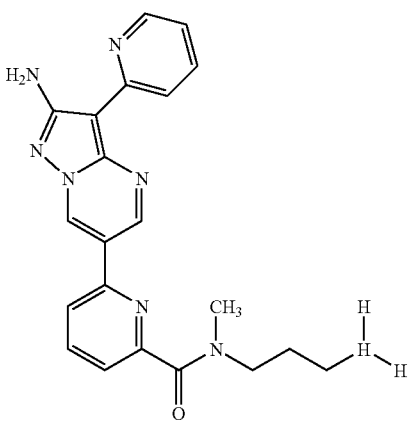 |

-continued

| Cmpd # (V-) | Compound |
|---|---|
| 156 | (structure) |
| 157 | (structure) |
| 158 | (structure) |

-continued

| Cmpd # (V-) | Compound |
|---|---|
| 159 | (structure) |
| 160 | (structure) |

| Cmpd # (V-) | Compound |
|---|---|
| 161 | 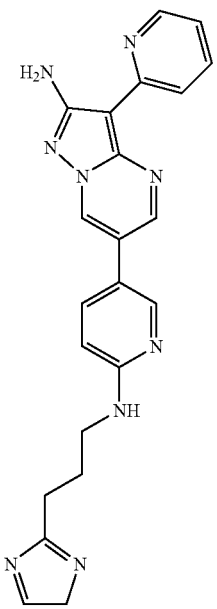 |
| 162 | 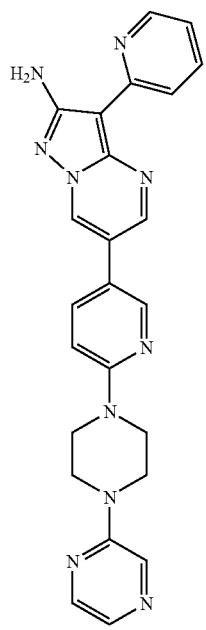 |
| Cmpd # (V-) | Compound |
|---|---|
| 163 | 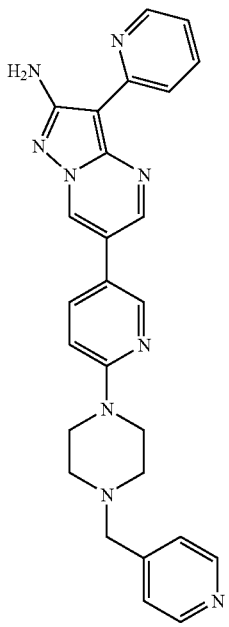 |
| 164 | 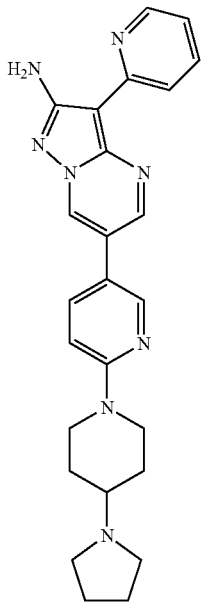 |

-continued
| Cmpd # (V-) | Compound |
|---|---|
| 165 | 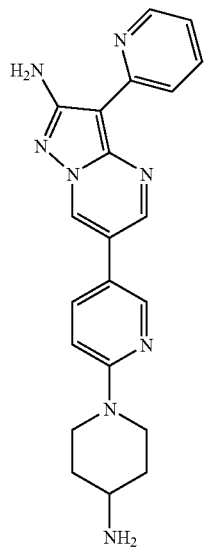 |
| 166 | 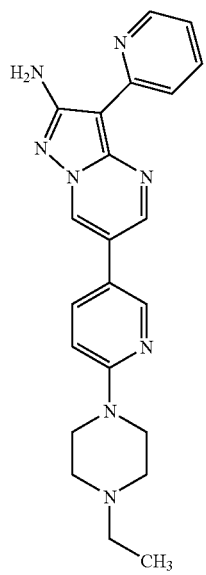 |
-continued
| Cmpd # (V-) | Compound |
|---|---|
| 167 | 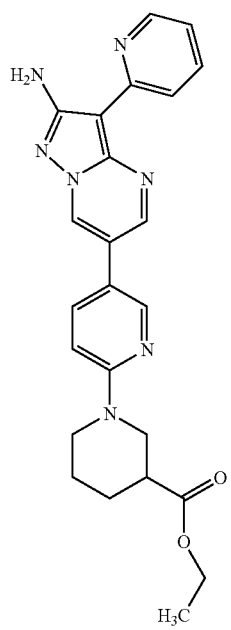 |
| 168 | 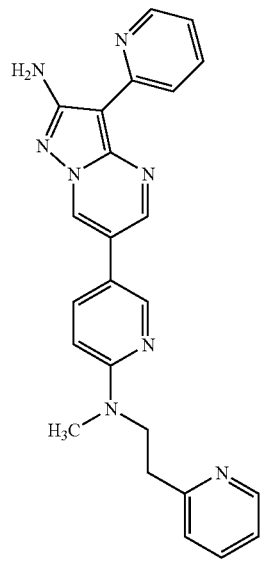 |

-continued
| Cmpd # (V-) | Compound |
|---|---|
| 169 | 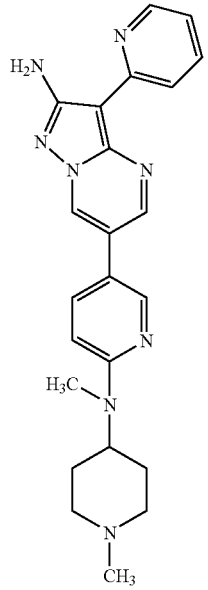 |
| 170 | 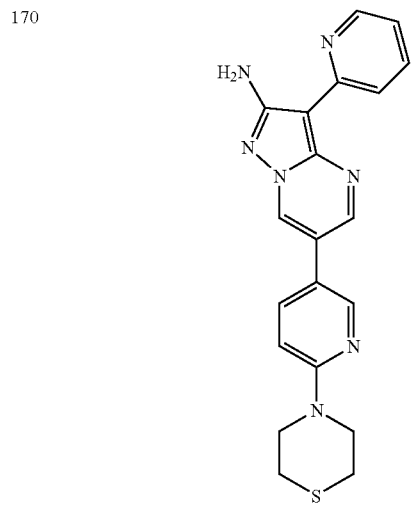 |
| 171 | 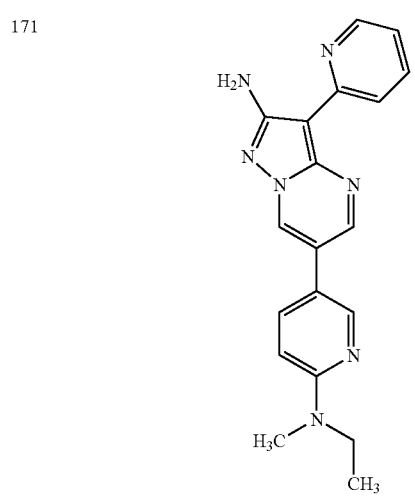 |
-continued
| Cmpd # (V-) | Compound |
|---|---|
| 172 | 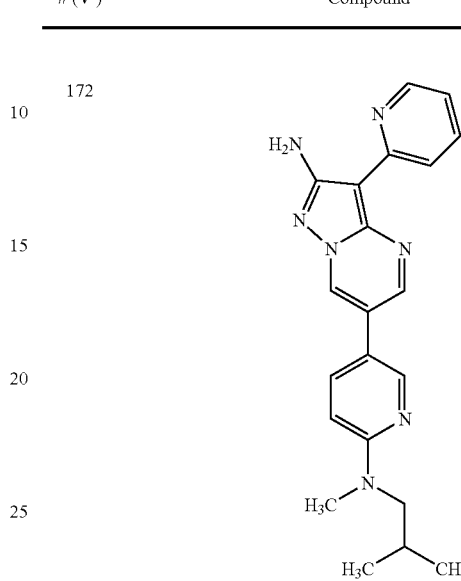 |
| 173 | 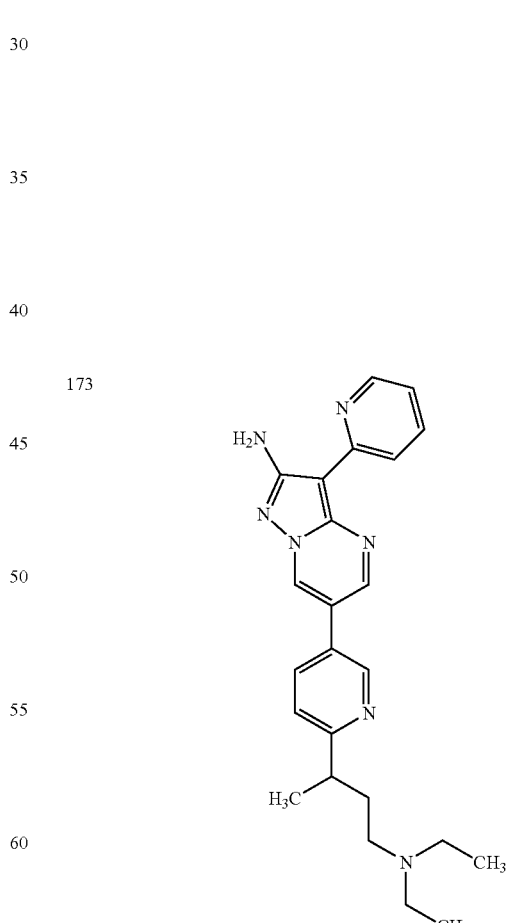 |

-continued
| Cmpd # (V-) | Compound |
|---|---|
| 174 | 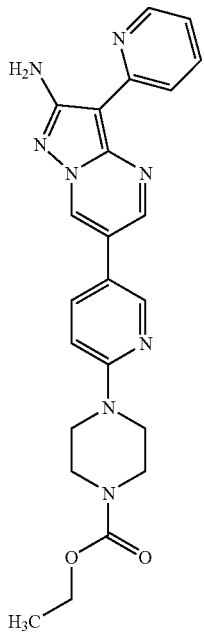 |
| 175 | 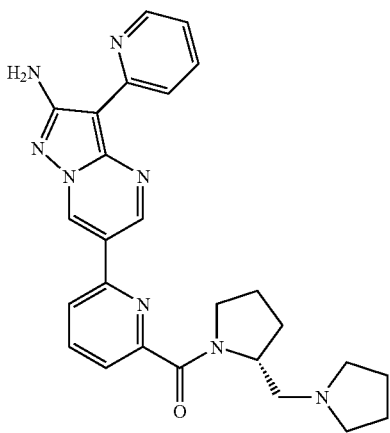 |
| 176 | 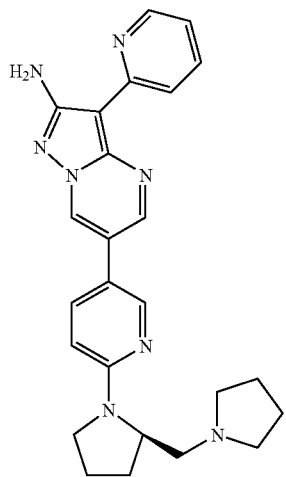 |
-continued
| Cmpd # (V-) | Compound |
|---|---|
| 177 | 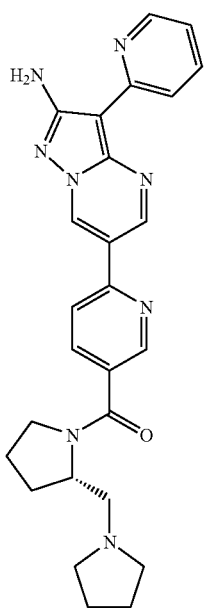 |
| 178 | 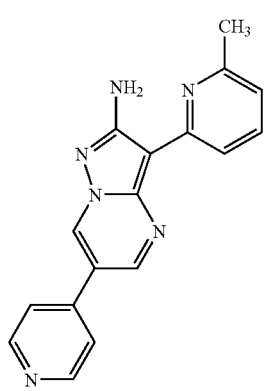 |
| 179 | 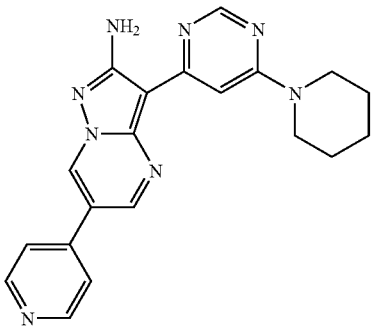 |

| Cmpd # (V-) | Compound |
|---|---|
| 180 | 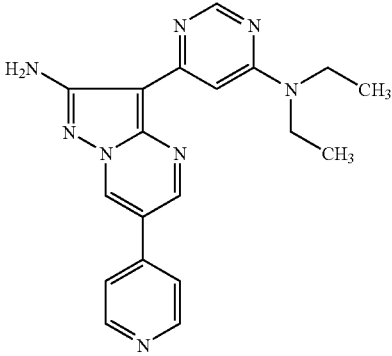 |
| 181 | 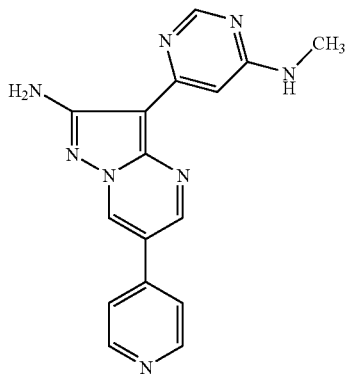 |
| 182 | 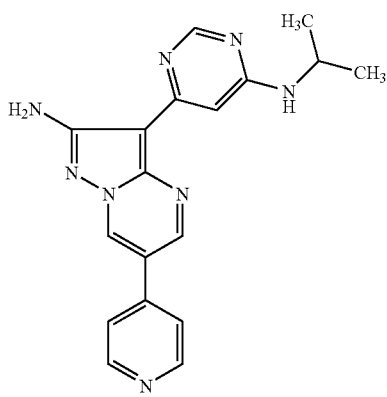 |
| 183 | 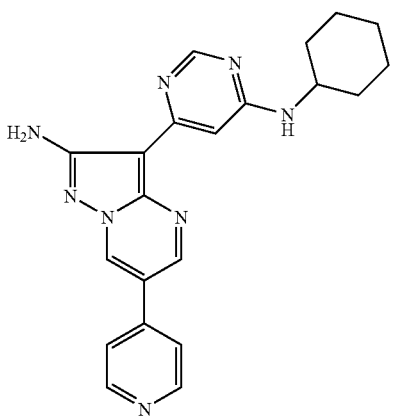 |
| Cmpd # (V-) | Compound |
|---|---|
| 184 | 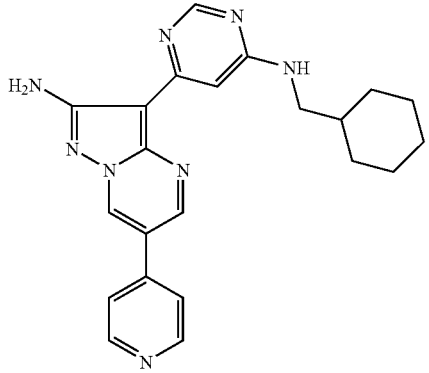 |
| 185 | 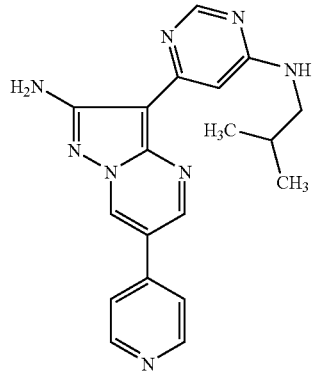 |
| 186 | 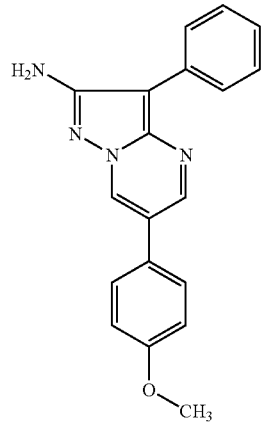 |
| 187 | 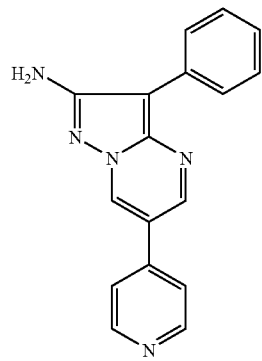 |

-continued
| Cmpd # (V-) | Compound |
|---|---|
| 188 | 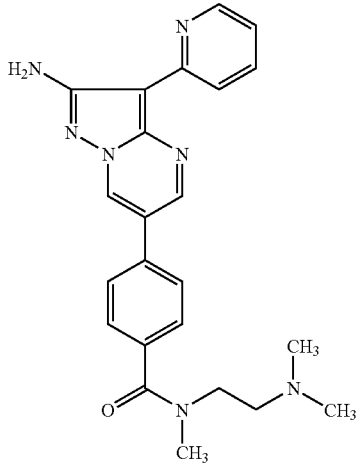 |
| 189 | 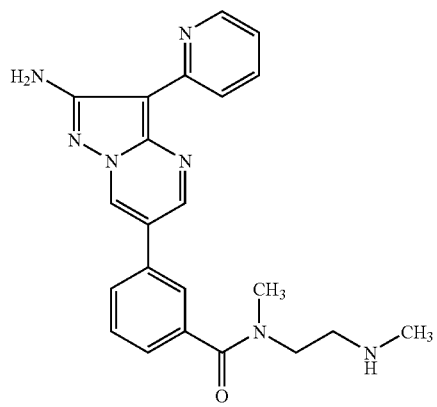 |
| 190 | 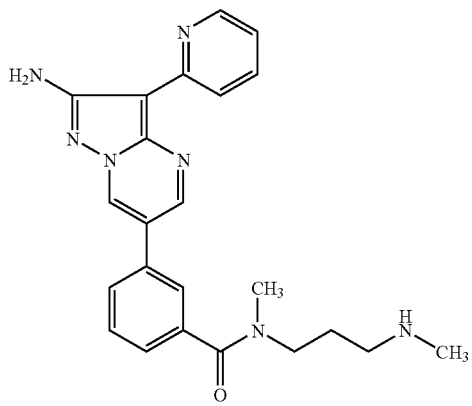 |
-continued
| Cmpd # (V-) | Compound |
|---|---|
| 191 | 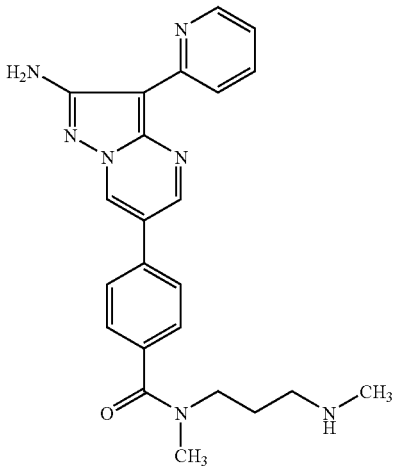 |
| 192 | 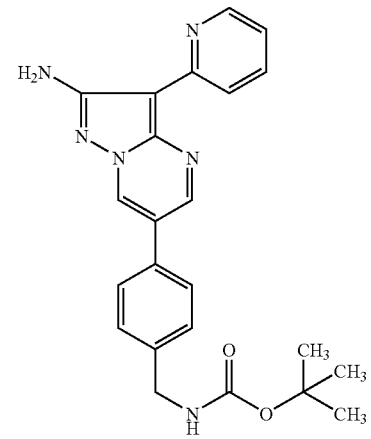 |
| 193 | 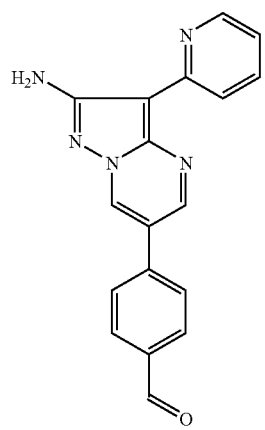 |

-continued
| Cmpd # (V-) | Compound |
|---|---|
| 194 | 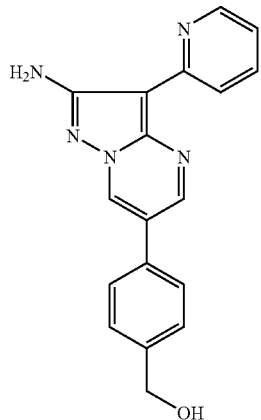 |
| 195 | 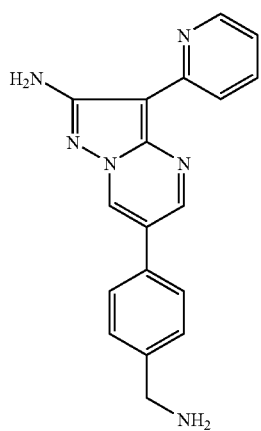 |
| 196 | 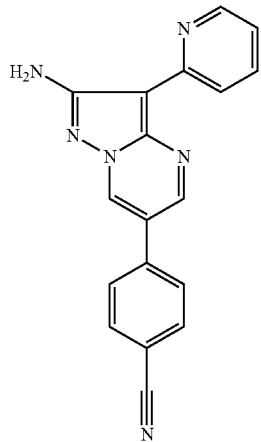 |
-continued
| Cmpd # (V-) | Compound |
|---|---|
| 197 | 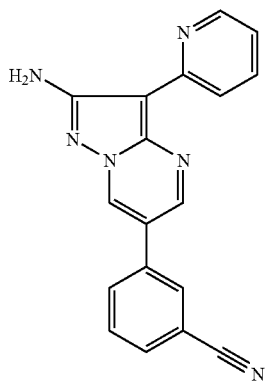 |
| 198 | 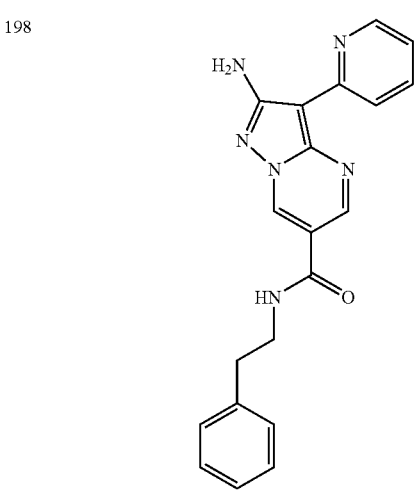 |
| 199 | 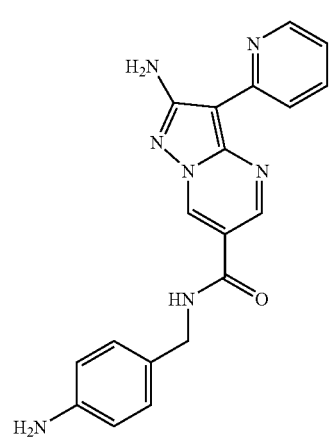 |

-continued
| Cmpd # (V-) | Compound |
|---|---|
| 200 | 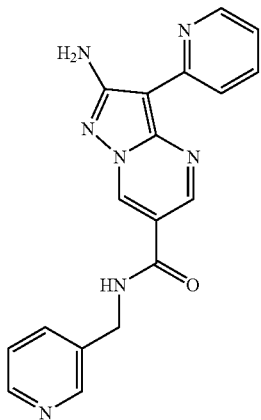 |
| 201 | 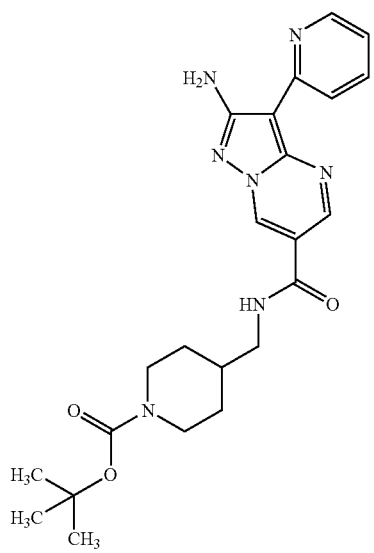 |
| 202 | 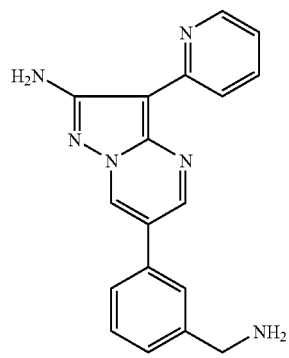 |
-continued
| Cmpd # (V-) | Compound |
|---|---|
| 203 | 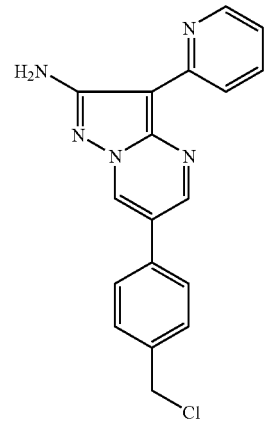 |
| 204 | 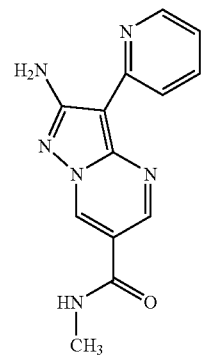 |
| 205 | 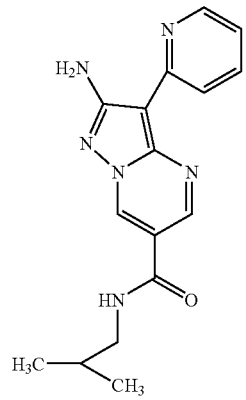 |

-continued
| Cmpd # (V-) | Compound |
|---|---|
| 206 | 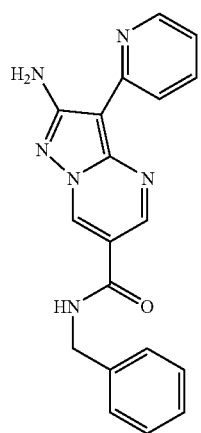 |
| 207 | 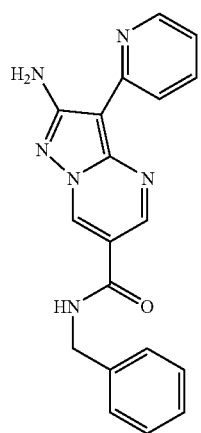 |
| 208 | 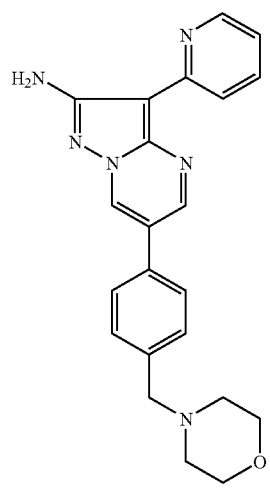 |
-continued
| Cmpd # (V-) | Compound |
|---|---|
| 209 | 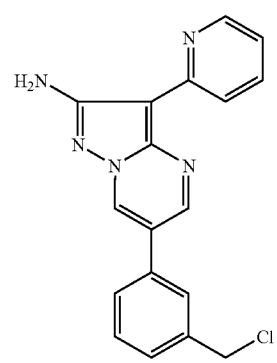 |
| 210 | 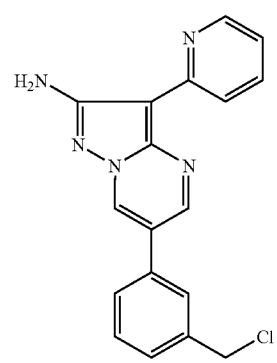 |
| 212 | 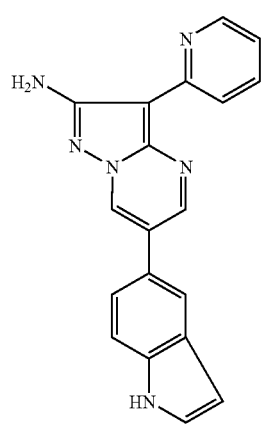 |

-continued
| Cmpd # (V-) | Compound |
|---|---|
| 213 | 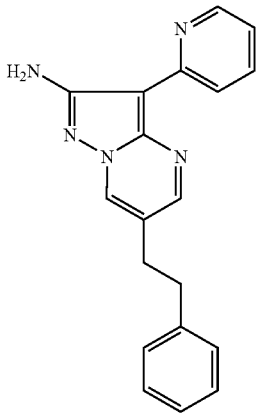 |
| 214 | 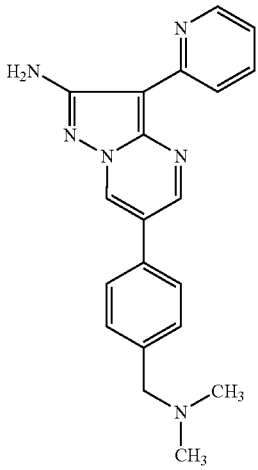 |
| 215 | 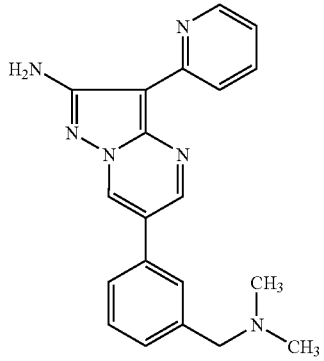 |
-continued
| Cmpd # (V-) | Compound |
|---|---|
| 216 | 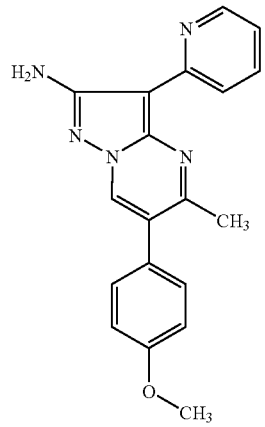 |
| 217 | 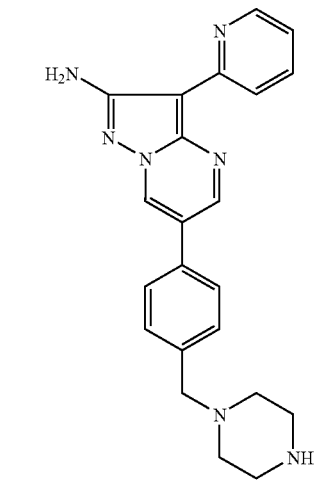 |
| 218 | 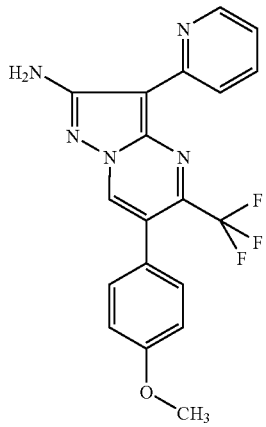 |

| Cmpd # (V-) | Compound |
|---|---|
| 219 | 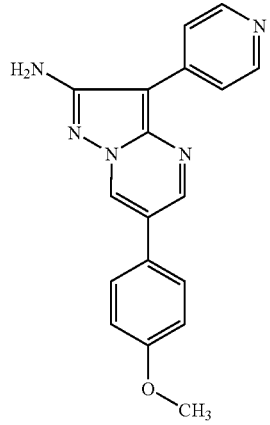 |
| 220 | 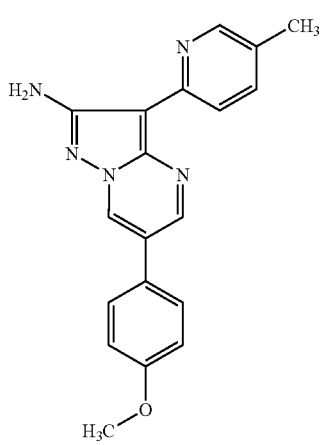 |
| 221 | 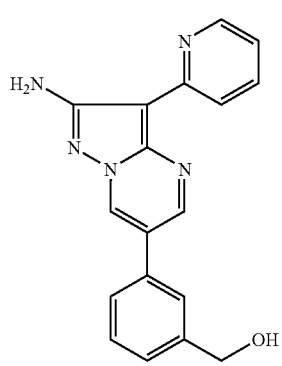 |
| Cmpd # (V-) | Compound |
|---|---|
| 222 | 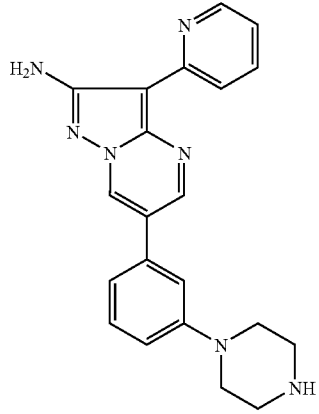 |
| 223 | 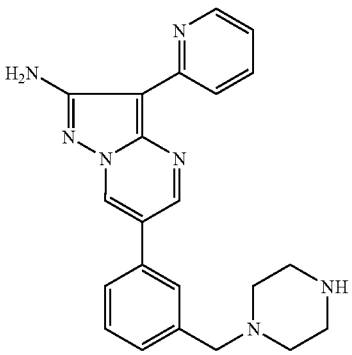 |
| 224 | 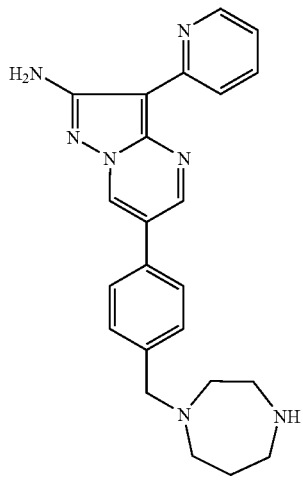 |

| Cmpd # (V-) | Compound |
|---|---|
| 225 | 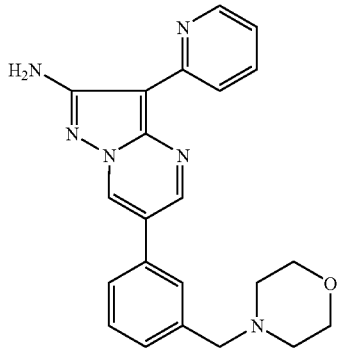 |
| 226 | 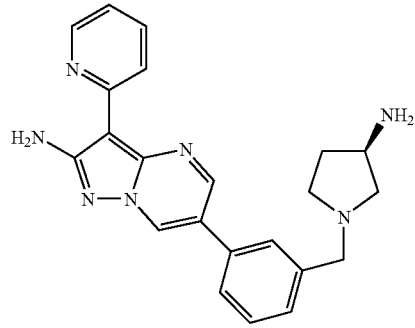 |
| 227 | 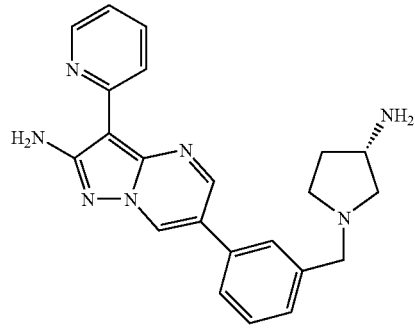 |
| 228 | 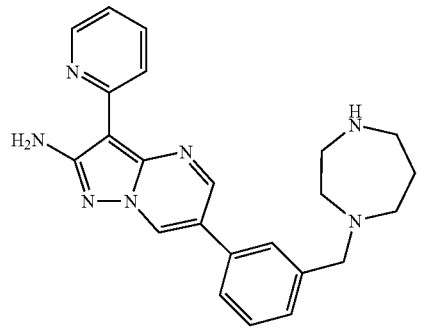 |
| Cmpd # (V-) | Compound |
|---|---|
| 229 | 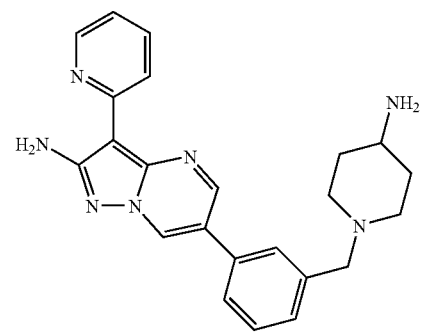 |
| 230 | 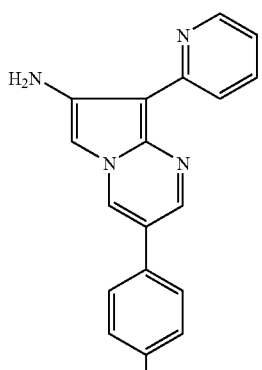 |
| 231 | 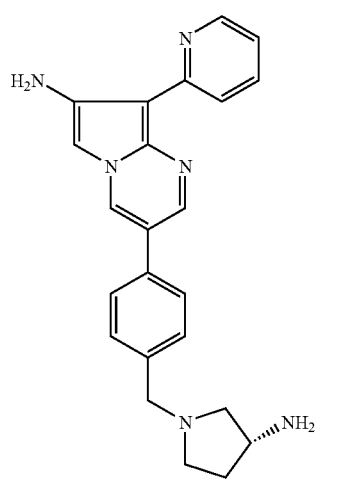 |

-continued
| Cmpd # (V-) | Compound |
|---|---|
| 232 | 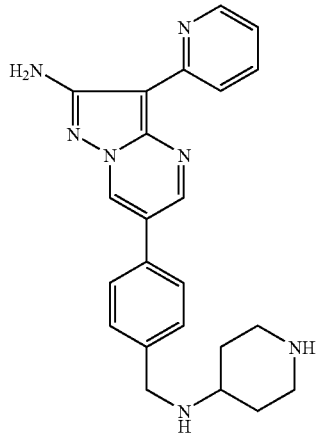 |
| 233 | 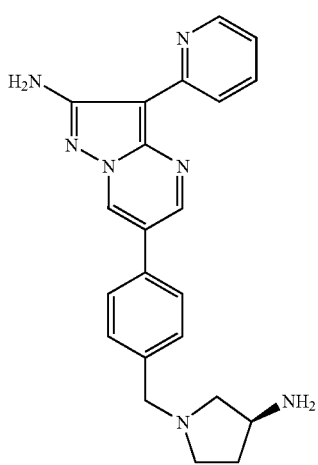 |
| 234 | 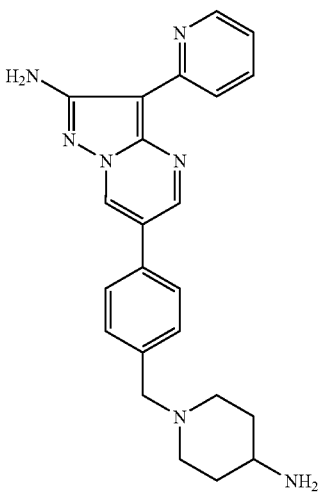 |
-continued
| Cmpd # (V-) | Compound |
|---|---|
| 235 | 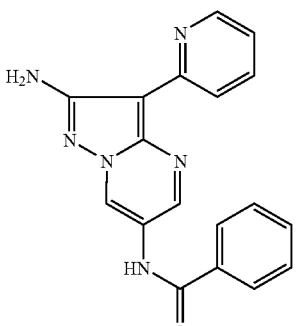 |
| 236 | 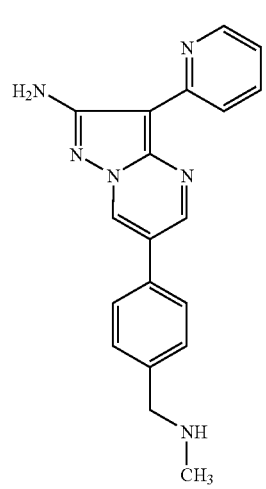 |
| 237 | 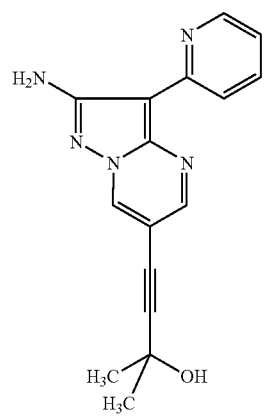 |

-continued
| Cmpd # (V-) | Compound |
|---|---|
| 238 | 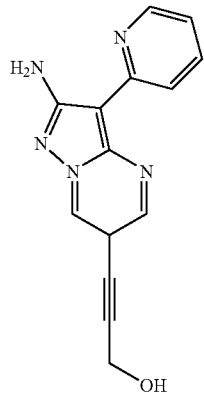 |
| 241 | 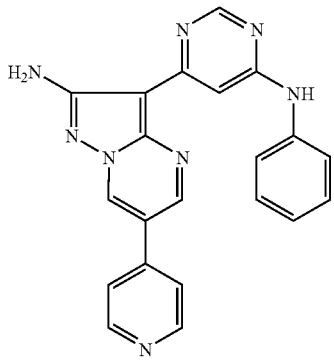 |
| 242 | 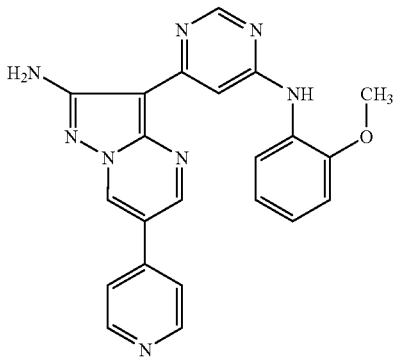 |
| 243 | 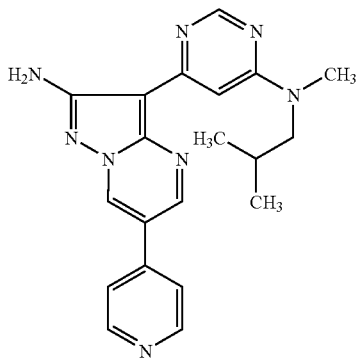 |
-continued
| Cmpd # (V-) | Compound |
|---|---|
| 244 | 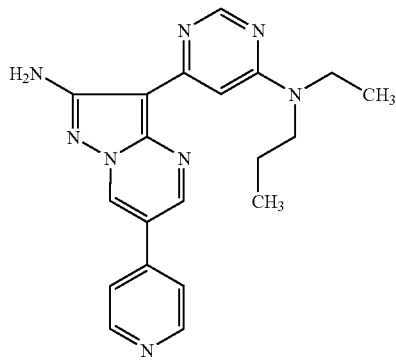 |
| 245 | 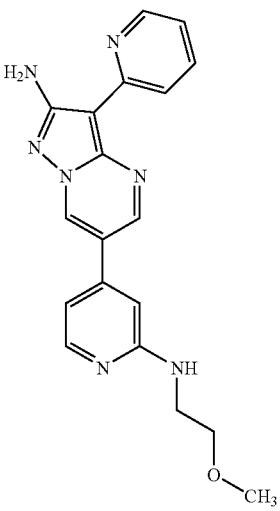 |
| 246 | 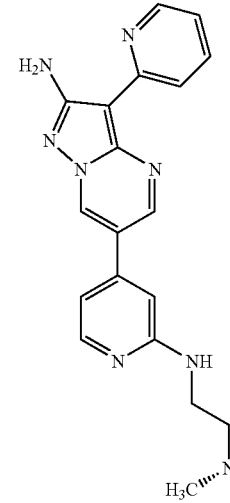 |

| Cmpd # (V-) | Compound |
|---|---|
| 247 | 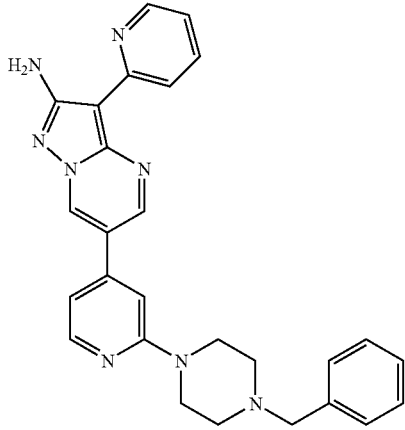 |
| 248 | 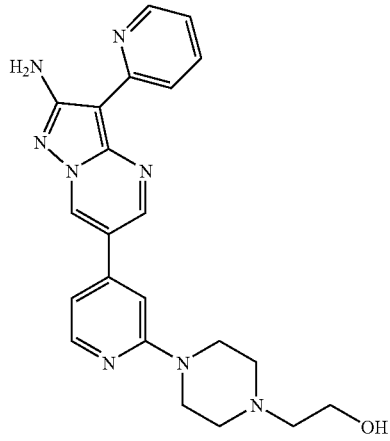 |
| 249 | 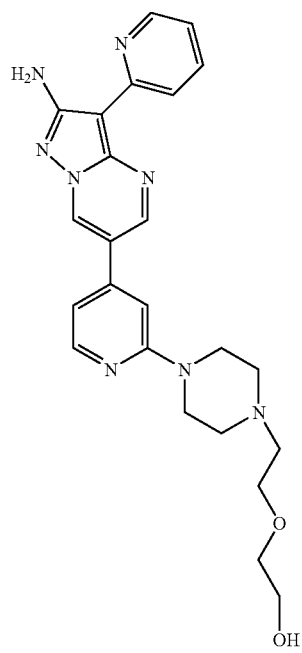 |
| Cmpd # (V-) | Compound |
|---|---|
| 250 | 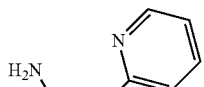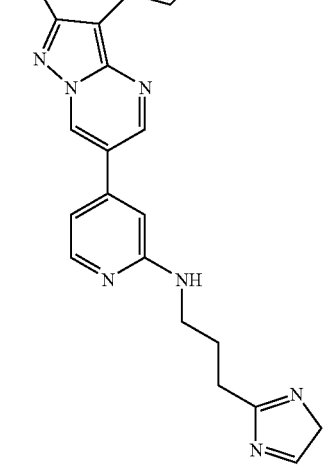 |
| 251 | 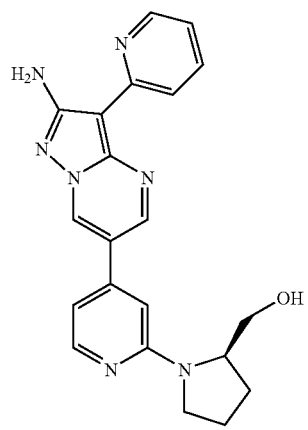 |
| 252 | 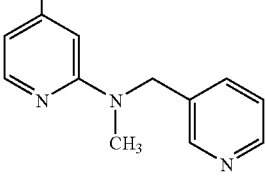 |

-continued
| Cmpd # (V-) | Compound |
|---|---|
| 253 | 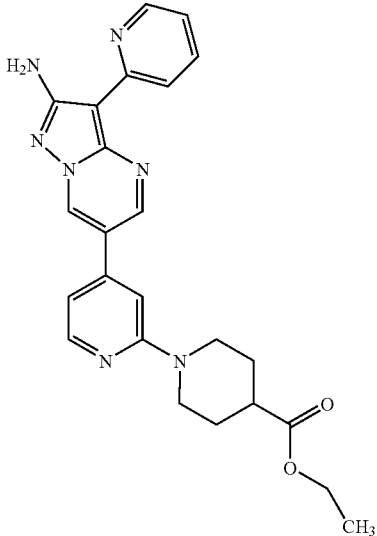 |
| 254 | 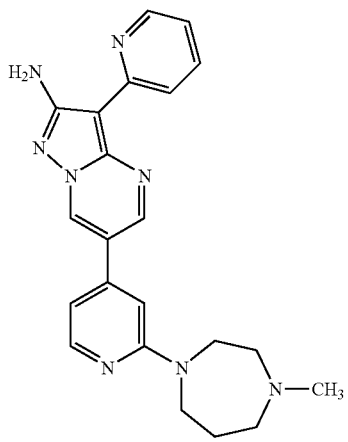 |
| 255 | 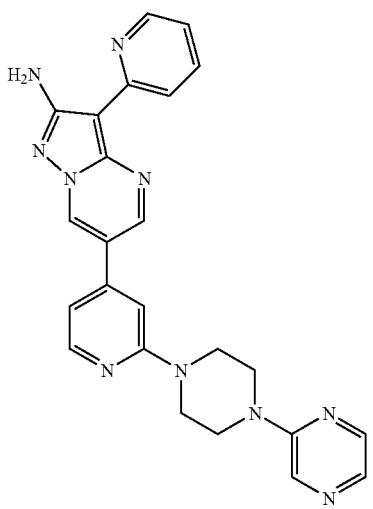 |
-continued
| Cmpd # (V-) | Compound |
|---|---|
| 256 | 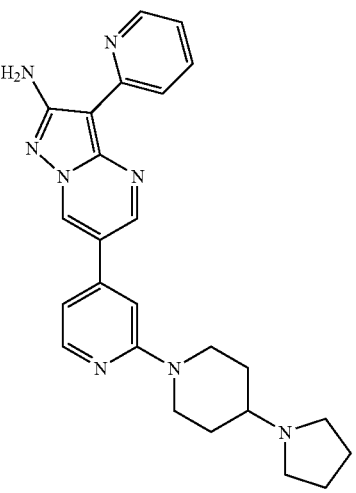 |
| 257 | 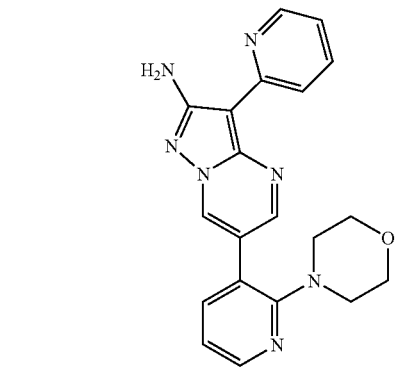 |
| 258 | 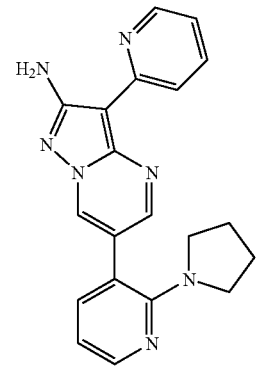 |

| Cmpd # (V-) | Compound |
|---|---|
| 259 | (structure) |
| 260 | (structure) |
| 261 | (structure) |
| 262 | (structure) |

| Cmpd # (V-) | Compound |
|---|---|
| 263 | (structure) |
| 264 | (structure) |
| 265 | (structure) |
| 266 | (structure) |

-continued

| Cmpd # (V-) | Compound |
|---|---|
| 267 | (structure) |
| 268 | (structure) |
| 269 | (structure) |
| 270 | (structure) |

-continued

| Cmpd # (V-) | Compound |
|---|---|
| 271 | (structure) |
| 272 | (structure) |
| 273 | (structure) |
| 274 | (structure) |
| 275 | (structure) |

-continued
| Cmpd # (V-) | Compound |
|---|---|
| 276 | 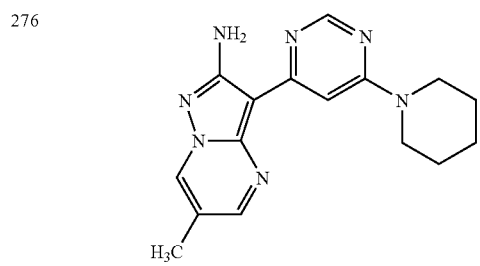 |
| 277 | 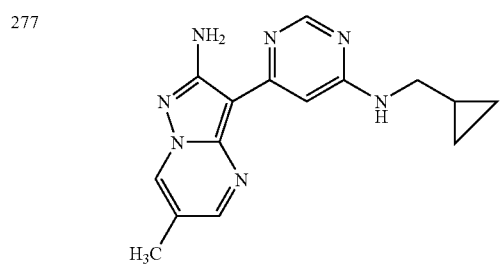 |
| 278 | 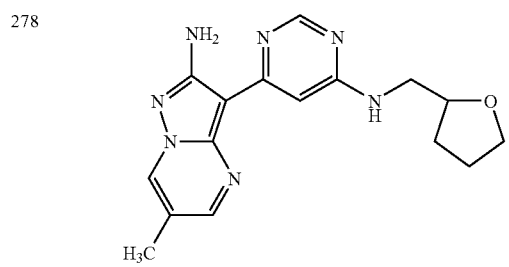 |
| 279 | 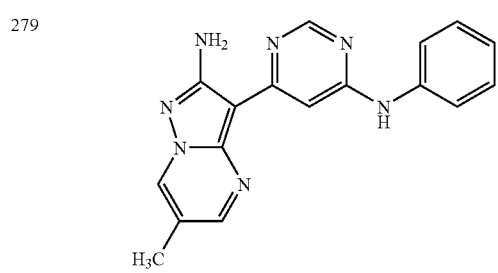 |
| 280 | 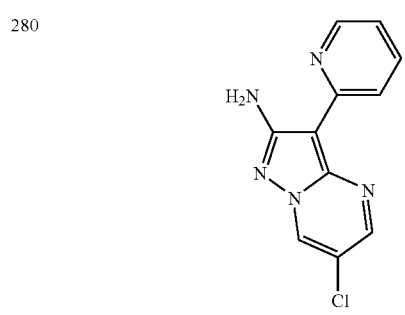 |
-continued
| Cmpd # (V-) | Compound |
|---|---|
| 281 | 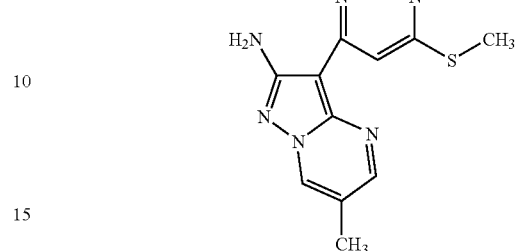 |
| 282 | 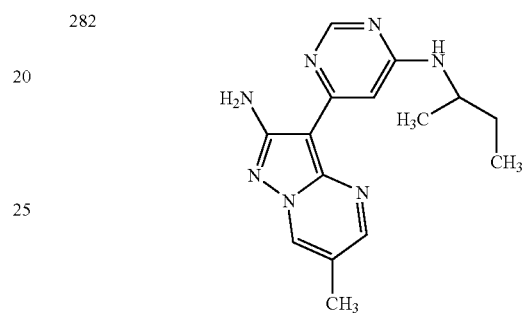 |
| 283 | 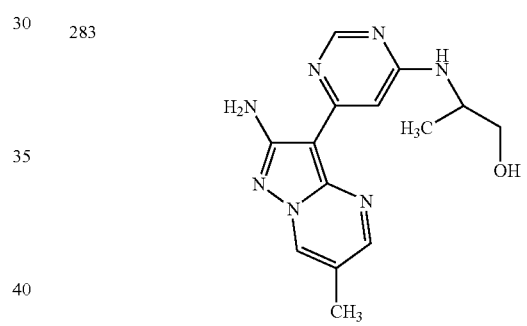 |
| 284 | 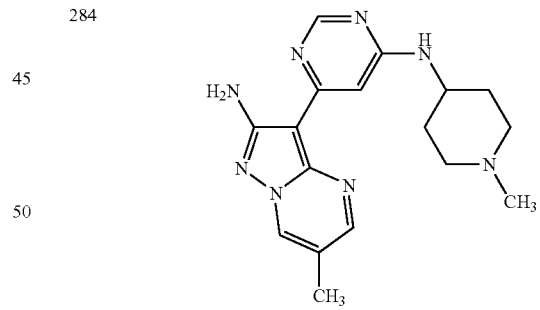 |
| 285 | 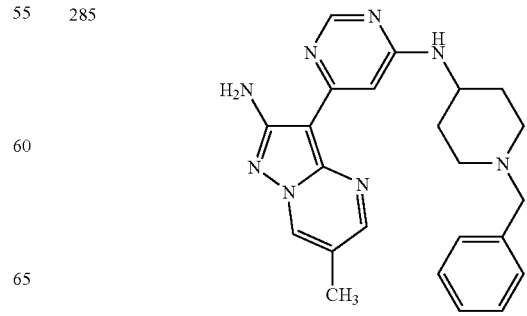 |

| Cmpd # (V-) | Compound |
|---|---|
| 286 | 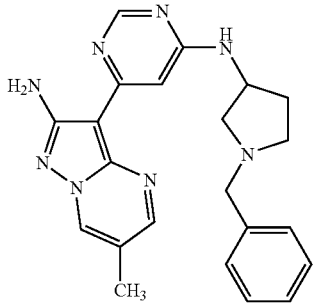 |
| 287 | 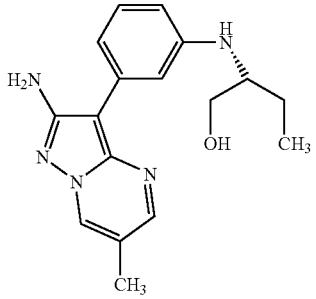 |
| 288 | 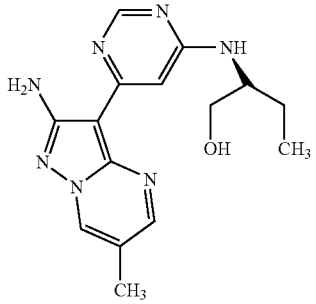 |
| 289 | 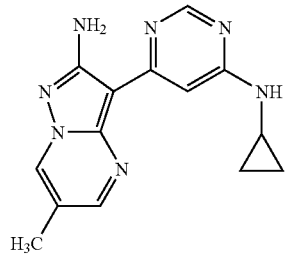 |
| 290 | 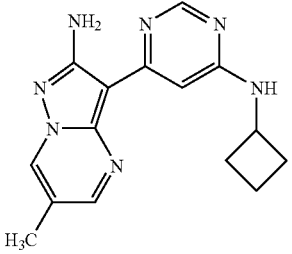 |
| Cmpd # (V-) | Compound |
|---|---|
| 291 | 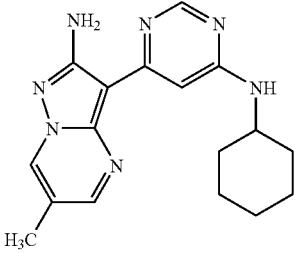 |
| 292 | 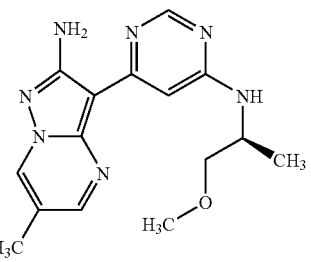 |
| 293 | 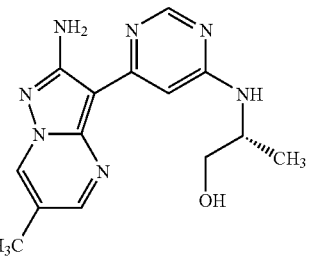 |
| 294 | 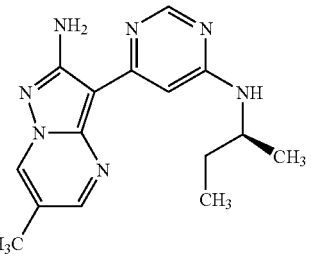 |
| 295 | 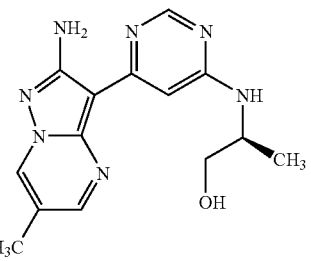 |

| Cmpd # (V-) | Compound |
|---|---|
| 296 | |
| 297 | |
| 298 | |
| 299 | |
| 300 | |

| Cmpd # (V-) | Compound |
|---|---|
| 301 | |
| 302 | |
| 303 | |
| 304 | |
| 305 | |

-continued
| Cmpd # (V-) | Compound |
|---|---|
| 306 | 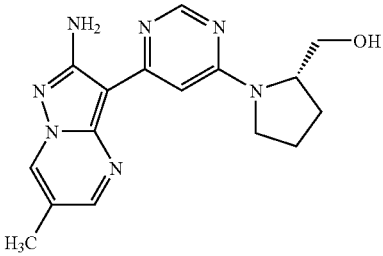 |
| 307 | 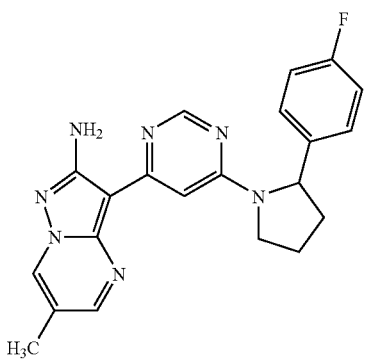 |
| 308 | 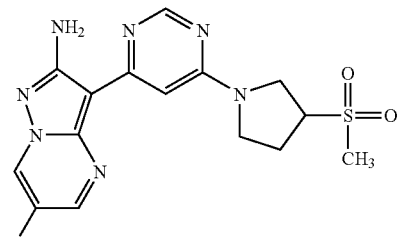 |
| 309 | 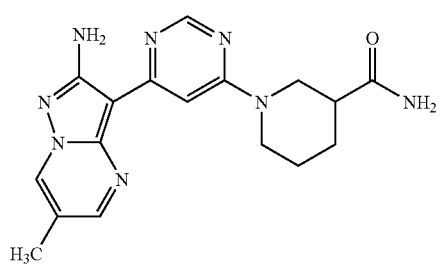 |
| 310 | 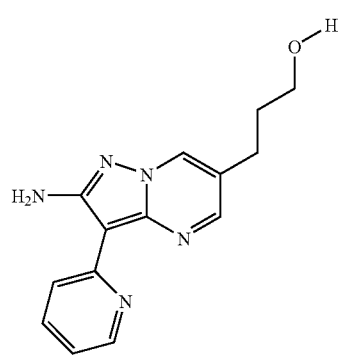 |
-continued
| Cmpd # (V-) | Compound |
|---|---|
| 311 | 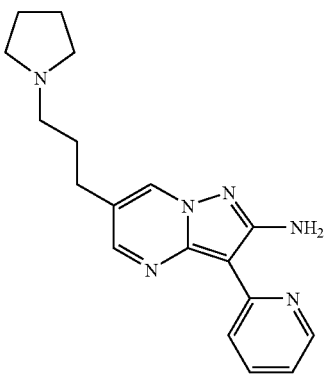 |
| 312 | 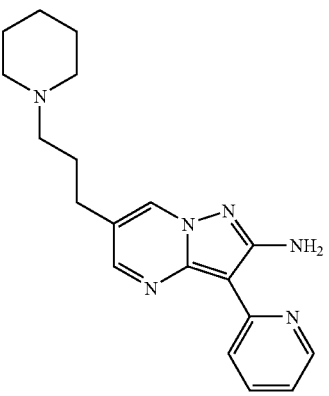 |
| 313 | 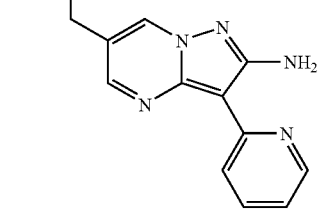 |

-continued
| Cmpd # (V-) | Compound |
|---|---|
| 314 | 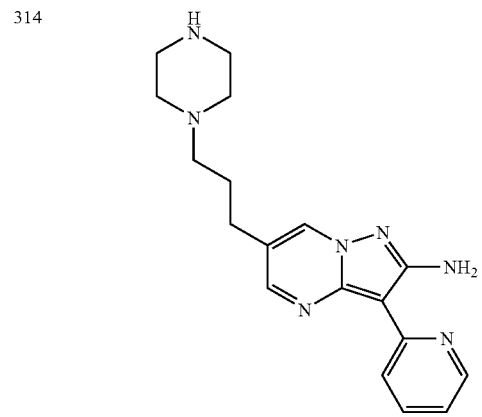 |
| 315 | 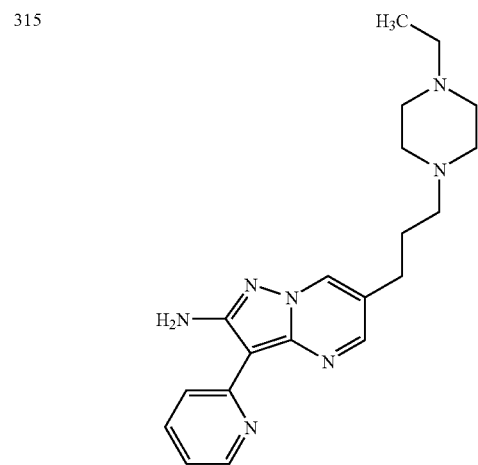 |
| 316 | 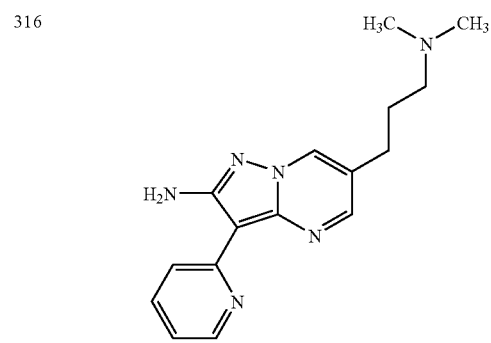 |
-continued
| Cmpd # (V-) | Compound |
|---|---|
| 317 | 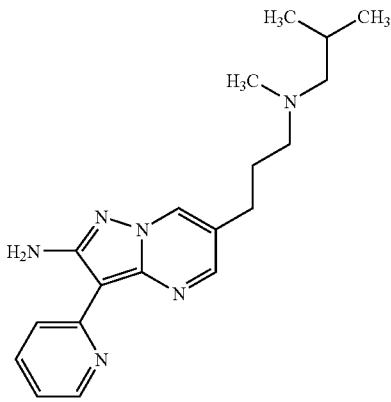 |
| 318 | 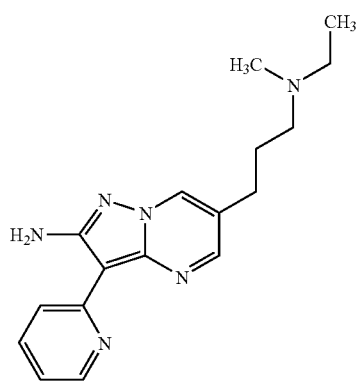 |
| 319 | 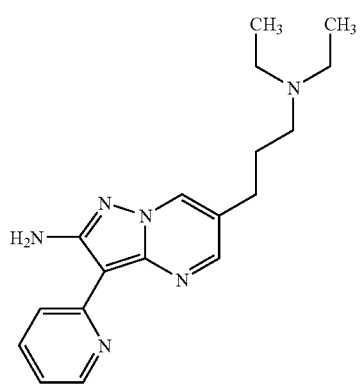 |
| 320 | 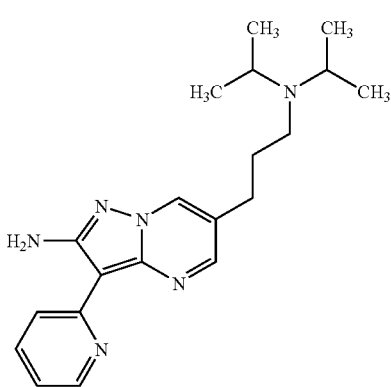 |

-continued
| Cmpd # (V-) | Compound |
|---|---|
| 321 | 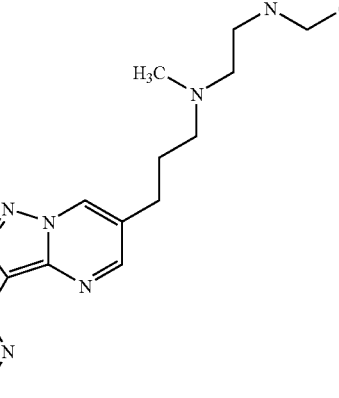 |
| 322 | 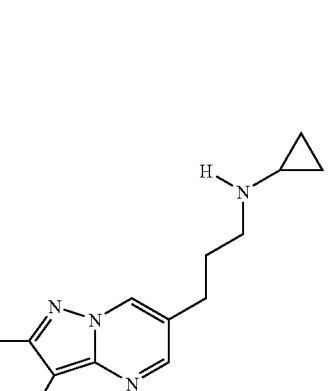 |
| 323 | 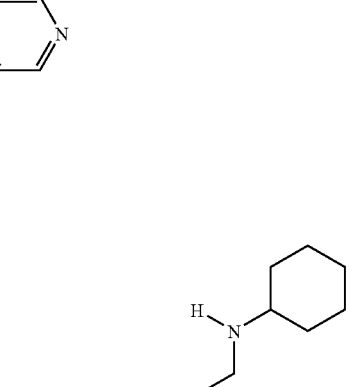 |
-continued
| Cmpd # (V-) | Compound |
|---|---|
| 324 | 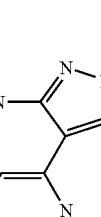 |
| 325 |  |
| 326 | 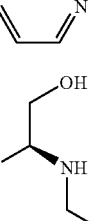 |
| 327 |  |

-continued

| Cmpd # (V-) | Compound |
|---|---|
| 328 | [structure: 7-(3-thiomorpholinopropyl)-3-(pyridin-2-yl)pyrazolo[1,5-a]pyrimidin-2-amine] |
| 329 | [structure: 2-amino-3-(pyridin-2-yl)pyrazolo[1,5-a]pyrimidine with 6-(3-((tetrahydrofuran-2-yl)methylamino)propyl) substituent] |
| 330 | [structure: ethyl 1-(3-(2-amino-3-(pyridin-2-yl)pyrazolo[1,5-a]pyrimidin-6-yl)propyl)piperidine-3-carboxylate] |

-continued

| Cmpd # (V-) | Compound |
|---|---|
| 331 | [structure: 6-(3-(4-isopropylpiperazin-1-yl)propyl)-3-(pyridin-2-yl)pyrazolo[1,5-a]pyrimidin-2-amine] |
| 332 | [structure: pyrazolo[1,5-a]pyrimidine with 6-amino-N-cyclopentylpyrimidin-4-yl and methyl substituents] |
| 333 | [structure: pyrazolo[1,5-a]pyrimidine with 6-amino-N-(norbornyl)pyrimidin-4-yl and methyl substituents] |
| 334 | [structure: pyrazolo[1,5-a]pyrimidine with 6-amino-N-(2-(benzyloxy)cyclopentyl)pyrimidin-4-yl substituent] |
| 335 | [structure: pyrazolo[1,5-a]pyrimidine with 6-amino-N-(tetrahydrofuran-3-yl)pyrimidin-4-yl and methyl substituents] |

-continued
| Cmpd # (V-) | Compound |
|---|---|
| 336 | 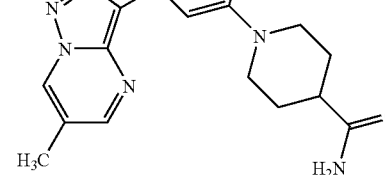 |
| 337 | 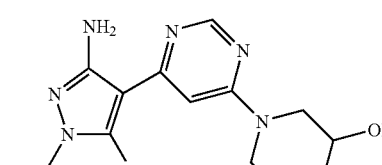 |
| 338 | 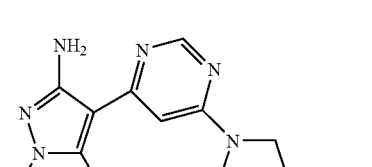 |
| 339 | 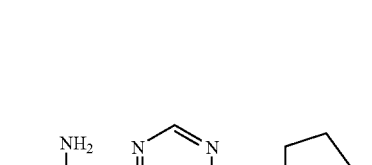 |
| 340 | 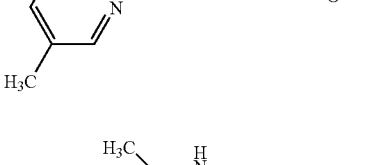 |
-continued
| Cmpd # (V-) | Compound |
|---|---|
| 341 | |
| 342 | |
| 343 | |
| 344 | |
| 345 | |

-continued
| Cmpd # (V-) | Compound |
|---|---|
| 346 | 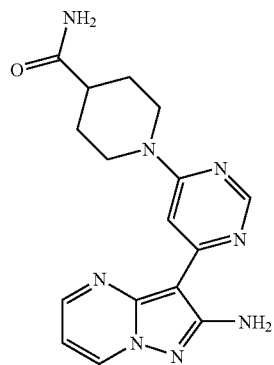 |
| 347 | 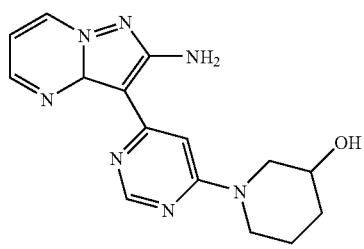 |
| 348 | 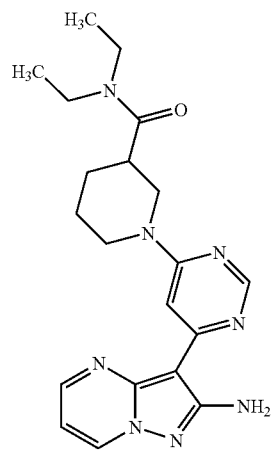 |
| 349 | 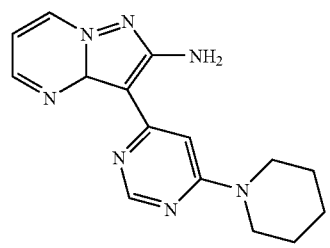 |
-continued
| Cmpd # (V-) | Compound |
|---|---|
| 350 | 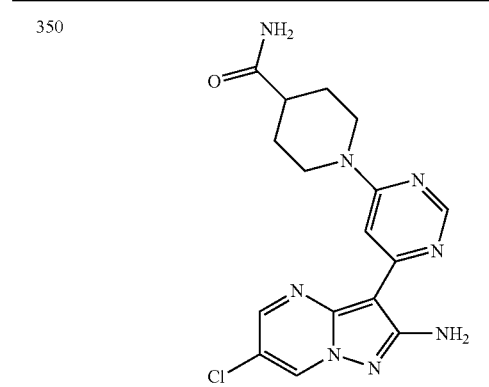 |
| 351 | 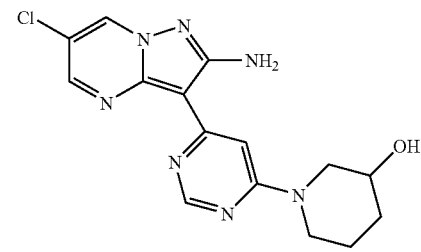 |
| 352 | 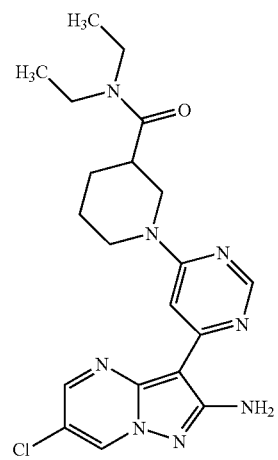 |
| 353 | 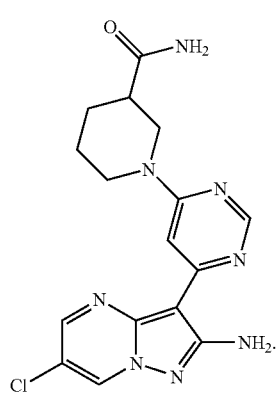 |

14. A pharmaceutical composition comprising a compound according to claim 1 or a pharmaceutically acceptable salt thereof, and a pharmaceutically acceptable carrier or diluent.

15. A method of treating a cancer selected from colon, breast, gastric, ovarian, prostate, or pancreatic cancer in a patient in need thereof, wherein said method comprises administering to said patient a compound according to claim 1 or a composition comprising said compound.

* * * * *